US012799230B2

(12) United States Patent
Liu et al.

(10) Patent No.: US 12,799,230 B2
(45) Date of Patent: *Nov. 17, 2026

(54) ANTI-SCLEROSTIN CONSTRUCTS AND USES THEREOF

(71) Applicant: Angitia Incorporated Limited, Westlake Village, CA (US)

(72) Inventors: Xiaofeng Liu, Guangzhou (CN); Kunfeng Liu, Guangzhou (CN); Baozhi Yuan, Guangzhou (CN); Muyu Li, Guangzhou (CN); Hua Zhu Ke, Guangzhou (CN)

(73) Assignee: Angitia Incorporated Limited, Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/573,405

(22) Filed: Mar. 20, 2026

(65) Prior Publication Data

US 2026/0201071 A1 Jul. 16, 2026

Related U.S. Application Data

(63) Continuation of application No. 17/982,481, filed on Nov. 7, 2022, now Pat. No. 12,630,651, which is a continuation of application No. PCT/CN2021/120612, filed on Sep. 26, 2021.

(30) Foreign Application Priority Data

Sep. 28, 2020 (WO) ................ PCT/CN2020/118387

(51) Int. Cl.

| | |
|---|---|
| ***C07K 16/22*** | (2006.01) |
| ***A61P 19/00*** | (2006.01) |
| ***C07K 14/71*** | (2006.01) |
| ***C07K 16/46*** | (2006.01) |

(52) U.S. Cl.

CPC ............ *C07K 16/468* (2013.01); *A61P 19/00* (2018.01); *C07K 2317/31* (2013.01); *C07K 2317/52* (2013.01); *C07K 2317/565* (2013.01); *C07K 2317/622* (2013.01)

(58) Field of Classification Search

CPC ..... C07K 16/22; C07K 14/71; C07K 2317/76

See application file for complete search history.

(56) References Cited

U.S. PATENT DOCUMENTS

| | | | |
|---|---|---|---|
| 4,816,567 | A | 3/1989 | Cabilly et al. |
| 5,500,362 | A | 3/1996 | Robinson et al. |
| 5,624,821 | A | 4/1997 | Winter et al. |
| 5,648,260 | A | 7/1997 | Winter et al. |
| 5,750,373 | A | 5/1998 | Garrard et al. |
| 5,770,429 | A | 6/1998 | Lonberg et al. |
| 5,821,337 | A | 10/1998 | Carter et al. |
| 6,075,181 | A | 6/2000 | Kucherlapati et al. |
| 6,150,584 | A | 11/2000 | Kucherlapati et al. |
| 6,194,551 | B1 | 2/2001 | Idusogie et al. |
| 6,602,684 | B1 | 8/2003 | Umana et al. |
| 6,737,056 | B1 | 5/2004 | Prest |
| 6,982,321 | B2 | 1/2006 | Winter |
| 7,041,870 | B2 | 5/2006 | Tomizuka et al. |
| 7,087,409 | B2 | 8/2006 | Barbas, III et al. |
| 7,189,826 | B2 | 3/2007 | Rodman |
| 7,332,581 | B2 | 2/2008 | Presta |
| 7,371,826 | B2 | 5/2008 | Presta |
| 7,371,849 | B2 | 5/2008 | Honda et al. |
| 7,521,541 | B2 | 4/2009 | Eigenbrot et al. |
| 7,527,791 | B2 | 5/2009 | Adams et al. |
| 7,592,429 | B2 | 9/2009 | Paszty et al. |
| 8,754,287 | B2 | 6/2014 | MacDonald et al. |
| 8,993,720 | B2 | 3/2015 | Dresner et al. |
| 9,511,111 | B2 | 12/2016 | Dresner et al. |
| 9,657,090 | B2 | 5/2017 | Ke et al. |
| 11,999,772 | B2 | 6/2024 | Adams et al. |
| 12,630,651 | B2 * | 5/2026 | Liu ......................... A61P 19/00 |
| 2002/0164328 | A1 | 11/2002 | Shinkawa et al. |
| 2003/0115614 | A1 | 6/2003 | Kanda et al. |
| 2003/0157108 | A1 | 8/2003 | Presta |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |

(Continued)

FOREIGN PATENT DOCUMENTS

| | | |
|---|---|---|
| CN | 107126560 A | 9/2017 |
| RU | 2548817 C2 | 4/2015 |

(Continued)

OTHER PUBLICATIONS

Li et al (J Orthop Translat. Jul. 10, 2025:54:1-7. doi: 10.1016/j.jot.2025.06.019. eCollection Sep. 2025).*
Morrell et al (Bone Aug. 2021: 149:115967. doi: 10.1016/j.bone.2021.115967. Epub Apr. 21, 2021).*
Florio et al (The Journal of Bone and Joint Surgery 105(15):p. 1145-1155, Aug. 2, 2023; abstract).*
Zhang et al (J Orthop Translat. Dec. 6, 2021;31:73-79).*
Promruk et al (Bone Res 14, 73 (Jul. 15, 2026).*
Wang et al (Oncogene vol. 44, pp. 2677-2688 (2025)).*
Abhinandan, K. R. et al. (2008). "Analysis and Improvements to Kabat and Structurally Correct Numbering of Antibody Variable Domains," Molecular Immunology 45:3832-3839.
Adolf-Bryfogle, J. et al. (2015). "PylgClassify: A Database of Antibody CDR Structural Classifications," Nucleic Acids Research 43:D432-D438.

(Continued)

*Primary Examiner* — Lynn A Bristol
(74) *Attorney, Agent, or Firm* — MORRISON & FOERSTER LLP

(57) ABSTRACT

The present application provides anti-Sclerostin constructs that bind to Sclerostin, nucleic acid molecules encoding an amino acid sequence of the anti-Sclerostin construct, vectors comprising the nucleic acid molecules, host cells containing the vectors, methods of preparing the anti-Sclerostin construct, pharmaceutical compositions containing the anti-Sclerostin construct, and methods of using the anti-Sclerostin construct or compositions.

2 Claims, 7 Drawing Sheets

Specification includes a Sequence Listing.

(56) References Cited

U.S. PATENT DOCUMENTS

| | | | |
|---|---|---|---|
| 2005/0014934 A1 | 1/2005 | Hinton et al. | |
| 2005/0079574 A1 | 4/2005 | Bond | |
| 2005/0119455 A1 | 6/2005 | Fuh et al. | |
| 2005/0123546 A1 | 6/2005 | Umana et al. | |
| 2005/0266000 A1 | 12/2005 | Bond et al. | |
| 2007/0061900 A1 | 3/2007 | Murphy et al. | |
| 2007/0117126 A1 | 5/2007 | Sidhu et al. | |
| 2007/0160598 A1 | 7/2007 | Dennis et al. | |
| 2007/0237764 A1 | 10/2007 | Birtalan et al. | |
| 2007/0292936 A1 | 12/2007 | Barthelemy et al. | |
| 2009/0002360 A1 | 1/2009 | Chen et al. | |
| 2009/0307787 A1 | 12/2009 | Grosveld et al. | |
| 2010/0122358 A1 | 5/2010 | Bruggemann et al. | |
| 2013/0337438 A1 | 12/2013 | Mori et al. | |
| 2015/0289489 A1 | 10/2015 | Macdonald et al. | |
| 2015/0368355 A1 | 12/2015 | Yoshida et al. | |
| 2016/0046705 A1 | 2/2016 | Kannan et al. | |
| 2019/0352387 A1 | 11/2019 | Sampei | |
| 2023/0312755 A1* | 10/2023 | Liu ......................... | A61P 19/00 424/136.1 |

FOREIGN PATENT DOCUMENTS

| | | |
|---|---|---|
| WO | WO-1994029351 A2 | 12/1994 |
| WO | WO-1987004462 A1 | 9/1996 |
| WO | WO-1996027011 A1 | 9/1996 |
| WO | WO-1996034103 A1 | 9/1996 |
| WO | WO-1997004801 A1 | 2/1997 |
| WO | WO-1997030087 A1 | 8/1997 |
| WO | WO-1998046755 A1 | 10/1998 |
| WO | WO-1999051642 A1 | 10/1999 |
| WO | WO-1999054440 A1 | 10/1999 |
| WO | WO-1998058964 A1 | 6/2000 |
| WO | WO-2000032773 A1 | 6/2000 |
| WO | WO-2000061739 A1 | 6/2000 |
| WO | WO-2003011878 A3 | 6/2000 |
| WO | WO-2002031140 A1 | 4/2002 |
| WO | WO-2002060919 A3 | 8/2002 |
| WO | WO-1999022764 A1 | 11/2002 |
| WO | WO-2001029246 A1 | 11/2002 |
| WO | WO-2002092015 A2 | 11/2002 |
| WO | WO-2003048731 A2 | 11/2002 |
| WO | WO-2002066509 A2 | 1/2003 |
| WO | WO-2003085107 A1 | 4/2003 |
| WO | WO-2003084570 A1 | 10/2003 |
| WO | WO-2003085119 A1 | 10/2003 |
| WO | WO-2003106657 A2 | 12/2003 |
| WO | WO-2004056312 A3 | 7/2004 |
| WO | WO-2004049794 A3 | 1/2005 |
| WO | WO-2005003158 A2 | 1/2005 |
| WO | WO-2005014650 A2 | 2/2005 |
| WO | WO-2005035586 A1 | 4/2005 |
| WO | WO-2005035778 A1 | 4/2005 |
| WO | WO-2005053742 A1 | 6/2005 |
| WO | WO-2005100402 A1 | 10/2005 |
| WO | WO-2006015373 A2 | 2/2006 |
| WO | WO-2006029879 A3 | 3/2006 |
| WO | WO-2008077546 A1 | 7/2008 |
| WO | WO-2009013155 A2 | 1/2009 |
| WO | WO-2009047356 A1 | 4/2009 |
| WO | WO-2009086320 A1 | 7/2009 |
| WO | WO-2010131185 A1 | 11/2010 |
| WO | WO-2010151792 A1 | 12/2010 |
| WO | WO-2012118903 A2 | 9/2012 |
| WO | WO-2013096291 A2 | 6/2013 |
| WO | WO-2014006100 A1 | 1/2014 |
| WO | WO-2014081955 A1 | 5/2014 |
| WO | WO-2018115879 A1 | 6/2018 |
| WO | WO-2018115880 A1 | 6/2018 |
| WO | WO-2018139623 A1 | 8/2018 |
| WO | WO-2020002673 A1 | 1/2020 |
| WO | WO-2021030179 A1 | 2/2021 |
| WO | WO-2022063262 A1 | 3/2022 |
| WO | WO-2022136582 A1 | 6/2022 |

OTHER PUBLICATIONS

Agholme, F. et al. (Oct. 2011). "Anti-Sclerostin Antibody and Mechanical Loading Appear to Influence Metaphyseal Bone Independently in Rats," Acta Orthopaedica 82(5):628-632.

Akolkar, P. N. et al. (1987). "Different VL and VH Germ-Line Genes are Used to Produce Similar Combining Sites With Specificity for Alpha(1→6) Dextrans," Journal of Immunology 138(12):4472-4479.

Al-Lazikani, B. et al. (1997). "Standard Conformations for The Canonical Structures of Immunoglobulins," Journal of Molecular Biology 273:927-948.

Almagro, J. C. et al. (2008). "Humanization of Antibodies," Frontiers in Bioscience 13:1619-1633.

Angal, S. et al. (1993). "A Single Amino Acid Substitution Abolishes The Heterogeneity of Chimeric Mouse/Human (IgG4) Antibody," Molecular Immunology 30(1):105-108.

Baca, M. et al. (1997). "Antibody Humanization Using Monovalent Phage Display," Journal of Biological Chemistry 272(16):10678-10684.

Balemans, W. et al. (2001). "Increased Bone Density in Sclerosteosis is Due to The Deficiency of A Novel Secreted Protein (SOST)," Human Molecular Genetics 10:537-543.

Ben-Yedidia, T. et al. (1997). "Design of Peptide and Polypeptide Vaccines," Current Opinion in Biotechnology 8:442-448.

Bijker, M. S. et al. (2007). "Design and Development of Synthetic Peptide Vaccines: Past, Present and Future," Expert Review of Vaccines 6(4):591-603.

Boerner, P. et al. (1991). "Production of Antigen-Specific Human Monoclonal Antibodies From In Vitro-Primed Human Splenocytes," Journal of Immunology 147(1):86-95.

Boschert, V. et al. (Aug. 2016). "The Sclerostin-Neutralizing Antibody AbD09097 Recognizes an Epitope Adjacent to Sclerostin's Binding Site for The Wnt Co-Receptor LRP6," Open Biology 6(8):160120,1-20.

Bruggemann, M. et al. (1987). "Comparison of The Effector Functions of Human Immunoglobulins Using A Matched Set of Chimeric Antibodies," Journal of Experimental Medicine 166:1351-1361.

Brunkow, M. E. et al. (2001). "Bone Dysplasia Sclerosteosis Results From Loss of The SOST Gene Product," American Journal of Human Genetics 68:577-589.

Burton, D. R. et al. (1985). "Immunoglobulin G: Functional Sites," Molecular Immunology 22(3):161-206.

Capel, P. J. et al. (1994). "Heterogeneity of Human IgG Fc Receptors," Immunomethods 4:25-34.

Carpenter, K. A. et al. (2023, e-pub. Oct. 10, 2023). "Sclerostin Antibody Improves Alveolar Bone Quality in The Hyp Mouse Model of X-Linked Hypophosphatemia (XLH)," International Journal of Oral Science 15(1):47, 10 pages.

Carpenter, K. A. et al. (Jan. 2022). "Sclerostin Antibody Improves Phosphate Metabolism Hormones, Bone Formation Rates, and Bone Mass in Adult Hyp Mice," Bone 154:116201, 30 pages.

Carpenter, K. A. et al. (Mar. 2020). "Sclerostin Antibody Treatment Increases Bone Mass and Normalizes Circulating Phosphate Levels in Growing Hyp Mice," Journal of Bone and Mineral Research 35(3):596-607.

Carter, P. et al. (1992). "Humanization of an Anti-p185HER2 Antibody for Human Cancer Therapy," PNAS USA 89:4285-4289.

Cheadle, J. P. et al. (1992). "Cloning and Expression of The Variable Regions of Mouse Myeloma Protein MOPC315 in *E. coli*: Recovery of Active Fv Fragments," Molecular Immunology 29(1):21-30.

Chen, W. et al. (2010). "A Large Human Domain Antibody Library Combining Heavy and Light Chain CDR3 Diversity," Molecular Immunology 47:912-921.

Chothia, C. et al. (1985). "Domain Association in Immunoglobulin Molecules," Journal of Molecular Biology 186:651-663.

Chothia, C. et al. (1987). "Canonical Structures for The Hypervariable Regions of Immunoglobulins," Journal of Molecular Biology 196:901-917.

Chothia, C. et al. (1989). "Conformations of Immunoglobulin Hypervariable Regions," Nature 342:877-883.

(56) References Cited

OTHER PUBLICATIONS

Chowdhury, P.S. (2008). "Engineering Hot Spots for Affinity Enhancement of Antibodies," Methods Mol Biol 207:179-196.
Ciulla, M. M. (Jun. 16, 2021). "Predictability in Contemporary Medicine," Frontiers in Medicine 8:510421.
Clackson, T. et al. (Aug. 15, 1991). "Making Antibody Fragments Using Phage Display Libraries," Nature 352:624-628.
Clynes, R. et al. (1998). "Fc Receptors are Required in Passive and Active Immunity to Melanoma," PNAS 95:652-656.
Cragg, M. S. et al. (2003). "Complement-Mediated Lysis by Anti-CD20 mAb Correlates With Segregation Into Lipid Rafts," Blood 101(3):1045-1052.
Cunningham, B. C. et al. (1989). "High-Resolution Epitope Mapping of hGH-Receptor Interactions by Alanine-Scanning Mutagenesis," Science 244:1081-1085.
Daeron, M. (1997). "Fc Receptor Biology," Annual Review of Immunology 15:203-234.
Dall'acqua, W. et al. (1998). "Contribution of Domain Interface Residues to The Stability of Antibody CH3 Domain Homodimers," Biochemistry 37:9266-9273.
Dall'acqua, W. et al. (2005). "Antibody Humanization by Framework Shuffling," Methods 36:43-60.
Dreyer, T. J. et al. (Apr. 3, 2023). "Novel Insights on The Effect of Sclerostin on Bone and Other Organs," Journal of Endocrinology 257(2):e220209, 17 pages.
Duncan, A.R. et al. (1988). "The Binding Site for Clq on IgG," Nature 332:738-740.
Edgar, R.C. et al. (2004). "Muscle: A Multiple Sequence Alignment Method With Reduced Time and Space Complexity," BMC Bioinformatics 5:113, 19 pages.
Edgar, R.C. et al. (2004). "Muscle: Multiple Sequence Alignment With High Accuracy and High Throughput," Nucleic Acids Research 32(5):1792-1797.
Ehrenmann, F. et al. (2009). "IMGT/3Dstructure-DB and IMGT/DomainGapAlign: A Database and a Tool for Immunoglobulins or Antibodies, T Cell Receptors, MHC, IgSF and MhcSF," Nucleic Acids Research 38:D301-D307.
Endo, Y. et al. (2003). "High-Throughput, Genome-Scale Protein Production Method Based on The Wheat Germ Cell-Free Expression System," Biotech Advan 21:695-713.
Fellouse, F. E. et al. (2004). "Synthetic Antibodies From A Four-Amino-Acid Code: A Dominant Role for Tyrosine in Antigen Recognition," PNAS 101(34):12467-12472.
Florio, M. et al. (May 27, 2016). "A Bispecific Antibody Targeting Sclerostin and DKK-Promotes Bone Mass Accrual and Fracture Repair," Nature Communications 7(1):11505, pp. 1-14.
Fulciniti, M. et al. (2009). "Anti-DKK1 Mab (BHQ880) as a Potential Therapeutic Agent for Multiple Myeloma," Blood 114(2):371-379.
Gazzano-Santoro, H. et al. (1997). "A Non-Radioactive Complement-Dependent Cytotoxicity Assay for Anti-CD20 Monoclonal Antibody," J Immunol Methods 202:163-171.
Glorieux, F. H. et al. (Jul. 2017). "BPS804 Anti-Sclerostin Antibody in Adults With Moderate Osteogenesis Imperfecta: Results of A Randomized Phase 2a Trial," Journal of Bone and Mineral Research 32(7):1496-1504.
Griffiths, A. D. et al. (1993). "Human Anti-Self Antibodies With High Specificity From Phage Display Libraries," The EMBO Journal 12(2):725-734.
Guyer, R. L. et al. (1976). "Immunoglobulin Binding by Mouse Intestinal Epithelial Cell Receptors," J Immunol 117(2):587-593.
Hannoush, R. N. et al. (2008). "Kinetics of Wnt-Driven Beta-Catenin Stabilization Revealed by Quantitative and Temporal Imaging," PLoS One 3(10):e3498, 6 pages.
Hellstrom, I. et al. (1985). "Strong Antitumor Activities of IgG3 Antibodies to a Human Melanoma-Associated Ganglioside," PNAS USA 82:1499-1502.
Hellstrom, I. et al. (1986). "Antitumor Effects of L6, an IgG2a Antibody That Reacts With Most Human Carcinomas," PNAS USA 83:7059-7063.
Holdsworth, G. et al. (2018). "Dampening of The Bone Formation Response Following Repeat Dosing With Sclerostin Antibody in Mice is Associated With Up-Regulation of Wnt Antagonists," Bone 107:93-103.
Honegger, A. et al. (2001). "Yet Another Numbering Scheme for Immunoglobulin Variable Domains: An Automatic Modeling and Analysis Tool," J Mol Biol 309:657-670.
Hoogenboom, H. R. et al. (1992). "By-Passing Immunisation: Human Antibodies From Synthetic Repertoires of Germline VH Gene Segments Rearranged In Vitro," J Mol Biol 227:381-388.
Idusogie, E. E. et al. (2000). "Mapping of The C1q Binding Site on Rituxan, A Chimeric Antibody With A Human IgG1 Fc," J Immunol 164:4178-4184.
International Preliminary Report on Patentability issued on Mar. 28, 2023 for PCT Application No. PCT/CN2021/120612, filed on Sep. 26, 2021, 5 pages.
International Search Report and Written Opinion of the International Searching Authority mailed on Sep. 26, 2021 for PCT Application No. PCT/CN2021/120612 filed on Sep. 26, 2021, 8 pages.
Jansen, F. K. et al. (1982). "Immunotoxins: Hybrid Molecules Combining High Specificity and Potent Cytotoxicity," Immunol Rev 62:185-216.
Jones, P. T. et al. (1986). "Replacing The Complementarity-Determining Regions in a Human Antibody With Those From A Mouse," Nature 321(6069):522-525.
Kabat, D. et al. (1977). "Competition Between Globin Messenger Ribonucleic Acids for a Discriminating Initiation Factor," J Biol Chem 252(8):2684-2690.
Kanda, Y. et al. (2005). "Comparison of Cell Lines for Stable Production of Fucose-Negative Antibodies With Enhanced ADCC," Biotechnology and Bioengineering 94(4):680-688.
Kashmiri, S. V. S. et al. (2005). "SDR grafting—a New Approach to Antibody Humanization," Methods 36:25-34.
Ke, H. Z. et al. (2012). "Sclerostin and Dickkopf-1 as Therapeutic Targets in Bone Diseases," Endocrine Reviews 33(5), 37 pages.
Kedlaya, R. et al. (Nov. 13, 2013). "IGF-I Regulates Phosphate Homeostasis by Mediating Renal Phosphate Reabsorption and Bone Mineralization," Science Translational Medicine 5(211):211ra158, 20 pages.
Kim, J. et al. (2020). "Sclerostin Inhibits Wnt Signaling Through Tandem Interaction With Two LRP6 Ectodomains," Nature Communications 11(1):5357, 11 pages.
Kleber, M. et al. (Jul. 3, 2019). "Monoclonal Antibodies Against RANKL and Sclerostin for Myeloma-Related Bone Disease: Can They Change The Standard of Care?," Expert Review of Hematology 12(8):651-663, 34 pages.
Klimka, A. et al. (2000). "Human Anti-CD30 Recombinant Antibodies by Guided Phage Antibody Selection Using Cell Panning," British Journal Of Cancer 83(2):252-260.
Kohler, G. et al. (1976). "Fusion Between Immunoglobulin-Secreting and Nonsecreting Myeloma Cell Lines," Eur J Immunol 6:292-295.
Kozbor, D. et al. (1984). "A Human Hybrid Myeloma for Production of Human Monoclonal Antibodies," J Immunol 133(6):3001-3005.
Lee, C. V. et al. (2004). "Bivalent Antibody Phage Display Mimics Natural Immunoglobulin," J Immunol Methods 284:119-132.
Lee, C. V. et al. (2004). "High-Affinity Human Antibodies From Phage-Displayed Synthetic Fab Libraries With A Single Framework Scaffold," J Mol Biol 340:1073-1093.
Lefranc, M. P. et al. (2003). "IMGT Unique Numbering for Immunoglobulin and T Cell Receptor Variable Domains and Ig Superfamily V-Like Domains," Dev Compar Immunol 27:55-77.
Li, J. et al. (2006). "Human Antibodies for Immunotherapy Development Generated via A Human B Cell Hybridoma Technology," PNAS 103(10):3557-3562.
Li, J. et al. (2009, e-pub. Dec. 1, 2008). "Sclerostin Antibody Treatment Increases Bone Formation, Bone Mass, and Bone Strength in a Rat Model of Postmenopausal Osteoporosis*," Journal of Bone and Mineral Research 24(4):578-588.
Lonberg, N. (2005). "Human Antibodies From Transgenic Animals," Nature Biotechnology 23(9):1117-1125.

(56) References Cited

OTHER PUBLICATIONS

Lonberg, N. (2008). "Fully Human Antibodies From Transgenic Mouse and Phage Display Platforms," Current Opinion in Immunology 20:450-459.

Long, J. et al. (Aug. 2021, e-pub. Jun. 4, 2021). "Multifunctional Magnesium Incorporated Scaffolds by 3D-Printing for Comprehensive Postsurgical Management of Osteosarcoma," Biomaterials 275:120950, 13 pages.

Maccallum, R. C. et al. (1996). "Antibody-Antigen Interactions: Contact Analysis and Binding Site Topography," J Mol Biol 262:732-745.

Manuel, M. (2013). "A New Semi-Subterranean Diving Beetle of The Hydroporus Normandi-Complex From South-Eastern France, With Notes on Other Taxa of The Complex (Coleoptera: Dytiscidae)," Zootaxa 3652(4):453-474.

Marks, J. D. et al. (1991). "By-Passing Immunization: Human Antibodies From V-Gene Libraries Displayed on Phage," J Mol Biol 222(3):581-597.

Marks, J. D. et al. (1992). "By-Passing Immunization: Building High Affinity Human Antibodies by Chain Shuffling," Biotechnology 10:779-783.

Mccafferty, J. et al. (1990). "Phage Antibodies: Filamentous Phage Displaying Antibody Variable Domains," Nature 348:552-554.

Mcclung, M. R. et al. (Jan. 30, 2014). "Romosozumab in Postmenopausal Women With Low Bone Mineral Density," New England Journal of Medicine 370(5):412-420.

Mcdonald, M.M. et al. (Jun. 29, 2017). "Inhibiting The Osteocyte-Specific Protein Sclerostin Increases Bone Mass and Fracture Resistance in Multiple Myeloma," Blood 129(26):3452-3464.

Morrison, S. L. et al. (1984). "Chimeric Human Antibody Molecules: Mouse Antigen-Binding Domains With Human Constant Region Domains," PNAS USA 81:6851-6855.

Munson, P. J. et al. (1980). "Ligand: A Versatile Computerized Approach for Characterization of Ligand-Binding Systems," Analytical Biochemistry 107:220-239.

Okazaki, A. et al. (2004). "Fucose Depletion From Human IgG1 Oligosaccharide Enhances Binding Enthalpy and Association Rate Between IgG1 and FcγRIIIa," J Mol Biol 336:1239-1249.

Ominsky, M. S. et al. (May 2011). "Inhibition of Sclerostin by Monoclonal Antibody Enhances Bone Healing and Improves Bone Density and Strength of Nonfractured Bones," Journal of Bone and Mineral Research 26(5):1012-1021.

Osbourn, J. et al. (2005). "From Rodent Reagents to Human Therapeutics Using Antibody Guided Selection," Methods 36:61-68.

Padlan, E. A. et al. (1991). "A Possible Procedure for Reducing The Immunogenicity of Antibody Variable Domains While Preserving Their Ligand-Binding Properties," Molecular Immunology 28:489-498.

Petkova, S. B. et al. (2006). "Enhanced Half-Life of Genetically Engineered Human IgG1 Antibodies in a Humanized FcRn Mouse Model: Potential Application in Humorally Mediated Autoimmune Disease," International Immunology 18(12):1759-1769.

Pluckthun, A. (1992). "Mono- and Bivalent Antibody Fragments Produced in *Escherichia coli*: Engineering, Folding and Antigen Binding," Immunological Reviews 130:151-188.

Presta, L. G. (1992). "Antibody Engineering," Current Opinion in Structural Biology 2:593-596.

Presta, L. G. et al. (1993). "Humanization of an Antibody Directed Against IgE," J Immunol 151(5):2623-2632.

Queen, C. et al. (1989). "A Humanized Antibody That Binds to The Interleukin 2 Receptor," PNAS USA 86:10029-10033.

Raag, R. et al. (1995). "Single-Chain Fvs," FASEB 9(1):73-80.

Ramakrishnan, S. et al. (1984). "Comparison of The Selective Cytotoxic Effects of Immunotoxins Containing Ricin A Chain or Pokeweed Antiviral Protein and Anti-Thy 1.1 Monoclonal Antibodies," Cancer Research 44:201-208.

Ravetch, J. V. et al. (1991). "Fc Receptors," Annu Rev Immunol 9:457-492.

Ren, Y. et al. (May-Jul. 2016). "Sclerostin Antibody (Scl-Ab) Improves Osteomalacia Phenotype in Dentin Matrix Protein 1 (Dmp1) Knockout Mice With Little Impact on Serum Levels of Phosphorus and FGF23," Matrix Biology 52:151-161, 11 pages.

Retter, I. et al. (2005). "VBASE2, An Integrative V Gene Database," Nucleic Acids Research 33:D671-D674.

Riechmann, L. et al. (1988). "Reshaping Human Antibodies for Therapy," Nature 332:323-327.

Ripka, J. et al. (1986). "Two Chinese Hamster Ovary Glycosylation Mutants Affected in The Conversion of GDP-Mannose to GDP-Fucose," Archives of Biochemistry and Biophysics 249(2):533-545.

Rosok, M. J. et al. (1996). "A Combinatorial Library Strategy for The Rapid Humanization of Anticarcinoma BR96 Fab," J Biol Chem 271:22611-22618.

Saag, K. G. et al. (Oct. 12, 2017). "Romosozumab or Alendronate for Fracture Prevention in Women With Osteoporosis," New England Journal of Medicine 377(15):1417-1427.

Seefried, L. et al. (Jun. 1, 2017). "Efficacy of Anti-Sclerostin Monoclonal Antibody BPS804 in Adult Patients With Hypophosphatasia," Journal of Clinical Investigation 127(6):2148-2158.

Shields, R. L. et al. (2001). "High Resolution Mapping of The Binding Site on Human IgG1 for FcyRI, FcyRII, FcyRIII, and FcRn and Design of IgG1 Variants With Improved Binding to The FcyR," J Biol Chem 276(9):6591-6604.

Sidhu, S. S. et al. (2004). "Phage-Displayed Antibody Libraries of Synthetic Heavy Chain Complementarity Determining Regions," J Mol Biol 338:299-310.

Sims, M. J. et al. (1993). "A Humanized CD18 Antibody Can Block Function Without Cell Destruction," J Immunol 151(4):2296-2308.

Sinder, B. P. et al. (Jan. 2013). "Sclerostin Antibody Improves Skeletal Parameters in a Brtl/b Mouse Model of Osteogenesis Imperfecta," Journal of Bone and Mineral Research 28(1):73-80.

Sitaraman, K. et al. (2009). "Chapter 15: High-Throughput Protein Expression Using Cell-Free System," Methods in Molecular Biology:High-Throughput Protein Expression and Purification 498:229-244.

Skerra, A. (1993). "Bacterial Expression of Immunoglobulin Fragments," Current Opinion in Immunology 5:256-262.

Spirin, A. S. (2004). "High-Throughput Cell-Free Systems for Synthesis of Functionally Active Proteins," Trends in Biotechnology 22:538-545.

Tian, Y. et al. (2018). "EIF3B Correlates With Advanced Disease Stages and Poor Prognosis, and it Promotes Proliferation and Inhibits Apoptosis in Non-Small Cell Lung Cancer," Cancer Biomarkers 23:219-300.

Tomlinson, I. M. et al. (1992). "The Repertoire of Human Germline VH Sequences Reveals About Fifty Groups of VH Segments With Different Hypervariable Loops," J Mol Biol 227:776-798.

Van Dijk, M. A. et al. (2001). "Human Antibodies as Next Generation Therapeutics," Current Opinion in Chemical Biology 5:368-374.

Vitetta, E. S. et al. (1987). "Redesigning Nature's Poisons to Create Anti-Tumor Reagents," Science 238:1098-1104.

Waterhouse, P. et al. (1993). "Combinatorial Infection and In Vivo Recombination: A Strategy for Making Large Phage Antibody Repertoires," Nucleic Acids Research 21(9):2265-2266.

Winter, G. et al. (1994). "Making Antibodies by Phage Display Technology," Annu Rev Immunol 12:433-455.

Wright, A. et al. (1997). "Effect of Glycosylation on Antibody Function: Implications for Genetic Engineering," Tibtech 26-32.

Yamane-Ohnuki, N. et al. (2003). "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnology and Bioengineering 87(5):614-622.

Yavropoulou, M. P. et al. (2012, e-pub. May 2, 2012). "Serum Sclerostin Levels in Paget's Disease and Prostate Cancer With Bone Metastases With A Wide Range of Bone Turnover," Bone 51(1):153-157.

(56) References Cited

OTHER PUBLICATIONS

Yu, S. et al. (May 2022). "Drug Discovery of Sclerostin Inhibitors," Acta Pharmaceutica Sinica B 12(5):2150-2170.

* cited by examiner

SEQUENCE LISTING

```
Sequence total quantity: 200
SEQ ID NO: 1            moltype = AA  length = 5
FEATURE                 Location/Qualifiers
REGION                  1..5
                        note = Synthetic Construct
source                  1..5
                        mol_type = protein
                        organism = synthetic construct
SEQUENCE: 1
DYEIH                                                                5

SEQ ID NO: 2            moltype = AA  length = 5
FEATURE                 Location/Qualifiers
REGION                  1..5
                        note = Synthetic Construct
source                  1..5
                        mol_type = protein
                        organism = synthetic construct
SEQUENCE: 2
DFEMH                                                                5

SEQ ID NO: 3            moltype = AA  length = 5
FEATURE                 Location/Qualifiers
REGION                  1..5
                        note = Synthetic Construct
source                  1..5
                        mol_type = protein
                        organism = synthetic construct
SEQUENCE: 3
DYEMH                                                                5

SEQ ID NO: 4            moltype = AA  length = 5
FEATURE                 Location/Qualifiers
REGION                  1..5
                        note = Synthetic Construct
source                  1..5
                        mol_type = protein
                        organism = synthetic construct
SEQUENCE: 4
SYWMH                                                                5

SEQ ID NO: 5            moltype = AA  length = 17
```

```
FEATURE                 Location/Qualifiers
REGION                  1..17
                        note = Synthetic Construct
source                  1..17
                        mol_type = protein
                        organism = synthetic construct
SEQUENCE: 5
AIDPETGGTA YNQKFKG                                              17

SEQ ID NO: 6            moltype = AA  length = 17
FEATURE                 Location/Qualifiers
REGION                  1..17
                        note = Synthetic Construct
source                  1..17
                        mol_type = protein
                        organism = synthetic construct
SEQUENCE: 6
AIDPETGGTA YNQKFKA                                              17

SEQ ID NO: 7            moltype = AA  length = 17
FEATURE                 Location/Qualifiers
REGION                  1..17
                        note = Synthetic Construct
source                  1..17
                        mol_type = protein
                        organism = synthetic construct
SEQUENCE: 7
AIDPETGGTA YNQKFTA                                              17

SEQ ID NO: 8            moltype = AA  length = 17
FEATURE                 Location/Qualifiers
REGION                  1..17
                        note = Synthetic Construct
source                  1..17
                        mol_type = protein
                        organism = synthetic construct
SEQUENCE: 8
MIHPNSGSSN YNEKFKS                                              17

SEQ ID NO: 9            moltype = AA  length = 6
FEATURE                 Location/Qualifiers
REGION                  1..6
                        note = Synthetic Construct
source                  1..6
                        mol_type = protein
                        organism = synthetic construct
SEQUENCE: 9
YDYVTY                                                          6

SEQ ID NO: 10           moltype = AA  length = 6
FEATURE                 Location/Qualifiers
REGION                  1..6
                        note = Synthetic Construct
source                  1..6
                        mol_type = protein
                        organism = synthetic construct
SEQUENCE: 10
YDYVSY                                                          6

SEQ ID NO: 11           moltype = AA  length = 9
FEATURE                 Location/Qualifiers
REGION                  1..9
                        note = Synthetic Construct
source                  1..9
                        mol_type = protein
                        organism = synthetic construct
SEQUENCE: 11
DYDDEGFAY                                                       9

SEQ ID NO: 12           moltype =   length =
SEQUENCE: 12
000

SEQ ID NO: 13           moltype = AA  length = 17
FEATURE                 Location/Qualifiers
REGION                  1..17
                        note = Synthetic Construct
VARIANT                 9
                        note = Xaa = T or S
```

```
VARIANT                 11
                        note = Xaa = Y or N
VARIANT                 16
                        note = Xaa = K or T
VARIANT                 17
                        note = Xaa = A, G, or S
source                  1..17
                        mol_type = protein
                        organism = synthetic construct
SEQUENCE: 13
AIDPETGGXA XNQKFXX                                                  17

SEQ ID NO: 14           moltype = AA  length = 6
FEATURE                 Location/Qualifiers
REGION                  1..6
                        note = Synthetic Construct
VARIANT                 5
                        note = Xaa = T or S
source                  1..6
                        mol_type = protein
                        organism = synthetic construct
SEQUENCE: 14
YDYVXY                                                              6

SEQ ID NO: 15           moltype = AA  length = 16
FEATURE                 Location/Qualifiers
REGION                  1..16
                        note = Synthetic Construct
source                  1..16
                        mol_type = protein
                        organism = synthetic construct
SEQUENCE: 15
KSSQSLLYSD GRTYLN                                                   16

SEQ ID NO: 16           moltype = AA  length = 16
FEATURE                 Location/Qualifiers
REGION                  1..16
                        note = Synthetic Construct
source                  1..16
                        mol_type = protein
                        organism = synthetic construct
SEQUENCE: 16
KSSQSLLYSD GKTYLN                                                   16

SEQ ID NO: 17           moltype = AA  length = 11
FEATURE                 Location/Qualifiers
REGION                  1..11
                        note = Synthetic Construct
source                  1..11
                        mol_type = protein
                        organism = synthetic construct
SEQUENCE: 17
KASQSVSNDV A                                                        11

SEQ ID NO: 18           moltype = AA  length = 7
FEATURE                 Location/Qualifiers
REGION                  1..7
                        note = Synthetic Construct
source                  1..7
                        mol_type = protein
                        organism = synthetic construct
SEQUENCE: 18
LVSKLDS                                                             7

SEQ ID NO: 19           moltype = AA  length = 7
FEATURE                 Location/Qualifiers
REGION                  1..7
                        note = Synthetic Construct
source                  1..7
                        mol_type = protein
                        organism = synthetic construct
SEQUENCE: 19
YASNRCT                                                             7

SEQ ID NO: 20           moltype = AA  length = 9
FEATURE                 Location/Qualifiers
REGION                  1..9
                        note = Synthetic Construct
```

```
source                1..9
                      mol_type = protein
                      organism = synthetic construct
SEQUENCE: 20
WQGTHLPHT                                                        9

SEQ ID NO: 21         moltype = AA  length = 9
FEATURE               Location/Qualifiers
REGION                1..9
                      note = Synthetic Construct
source                1..9
                      mol_type = protein
                      organism = synthetic construct
SEQUENCE: 21
QQDYSSPWT                                                        9

SEQ ID NO: 22         moltype = AA  length = 115
FEATURE               Location/Qualifiers
REGION                1..115
                      note = Synthetic Construct
source                1..115
                      mol_type = protein
                      organism = synthetic construct
SEQUENCE: 22
QAQLQQSGAE LVRPGASVTL SCKASGYTFT DYEIHWMKQT PVHGLEWIGA IDPETGGTAY  60
NQKFKGKAIL TADRSSSTAY LELRSLTSED SAVYYCYSYD YVTYWGQGTL VTVSA       115

SEQ ID NO: 23         moltype = AA  length = 112
FEATURE               Location/Qualifiers
REGION                1..112
                      note = Synthetic Construct
source                1..112
                      mol_type = protein
                      organism = synthetic construct
SEQUENCE: 23
DVVMTQTPLT WSITIGQPAS ISCKSSQSLL YSDGRTYLNW LLQRPGQSPK RLIYLVSKLD  60
SGVPDRFSGS GSGTDFTLKI SRVEAEDLGF YYCWQGTHLP HTFGAGTKLE LK          112

SEQ ID NO: 24         moltype = AA  length = 115
FEATURE               Location/Qualifiers
REGION                1..115
                      note = Synthetic Construct
source                1..115
                      mol_type = protein
                      organism = synthetic construct
SEQUENCE: 24
QVQLQQSGAE LVRPGASVTL SCKASGYTFT DYEIHWVKQT PVHGLEWIGA IDPETGGTAY  60
NQKFKAKAIL TADRSSSTAY MELRSLTSED SAVYYSFSYD YVSYWGQGTL VTVSA       115

SEQ ID NO: 25         moltype = AA  length = 112
FEATURE               Location/Qualifiers
REGION                1..112
                      note = Synthetic Construct
source                1..112
                      mol_type = protein
                      organism = synthetic construct
SEQUENCE: 25
DVVMTQTPLT LSVTIGQPAS ISCKSSQSLL YSDGRTYLNW LLQRPGQSPK RLIYLVSKLD  60
SGVPDRFAGS GSGTDFSLKI SRVEAEDLGV YYCWQGTHLP HTFGAGTKLE LK          112

SEQ ID NO: 26         moltype = AA  length = 115
FEATURE               Location/Qualifiers
REGION                1..115
                      note = Synthetic Construct
source                1..115
                      mol_type = protein
                      organism = synthetic construct
SEQUENCE: 26
QAQLQQSGAE LVRPGASVTL SCKASGYTFT DYEIHWVKQT PVHGLEWIGA IDPETGGTAY  60
NQKFKGKAIL TADRSSSTAY LELRSLTSED SAVYYCFSYD YVTYWGQGTL VTVTA       115

SEQ ID NO: 27         moltype = AA  length = 112
FEATURE               Location/Qualifiers
REGION                1..112
                      note = Synthetic Construct
source                1..112
                      mol_type = protein
                      organism = synthetic construct
```

```
SEQUENCE: 27
DVVMTQTPLT WSITIGQPAS ISCKSSQSLL YSDGRTYLNW LLQRPGQSPK RLIYLVSKLD  60
SGVPDRFTGS GSGTDFTLKI SRVEAEDLGF YYCWQGTHLP HTFGAGTKLE LK          112

SEQ ID NO: 28           moltype = AA  length = 115
FEATURE                 Location/Qualifiers
REGION                  1..115
                        note = Synthetic Construct
source                  1..115
                        mol_type = protein
                        organism = synthetic construct
SEQUENCE: 28
QVQLQQSGAE LVRPGASVTL SCKASGYTFT DFEMHWVKQT PVHGLEWIGA IDPETGGTAY  60
NQKFTAKAIL TADRSSSTAY MELRSLTSED SAVYYCFSYD YVSYWGQGTL VTVSA       115

SEQ ID NO: 29           moltype = AA  length = 112
FEATURE                 Location/Qualifiers
REGION                  1..112
                        note = Synthetic Construct
source                  1..112
                        mol_type = protein
                        organism = synthetic construct
SEQUENCE: 29
DVMMTQTPLT LSVTIGQPAS ISCKSSQSLL YSDGRTYLNW LLQRPGQSPK RLIYLVSKLD  60
SGVPDRFTGS GSGTDFTLKI SRVEAEDLGV YYCWQGTHLP HTFGAGTKLE LK          112

SEQ ID NO: 30           moltype = AA  length = 115
FEATURE                 Location/Qualifiers
REGION                  1..115
                        note = Synthetic Construct
source                  1..115
                        mol_type = protein
                        organism = synthetic construct
SEQUENCE: 30
QVQLQQSGAE LVRPGASVTL SCKASGYTFT DYEMHWVKQT PVHGLEWIGA IDPETGGTAY  60
NQKFKAKAIL TADRSSSTAY MELRSLTSED SAVYYCFSYD YVSYWGQGTL VTVSA       115

SEQ ID NO: 31           moltype = AA  length = 112
FEATURE                 Location/Qualifiers
REGION                  1..112
                        note = Synthetic Construct
source                  1..112
                        mol_type = protein
                        organism = synthetic construct
SEQUENCE: 31
DVVMTQTPLT LSVTIGQPAS ISCKSSQSLL YSDGRTYLNW LLQRPGQSPK RLIYLVSKLD  60
SGVPDRFTGS GSGTDFTLKI SRVEAEDLGV YYCWQGTHLP HTFGVGTKLE LK          112

SEQ ID NO: 32           moltype = AA  length = 115
FEATURE                 Location/Qualifiers
REGION                  1..115
                        note = Synthetic Construct
source                  1..115
                        mol_type = protein
                        organism = synthetic construct
SEQUENCE: 32
QVQLQQSGAE LVRPGASVTL SCKASGYTFT DFEIHWMKQT PVPGLEWIGA IDPETGGTAY  60
NQKFKGKALL TADKSSSTAY MDLRSLTSED SAVYFCFSYD YVSYWGQGTL VTVSA       115

SEQ ID NO: 33           moltype = AA  length = 112
FEATURE                 Location/Qualifiers
REGION                  1..112
                        note = Synthetic Construct
source                  1..112
                        mol_type = protein
                        organism = synthetic construct
SEQUENCE: 33
DVVMTQTPLT LSVTFGQPAS ISCKSSQSLL YSDGKTYLNW LLQRPGQSPK RLIYLVSKLD  60
SGVPDRFTGS GSGTAFTLKI SRVEAEDLGV YYCWQGTHLP HTFGAGTKLE LR          112

SEQ ID NO: 34           moltype = AA  length = 115
FEATURE                 Location/Qualifiers
REGION                  1..115
                        note = Synthetic Construct
source                  1..115
                        mol_type = protein
                        organism = synthetic construct
```

```
SEQUENCE: 34
QVQLQQSGAE LVRPGASVTL SCKASGYTFT DYEMHWVKQT PVHGLEWIGA IDPETGGSAN  60
NQKFKAKAIL TADRSSSTAY MELRSLTSED SAVYYCFSYD YVSYWGQGTL VTVSA       115

SEQ ID NO: 35          moltype = AA  length = 112
FEATURE                Location/Qualifiers
REGION                 1..112
                       note = Synthetic Construct
source                 1..112
                       mol_type = protein
                       organism = synthetic construct
SEQUENCE: 35
DVVMTQTPLT LSVTIGQPAS ISCKSSQSLL YSDGRTYLNW LLQRPGQSPK RLIYLVSKLD  60
SGVPDRFTGS GSGTDFTLKI GRVEAEDLGV YYCWQGTHLP HTFGAGTKLE LK          112

SEQ ID NO: 36          moltype = AA  length = 115
FEATURE                Location/Qualifiers
REGION                 1..115
                       note = Synthetic Construct
source                 1..115
                       mol_type = protein
                       organism = synthetic construct
SEQUENCE: 36
QVQLQQSGAE LVRPGASVTL SCKASGYTFT DYEMHWVKQT PVHGLEWIGA IDPETGGTAY  60
NQKFKAKAIL TADRSSSTAY MELRSLTSED SAVYYCFSYD YVSYWGQGTL VTVSA       115

SEQ ID NO: 37          moltype = AA  length = 112
FEATURE                Location/Qualifiers
REGION                 1..112
                       note = Synthetic Construct
source                 1..112
                       mol_type = protein
                       organism = synthetic construct
SEQUENCE: 37
DVVMTQTPLT LSVTLGQPAS ISCKSSQSLL YSDGRTYLNW LLQRPGQSPK RLIYLVSKLD  60
SGVPDRFTGS GSGTDFTLKI SRVEAEDLGL YYCWQGTHLP HTFGAGTKLE LK          112

SEQ ID NO: 38          moltype = AA  length = 115
FEATURE                Location/Qualifiers
REGION                 1..115
                       note = Synthetic Construct
source                 1..115
                       mol_type = protein
                       organism = synthetic construct
SEQUENCE: 38
QVQLQQSGAE LVRPGASVTL SCKASGYTFT DFEIHWLKQT PVPGLEWIGA IDPETGGTAY  60
NQKFKGKALL TADKSSSTAY MELRSLTSED SAVYYCFSYD YVSYWGQGTL VTVSA       115

SEQ ID NO: 39          moltype = AA  length = 112
FEATURE                Location/Qualifiers
REGION                 1..112
                       note = Synthetic Construct
source                 1..112
                       mol_type = protein
                       organism = synthetic construct
SEQUENCE: 39
DVVMTQTPLT LSVTIGQPAS ISCKSSQSLL YSDGKTYLNW LLQRPGQSPK RLIYLVSKLD  60
SGVPDRFTGS GSGTAFTLKI SRVEAEDLGV YYCWQGTHLP HTFGAGTKLE LR          112

SEQ ID NO: 40          moltype = AA  length = 118
FEATURE                Location/Qualifiers
REGION                 1..118
                       note = Synthetic Construct
source                 1..118
                       mol_type = protein
                       organism = synthetic construct
SEQUENCE: 40
QVQLQQPGAE LVKPGASVKL SCKASGYTFT SYWMHWVKQR PGQGLEWIGM IHPNSGSSNY  60
NEKFKSKATL TVDKSSSTAY MQLSSLTSED SAVYYCANDY DDEGFAYWGQ GTLVTVSA    118

SEQ ID NO: 41          moltype = AA  length = 107
FEATURE                Location/Qualifiers
REGION                 1..107
                       note = Synthetic Construct
source                 1..107
                       mol_type = protein
                       organism = synthetic construct
```

```
SEQUENCE: 41
SIVMTQTPKF LLVSAGDRVT ITCKASQSVS NDVAWYQQKP GQSPKLLIYY ASNRCTGVPD  60
RFTGSGYGTD FTFTISTVQA EDLAVYFCQQ DYSSPWTFGG GTKLEIK                107

SEQ ID NO: 42           moltype = AA  length = 10
FEATURE                 Location/Qualifiers
REGION                  1..10
                        note = Synthetic Construct
source                  1..10
                        mol_type = protein
                        organism = synthetic construct
SEQUENCE: 42
GFTFSDYAMA                                                         10

SEQ ID NO: 43           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 43
TIIYDGSSTY YRDSVKG                                                 17

SEQ ID NO: 44           moltype = AA  length = 11
FEATURE                 Location/Qualifiers
REGION                  1..11
                        note = Synthetic Construct
source                  1..11
                        mol_type = protein
                        organism = synthetic construct
SEQUENCE: 44
GLGIATDYFD Y                                                       11

SEQ ID NO: 45           moltype = AA  length = 11
FEATURE                 Location/Qualifiers
REGION                  1..11
                        note = Synthetic Construct
source                  1..11
                        mol_type = protein
                        organism = synthetic construct
SEQUENCE: 45
LASEDIYSDL A                                                       11

SEQ ID NO: 46           moltype = AA  length = 7
FEATURE                 Location/Qualifiers
REGION                  1..7
                        note = Synthetic Construct
source                  1..7
                        mol_type = protein
                        organism = synthetic construct
SEQUENCE: 46
NANSLQN                                                            7

SEQ ID NO: 47           moltype = AA  length = 9
FEATURE                 Location/Qualifiers
REGION                  1..9
                        note = Synthetic Construct
source                  1..9
                        mol_type = protein
                        organism = synthetic construct
SEQUENCE: 47
QQYNNYPPT                                                          9

SEQ ID NO: 48           moltype = AA  length = 10
FEATURE                 Location/Qualifiers
REGION                  1..10
                        note = Synthetic Construct
source                  1..10
                        mol_type = protein
                        organism = synthetic construct
SEQUENCE: 48
GYTFTDYYIH                                                         10

SEQ ID NO: 49           moltype = AA  length = 17
FEATURE                 Location/Qualifiers
REGION                  1..17
                        note = Synthetic Construct
```

```
source                  1..17
                        mol_type = protein
                        organism = synthetic construct
SEQUENCE: 49
WIHSNSGATT YAQKFQA                                                   17

SEQ ID NO: 50           moltype =   length =
SEQUENCE: 50
000

SEQ ID NO: 51           moltype = AA  length = 13
FEATURE                 Location/Qualifiers
REGION                  1..13
                        note = Synthetic Construct
source                  1..13
                        mol_type = protein
                        organism = synthetic construct
SEQUENCE: 51
TGSSNIGAGY DVH                                                       13

SEQ ID NO: 52           moltype = AA  length = 7
FEATURE                 Location/Qualifiers
REGION                  1..7
                        note = Synthetic Construct
source                  1..7
                        mol_type = protein
                        organism = synthetic construct
SEQUENCE: 52
GYSNRPS                                                              7

SEQ ID NO: 53           moltype = AA  length = 11
FEATURE                 Location/Qualifiers
REGION                  1..11
                        note = Synthetic Construct
source                  1..11
                        mol_type = protein
                        organism = synthetic construct
SEQUENCE: 53
QSYDNSLSSY V                                                         11

SEQ ID NO: 54           moltype = AA  length = 10
FEATURE                 Location/Qualifiers
REGION                  1..10
                        note = Synthetic Construct
source                  1..10
                        mol_type = protein
                        organism = synthetic construct
SEQUENCE: 54
GFTFSSYAIS                                                           10

SEQ ID NO: 55           moltype = AA  length = 19
FEATURE                 Location/Qualifiers
REGION                  1..19
                        note = Synthetic Construct
source                  1..19
                        mol_type = protein
                        organism = synthetic construct
SEQUENCE: 55
SVSGTGLGFQ TYYPDSVKG                                                 19

SEQ ID NO: 56           moltype = AA  length = 9
FEATURE                 Location/Qualifiers
REGION                  1..9
                        note = Synthetic Construct
source                  1..9
                        mol_type = protein
                        organism = synthetic construct
SEQUENCE: 56
SLENYAFDY                                                            9

SEQ ID NO: 57           moltype = AA  length = 15
FEATURE                 Location/Qualifiers
REGION                  1..15
                        note = Synthetic Construct
source                  1..15
                        mol_type = protein
                        organism = synthetic construct
SEQUENCE: 57
RASESVDDFG ISFIN                                                     15
```

```
SEQ ID NO: 58          moltype = AA  length = 7
FEATURE                Location/Qualifiers
REGION                 1..7
                       note = Synthetic Construct
source                 1..7
                       mol_type = protein
                       organism = synthetic construct
SEQUENCE: 58
AGSKQGS                                                            7

SEQ ID NO: 59          moltype = AA  length = 9
FEATURE                Location/Qualifiers
REGION                 1..9
                       note = Synthetic Construct
source                 1..9
                       mol_type = protein
                       organism = synthetic construct
SEQUENCE: 59
QQLKEVPPT                                                          9

SEQ ID NO: 60          moltype = AA  length = 120
FEATURE                Location/Qualifiers
REGION                 1..120
                       note = Synthetic Construct
source                 1..120
                       mol_type = protein
                       organism = synthetic construct
SEQUENCE: 60
EVQLVESGGG VVQPGRSLRL SCAASGFTFS DYAMAWVRQA PGKGLEWVAT IIYDGSSTYY  60
RDSVKGRFTI SRDNSKNTLY LQMNSLRAED TAVYYCATGL GIATDYFDYW GQGTLVTVSS  120

SEQ ID NO: 61          moltype = AA  length = 107
FEATURE                Location/Qualifiers
REGION                 1..107
                       note = Synthetic Construct
source                 1..107
                       mol_type = protein
                       organism = synthetic construct
SEQUENCE: 61
DIRMTQSPFS LSASVGDRVT ITCLASEDIY SDLAWYQQKP AKAPKLFIYN ANSLQNGVPS  60
RFSGSGSGTD YTLTISSLQP EDFATYYCQQ YNNYPPTFGG GTKVEIK                107

SEQ ID NO: 62          moltype = AA  length = 112
FEATURE                Location/Qualifiers
REGION                 1..112
                       note = Synthetic Construct
source                 1..112
                       mol_type = protein
                       organism = synthetic construct
SEQUENCE: 62
EVQLVQSGAE VKKPGASVKV SCKASGYTFT DYYIHWVRQA PGQGLEWMGW IHSNSGATTY  60
AQKFQARVTM SRDTSSSTAY MELSRLESDD TAMYFCSRED YWGQGTLVTV SS          112

SEQ ID NO: 63          moltype = AA  length = 110
FEATURE                Location/Qualifiers
REGION                 1..110
                       note = Synthetic Construct
source                 1..110
                       mol_type = protein
                       organism = synthetic construct
SEQUENCE: 63
QSVLTQPPSV SGAPGQRVTI SCTGSSNIGA GYDVHWYQQL PGTAPKLLIY GYSNRPSGVP  60
DRFSGSKSGA SASLAITGLR PDDEADYYCQ SYDNSLSSYV FGGGTQLTVL             110

SEQ ID NO: 64          moltype = AA  length = 120
FEATURE                Location/Qualifiers
REGION                 1..120
                       note = Synthetic Construct
source                 1..120
                       mol_type = protein
                       organism = synthetic construct
SEQUENCE: 64
EVQLVESGGG LVQPGGSLRL SCAASGFTFS SYAISWVRQA PGKGLEWVAS VSGTGLGFQT  60
YYPDSVKGRF TISRDNAKNS LYLQMNSLRA EDTAVYYCAT SLENYAFDYW GQGTTVTVSS  120

SEQ ID NO: 65          moltype = AA  length = 111
FEATURE                Location/Qualifiers
```

```
REGION                1..111
                      note = Synthetic Construct
source                1..111
                      mol_type = protein
                      organism = synthetic construct
SEQUENCE: 65
EIVLTQSPAT LSLSPGERAT LSCRASESVD DFGISFINWY QQKPGQAPRL LIYAGSKQGS  60
GIPARFSGSG SGTDFTLTIS SLEPEDFAVY YCQQLKEVPP TFGGGTKVEI K           111

SEQ ID NO: 66         moltype = AA  length = 10
FEATURE               Location/Qualifiers
REGION                1..10
                      note = Synthetic Construct
source                1..10
                      mol_type = protein
                      organism = synthetic construct
SEQUENCE: 66
GFTFSSYAMS                                                         10

SEQ ID NO: 67         moltype = AA  length = 17
FEATURE               Location/Qualifiers
REGION                1..17
                      note = Synthetic Construct
source                1..17
                      mol_type = protein
                      organism = synthetic construct
SEQUENCE: 67
GITGSGGSTY YADSVKG                                                 17

SEQ ID NO: 68         moltype = AA  length = 13
FEATURE               Location/Qualifiers
REGION                1..13
                      note = Synthetic Construct
source                1..13
                      mol_type = protein
                      organism = synthetic construct
SEQUENCE: 68
DPGTTVIMSW FDP                                                     13

SEQ ID NO: 69         moltype = AA  length = 12
FEATURE               Location/Qualifiers
REGION                1..12
                      note = Synthetic Construct
source                1..12
                      mol_type = protein
                      organism = synthetic construct
SEQUENCE: 69
RASQSVRGRY LA                                                      12

SEQ ID NO: 70         moltype = AA  length = 7
FEATURE               Location/Qualifiers
REGION                1..7
                      note = Synthetic Construct
source                1..7
                      mol_type = protein
                      organism = synthetic construct
SEQUENCE: 70
GASSRAT                                                            7

SEQ ID NO: 71         moltype = AA  length = 9
FEATURE               Location/Qualifiers
REGION                1..9
                      note = Synthetic Construct
source                1..9
                      mol_type = protein
                      organism = synthetic construct
SEQUENCE: 71
QQYGSSPRT                                                          9

SEQ ID NO: 72         moltype = AA  length = 122
FEATURE               Location/Qualifiers
REGION                1..122
                      note = Synthetic Construct
source                1..122
                      mol_type = protein
                      organism = synthetic construct
```

```
SEQUENCE: 72
EVQLLESGGG LVQPGGSLRL SCAASGFTFS SYAMSWVRQA PGKGLEWVSG ITGSGGSTYY  60
ADSVKGRFTI SRDNSKNTLY LQMNSLRAED TAVYYCAKDP GTTVIMSWFD PWGQGTLVTV  120
SS                                                                 122

SEQ ID NO: 73          moltype = AA  length = 108
FEATURE                Location/Qualifiers
REGION                 1..108
                       note = Synthetic Construct
source                 1..108
                       mol_type = protein
                       organism = synthetic construct
SEQUENCE: 73
EIVLTQSPGT LSLSPGERAT LSCRASQSVR GRYLAWYQQK PGQAPRLLIY GASSRATGIP  60
DRFSGSGSGT DFTLTISRLE PEDFAVFYCQ QYGSSPRTFG QGTKVEIK               108

SEQ ID NO: 74          moltype = AA  length = 5
FEATURE                Location/Qualifiers
REGION                 1..5
                       note = Synthetic Construct
source                 1..5
                       mol_type = protein
                       organism = synthetic construct
SEQUENCE: 74
GGGGS                                                              5

SEQ ID NO: 75          moltype = AA  length = 10
FEATURE                Location/Qualifiers
REGION                 1..10
                       note = Synthetic Construct
source                 1..10
                       mol_type = protein
                       organism = synthetic construct
SEQUENCE: 75
GGGGSGGGGS                                                         10

SEQ ID NO: 76          moltype = AA  length = 15
FEATURE                Location/Qualifiers
REGION                 1..15
                       note = Synthetic Construct
source                 1..15
                       mol_type = protein
                       organism = synthetic construct
SEQUENCE: 76
GGGGSGGGGS GGGGS                                                   15

SEQ ID NO: 77          moltype = AA  length = 20
FEATURE                Location/Qualifiers
REGION                 1..20
                       note = Synthetic Construct
source                 1..20
                       mol_type = protein
                       organism = synthetic construct
SEQUENCE: 77
GGGGSGGGGS GGGGSGGGGS                                              20

SEQ ID NO: 78          moltype = AA  length = 4
FEATURE                Location/Qualifiers
source                 1..4
                       mol_type = protein
                       organism = synthetic construct
VARIANT                2..4
                       note = Can be absent
VARIANT                1
                       note = Can be present in repeats of any integer
REGION                 1..4
                       note = Synthetic Construct
SEQUENCE: 78
GGGG                                                               4

SEQ ID NO: 79          moltype = AA  length = 4
FEATURE                Location/Qualifiers
source                 1..4
                       mol_type = protein
                       organism = synthetic construct
VARIANT                3..4
                       note = Can be absent, or present in repeats of any integer
                        up to 7
```

```
REGION                  1..4
                        note = Synthetic Construct
SEQUENCE: 79
GSGS                                                                        4

SEQ ID NO: 80           moltype = AA  length = 5
FEATURE                 Location/Qualifiers
REGION                  1..5
                        note = Synthetic Construct
VARIANT                 1..5
                        note = Can be present in repeats of any integer up to 8
source                  1..5
                        mol_type = protein
                        organism = synthetic construct
SEQUENCE: 80
GSGGS                                                                       5

SEQ ID NO: 81           moltype = AA  length = 5
FEATURE                 Location/Qualifiers
REGION                  1..5
                        note = Synthetic Construct
VARIANT                 1..5
                        note = Can be present in repeats of any integer up to 8
source                  1..5
                        mol_type = protein
                        organism = synthetic construct
SEQUENCE: 81
GGGGS                                                                       5

SEQ ID NO: 82           moltype = AA  length = 4
FEATURE                 Location/Qualifiers
REGION                  1..4
                        note = Synthetic Construct
VARIANT                 1..4
                        note = Can be present in repeats of any integer up to 8
source                  1..4
                        mol_type = protein
                        organism = synthetic construct
SEQUENCE: 82
GGGS                                                                        4

SEQ ID NO: 83           moltype = AA  length = 30
FEATURE                 Location/Qualifiers
REGION                  1..30
                        note = Synthetic Construct
source                  1..30
                        mol_type = protein
                        organism = synthetic construct
SEQUENCE: 83
GGGGSGGGGS GGGGSGGGGS GGGGSGGGGS                                            30

SEQ ID NO: 84           moltype = AA  length = 15
FEATURE                 Location/Qualifiers
REGION                  1..15
                        note = Synthetic Construct
VARIANT                 1..15
                        note = Can be present in repeats of any integer up to 3
source                  1..15
                        mol_type = protein
                        organism = synthetic construct
SEQUENCE: 84
GSTSGSGKPG SGEGS                                                            15

SEQ ID NO: 85           moltype = AA  length = 16
FEATURE                 Location/Qualifiers
REGION                  1..16
                        note = Synthetic Construct
source                  1..16
                        mol_type = protein
                        organism = synthetic construct
SEQUENCE: 85
RSSQSLLYSD GRTYLN                                                           16

SEQ ID NO: 86           moltype = AA  length = 16
FEATURE                 Location/Qualifiers
REGION                  1..16
                        note = Synthetic Construct
```

```
source                  1..16
                        mol_type = protein
                        organism = synthetic construct
SEQUENCE: 86
RSSQSLLYSD SRTYLN                                              16

SEQ ID NO: 87           moltype = AA  length = 115
FEATURE                 Location/Qualifiers
REGION                  1..115
                        note = Synthetic Construct
source                  1..115
                        mol_type = protein
                        organism = synthetic construct
SEQUENCE: 87
EVQLVQSGAE VKKPGASVKV SCKASGYTFT DYEIHWVRQA PGKGLEWMGA IDPETGGTAY  60
NQKFKGRVTM TTDTSTSTAY MELRSLRSDD TAVYYCYSYD YVTYWGQGTT VTVSS       115

SEQ ID NO: 88           moltype = AA  length = 112
FEATURE                 Location/Qualifiers
REGION                  1..112
                        note = Synthetic Construct
source                  1..112
                        mol_type = protein
                        organism = synthetic construct
SEQUENCE: 88
DVVMTQSPLS LSVSPGERAS LSCKSSQSLL YSDGRTYLNW YLQKPGQSPQ RLIYLVSKLD  60
SGVPDRFSGS GSGTDFTLKI SRVQSEDVGV YYCWQGTHLP HTFGGGTKVE IK          112

SEQ ID NO: 89           moltype = AA  length = 112
FEATURE                 Location/Qualifiers
REGION                  1..112
                        note = Synthetic Construct
source                  1..112
                        mol_type = protein
                        organism = synthetic construct
SEQUENCE: 89
DIQMTQSPSS LSASVGDRVT ITCRSSQSLL YSDGRTYLNW YQQKPGKSPK RLIYLVSKLD  60
SGVPDRFSGS GSGTDFTLTI SSLQPEDFAT YYCWQGTHLP HTFGGGTKVE IK          112

SEQ ID NO: 90           moltype = AA  length = 112
FEATURE                 Location/Qualifiers
REGION                  1..112
                        note = Synthetic Construct
source                  1..112
                        mol_type = protein
                        organism = synthetic construct
SEQUENCE: 90
DIQMTQSPSS LSASVGDRVT ITCRSSQSLL YSDSRTYLNW LQQKPGKSPK RLIYLVSKLD  60
SGVPDRFSGS GSGTDFTLTI SSLQPEDFAT YYCWQGTHLP HTFGGGTKVE IK          112

SEQ ID NO: 91           moltype = AA  length = 708
FEATURE                 Location/Qualifiers
REGION                  1..708
                        note = Synthetic Construct
source                  1..708
                        mol_type = protein
                        organism = synthetic construct
SEQUENCE: 91
EVQLVESGGG LVQPANSLKL SCAASGFTFS DYAMAWVRQS PKKGLEWVAT IIYDGSSTYY  60
RDSVKGRFTI SRDNAKSTLY LQMDSLRSED TATYYCATGL GIATDYFDYW GQGVLVTVSS  120
AETTAPSVYP LAPGTALKSN SMVTLGCLVK GYFPEPVTVT WNSGALSSGV HTFPAVLQSG  180
LYTLTSSVTV PSSTWPSQTV TCNVAHPASS TKVDKKIVPR NCGGDCKPCI CTGSEVSSVF  240
IFPPKPKDVL TITLTPKVTC VVVDISQDDP EVHFSWFVDD VEVHTAQTRP PEEQFNSTFR  300
SVSELPILHQ DWLNGRTFRC KVTSAAFPSP IEKTISKPEG RTQVPHVYTM SPTKEEMTQN  360
EVSITCMVKG FYPPDIYVEW QMNGQPQENY KNTPPTMDTD GSYFLYSKLN VKKEKWQQGN  420
TFTCSVLHEG LHNHHTEKSL SHSPGKGGGG SGGGGSGGGG SQAQLQQSGA ELVRPGASVT  480
LSCKASGYTF TDYEIHWMKQ TPVHGLEWIG AIDPETGGTA YNQKFKGKAI LTADRSSSTA  540
YLELRSLTSE DSAVYYCYSY DYVTYWGQGT LVTVSAGGGG SGGGGSGGGG SGGGGSDVVM  600
TQTPLTWSIT IGQPASISCK SSQSLLYSDG RTYLNWLLQR PGQSPKRLIY LVSKLDSGVP  660
DRFSGSGSGT DFTLKISRVE AEDLGFYYCW QGTHLPHTFG AGTKLELK              708

SEQ ID NO: 92           moltype = AA  length = 708
FEATURE                 Location/Qualifiers
REGION                  1..708
                        note = Synthetic Construct
source                  1..708
                        mol_type = protein
                        organism = synthetic construct
```

```
SEQUENCE: 92
EVQLVESGGG LVQPANSLKL SCAASGFTFS DYAMAWVRQS PKKGLEWVAT IIYDGSSTYY  60
RDSVKGRFTI SRDNAKSTLY LQMDSLRSED TATYYCATGL GIATDYFDYW GQGVLVTVSS  120
AETTAPSVYP LAPGTALKSN SMVTLGCLVK GYFPEPVTVT WNSGALSSGV HTFPAVLQSG  180
LYTLTSSVTV PSSTWPSQTV TCNVAHPASS TKVDKKIVPR NCGGDCKPCI CTGSEVSSVF  240
IFPPKPKDVL TITLTPKVTC VVVDISQDDP EVHFSWFVDD VEVHTAQTRP PEEQFNSTFR  300
SVSELPILHQ DWLNGRTFRC KVTSAAFPSP IEKTISKPEG RTQVPHVYTM SPTKEEMTQN  360
EVSITCMVKG FYPPDIYVEW QMNGQPQENY KNTPPTMDTD GSYFLYSKLN VKKEKWQQGN  420
TFTCSVLHEG LHNHHTEKSL SHSPGKGGGG SGGGGSGGGG SDVVMTQTPL TWSITIGQPA  480
SISCKSSQSL LYSDGRTYLN WLLQRPGQSP KRLIYLVSKL DSGVPDRFSG SGSGTDFTLK  540
ISRVEAEDLG FYYCWQGTHL PHTFGAGTKL ELKGGGGSGG GGSGGGGSGG GGSQAQLQQS  600
GAELVRPGAS VTLSCKASGY TFTDYEIHWM KQTPVHGLEW IGAIDPETGG TAYNQKFKGK  660
AILTADRSSS TAYLELRSLT SEDSAVYYCY SYDYVTYWGQ GTLVTVSA              708

SEQ ID NO: 93          moltype = AA  length = 214
FEATURE                Location/Qualifiers
REGION                 1..214
                       note = Synthetic Construct
source                 1..214
                       mol_type = protein
                       organism = synthetic construct
SEQUENCE: 93
DIRMTQSPAS LSASLGETVN IECLASEDIY SDLAWYQQKP GKSPQLLIYN ANSLQNGVPS  60
RFSGSGSGTQ YSLKINSLQS EDVATYFCQQ YNNYPPTFGG GTKLELKRAD AAPTVSIFPP  120
STEQLATGGA SVVCLMNNFY PRDISVKWKI DGTERRDGVL DSVTDQDSKD STYSMSSTLS  180
LTKADYESHN LYTCEVVHKT SSSPVVKSFN RNEC                              214

SEQ ID NO: 94          moltype = AA  length = 701
FEATURE                Location/Qualifiers
REGION                 1..701
                       note = Synthetic Construct
source                 1..701
                       mol_type = protein
                       organism = synthetic construct
SEQUENCE: 94
QAQLQQSGAE LVRPGASVTL SCKASGYTFT DYEIHWMKQT PVHGLEWIGA IDPETGGTAY  60
NQKFKGKAIL TADRSSSTAY LELRSLTSED SAVYYCYSYD YVTYWGQGTL VTVSAAKTTP  120
PSVYPLAPGS AAQTNSMVTL GCLVKGYFPE PVTVTWNSGS LSSGVHTFPA VLQSDLYTLS  180
SSVTVPSSPR PSETVTCNVA HPASSTKVDK KIVPRDCGCK PCICTVPEVS SVFIFPPKPK  240
DVLTITLTPK VTCVVVDISK DDPEVQFSWF VDDVEVHTAQ TQPREEQFNS TFRSVSELPI  300
MHQDWLNGKE FKCRVNSAAF PAPIEKTISK TKGRPKAPQV YTIPPPKEQM AKDKVSLTCM  360
ITDFFPEDIT VEWQWNGQPA ENYKNTQPIM NTNGSYFVYS KLNVQKSNWE AGNTFTCSVL  420
HEGLHNHHTE KSLSHSPGKG GGGSGGGGSG GGGSEVQLVE SGGGLVQPAN SLKLSCAASG  480
FTFSDYAMAW VRQSPKKGLE WVATIIYDGS STYYRDSVKG RFTISRDNAK STLYLQMDSL  540
RSEDTATYYC ATGLGIATDY FDYWGQGVLV TVSSGGGGSG GGGSGGGGSG GGGSDIRMTQ  600
SPASLSASLG ETVNIECLAS EDIYSDLAWY QQKPGKSPQL LIYNANSLQN GVPSRFSGSG  660
SGTQYSLKIN SLQSEDVATY FCQQYNNYPP TFGGGTKLEL K                      701

SEQ ID NO: 95          moltype = AA  length = 701
FEATURE                Location/Qualifiers
REGION                 1..701
                       note = Synthetic Construct
source                 1..701
                       mol_type = protein
                       organism = synthetic construct
SEQUENCE: 95
QAQLQQSGAE LVRPGASVTL SCKASGYTFT DYEIHWMKQT PVHGLEWIGA IDPETGGTAY  60
NQKFKGKAIL TADRSSSTAY LELRSLTSED SAVYYCYSYD YVTYWGQGTL VTVSAAKTTP  120
PSVYPLAPGS AAQTNSMVTL GCLVKGYFPE PVTVTWNSGS LSSGVHTFPA VLQSDLYTLS  180
SSVTVPSSPR PSETVTCNVA HPASSTKVDK KIVPRDCGCK PCICTVPEVS SVFIFPPKPK  240
DVLTITLTPK VTCVVVDISK DDPEVQFSWF VDDVEVHTAQ TQPREEQFNS TFRSVSELPI  300
MHQDWLNGKE FKCRVNSAAF PAPIEKTISK TKGRPKAPQV YTIPPPKEQM AKDKVSLTCM  360
ITDFFPEDIT VEWQWNGQPA ENYKNTQPIM NTNGSYFVYS KLNVQKSNWE AGNTFTCSVL  420
HEGLHNHHTE KSLSHSPGKG GGGSGGGGSG GGGSDIRMTQ SPASLSASLG ETVNIECLAS  480
EDIYSDLAWY QQKPGKSPQL LIYNANSLQN GVPSRFSGSG SGTQYSLKIN SLQSEDVATY  540
FCQQYNNYPP TFGGGTKLEL KGGGGSGGGG SGGGGSGGGG SEVQLVESGG GLVQPANSLK  600
LSCAASGFTF SDYAMAWVRQ SPKKGLEWVA TIIYDGSSTY YRDSVKGRFT ISRDNAKSTL  660
YLQMDSLRSE DTATYYCATG LGIATDYFDY WGQGVLVTVS S                      701

SEQ ID NO: 96          moltype = AA  length = 219
FEATURE                Location/Qualifiers
REGION                 1..219
                       note = Synthetic Construct
source                 1..219
                       mol_type = protein
                       organism = synthetic construct
SEQUENCE: 96
DVVMTQTPLT WSITIGQPAS ISCKSSQSLL YSDGRTYLNW LLQRPGQSPK RLIYLVSKLD  60
SGVPDRFSGS GSGTDFTLKI SRVEAEDLGF YYCWQGTHLP HTFGAGTKLE LKRADAAPTV  120
```

```
SIFPPSSEQL TSGGASVVCF LNNFYPKDIN VKWKIDGSER QNGVLNSWTD QDSKDSTYSM  180
SSTLTLTKDE YERHNSYTCE ATHKTSTSPI VKSFNRNEC                         219

SEQ ID NO: 97           moltype = AA  length = 708
FEATURE                 Location/Qualifiers
REGION                  1..708
                        note = Synthetic Construct
source                  1..708
                        mol_type = protein
                        organism = synthetic construct
SEQUENCE: 97
QAQLQQSGAE LVRPGASVTL SCKASGYTFT DYEIHWMKQT PVHGLEWIGA IDPETGGTAY  60
NQKFKGKAIL TADRSSSTAY LELRSLTSED SAVYYCYSYD YVTYWGQGTL VTVSAGGGGS  120
GGGGSGGGGS GGGGSDVVMT QTPLTWSITI GQPASISCKS SQSLLYSDGR TYLNWLLQRP  180
GQSPKRLIYL VSKLDSGVPD RFSGSGSGTD FTLKISRVEA EDLGFYYCWQ GTHLPHTFGA  240
GTKLELKGGG GSGGGGSGGG GSEVQLVESG GGLVQPANSL KLSCAASGFT FSDYAMAWVR  300
QSPKKGLEWV ATIIYDGSST YYRDSVKGRF TISRDNAKST LYLQMDSLRS EDTATYYCAT  360
GLGIATDYFD YWGQGVLVTV SSAETTAPSV YPLAPGTALK SNSMVTLGCL VKGYFPEPVT  420
VTWNSGALSS GVHTFPAVLQ SGLYTLTSSV TVPSSTWPSQ TVTCNVAHPA SSTKVDKKIV  480
PRNCGGDCKP CICTGSEVSS VFIFPPKPKD VLTITLTPKV TCVVVDISQD DPEVHFSWFV  540
DDVEVHTAQT RPPEEQFNST FRSVSELPIL HQDWLNGRTF RCKVTSAAFP SPIEKTISKP  600
EGRTQVPHVY TMSPTKEEMT QNEVSITCMV KGFYPPDIYV EWQMNGQPQE NYKNTPPTMD  660
TDGSYFLYSK LNVKKEKWQQ GNTFTCSVLH EGLHNHHTEK SLSHSPGK               708

SEQ ID NO: 98           moltype = AA  length = 708
FEATURE                 Location/Qualifiers
REGION                  1..708
                        note = Synthetic Construct
source                  1..708
                        mol_type = protein
                        organism = synthetic construct
SEQUENCE: 98
DVVMTQTPLT WSITIGQPAS ISCKSSQSLL YSDGRTYLNW LLQRPGQSPK RLIYLVSKLD  60
SGVPDRFSGS GSGTDFTLKI SRVEAEDLGF YYCWQGTHLP HTFGAGTKLE LKGGGGSGGG  120
GSGGGGSGGG GSQAQLQQSG AELVRPGASV TLSCKASGYT FTDYEIHWMK QTPVHGLEWI  180
GAIDPETGGT AYNQKFKGKA ILTADRSSST AYLELRSLTS EDSAVYYCYS YDYVTYWGQG  240
TLVTVSAGGG GSGGGGSGGG GSEVQLVESG GGLVQPANSL KLSCAASGFT FSDYAMAWVR  300
QSPKKGLEWV ATIIYDGSST YYRDSVKGRF TISRDNAKST LYLQMDSLRS EDTATYYCAT  360
GLGIATDYFD YWGQGVLVTV SSAETTAPSV YPLAPGTALK SNSMVTLGCL VKGYFPEPVT  420
VTWNSGALSS GVHTFPAVLQ SGLYTLTSSV TVPSSTWPSQ TVTCNVAHPA SSTKVDKKIV  480
PRNCGGDCKP CICTGSEVSS VFIFPPKPKD VLTITLTPKV TCVVVDISQD DPEVHFSWFV  540
DDVEVHTAQT RPPEEQFNST FRSVSELPIL HQDWLNGRTF RCKVTSAAFP SPIEKTISKP  600
EGRTQVPHVY TMSPTKEEMT QNEVSITCMV KGFYPPDIYV EWQMNGQPQE NYKNTPPTMD  660
TDGSYFLYSK LNVKKEKWQQ GNTFTCSVLH EGLHNHHTEK SLSHSPGK               708

SEQ ID NO: 99           moltype = AA  length = 214
FEATURE                 Location/Qualifiers
REGION                  1..214
                        note = Synthetic Construct
source                  1..214
                        mol_type = protein
                        organism = synthetic construct
SEQUENCE: 99
DIRMTQSPAS LSASLGETVN IECLASEDIY SDLAWYQQKP GKSPQLLIYN ANSLQNGVPS  60
RFSGSGSGTQ YSLKINSLQS EDVATYFCQQ YNNYPPTFGG GTKLELKRAD AAPTVSIFPP  120
STEQLATGGA SVVCLMNNFY PRDISVKWKI DGTERRDGVL DSVTDQDSKD STYSMSSTLS  180
LTKADYESHN LYTCEVVHKT SSSPVVKSFN RNEC                              214

SEQ ID NO: 100          moltype = AA  length = 701
FEATURE                 Location/Qualifiers
REGION                  1..701
                        note = Synthetic Construct
source                  1..701
                        mol_type = protein
                        organism = synthetic construct
SEQUENCE: 100
EVQLVESGGG LVQPANSLKL SCAASGFTFS DYAMAWVRQS PKKGLEWVAT IIYDGSSTYY  60
RDSVKGRFTI SRDNAKSTLY LQMDSLRSED TATYYCATGL GIATDYFDYW GQGVLVTVSS  120
GGGGSGGGGS GGGGSGGGGS DIRMTQSPAS LSASLGETVN IECLASEDIY SDLAWYQQKP  180
GKSPQLLIYN ANSLQNGVPS RFSGSGSGTQ YSLKINSLQS EDVATYFCQQ YNNYPPTFGG  240
GTKLELKGGG GSGGGGSGGG GSQAQLQQSG AELVRPGASV TLSCKASGYT FTDYEIHWMK  300
QTPVHGLEWI GAIDPETGGT AYNQKFKGKA ILTADRSSST AYLELRSLTS EDSAVYYCYS  360
YDYVTYWGQG TLVTVSAAKT TPPSVYPLAP GSAAQTNSMV TLGCLVKGYF PEPVTVTWNS  420
GSLSSGVHTF PAVLQSDLYT LSSSVTVPSS PRPSETVTCN VAHPASSTKV DKKIVPRDCG  480
CKPCICTVPE VSSVFIFPPK PKDVLTITLT PKVTCVVVDI SKDDPEVQFS WFVDDVEVHT  540
AQTQPREEQF NSTFRSVSEL PIMHQDWLNG KEFKCRVNSA AFPAPIEKTI SKTKGRPKAP  600
QVYTIPPPKE QMAKDKVSLT CMITDFFPED ITVEWQWNGQ PAENYKNTQP IMNTNGSYFV  660
YSKLNVQKSN WEAGNTFTCS VLHEGLHNHH TEKSLSHSPG K                      701
```

```
SEQ ID NO: 101          moltype = AA  length = 701
FEATURE                 Location/Qualifiers
REGION                  1..701
                        note = Synthetic Construct
source                  1..701
                        mol_type = protein
                        organism = synthetic construct
SEQUENCE: 101
DIRMTQSPAS LSASLGETVN IECLASEDIY SDLAWYQQKP GKSPQLLIYN ANSLQNGVPS  60
RFSGSGSGTQ YSLKINSLQS EDVATYFCQQ YNNYPPTFGG GTKLELKGGG GSGGGGSGGG  120
GSGGGGSEVQ LVESGGGLVQ PANSLKLSCA ASGFTFSDYA MAWVRQSPKK GLEWVATIIY  180
DGSSTYYRDS VKGRFTISRD NAKSTLYLQM DSLRSEDTAT YYCATGLGIA TDYFDYWGQG  240
VLVTVSSGGG GSGGGGSGGG GSQAQLQQSG AELVRPGASV TLSCKASGYT FTDYEIHWMK  300
QTPVHGLEWI GAIDPETGGT AYNQKFKGKA ILTADRSSST AYLELRSLTS EDSAVYYCYS  360
YDYVTYWGQG TLVTVSAAKT TPPSVYPLAP GSAAQTNSMV TLGCLVKGYF PEPVTVTWNS  420
GSLSSGVHTF PAVLQSDLYT LSSSVTVPSS PRPSETVTCN VAHPASSTKV DKKIVPRDCG  480
CKPCICTVPE VSSVFIFPPK PKDVLTITLT PKVTCVVVDI SKDDPEVQFS WFVDDVEVHT  540
AQTQPREEQF NSTFRSVSEL PIMHQDWLNG KEFKCRVNSA AFPAPIEKTI SKTKGRPKAP  600
QVYTIPPPKE QMAKDKVSLT CMITDFFPED ITVEWQWNGQ PAENYKNTQP IMNTNGSYFV  660
YSKLNVQKSN WEAGNTFTCS VLHEGLHNHH TEKSLSHSPG K                      701

SEQ ID NO: 102          moltype = AA  length = 219
FEATURE                 Location/Qualifiers
REGION                  1..219
                        note = Synthetic Construct
source                  1..219
                        mol_type = protein
                        organism = synthetic construct
SEQUENCE: 102
DVVMTQTPLT WSITIGQPAS ISCKSSQSLL YSDGRTYLNW LLQRPGQSPK RLIYLVSKLD  60
SGVPDRFSGS GSGTDFTLKI SRVEAEDLGF YYCWQGTHLP HTFGAGTKLE LKRADAAPTV  120
SIFPPSSEQL TSGGASVVCF LNNFYPKDIN VKWKIDGSER QNGVLNSWTD QDSKDSTYSM  180
SSTLTLTKDE YERHNSYTCE ATHKTSTSPI VKSFNRNEC                          219

SEQ ID NO: 103          moltype = AA  length = 446
FEATURE                 Location/Qualifiers
REGION                  1..446
                        note = Synthetic Construct
source                  1..446
                        mol_type = protein
                        organism = synthetic construct
SEQUENCE: 103
EVQLVESGGG LVQPANSLKL SCAASGFTFS DYAMAWVRQS PKKGLEWVAT IIYDGSSTYY  60
RDSVKGRFTI SRDNAKSTLY LQMDSLRSED TATYYCATGL GIATDYFDYW GQGVLVTVSS  120
AETTAPSVYP LAPGTALKSN SMVTLGCLVK GYFPEPVTVT WNSGALSSGV HTFPAVLQSG  180
LYTLTSSVTV PSSTWPSQTV TCNVAHPASS TKVDKKIVPR NCGGDCKPCI CTGSEVSSVF  240
IFPPKPKDVL TITLTPKVTC VVVDISQDDP EVHFSWFVDD VEVHTAQTRP PEEQFNSTFR  300
SVSELPILHQ DWLNGRTFRC KVTSAAFPSP IEKTISKPEG RTQVPHVYTM SPTKEEMTQN  360
EVSITCMVKG FYPPDIYVEW QMNGQPQENY KNTPPTMDTD GSYFLYSKLN VKKEKWQQGN  420
TFTCSVLHEG LHNHHTEKSL SHSPGK                                        446

SEQ ID NO: 104          moltype = AA  length = 476
FEATURE                 Location/Qualifiers
REGION                  1..476
                        note = Synthetic Construct
source                  1..476
                        mol_type = protein
                        organism = synthetic construct
SEQUENCE: 104
QAQLQQSGAE LVRPGASVTL SCKASGYTFT DYEIHWMKQT PVHGLEWIGA IDPETGGTAY  60
NQKFKGKAIL TADRSSSTAY LELRSLTSED SAVYYCYSYD YVTYWGQGTL VTVSAGGGGS  120
GGGGSGGGGS GGGGSDVVMT QTPLTWSITI GQPASISCKS SQSLLYSDGR TYLNWLLQRP  180
GQSPKRLIYL VSKLDSGVPD RFSGSGSGTD FTLKISRVEA EDLGFYYCWQ GTHLPHTFGA  240
GTKLELKGGG GSGGGGSGGG GSDIRMTQSP ASLSASLGET VNIECLASED IYSDLAWYQQ  300
KPGKSPQLLI YNANSLQNGV PSRFSGSGSG TQYSLKINSL QSEDVATYFC QQYNNYPPTF  360
GGGTKLELKR ADAAPTVSIF PPSTEQLATG GASVVCLMNN FYPRDISVKW KIDGTERRDG  420
VLDSVTDQDS KDSTYSMSST LSLTKADYES HNLYTCEVVH KTSSSPVVKS FNRNEC       476

SEQ ID NO: 105          moltype = AA  length = 476
FEATURE                 Location/Qualifiers
REGION                  1..476
                        note = Synthetic Construct
source                  1..476
                        mol_type = protein
                        organism = synthetic construct
SEQUENCE: 105
DVVMTQTPLT WSITIGQPAS ISCKSSQSLL YSDGRTYLNW LLQRPGQSPK RLIYLVSKLD  60
SGVPDRFSGS GSGTDFTLKI SRVEAEDLGF YYCWQGTHLP HTFGAGTKLE LKGGGGSGGG  120
GSGGGGSGGG GSQAQLQQSG AELVRPGASV TLSCKASGYT FTDYEIHWMK QTPVHGLEWI  180
```

-continued

```
GAIDPETGGT AYNQKFKGKA ILTADRSSST AYLELRSLTS EDSAVYYCYS YDYVTYWGQG  240
TLVTVSAGGG GSGGGGSGGG GSDIRMTQSP ASLSASLGET VNIECLASED IYSDLAWYQQ  300
KPGKSPQLLI YNANSLQNGV PSRFSGSGSG TQYSLKINSL QSEDVATYFC QQYNNYPPTF  360
GGGTKLELKR ADAAPTVSIF PPSTEQLATG GASVVCLMNN FYPRDISVKW KIDGTERRDG  420
VLDSVTDQDS KDSTYSMSST LSLTKADYES HNLYTCEVVH KTSSSPVVKS FNRNEC      476

SEQ ID NO: 106          moltype = AA  length = 439
FEATURE                 Location/Qualifiers
REGION                  1..439
                        note = Synthetic Construct
source                  1..439
                        mol_type = protein
                        organism = synthetic construct
SEQUENCE: 106
QAQLQQSGAE LVRPGASVTL SCKASGYTFT DYEIHWMKQT PVHGLEWIGA IDPETGGTAY  60
NQKFKGKAIL TADRSSSTAY LELRSLTSED SAVYYCYSYD YVTYWGQGTL VTVSAAKTTP  120
PSVYPLAPGS AAQTNSMVTL GCLVKGYFPE PVTVTWNSGS LSSGVHTFPA VLQSDLYTLS  180
SSVTVPSSPR PSETVTCNVA HPASSTKVDK KIVPRDCGCK PCICTVPEVS SVFIFPPKPK  240
DVLTITLTPK VTCVVVDISK DDPEVQFSWF VDDVEVHTAQ TQPREEQFNS TFRSVSELPI  300
MHQDWLNGKE FKCRVNSAAF PAPIEKTISK TKGRPKAPQV YTIPPPKEQM AKDKVSLTCM  360
ITDFFPEDIT VEWQWNGQPA ENYKNTQPIM NTNGSYFVYS KLNVQKSNWE AGNTFTCSVL  420
HEGLHNHHTE KSLSHSPGK                                             439

SEQ ID NO: 107          moltype = AA  length = 481
FEATURE                 Location/Qualifiers
REGION                  1..481
                        note = Synthetic Construct
source                  1..481
                        mol_type = protein
                        organism = synthetic construct
SEQUENCE: 107
EVQLVESGGG LVQPANSLKL SCAASGFTFS DYAMAWVRQS PKKGLEWVAT IIYDGSSTYY  60
RDSVKGRFTI SRDNAKSTLY LQMDSLRSED TATYYCATGL GIATDYFDYW GQGVLVTVSS  120
GGGGSGGGGS GGGGSGGGGS DIRMTQSPAS LSASLGETVN IECLASEDIY SDLAWYQQKP  180
GKSPQLLIYN ANSLQNGVPS RFSGSGSGTQ YSLKINSLQS EDVATYFCQQ YNNYPPTFGG  240
GTKLELKGGG GSGGGGSGGG GSDVVMTQTP LTWSITIGQP ASISCKSSQS LLYSDGRTYL  300
NWLLQRPGQS PKRLIYLVSK LDSGVPDRFS GSGSGTDFTL KISRVEAEDL GFYYCWQGTH  360
LPHTFGAGTK LELKRADAAP TVSIFPPSSE QLTSGGASVV CFLNNFYPKD INVKWKIDGS  420
ERQNGVLNSW TDQDSKDSTY SMSSTLTLTK DEYERHNSYT CEATHKTSTS PIVKSFNRNE  480
C                                                                481

SEQ ID NO: 108          moltype = AA  length = 481
FEATURE                 Location/Qualifiers
REGION                  1..481
                        note = Synthetic Construct
source                  1..481
                        mol_type = protein
                        organism = synthetic construct
SEQUENCE: 108
DIRMTQSPAS LSASLGETVN IECLASEDIY SDLAWYQQKP GKSPQLLIYN ANSLQNGVPS  60
RFSGSGSGTQ YSLKINSLQS EDVATYFCQQ YNNYPPTFGG GTKLELKGGG GSGGGGSGGG  120
GSGGGGSEVQ LVESGGGLVQ PANSLKLSCA ASGFTFSDYA MAWVRQSPKK GLEWVATIIY  180
DGSSTYYRDS VKGRFTISRD NAKSTLYLQM DSLRSEDTAT YYCATGLGIA TDYFDYWGQG  240
VLVTVSSGGG GSGGGGSGGG GSDVVMTQTP LTWSITIGQP ASISCKSSQS LLYSDGRTYL  300
NWLLQRPGQS PKRLIYLVSK LDSGVPDRFS GSGSGTDFTL KISRVEAEDL GFYYCWQGTH  360
LPHTFGAGTK LELKRADAAP TVSIFPPSSE QLTSGGASVV CFLNNFYPKD INVKWKIDGS  420
ERQNGVLNSW TDQDSKDSTY SMSSTLTLTK DEYERHNSYT CEATHKTSTS PIVKSFNRNE  480
C                                                                481

SEQ ID NO: 109          moltype = AA  length = 446
FEATURE                 Location/Qualifiers
REGION                  1..446
                        note = Synthetic Construct
source                  1..446
                        mol_type = protein
                        organism = synthetic construct
SEQUENCE: 109
EVQLVESGGG LVQPANSLKL SCAASGFTFS DYAMAWVRQS PKKGLEWVAT IIYDGSSTYY  60
RDSVKGRFTI SRDNAKSTLY LQMDSLRSED TATYYCATGL GIATDYFDYW GQGVLVTVSS  120
AETTAPSVYP LAPGTALKSN SMVTLGCLVK GYFPEPVTVT WNSGALSSGV HTFPAVLQSG  180
LYTLTSSVTV PSSTWPSQTV TCNVAHPASS TKVDKKIVPR NCGGDCKPCI CTGSEVSSVF  240
IFPPKPKDVL TITLTPKVTC VVVDISQDDP EVHFSWFVDD VEVHTAQTRP PEEQFNSTFR  300
SVSELPILHQ DWLNGRTFRC KVTSAAFPSP IEKTISKPEG RTQVPHVYTM SPTKEEMTQN  360
EVSITCMVKG FYPPDIYVEW QMNGQPQENY KNTPPTMDTD GSYFLYSKLN VKKEKWQQGN  420
TFTCSVLHEG LHNHHTEKSL SHSPGK                                     446

SEQ ID NO: 110          moltype = AA  length = 476
FEATURE                 Location/Qualifiers
```

-continued

```
REGION                  1..476
                        note = Synthetic Construct
source                  1..476
                        mol_type = protein
                        organism = synthetic construct
SEQUENCE: 110
DIRMTQSPAS LSASLGETVN IECLASEDIY SDLAWYQQKP GKSPQLLIYN ANSLQNGVPS  60
RFSGSGSGTQ YSLKINSLQS EDVATYFCQQ YNNYPPTFGG GTKLELKRAD AAPTVSIFPP  120
STEQLATGGA SVVCLMNNFY PRDISVKWKI DGTERRDGVL DSVTDQDSKD STYSMSSTLS  180
LTKADYESHN LYTCEVVHKT SSSPVVKSFN RNECGGGGSG GGGSGGGGSQ AQLQQSGAEL  240
VRPGASVTLS CKASGYTFTD YEIHWMKQTP VHGLEWIGAI DPETGGTAYN QKFKGKAILT  300
ADRSSSTAYL ELRSLTSEDS AVYYCSYDY VTYWGQGTLV TVSAGGGGSG GGGSGGGGSG  360
GGGSDVVMTQ TPLTWSITIG QPASISCKSS QSLLYSDGRT YLNWLLQRPG QSPKRLIYLV  420
SKLDSGVPDR FSGSGSGTDF TLKISRVEAE DLGFYYCWQG THLPHTFGAG TKLELK      476

SEQ ID NO: 111          moltype = AA  length = 476
FEATURE                 Location/Qualifiers
REGION                  1..476
                        note = Synthetic Construct
source                  1..476
                        mol_type = protein
                        organism = synthetic construct
SEQUENCE: 111
DIRMTQSPAS LSASLGETVN IECLASEDIY SDLAWYQQKP GKSPQLLIYN ANSLQNGVPS  60
RFSGSGSGTQ YSLKINSLQS EDVATYFCQQ YNNYPPTFGG GTKLELKRAD AAPTVSIFPP  120
STEQLATGGA SVVCLMNNFY PRDISVKWKI DGTERRDGVL DSVTDQDSKD STYSMSSTLS  180
LTKADYESHN LYTCEVVHKT SSSPVVKSFN RNECGGGGSG GGGSGGGGSD VVMTQTPLTW  240
SITIGQPASI SCKSSQSLLY SDGRTYLNWL LQRPGQSPKR LIYLVSKLDS GVPDRFSGSG  300
SGTDFTLKIS RVEAEDLGFY YCWQGTHLPH TFGAGTKLEL KGGGGSGGGG SGGGGSGGGG  360
SQAQLQQSGA ELVRPGASVT LSCKASGYTF TDYEIHWMKQ TPVHGLEWIG AIDPETGGTA  420
YNQKFKGKAI LTADRSSSTA YLELRSLTSE DSAVYYCYSY DYVTYWGQGT LVTVSA      476

SEQ ID NO: 112          moltype = AA  length = 439
FEATURE                 Location/Qualifiers
REGION                  1..439
                        note = Synthetic Construct
source                  1..439
                        mol_type = protein
                        organism = synthetic construct
SEQUENCE: 112
QAQLQQSGAE LVRPGASVTL SCKASGYTFT DYEIHWMKQT PVHGLEWIGA IDPETGGTAY  60
NQKFKGKAIL TADRSSSTAY LELRSLTSED SAVYYCYSYD YVTYWGQGTL VTVSAAKTTP  120
PSVYPLAPGS AAQTNSMVTL GCLVKGYFPE PVTVTWNSGS LSSGVHTFPA VLQSDLYTLS  180
SSVTVPSSPR PSETVTCNVA HPASSTKVDK KIVPRDCGCK PCICTVPEVS SVFIFPPKPK  240
DVLTITLTPK VTCVVVDISK DDPEVQFSWF VDDVEVHTAQ TQPREEQFNS TFRSVSELPI  300
MHQDWLNGKE FKCRVNSAAF PAPIEKTISK TKGRPKAPQV YTIPPPKEQM AKDKVSLTCM  360
ITDFFPEDIT VEWQWNGQPA ENYKNTQPIM NTNGSYFVYS KLNVQKSNWE AGNTFTCSVL  420
HEGLHNHHTE KSLSHSPGK                                             439

SEQ ID NO: 113          moltype = AA  length = 481
FEATURE                 Location/Qualifiers
REGION                  1..481
                        note = Synthetic Construct
source                  1..481
                        mol_type = protein
                        organism = synthetic construct
SEQUENCE: 113
DVVMTQTPLT WSITIGQPAS ISCKSSQSLL YSDGRTYLNW LLQRPGQSPK RLIYLVSKLD  60
SGVPDRFSGS GSGTDFTLKI SRVEAEDLGF YYCWQGTHLP HTFGAGTKLE LKRADAAPTV  120
SIFPPSSEQL TSGGASVVCF LNNFYPKDIN VKWKIDGSER QNGVLNSWTD QDSKDSTYSM  180
SSTLTLTKDE YERHNSYTCE ATHKTSTSPI VKSFNRNECG GGGSGGGGSG GGGSEVQLVE  240
SGGGLVQPAN SLKLSCAASG FTFSDYAMAW VRQSPKKGLE WVATIIYDGS STYYRDSVKG  300
RFTISRDNAK STLYLQMDSL RSEDTATYYC ATGLGIATDY FDYWGQGVLV TVSSGGGGSG  360
GGGSGGGGSG GGGSDIRMTQ SPASLSASLG ETVNIECLAS EDIYSDLAWY QQKPGKSPQL  420
LIYNANSLQN GVPSRFSGSG SGTQYSLKIN SLQSEDVATY FCQQYNNYPP TFGGGTKLEL  480
K                                                                481

SEQ ID NO: 114          moltype = AA  length = 481
FEATURE                 Location/Qualifiers
REGION                  1..481
                        note = Synthetic Construct
source                  1..481
                        mol_type = protein
                        organism = synthetic construct
SEQUENCE: 114
DVVMTQTPLT WSITIGQPAS ISCKSSQSLL YSDGRTYLNW LLQRPGQSPK RLIYLVSKLD  60
SGVPDRFSGS GSGTDFTLKI SRVEAEDLGF YYCWQGTHLP HTFGAGTKLE LKRADAAPTV  120
SIFPPSSEQL TSGGASVVCF LNNFYPKDIN VKWKIDGSER QNGVLNSWTD QDSKDSTYSM  180
SSTLTLTKDE YERHNSYTCE ATHKTSTSPI VKSFNRNECG GGGSGGGGSG GGGSDIRMTQ  240
```

```
SPASLSASLG ETVNIECLAS EDIYSDLAWY QQKPGKSPQL LIYNANSLQN GVPSRFSGSG  300
SGTQYSLKIN SLQSEDVATY FCQQYNNYPP TFGGGTKLEL KGGGGSGGGG SGGGGSGGGG  360
SEVQLVESGG GLVQPANSLK LSCAASGFTF SDYAMAWVRQ SPKKGLEWVA TIIYDGSSTY  420
YRDSVKGRFT ISRDNAKSTL YLQMDSLRSE DTATYYCATG LGIATDYFDY WGQGVLVTVS  480
A                                                                 481

SEQ ID NO: 115         moltype = AA  length = 709
FEATURE                Location/Qualifiers
REGION                 1..709
                       note = Synthetic Construct
source                 1..709
                       mol_type = protein
                       organism = synthetic construct
SEQUENCE: 115
EVQLVESGGG VVQPGRSLRL SCAASGFTFS DYAMAWVRQA PGKGLEWVAT IIYDGSSTYY  60
RDSVKGRFTI SRDNSKNTLY LQMNSLRAED TAVYYCATGL GIATDYFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGKGGG GSGGGGSGGG GSDIQMTQSP SSLSASVGDR  480
VTITCRSSQS LLYSDGRTYL NWYQQKPGKS PKRLIYLVSK LDSGVPDRFS GSGSGTDFTL  540
TISSLQPEDF ATYYCWQGTH LPHTFGCGTK VEIKGGGGSG GGGSGGGGSG GGGSEVQLVQ  600
SGAEVKKPGA SVKVSCKASG YTFTDYEIHW VRQAPGKCLE WMGAIDPETG GTAYNQKFKG  660
RVTMTTDTST STAYMELRSL RSDDTAVYYC YSYDYVTYWG QGTTVTVSA             709

SEQ ID NO: 116         moltype = AA  length = 709
FEATURE                Location/Qualifiers
REGION                 1..709
                       note = Synthetic Construct
source                 1..709
                       mol_type = protein
                       organism = synthetic construct
SEQUENCE: 116
EVQLVESGGG VVQPGRSLRL SCAASGFTFS DYAMAWVRQA PGKGLEWVAT IIYDGSSTYY  60
RDSVKGRFTI SRDNSKNTLY LQMNSLRAED TAVYYCATGL GIATDYFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGKGGG GSGGGGSGGG GSEVQLVQSG AEVKKPGASV  480
KVSCKASGYT FTDYEIHWVR QAPGKCLEWM GAIDPETGGT AYNQKFKGRV TMTTDTSTST  540
AYMELRSLRS DDTAVYYCYS YDYVTYWGQG TTVTVSSGGG GSGGGGSGGG GSGGGGSDIQ  600
MTQSPSSLSA SVGDRVTITC RSSQSLLYSD GRTYLNWYQQ KPGKSPKRLI YLVSKLDSGV  660
PDRFSGSGSG TDFTLTISSL QPEDFATYYC WQGTHLPHTF GCGTKVEIK             709

SEQ ID NO: 117         moltype = AA  length = 709
FEATURE                Location/Qualifiers
REGION                 1..709
                       note = Synthetic Construct
source                 1..709
                       mol_type = protein
                       organism = synthetic construct
SEQUENCE: 117
EVQLVESGGG VVQPGRSLRL SCAASGFTFS DYAMAWVRQA PGKGLEWVAT IIYDGSSTYY  60
RDSVKGRFTI SRDNSKNTLY LQMNSLRAED TAVYYCATGL GIATDYFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGKGGG GSGGGGSGGG GSDVVMTQSP LSLSVSPGER  480
ASLSCKSSQS LLYSDGRTYL NWYLQKPGQS PQRLIYLVSK LDSGVPDRFS GSGSGTDFTL  540
KISRVQSEDV GVYYCWQGTH LPHTFGCGTK VEIKGGGGSG GGGSGGGGSG GGGSEVQLVQ  600
SGAEVKKPGA SVKVSCKASG YTFTDYEIHW VRQAPGKCLE WMGAIDPETG GTAYNQKFKG  660
RVTMTTDTST STAYMELRSL RSDDTAVYYC YSYDYVTYWG QGTTVTVSA             709

SEQ ID NO: 118         moltype = AA  length = 709
FEATURE                Location/Qualifiers
REGION                 1..709
                       note = Synthetic Construct
source                 1..709
                       mol_type = protein
                       organism = synthetic construct
SEQUENCE: 118
EVQLVESGGG VVQPGRSLRL SCAASGFTFS DYAMAWVRQA PGKGLEWVAT IIYDGSSTYY  60
RDSVKGRFTI SRDNSKNTLY LQMNSLRAED TAVYYCATGL GIATDYFDYW GQGTLVTVSS  120
```

```
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGKGGG GSGGGGSGGG GSEVQLVQSG AEVKKPGASV  480
KVSCKASGYT FTDYEIHWVR QAPGKCLEWM GAIDPETGGT AYNQKFKGRV TMTTDTSTST  540
AYMELRSLRS DDTAVYYCYS YDYVTYWGQG TTVTVSSGGG GSGGGGSGGG GSGGGGSDVV  600
MTQSPLSLSV SPGERASLSC KSSQSLLYSD GRTYLNWYLQ KPGQSPQRLI YLVSKLDSGV  660
PDRFSGSGSG TDFTLKISRV QSEDVGVYYC WQGTHLPHTF GCGTKVEIK             709

SEQ ID NO: 119          moltype = AA  length = 214
FEATURE                 Location/Qualifiers
REGION                  1..214
                        note = Synthetic Construct
source                  1..214
                        mol_type = protein
                        organism = synthetic construct
SEQUENCE: 119
DIRMTQSPFS LSASVGDRVT ITCLASEDIY SDLAWYQQKP AKAPKLFIYN ANSLQNGVPS  60
RFSGSGSGTD YTLTISSLQP EDFATYYCQQ YNNYPPTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 120          moltype = AA  length = 704
FEATURE                 Location/Qualifiers
REGION                  1..704
                        note = Synthetic Construct
source                  1..704
                        mol_type = protein
                        organism = synthetic construct
SEQUENCE: 120
EVQLVQSGAE VKKPGASVKV SCKASGYTFT DYEIHWVRQA PGKGLEWMGA IDPETGGTAY  60
NQKFKGRVTM TTDTSTSTAY MELRSLRSDD TAVYYCYSYD YVTYWGQGTT VTVSSASTKG  120
PSVFPLAPCS RSTSESTAAL GCLVKDYFPE PVTVSWNSGA LTSGVHTFPA VLQSSGLYSL  180
SSVVTVPSSS LGTKTYTCNV DHKPSNTKVD KRVESKYGPP CPPCPAPEFL GGPSVFLFPP  240
KPKDTLMISR TPEVTCVVVD VSQEDPEVQF NWYVDGVEVH NAKTKPREEQ FNSTYRVVSV  300
LTVLHQDWLN GKEYKCKVSN KGLPSSIEKT ISKAKGQPRE PQVYTLPPSQ EEMTKNQVSL  360
TCLVKGFYPS DIAVEWESNG QPENNYKTTP PVLDSDGSFF LYSRLTVDKS RWQEGNVFSC  420
SVMHEALHNH YTQKSLSLSL GKGGGGSGGG GSGGGGSEVQ LVESGGGVVQ PGRSLRLSCA  480
ASGFTFSDYA MAWVRQAPGK CLEWVATIIY DGSSTYYRDS VKGRFTISRD NSKNTLYLQM  540
NSLRAEDTAV YYCATGLGIA TDYFDYWGQG TLVTVSSGGG GSGGGGSGGG GSGGGGSDIR  600
MTQSPFSLSA SVGDRVTITC LASEDIYSDL AWYQQKPAKA PKLFIYNANS LQNGVPSRFS  660
GSGSGTDYTL TISSLQPEDF ATYYCQQYNN YPPTFGCGTK VEIK                  704

SEQ ID NO: 121          moltype = AA  length = 704
FEATURE                 Location/Qualifiers
REGION                  1..704
                        note = Synthetic Construct
source                  1..704
                        mol_type = protein
                        organism = synthetic construct
SEQUENCE: 121
EVQLVQSGAE VKKPGASVKV SCKASGYTFT DYEIHWVRQA PGKGLEWMGA IDPETGGTAY  60
NQKFKGRVTM TTDTSTSTAY MELRSLRSDD TAVYYCYSYD YVTYWGQGTT VTVSSASTKG  120
PSVFPLAPCS RSTSESTAAL GCLVKDYFPE PVTVSWNSGA LTSGVHTFPA VLQSSGLYSL  180
SSVVTVPSSS LGTKTYTCNV DHKPSNTKVD KRVESKYGPP CPPCPAPEFL GGPSVFLFPP  240
KPKDTLMISR TPEVTCVVVD VSQEDPEVQF NWYVDGVEVH NAKTKPREEQ FNSTYRVVSV  300
LTVLHQDWLN GKEYKCKVSN KGLPSSIEKT ISKAKGQPRE PQVYTLPPSQ EEMTKNQVSL  360
TCLVKGFYPS DIAVEWESNG QPENNYKTTP PVLDSDGSFF LYSRLTVDKS RWQEGNVFSC  420
SVMHEALHNH YTQKSLSLSL GKGGGGSGGG GSGGGGSDIR MTQSPFSLSA SVGDRVTITC  480
LASEDIYSDL AWYQQKPAKA PKLFIYNANS LQNGVPSRFS GSGSGTDYTL TISSLQPEDF  540
ATYYCQQYNN YPPTFGCGTK VEIKGGGGSG GGGSGGGGSG GGGSEVQLVE SGGGVVQPGR  600
SLRLSCAASG FTFSDYAMAW VRQAPGKCLE WVATIIYDGS STYYRDSVKG RFTISRDNSK  660
NTLYLQMNSL RAEDTAVYYC ATGLGIATDY FDYWGQGTLV TVSA                  704

SEQ ID NO: 122          moltype = AA  length = 219
FEATURE                 Location/Qualifiers
REGION                  1..219
                        note = Synthetic Construct
source                  1..219
                        mol_type = protein
                        organism = synthetic construct
SEQUENCE: 122
DIQMTQSPSS LSASVGDRVT ITCRSSQSLL YSDGRTYLNW YQQKPGKSPK RLIYLVSKLD  60
SGVPDRFSGS GSGTDFTLTI SSLQPEDFAT YYCWQGTHLP HTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219
```

```
SEQ ID NO: 123         moltype = AA  length = 704
FEATURE                Location/Qualifiers
REGION                 1..704
                       note = Synthetic Construct
source                 1..704
                       mol_type = protein
                       organism = synthetic construct
SEQUENCE: 123
EVQLVQSGAE VKKPGASVKV SCKASGYTFT DYEIHWVRQA PGKGLEWMGA IDPETGGTAY  60
NQKFKGRVTM TTDTSTSTAY MELRSLRSDD TAVYYCYSYD YVTYWGQGTT VTVSSASTKG  120
PSVFPLAPCS RSTSESTAAL GCLVKDYFPE PVTVSWNSGA LTSGVHTFPA VLQSSGLYSL  180
SSVVTVPSSS LGTKTYTCNV DHKPSNTKVD KRVESKYGPP CPPCPAPEFL GGPSVFLFPP  240
KPKDTLMISR TPEVTCVVVD VSQEDPEVQF NWYVDGVEVH NAKTKPREEQ FNSTYRVVSV  300
LTVLHQDWLN GKEYKCKVSN KGLPSSIEKT ISKAKGQPRE PQVYTLPPSQ EEMTKNQVSL  360
TCLVKGFYPS DIAVEWESNG QPENNYKTTP PVLDSDGSFF LYSRLTVDKS RWQEGNVFSC  420
SVMHEALHNH YTQKSLSLSL GKGGGGSGGG GSGGGGSEVQ LVESGGGVVQ PGRSLRLSCA  480
ASGFTFSDYA MAWVRQAPGK CLEWVATIIY DGSSTYYRDS VKGRFTISRD NSKNTLYLQM  540
NSLRAEDTAV YYCATGLGIA TDYFDYWGQG TLVTVSSGGG GSGGGGSGGG GSGGGGSDIR  600
MTQSPFSLSA SVGDRVTITC LASEDIYSDL AWYQQKPAKA PKLFIYNANS LQNGVPSRFS  660
GSGSGTDYTL TISSLQPEDF ATYYCQQYNN YPPTFGCGTK VEIK                    704

SEQ ID NO: 124         moltype = AA  length = 704
FEATURE                Location/Qualifiers
REGION                 1..704
                       note = Synthetic Construct
source                 1..704
                       mol_type = protein
                       organism = synthetic construct
SEQUENCE: 124
EVQLVQSGAE VKKPGASVKV SCKASGYTFT DYEIHWVRQA PGKGLEWMGA IDPETGGTAY  60
NQKFKGRVTM TTDTSTSTAY MELRSLRSDD TAVYYCYSYD YVTYWGQGTT VTVSSASTKG  120
PSVFPLAPCS RSTSESTAAL GCLVKDYFPE PVTVSWNSGA LTSGVHTFPA VLQSSGLYSL  180
SSVVTVPSSS LGTKTYTCNV DHKPSNTKVD KRVESKYGPP CPPCPAPEFL GGPSVFLFPP  240
KPKDTLMISR TPEVTCVVVD VSQEDPEVQF NWYVDGVEVH NAKTKPREEQ FNSTYRVVSV  300
LTVLHQDWLN GKEYKCKVSN KGLPSSIEKT ISKAKGQPRE PQVYTLPPSQ EEMTKNQVSL  360
TCLVKGFYPS DIAVEWESNG QPENNYKTTP PVLDSDGSFF LYSRLTVDKS RWQEGNVFSC  420
SVMHEALHNH YTQKSLSLSL GKGGGGSGGG GSGGGGSDIR MTQSPFSLSA SVGDRVTITC  480
LASEDIYSDL AWYQQKPAKA PKLFIYNANS LQNGVPSRFS GSGSGTDYTL TISSLQPEDF  540
ATYYCQQYNN YPPTFGCGTK VEIKGGGGSG GGGSGGGGSG GGGSEVQLVE SGGGVVQPGR  600
SLRLSCAASG FTFSDYAMAW VRQAPGKCLE WVATIIYDGS STYYRDSVKG RFTISRDNSK  660
NTLYLQMNSL RAEDTAVYYC ATGLGIATDY FDYWGQGTLV TVSA                    704

SEQ ID NO: 125         moltype = AA  length = 219
FEATURE                Location/Qualifiers
REGION                 1..219
                       note = Synthetic Construct
source                 1..219
                       mol_type = protein
                       organism = synthetic construct
SEQUENCE: 125
DVVMTQSPLS LSVSPGERAS LSCKSSQSLL YSDGRTYLNW YLQKPGQSPQ RLIYLVSKLD  60
SGVPDRFSGS GSGTDFTLKI SRVQSEDVGV YYCWQGTHLP HTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                          219

SEQ ID NO: 126         moltype = AA  length = 710
FEATURE                Location/Qualifiers
REGION                 1..710
                       note = Synthetic Construct
source                 1..710
                       mol_type = protein
                       organism = synthetic construct
SEQUENCE: 126
EVQLLESGGG LVQPGGSLRL SCAASGFTFS SYAMSWVRQA PGKGLEWVSG ITGSGGSTYY  60
ADSVKGRFTI SRDNSKNTLY LQMNSLRAED TAVYYCAKDP GTTVIMSWFD PWGQGTLVTV  120
SSASTKGPSV FPLAPCSRST SESTAALGCL VKDYFPEPVT VSWNSGALTS GVHTFPAVLQ  180
SSGLYSLSSV VTVPSSNFGT QTYTCNVDHK PSNTKVDKTV ERKCCVECPP CPAPPVAGPS  240
VFLFPPKPKD TLMISRTPEV TCVVVDVSHE DPEVQFNWYV DGVEVHNAKT KPREEQFNST  300
FRVVSVLTVV HQDWLNGKEY KCKVSNKGLP APIEKTISKT KGQPREPQVY TLPPSREEMT  360
KNQVSLTCLV KGFYPSDIAV EWESNGQPEN NYKTTPPMLD SDGSFFLYSK LTVDKSRWQQ  420
GNVFSCSVMH EALHNHYTQK SLSLSPGKGG GGSGGGGSGG GGSDIQMTQS PSSLSASVGD  480
RVTITCRSSQ SLLYSDGRTY LNWYQQKPGK SPKRLIYLVS KLDSGVPDRF SGSGSGTDFT  540
LTISSLQPED FATYYCWQGT HLPHTFGCGT KVEIKGGGGS GGGGSGGGGS GGGGSEVQLV  600
QSGAEVKKPG ASVKVSCKAS GYTFTDYEIH WVRQAPGKCL EWMGAIDPET GGTAYNQKFK  660
GRVTMTTDTS TSTAYMELRS LRSDDTAVYY CYSYDYVTYW GQGTTVTVSA              710

SEQ ID NO: 127         moltype = AA  length = 710
FEATURE                Location/Qualifiers
```

```
REGION                 1..710
                       note = Synthetic Construct
source                 1..710
                       mol_type = protein
                       organism = synthetic construct
SEQUENCE: 127
DIQMTQSPSS LSASVGDRVT ITCRSSQSLL YSDGRTYLNW YQQKPGKSPK RLIYLVSKLD  60
SGVPDRFSGS GSGTDFTLTI SSLQPEDFAT YYCWQGTHLP HTFGCGTKVE IKGGGGSGGG  120
GSGGGGSGGG GSEVQLVQSG AEVKKPGASV KVSCKASGYT FTDYEIHWVR QAPGKCLEWM  180
GAIDPETGGT AYNQKFKGRV TMTTDTSTST AYMELRSLRS DDTAVYYCYS YDYVTYWGQG  240
TTVTVSSGGG GSGGGGSGGG GSEVQLLESG GGLVQPGGSL RLSCAASGFT FSSYAMSWVR  300
QAPGKGLEWV SGITGSGGST YYADSVKGRF TISRDNSKNT LYLQMNSLRA EDTAVYYCAK  360
DPGTTVIMSW FDPWGQGTLV TVSSASTKGP SVFPLAPCSR STSESTAALG CLVKDYFPEP  420
VTVSWNSGAL TSGVHTFPAV LQSSGLYSLS SVVTVPSSNF GTQTYTCNVD HKPSNTKVDK  480
TVERKCCVEC PPCPAPPVAG PSVFLFPPKP KDTLMISRTP EVTCVVVDVS HEDPEVQFNW  540
YVDGVEVHNA KTKPREEQFN STFRVVSVLT VVHQDWLNGK EYKCKVSNKG LPAPIEKTIS  600
KTKGQPREPQ VYTLPPSREE MTKNQVSLTC LVKGFYPSDI AVEWESNGQP ENNYKTTPPM  660
LDSDGSFFLY SKLTVDKSRW QQGNVFSCSV MHEALHNHYT QKSLSLSPGK             710

SEQ ID NO: 128         moltype = AA  length = 710
FEATURE                Location/Qualifiers
REGION                 1..710
                       note = Synthetic Construct
source                 1..710
                       mol_type = protein
                       organism = synthetic construct
SEQUENCE: 128
EVQLLESGGG LVQPGGSLRL SCAASGFTFS SYAMSWVRQA PGKGLEWVSG ITGSGGSTYY  60
ADSVKGRFTI SRDNSKNTLY LQMNSLRAED TAVYYCAKDP GTTVIMSWFD PWGQGTLVTV  120
SSASTKGPSV FPLAPCSRST SESTAALGCL VKDYFPEPVT VSWNSGALTS GVHTFPAVLQ  180
SSGLYSLSSV VTVPSSNFGT QTYTCNVDHK PSNTKVDKTV ERKCCVECPP CPAPPVAGPS  240
VFLFPPKPKD TLMISRTPEV TCVVVDVSHE DPEVQFNWYV DGVEVHNAKT KPREEQFNST  300
FRVVSVLTVV HQDWLNGKEY KCKVSNKGLP APIEKTISKT KGQPREPQVY TLPPSREEMT  360
KNQVSLTCLV KGFYPSDIAV EWESNGQPEN NYKTTPPMLD SDGSFFLYSK LTVDKSRWQQ  420
GNVFSCSVMH EALHNHYTQK SLSLSPGKGG GGSGGGGSGG GGSDVVMTQS PLSLSVSPGE  480
RASLSCKSSQ SLLYSDGRTY LNWYLQKPGQ SPQRLIYLVS KLDSGVPDRF SGSGSGTDFT  540
LKISRVQSED VGVYYCWQGT HLPHTFGCGT KVEIKGGGGS GGGGSGGGGS GGGGSEVQLV  600
QSGAEVKKPG ASVKVSCKAS GYTFTDYEIH WVRQAPGKCL EWMGAIDPET GGTAYNQKFK  660
GRVTMTTDTS TSTAYMELRS LRSDDTAVYY CYSYDYVTYW GQGTTVTVSA             710

SEQ ID NO: 129         moltype = AA  length = 215
FEATURE                Location/Qualifiers
REGION                 1..215
                       note = Synthetic Construct
source                 1..215
                       mol_type = protein
                       organism = synthetic construct
SEQUENCE: 129
EIVLTQSPGT LSLSPGERAT LSCRASQSVR GRYLAWYQQK PGQAPRLLIY GASSRATGIP  60
DRFSGSGSGT DFTLTISRLE PEDFAVFYCQ QYGSSPRTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 130         moltype = AA  length = 477
FEATURE                Location/Qualifiers
REGION                 1..477
                       note = Synthetic Construct
source                 1..477
                       mol_type = protein
                       organism = synthetic construct
SEQUENCE: 130
EIVLTQSPGT LSLSPGERAT LSCRASQSVR GRYLAWYQQK PGQAPRLLIY GASSRATGIP  60
DRFSGSGSGT DFTLTISRLE PEDFAVFYCQ QYGSSPRTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGECGGGGS GGGGSGGGGS DIQMTQSPSS  240
LSASVGDRVT ITCRSSQSLL YSDGRTYLNW YQQKPGKSPK RLIYLVSKLD SGVPDRFSGS  300
GSGTDFTLTI SSLQPEDFAT YYCWQGTHLP HTFGCGTKVE IKGGGGSGGG GSGGGGSGGG  360
GSEVQLVQSG AEVKKPGASV KVSCKASGYT FTDYEIHWVR QAPGKCLEWM GAIDPETGGT  420
AYNQKFKGRV TMTTDTSTST AYMELRSLRS DDTAVYYCYS YDYVTYWGQG TTVTVSA     477

SEQ ID NO: 131         moltype = AA  length = 477
FEATURE                Location/Qualifiers
REGION                 1..477
                       note = Synthetic Construct
source                 1..477
                       mol_type = protein
                       organism = synthetic construct
```

```
SEQUENCE: 131
DIQMTQSPSS LSASVGDRVT ITCRSSQSLL YSDGRTYLNW YQQKPGKSPK RLIYLVSKLD  60
SGVPDRFSGS GSGTDFTLTI SSLQPEDFAT YYCWQGTHLP HTFGCGTKVE IKGGGGSGGG  120
GSGGGGSGGG GSEVQLVQSG AEVKKPGASV KVSCKASGYT FTDYEIHWVR QAPGKCLEWM  180
GAIDPETGGT AYNQKFKGRV TMTTDTSTST AYMELRSLRS DDTAVYYCYS YDYVTYWGQG  240
TTVTVSSGGG GSGGGGSGGG GSEIVLTQSP GTLSLSPGER ATLSCRASQS VRGRYLAWYQ  300
QKPGQAPRLL IYGASSRATG IPDRFSGSGS GTDFTLTISR LEPEDFAVFY CQQYGSSPRT  360
FGQGTKVEIK RTVAAPSVFI FPPSDEQLKS GTASVVCLLN NFYPREAKVQ WKVDNALQSG  420
NSQESVTEQD SKDSTYSLSS TLTLSKADYE KHKVYACEVT HQGLSSPVTK SFNRGEC     477

SEQ ID NO: 132          moltype = AA  length = 477
FEATURE                 Location/Qualifiers
REGION                  1..477
                        note = Synthetic Construct
source                  1..477
                        mol_type = protein
                        organism = synthetic construct
SEQUENCE: 132
EIVLTQSPGT LSLSPGERAT LSCRASQSVR GRYLAWYQQK PGQAPRLLIY GASSRATGIP  60
DRFSGSGSGT DFTLTISRLE PEDFAVFYCQ QYGSSPRTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGECGGGGS GGGGSGGGGS DVVMTQSPLS  240
LSVSPGERAS LSCKSSQSLL YSDGRTYLNW YLQKPGQSPQ RLIYLVSKLD SGVPDRFSGS  300
GSGTDFTLKI SRVQSEDVGV YYCWQGTHLP HTFGCGTKVE IKGGGGSGGG GSGGGGSGGG  360
GSEVQLVQSG AEVKKPGASV KVSCKASGYT FTDYEIHWVR QAPGKCLEWM GAIDPETGGT  420
AYNQKFKGRV TMTTDTSTST AYMELRSLRS DDTAVYYCYS YDYVTYWGQG TTVTVSA     477

SEQ ID NO: 133          moltype = AA  length = 448
FEATURE                 Location/Qualifiers
REGION                  1..448
                        note = Synthetic Construct
source                  1..448
                        mol_type = protein
                        organism = synthetic construct
SEQUENCE: 133
EVQLLESGGG LVQPGGSLRL SCAASGFTFS SYAMSWVRQA PGKGLEWVSG ITGSGGSTYY  60
ADSVKGRFTI SRDNSKNTLY LQMNSLRAED TAVYYCAKDP GTTVIMSWFD PWGQGTLVTV  120
SSASTKGPSV FPLAPCSRST SESTAALGCL VKDYFPEPVT VSWNSGALTS GVHTFPAVLQ  180
SSGLYSLSSV VTVPSSNFGT QTYTCNVDHK PSNTKVDKTV ERKCCVECPP CPAPPVAGPS  240
VFLFPPKPKD TLMISRTPEV TCVVVDVSHE DPEVQFNWYV DGVEVHNAKT KPREEQFNST  300
FRVVSVLTVV HQDWLNGKEY KCKVSNKGLP APIEKTISKT KGQPREPQVY TLPPSREEMT  360
KNQVSLTCLV KGFYPSDIAV EWESNGQPEN NYKTTPPMLD SDGSFFLYSK LTVDKSRWQQ  420
GNVFSCSVMH EALHNHYTQK SLSLSPGK                                    448

SEQ ID NO: 134          moltype = AA  length = 442
FEATURE                 Location/Qualifiers
REGION                  1..442
                        note = Synthetic Construct
source                  1..442
                        mol_type = protein
                        organism = synthetic construct
SEQUENCE: 134
QAQLQQSGAE LVRPGASVTL SCKASGYTFT DYEIHWMKQT PVHGLEWIGA IDPETGGTAY  60
NQKFKGKAIL TADRSSSTAY LELRSLTSED SAVYYCYSYD YVTYWGQGTL VTVSSASTKG  120
PSVFPLAPCS RSTSESTAAL GCLVKDYFPE PVTVSWNSGA LTSGVHTFPA VLQSSGLYSL  180
SSVVTVPSSS LGTKTYTCNV DHKPSNTKVD KRVESKYGPP CPPCPAPEFL GGPSVFLFPP  240
KPKDTLMISR TPEVTCVVVD VSQEDPEVQF NWYVDGVEVH NAKTKPREEQ FNSTYRVVSV  300
LTVLHQDWLN GKEYKCKVSN KGLPSSIEKT ISKAKGQPRE PQVYTLPPSQ EEMTKNQVSL  360
SCAVKGFYPS DIAVEWESNG QPENNYKTTP PVLDSDGSFF LVSRLTVDKS RWQEGNVFSC  420
SVMHEALHNR FTQKSLSLSL GK                                          442

SEQ ID NO: 135          moltype = AA  length = 219
FEATURE                 Location/Qualifiers
REGION                  1..219
                        note = Synthetic Construct
source                  1..219
                        mol_type = protein
                        organism = synthetic construct
SEQUENCE: 135
DVVMTQTPLT WSITIGQPAS ISCKSSQSLL YSDGRTYLNW LLQRPGQSPK RLIYLVSKLD  60
SGVPDRFSGS GSGTDFTLKI SRVEAEDLGF YYCWQGTHLP HTFGAGTKLE LKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 136          moltype = AA  length = 447
FEATURE                 Location/Qualifiers
REGION                  1..447
                        note = Synthetic Construct
```

```
source                1..447
                      mol_type = protein
                      organism = synthetic construct
SEQUENCE: 136
EVQLVESGGG LVQPANSLKL SCAASGFTFS DYAMAWVRQS PKKGLEWVAT IIYDGSSTYY  60
RDSVKGRFTI SRDNAKSTLY LQMDSLRSED TATYYCATGL GIATDYFDYW GQGVLVTVSS  120
ASTKGPSVCP LAPSSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLWCLVK GFYPSDIAVE WESNGQPENN YKTTPPVLDS DGSFFLYSRL TVDKSRWQEG  420
NVFSCSVMHE ALHNHYTQKS LSLSLGK                                    447

SEQ ID NO: 137        moltype = AA  length = 214
FEATURE               Location/Qualifiers
REGION                1..214
                      note = Synthetic Construct
source                1..214
                      mol_type = protein
                      organism = synthetic construct
SEQUENCE: 137
DIRMTQSPAS LSASLGETVN IECLASEDIY SDLAWYQQKP GKSPQLLIYN ANSLQNGVPS  60
RFSGSGSGTQ YSLKINSLQS EDVATYFCQQ YNNYPPTFGG GTKLELKRTV AAPSVFIFPP  120
CDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGES                             214

SEQ ID NO: 138        moltype = AA  length = 447
FEATURE               Location/Qualifiers
REGION                1..447
                      note = Synthetic Construct
source                1..447
                      mol_type = protein
                      organism = synthetic construct
SEQUENCE: 138
EVQLVESGGG LVQPANSLKL SCAASGFTFS DYAMAWVRQS PKKGLEWVAT IIYDGSSTYY  60
RDSVKGRFTI SRDNAKSTLY LQMDSLRSED TATYYCATGL GIATDYFDYW GQGVLVTVSS  120
ASTKGPSVFP CAPSSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLWCLVK GFYPSDIAVE WESNGQPENN YKTTPPVLDS DGSFFLYSRL TVDKSRWQEG  420
NVFSCSVMHE ALHNHYTQKS LSLSLGK                                    447

SEQ ID NO: 139        moltype = AA  length = 214
FEATURE               Location/Qualifiers
REGION                1..214
                      note = Synthetic Construct
source                1..214
                      mol_type = protein
                      organism = synthetic construct
SEQUENCE: 139
DIRMTQSPAS LSASLGETVN IECLASEDIY SDLAWYQQKP GKSPQLLIYN ANSLQNGVPS  60
RFSGSGSGTQ YSLKINSLQS EDVATYFCQQ YNNYPPTFGG GTKLELKRTV AAPSVFICPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGES                             214

SEQ ID NO: 140        moltype = AA  length = 447
FEATURE               Location/Qualifiers
REGION                1..447
                      note = Synthetic Construct
source                1..447
                      mol_type = protein
                      organism = synthetic construct
SEQUENCE: 140
EVQLVESGGG LVQPANSLKL SCAASGFTFS DYAMAWVRQS PKKGLEWVAT IIYDGSSTYY  60
RDSVKGRFTI SRDNAKSTLY LQMDSLRSED TATYYCATGL GIATDYFDYW GQGVLVTVSS  120
ASTKGPSVFP LAPSSRSTSE STAALGCLVK DYFPEPVTVS WNSGALTSGV HTCPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLWCLVK GFYPSDIAVE WESNGQPENN YKTTPPVLDS DGSFFLYSRL TVDKSRWQEG  420
NVFSCSVMHE ALHNHYTQKS LSLSLGK                                    447

SEQ ID NO: 141        moltype = AA  length = 214
FEATURE               Location/Qualifiers
REGION                1..214
                      note = Synthetic Construct
```

```
source                1..214
                      mol_type = protein
                      organism = synthetic construct
SEQUENCE: 141
DIRMTQSPAS LSASLGETVN IECLASEDIY SDLAWYQQKP GKSPQLLIYN ANSLQNGVPS  60
RFSGSGSGTQ YSLKINSLQS EDVATYFCQQ YNNYPPTFGG GTKLELKRTV AAPSVFIFPP  120
SDEQLKSGTA SVVCLLNNFY PREAKVQWKV DNALQSGNSQ ESVTEQDSKD STYSLCSTLT  180
LSKADYEKHK VYACEVTHQG LSSPVTKSFN RGES                             214

SEQ ID NO: 142        moltype = AA  length = 447
FEATURE               Location/Qualifiers
REGION                1..447
                      note = Synthetic Construct
source                1..447
                      mol_type = protein
                      organism = synthetic construct
SEQUENCE: 142
EVQLVESGGG LVQPANSLKL SCAASGFTFS DYAMAWVRQS PKKGLEWVAT IIYDGSSTYY  60
RDSVKGRFTI SRDNAKSTLY LQMDSLRSED TATYYCATGL GIATDYFDYW GQGVLVTVSS  120
ASTKGPSVFP LAPSSRSTSE STAALGCLVK DYFPEPVTVS WNSGALTSGV HTFPACLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLWCLVK GFYPSDIAVE WESNGQPENN YKTTPPVLDS DGSFFLYSRL TVDKSRWQEG  420
NVFSCSVMHE ALHNHYTQKS LSLSLGK                                     447

SEQ ID NO: 143        moltype = AA  length = 214
FEATURE               Location/Qualifiers
REGION                1..214
                      note = Synthetic Construct
source                1..214
                      mol_type = protein
                      organism = synthetic construct
SEQUENCE: 143
DIRMTQSPAS LSASLGETVN IECLASEDIY SDLAWYQQKP GKSPQLLIYN ANSLQNGVPS  60
RFSGSGSGTQ YSLKINSLQS EDVATYFCQQ YNNYPPTFGG GTKLELKRTV AAPSVFIFPP  120
SDEQLKSGTA SVVCLLNNFY PREAKVQWKV DNALQSGNSC ESVTEQDSKD STYSLSSTLT  180
LSKADYEKHK VYACEVTHQG LSSPVTKSFN RGES                             214

SEQ ID NO: 144        moltype = AA  length = 447
FEATURE               Location/Qualifiers
REGION                1..447
                      note = Synthetic Construct
source                1..447
                      mol_type = protein
                      organism = synthetic construct
SEQUENCE: 144
EVQLVESGGG LVQPANSLKL SCAASGFTFS DYAMAWVRQS PKKGLEWVAT IIYDGSSTYY  60
RDSVKGRFTI SRDNAKSTLY LQMDSLRSED TATYYCATGL GIATDYFDYW GQGVLVTVSS  120
ASTKGPSVFP LAPSSRSTSE STAALGCLVK DYFPEPVTVS WNSGALTSGV HTFPACLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLWCLVK GFYPSDIAVE WESNGQPENN YKTTPPVLDS DGSFFLYSRL TVDKSRWQEG  420
NVFSCSVMHE ALHNHYTQKS LSLSLGK                                     447

SEQ ID NO: 145        moltype = AA  length = 214
FEATURE               Location/Qualifiers
REGION                1..214
                      note = Synthetic Construct
source                1..214
                      mol_type = protein
                      organism = synthetic construct
SEQUENCE: 145
DIRMTQSPAS LSASLGETVN IECLASEDIY SDLAWYQQKP GKSPQLLIYN ANSLQNGVPS  60
RFSGSGSGTQ YSLKINSLQS EDVATYFCQQ YNNYPPTFGG GTKLELKRTV AAPSVFIFPP  120
SDEQLKSGTA SVVCLLNNFY PREAKVQWKV DNALQSGNSC ESVTEQDSKD STYSLSSTLT  180
LSKADYEKHK VYACEVTHQG LSSPVTKSFN RGES                             214

SEQ ID NO: 146        moltype = AA  length = 442
FEATURE               Location/Qualifiers
REGION                1..442
                      note = Synthetic Construct
source                1..442
                      mol_type = protein
                      organism = synthetic construct
SEQUENCE: 146
EVQLVQSGAE VKKPGASVKV SCKASGYTFT DYEIHWVRQA PGKGLEWMGA IDPETGGTAY  60
NQKFKGRVTM TTDTSTSTAY MELRSLRSDD TAVYYCYSYD YVTYWGQGTT VTVSSASTKG  120
```

```
PSVFPLAPCS RSTSESTAAL GCLVKDYFPE PVTVSWNSGA LTSGVHTFPA VLQSSGLYSL  180
SSVVTVPSSS LGTKTYTCNV DHKPSNTKVD KRVESKYGPP CPPCPAPEFL GGPSVFLFPP  240
KPKDTLMISR TPEVTCVVVD VSQEDPEVQF NWYVDGVEVH NAKTKPREEQ FNSTYRVVSV  300
LTVLHQDWLN GKEYKCKVSN KGLPSSIEKT ISKAKGQPRE PQVYTLPPSQ EEMTKNQVSL  360
SCAVKGFYPS DIAVEWESNG QPENNYKTTP PVLDSDGSFF LVSRLTVDKS RWQEGNVFSC  420
SVMHEALHNR FTQKSLSLSL GK                                          442

SEQ ID NO: 147         moltype = AA  length = 219
FEATURE                Location/Qualifiers
REGION                 1..219
                       note = Synthetic Construct
source                 1..219
                       mol_type = protein
                       organism = synthetic construct
SEQUENCE: 147
DIQMTQSPSS LSASVGDRVT ITCRSSQSLL YSDGRTYLNW YQQKPGKSPK RLIYLVSKLD  60
SGVPDRFSGS GSGTDFTLTI SSLQPEDFAT YYCWQGTHLP HTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 148         moltype = AA  length = 447
FEATURE                Location/Qualifiers
REGION                 1..447
                       note = Synthetic Construct
source                 1..447
                       mol_type = protein
                       organism = synthetic construct
SEQUENCE: 148
EVQLVESGGG VVQPGRSLRL SCAASGFTFS DYAMAWVRQA PGKGLEWVAT IIYDGSSTYY  60
RDSVKGRFTI SRDNSKNTLY LQMNSLRAED TAVYYCATGL GIATDYFDYW GQGTLVTVSS  120
ASTKGPSVFP CAPSSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLWCLVK GFYPSDIAVE WESNGQPENN YKTTPPVLDS DGSFFLYSRL TVDKSRWQEG  420
NVFSCSVMHE ALHNHYTQKS LSLSLGK                                     447

SEQ ID NO: 149         moltype = AA  length = 214
FEATURE                Location/Qualifiers
REGION                 1..214
                       note = Synthetic Construct
source                 1..214
                       mol_type = protein
                       organism = synthetic construct
SEQUENCE: 149
DIRMTQSPFS LSASVGDRVT ITCLASEDIY SDLAWYQQKP AKAPKLFIYN ANSLQNGVPS  60
RFSGSGSGTD YTLTISSLQP EDFATYYCQQ YNNYPPTFGG GTKVEIKRTV AAPSVFICPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGES                              214

SEQ ID NO: 150         moltype = AA  length = 447
FEATURE                Location/Qualifiers
REGION                 1..447
                       note = Synthetic Construct
source                 1..447
                       mol_type = protein
                       organism = synthetic construct
SEQUENCE: 150
EVQLVESGGG VVQPGRSLRL SCAASGFTFS DYAMAWVRQA PGKGLEWVAT IIYDGSSTYY  60
RDSVKGRFTI SRDNSKNTLY LQMNSLRAED TAVYYCATGL GIATDYFDYW GQGTLVTVSS  120
ASTKGPSVFP LAPSSRSTSE STAALGCLVK DYFPEPVTVS WNSGALTSGV HTCPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLWCLVK GFYPSDIAVE WESNGQPENN YKTTPPVLDS DGSFFLYSRL TVDKSRWQEG  420
NVFSCSVMHE ALHNHYTQKS LSLSLGK                                     447

SEQ ID NO: 151         moltype = AA  length = 214
FEATURE                Location/Qualifiers
REGION                 1..214
                       note = Synthetic Construct
source                 1..214
                       mol_type = protein
                       organism = synthetic construct
SEQUENCE: 151
DIRMTQSPFS LSASVGDRVT ITCLASEDIY SDLAWYQQKP AKAPKLFIYN ANSLQNGVPS  60
RFSGSGSGTD YTLTISSLQP EDFATYYCQQ YNNYPPTFGG GTKVEIKRTV AAPSVFIFPP  120
SDEQLKSGTA SVVCLLNNFY PREAKVQWKV DNALQSGNSQ ESVTEQDSKD STYSLCSTLT  180
LSKADYEKHK VYACEVTHQG LSSPVTKSFN RGES                              214
```

```
SEQ ID NO: 152          moltype = AA  length = 447
FEATURE                 Location/Qualifiers
REGION                  1..447
                        note = Synthetic Construct
source                  1..447
                        mol_type = protein
                        organism = synthetic construct
SEQUENCE: 152
EVQLVESGGG VVQPGRSLRL SCAASGFTFS DYAMAWVRQA PGKGLEWVAT IIYDGSSTYY  60
RDSVKGRFTI SRDNSKNTLY LQMNSLRAED TAVYYCATGL GIATDYFDYW GQGTLVTVSS  120
ASTKGPSVFP LAPSSRSTSE STAALGCLVK DYFPEPVTVS WNSGALTSGV HTFPACLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLWCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 153          moltype = AA  length = 214
FEATURE                 Location/Qualifiers
REGION                  1..214
                        note = Synthetic Construct
source                  1..214
                        mol_type = protein
                        organism = synthetic construct
SEQUENCE: 153
DIRMTQSPFS LSASVGDRVT ITCLASEDIY SDLAWYQQKP AKAPKLFIYN ANSLQNGVPS  60
RFSGSGSGTD YTLTISSLQP EDFATYYCQQ YNNYPPTFGG GTKVEIKRTV AAPSVFIFPP  120
SDEQLKSGTA SVVCLLNNFY PREAKVQWKV DNALQSGNSC ESVTEQDSKD STYSLSSTLT  180
LSKADYEKHK VYACEVTHQG LSSPVTKSFN RGES                              214

SEQ ID NO: 154          moltype = AA  length = 447
FEATURE                 Location/Qualifiers
REGION                  1..447
                        note = Synthetic Construct
source                  1..447
                        mol_type = protein
                        organism = synthetic construct
SEQUENCE: 154
EVQLVESGGG VVQPGRSLRL SCAASGFTFS DYAMAWVRQA PGKGLEWVAT IIYDGSSTYY  60
RDSVKGRFTI SRDNSKNTLY LQMNSLRAED TAVYYCATGL GIATDYFDYW GQGTLVTVSS  120
ASTKGPSVCP LAPSSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLWCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 155          moltype = AA  length = 214
FEATURE                 Location/Qualifiers
REGION                  1..214
                        note = Synthetic Construct
source                  1..214
                        mol_type = protein
                        organism = synthetic construct
SEQUENCE: 155
DIRMTQSPFS LSASVGDRVT ITCLASEDIY SDLAWYQQKP AKAPKLFIYN ANSLQNGVPS  60
RFSGSGSGTD YTLTISSLQP EDFATYYCQQ YNNYPPTFGG GTKVEIKRTV AAPSVFICPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGES                              214

SEQ ID NO: 156          moltype = AA  length = 449
FEATURE                 Location/Qualifiers
REGION                  1..449
                        note = Synthetic Construct
source                  1..449
                        mol_type = protein
                        organism = synthetic construct
SEQUENCE: 156
EVQLLESGGG LVQPGGSLRL SCAASGFTFS SYAMSWVRQA PGKGLEWVSG ITGSGGSTYY  60
ADSVKGRFTI SRDNSKNTLY LQMNSLRAED TAVYYCAKDP GTTVIMSWFD PWGQGTLVTV  120
SSASTKGPSV FPCAPSSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLWCL VKGFYPSDIA VEWESNGQPE NNYKTTPPVL DSDGSFFLYS RLTVDKSRWQ  420
EGNVFSCSVM HEALHNHYTQ KSLSLSLGK                                    449

SEQ ID NO: 157          moltype = AA  length = 215
```

```
FEATURE                Location/Qualifiers
REGION                 1..215
                       note = Synthetic Construct
source                 1..215
                       mol_type = protein
                       organism = synthetic construct
SEQUENCE: 157
EIVLTQSPGT LSLSPGERAT LSCRASQSVR GRYLAWYQQK PGQAPRLLIY GASSRATGIP  60
DRFSGSGSGT DFTLTISRLE PEDFAVFYCQ QYGSSPRTFG QGTKVEIKRT VAAPSVFICP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGES                              215

SEQ ID NO: 158         moltype = AA  length = 449
FEATURE                Location/Qualifiers
REGION                 1..449
                       note = Synthetic Construct
source                 1..449
                       mol_type = protein
                       organism = synthetic construct
SEQUENCE: 158
EVQLLESGGG LVQPGGSLRL SCAASGFTFS SYAMSWVRQA PGKGLEWVSG ITGSGGSTYY  60
ADSVKGRFTI SRDNSKNTLY LQMNSLRAED TAVYYCAKDP GTTVIMSWFD PWGQGTLVTV  120
SSASTKGPSV FPLAPSSRST SESTAALGCL VKDYFPEPVT VSWNSGALTS GVHTCPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLWCL VKGFYPSDIA VEWESNGQPE NNYKTTPPVL DSDGSFFLYS RLTVDKSRWQ  420
EGNVFSCSVM HEALHNHYTQ KSLSLSLGK                                     449

SEQ ID NO: 159         moltype = AA  length = 215
FEATURE                Location/Qualifiers
REGION                 1..215
                       note = Synthetic Construct
source                 1..215
                       mol_type = protein
                       organism = synthetic construct
SEQUENCE: 159
EIVLTQSPGT LSLSPGERAT LSCRASQSVR GRYLAWYQQK PGQAPRLLIY GASSRATGIP  60
DRFSGSGSGT DFTLTISRLE PEDFAVFYCQ QYGSSPRTFG QGTKVEIKRT VAAPSVFIFP  120
PSDEQLKSGT ASVVCLLNNF YPREAKVQWK VDNALQSGNS QESVTEQDSK DSTYSLCSTL  180
TLSKADYEKH KVYACEVTHQ GLSSPVTKSF NRGES                              215

SEQ ID NO: 160         moltype = AA  length = 449
FEATURE                Location/Qualifiers
REGION                 1..449
                       note = Synthetic Construct
source                 1..449
                       mol_type = protein
                       organism = synthetic construct
SEQUENCE: 160
EVQLLESGGG LVQPGGSLRL SCAASGFTFS SYAMSWVRQA PGKGLEWVSG ITGSGGSTYY  60
ADSVKGRFTI SRDNSKNTLY LQMNSLRAED TAVYYCAKDP GTTVIMSWFD PWGQGTLVTV  120
SSASTKGPSV CPLAPSSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLWCL VKGFYPSDIA VEWESNGQPE NNYKTTPPVL DSDGSFFLYS RLTVDKSRWQ  420
EGNVFSCSVM HEALHNHYTQ KSLSLSLGK                                     449

SEQ ID NO: 161         moltype = AA  length = 215
FEATURE                Location/Qualifiers
REGION                 1..215
                       note = Synthetic Construct
source                 1..215
                       mol_type = protein
                       organism = synthetic construct
SEQUENCE: 161
EIVLTQSPGT LSLSPGERAT LSCRASQSVR GRYLAWYQQK PGQAPRLLIY GASSRATGIP  60
DRFSGSGSGT DFTLTISRLE PEDFAVFYCQ QYGSSPRTFG QGTKVEIKRT VAAPSVFICP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGES                              215

SEQ ID NO: 162         moltype = AA  length = 449
FEATURE                Location/Qualifiers
REGION                 1..449
                       note = Synthetic Construct
source                 1..449
                       mol_type = protein
                       organism = synthetic construct
```

```
SEQUENCE: 162
EVQLLESGGG LVQPGGSLRL SCAASGFTFS SYAMSWVRQA PGKGLEWVSG ITGSGGSTYY  60
ADSVKGRFTI SRDNSKNTLY LQMNSLRAED TAVYYCAKDP GTTVIMSWFD PWGQGTLVTV  120
SSASTKGPSV FPLAPSSRST SESTAALGCL VKDYFPEPVT VSWNSGALTS GVHTFPACLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLWCL VKGFYPSDIA VEWESNGQPE NNYKTTPPVL DSDGSFFLYS RLTVDKSRWQ  420
EGNVFSCSVM HEALHNHYTQ KSLSLSLGK                                   449

SEQ ID NO: 163         moltype = AA  length = 215
FEATURE                Location/Qualifiers
REGION                 1..215
                       note = Synthetic Construct
source                 1..215
                       mol_type = protein
                       organism = synthetic construct
SEQUENCE: 163
EIVLTQSPGT LSLSPGERAT LSCRASQSVR GRYLAWYQQK PGQAPRLLIY GASSRATGIP  60
DRFSGSGSGT DFTLTISRLE PEDFAVFYCQ QYGSSPRTFG QGTKVEIKRT VAAPSVFIFP  120
PSDEQLKSGT ASVVCLLNNF YPREAKVQWK VDNALQSGNS CESVTEQDSK DSTYSLSSTL  180
TLSKADYEKH KVYACEVTHQ GLSSPVTKSF NRGES                            215

SEQ ID NO: 164         moltype = AA  length = 120
FEATURE                Location/Qualifiers
REGION                 1..120
                       note = Synthetic Construct
source                 1..120
                       mol_type = protein
                       organism = synthetic construct
SEQUENCE: 164
EVQLVESGGG LVQPANSLKL SCAASGFTFS DYAMAWVRQS PKKGLEWVAT IIYDGSSTYY  60
RDSVKGRFTI SRDNAKSTLY LQMDSLRSED TATYYCATGL GIATDYFDYW GQGVLVTVSS  120

SEQ ID NO: 165         moltype = AA  length = 107
FEATURE                Location/Qualifiers
REGION                 1..107
                       note = Synthetic Construct
source                 1..107
                       mol_type = protein
                       organism = synthetic construct
SEQUENCE: 165
DIRMTQSPAS LSASLGETVN IECLASEDIY SDLAWYQQKP GKSPQLLIYN ANSLQNGVPS  60
RFSGSGSGTQ YSLKINSLQS EDVATYFCQQ YNNYPPTFGG GTKLELK               107

SEQ ID NO: 166         moltype = AA  length = 120
FEATURE                Location/Qualifiers
REGION                 1..120
                       note = Synthetic Construct
source                 1..120
                       mol_type = protein
                       organism = synthetic construct
SEQUENCE: 166
EVQLVESGGG VVQPGRSLRL SCAASGFTFS DYAMAWVRQA PGKCLEWVAT IIYDGSSTYY  60
RDSVKGRFTI SRDNSKNTLY LQMNSLRAED TAVYYCATGL GIATDYFDYW GQGTLVTVSS  120

SEQ ID NO: 167         moltype = AA  length = 107
FEATURE                Location/Qualifiers
REGION                 1..107
                       note = Synthetic Construct
source                 1..107
                       mol_type = protein
                       organism = synthetic construct
SEQUENCE: 167
DIRMTQSPFS LSASVGDRVT ITCLASEDIY SDLAWYQQKP AKAPKLFIYN ANSLQNGVPS  60
RFSGSGSGTD YTLTISSLQP EDFATYYCQQ YNNYPPTFGC GTKVEIK               107

SEQ ID NO: 168         moltype = AA  length = 115
FEATURE                Location/Qualifiers
REGION                 1..115
                       note = Synthetic Construct
source                 1..115
                       mol_type = protein
                       organism = synthetic construct
SEQUENCE: 168
EVQLVQSGAE VKKPGASVKV SCKASGYTFT DYEIHWVRQA PGKCLEWMGA IDPETGGTAY  60
NQKFKGRVTM TTDTSTSTAY MELRSLRSDD TAVYYCYSYD YVTYWGQGTT VTVSS      115

SEQ ID NO: 169         moltype = AA  length = 112
```

```
FEATURE                 Location/Qualifiers
REGION                  1..112
                        note = Synthetic Construct
source                  1..112
                        mol_type = protein
                        organism = synthetic construct
SEQUENCE: 169
DVVMTQSPLS LSVSPGERAS LSCKSSQSLL YSDGRTYLNW YLQKPGQSPQ RLIYLVSKLD  60
SGVPDRFSGS GSGTDFTLKI SRVQSEDVGV YYCWQGTHLP HTFGCGTKVE IK          112

SEQ ID NO: 170          moltype = AA  length = 112
FEATURE                 Location/Qualifiers
REGION                  1..112
                        note = Synthetic Construct
source                  1..112
                        mol_type = protein
                        organism = synthetic construct
SEQUENCE: 170
DIQMTQSPSS LSASVGDRVT ITCRSSQSLL YSDGRTYLNW YQQKPGKSPK RLIYLVSKLD  60
SGVPDRFSGS GSGTDFTLTI SSLQPEDFAT YYCWQGTHLP HTFGCGTKVE IK          112

SEQ ID NO: 171          moltype = AA  length = 441
FEATURE                 Location/Qualifiers
REGION                  1..441
                        note = Synthetic Construct
source                  1..441
                        mol_type = protein
                        organism = synthetic construct
SEQUENCE: 171
EVQLVQSGAE VKKPGASVKV SCKASGYTFT DYEIHWVRQA PGKGLEWMGA IDPETGGTAY  60
NQKFKGRVTM TTDTSTSTAY MELRSLRSDD TAVYYCYSYD YVTYWGQGTT VTVSSASTKG  120
PSVFPLAPCS RSTSESTAAL GCLVKDYFPE PVTVSWNSGA LTSGVHTFPA VLQSSGLYSL  180
SSVVTVPSSN FGTQTYTCNV DHKPSNTKVD KTVERKCCVE CPPCPAPPVA GPSVFLFPPK  240
PKDTLMISRT PEVTCVVVDV SHEDPEVQFN WYVDGVEVHN AKTKPREEQF NSTFRVVSVL  300
TVVHQDWLNG KEYKCKVSNK GLPAPIEKTI SKTKGQPREP QVYTLPPCRE EMTKNQVSLW  360
CLVKGFYPSD IAVEWESNGQ PENNYKTTPP MLDSDGSFFL YSKLTVDKSR WQQGNVFSCS  420
VMHEALHNHY TQKSLSLSPG K                                            441

SEQ ID NO: 172          moltype = AA  length = 448
FEATURE                 Location/Qualifiers
REGION                  1..448
                        note = Synthetic Construct
source                  1..448
                        mol_type = protein
                        organism = synthetic construct
SEQUENCE: 172
EVQLLESGGG LVQPGGSLRL SCAASGFTFS SYAMSWVRQA PGKGLEWVSG ITGSGGSTYY  60
ADSVKGRFTI SRDNSKNTLY LQMNSLRAED TAVYYCAKDP GTTVIMSWFD PWGQGTLVTV  120
SSASTKGPSV FPLAPSSRST SESTAALGCL VKDYFPEPVT VSWNSGALTS GVHTFPACLQ  180
SSGLYSLSSV VTVPSSNFGT QTYTCNVDHK PSNTKVDKTV ERKCCVECPP CPAPPVAGPS  240
VFLFPPKPKD TLMISRTPEV TCVVVDVSHE DPEVQFNWYV DGVEVHNAKT KPREEQFNST  300
FRVVSVLTVV HQDWLNGKEY KCKVSNKGLP APIEKTISKT KGQPREPQVC TLPPSREEMT  360
KNQVSLSCAV KGFYPSDIAV EWESNGQPEN NYKTTPPMLD SDGSFFLVSK LTVDKSRWQQ  420
GNVFSCSVMH EALHNRFTQK SLSLSPGK                                     448

SEQ ID NO: 173          moltype = AA  length = 445
FEATURE                 Location/Qualifiers
REGION                  1..445
                        note = Synthetic Construct
source                  1..445
                        mol_type = protein
                        organism = synthetic construct
SEQUENCE: 173
EVQLVQSGAE VKKPGASVKV SCKASGYTFT DYEIHWVRQA PGKGLEWMGA IDPETGGTAY  60
NQKFKGRVTM TTDTSTSTAY MELRSLRSDD TAVYYCYSYD YVTYWGQGTT VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP EAAGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVCTLP PSRDELTKNQ  360
VSLSCAVKGF YPSDIAVEWE SNGQPENNYK TTPPVLDSDG SFFLVSKLTV DKSRWQQGNV  420
FSCSVMHEAL HNRFTQKSLS LSPGK                                        445

SEQ ID NO: 174          moltype = AA  length = 452
FEATURE                 Location/Qualifiers
REGION                  1..452
                        note = Synthetic Construct
source                  1..452
                        mol_type = protein
                        organism = synthetic construct
```

```
SEQUENCE: 174
EVQLLESGGG LVQPGGSLRL SCAASGFTFS SYAMSWVRQA PGKGLEWVSG ITGSGGSTYY  60
ADSVKGRFTI SRDNSKNTLY LQMNSLRAED TAVYYCAKDP GTTVIMSWFD PWGQGTLVTV  120
SSASTKGPSV FPLAPSSKST SGGTAALGCL VKDYFPEPVT VSWNSGALTS GVHTFPACLQ  180
SSGLYSLSSV VTVPSSSLGT QTYICNVNHK PSNTKVDKKV EPKSSDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPCR  360
DELTKNQVSL WCLVKGFYPS DIAVEWESNG QPENNYKTTP PVLDSDGSFF LYSKLTVDKS  420
RWQQGNVFSC SVMHEALHNH YTQKSLSLSP GK                               452

SEQ ID NO: 175          moltype = AA  length = 445
FEATURE                 Location/Qualifiers
REGION                  1..445
                        note = Synthetic Construct
source                  1..445
                        mol_type = protein
                        organism = synthetic construct
SEQUENCE: 175
EVQLVQSGAE VKKPGASVKV SCKASGYTFT DYEIHWVRQA PGKGLEWMGA IDPETGGTAY  60
NQKFKGRVTM TTDTSTSTAY MELRSLRSDD TAVYYCYSYD YVTYWGQGTT VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP EAAGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVCTLP PSRDELTKNQ  360
VSLSCAVKGF YPSDIAVEWE SNGQPENNYK TTPPVLDSDG SFFLVSKLTV DKSRWQQGNV  420
FSCSVLHEAL HARFTQKSLS LSPGK                                       445

SEQ ID NO: 176          moltype = AA  length = 452
FEATURE                 Location/Qualifiers
REGION                  1..452
                        note = Synthetic Construct
source                  1..452
                        mol_type = protein
                        organism = synthetic construct
SEQUENCE: 176
EVQLLESGGG LVQPGGSLRL SCAASGFTFS SYAMSWVRQA PGKGLEWVSG ITGSGGSTYY  60
ADSVKGRFTI SRDNSKNTLY LQMNSLRAED TAVYYCAKDP GTTVIMSWFD PWGQGTLVTV  120
SSASTKGPSV FPLAPSSKST SGGTAALGCL VKDYFPEPVT VSWNSGALTS GVHTFPACLQ  180
SSGLYSLSSV VTVPSSSLGT QTYICNVNHK PSNTKVDKKV EPKSSDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPCR  360
DELTKNQVSL WCLVKGFYPS DIAVEWESNG QPENNYKTTP PVLDSDGSFF LYSKLTVDKS  420
RWQQGNVFSC SVLHEALHAH YTQKSLSLSP GK                               452

SEQ ID NO: 177          moltype = AA  length = 707
FEATURE                 Location/Qualifiers
REGION                  1..707
                        note = Synthetic Construct
source                  1..707
                        mol_type = protein
                        organism = synthetic construct
SEQUENCE: 177
EVQLVQSGAE VKKPGASVKV SCKASGYTFT DYEIHWVRQA PGKGLEWMGA IDPETGGTAY  60
NQKFKGRVTM TTDTSTSTAY MELRSLRSDD TAVYYCYSYD YVTYWGQGTT VTVSSASTKG  120
PSVFPLAPCS RSTSESTAAL GCLVKDYFPE PVTVSWNSGA LTSGVHTFPA VLQSSGLYSL  180
SSVVTVPSSS LGTKTYTCNV DHKPSNTKVD KRVESKYGPP CPPCPAPEAA GGPSVFLFPP  240
KPKDTLMISR TPEVTCVVVD VSQEDPEVQF NWYVDGVEVH NAKTKPREEQ FNSTYRVVSV  300
LTVLHQDWLN GKEYKCKVSN KGLPSSIEKT ISKAKGQPRE PQVYTLPPSQ EEMTKNQVSL  360
TCLVKGFYPS DIAVEWESNG QPENNYKTTP PVLDSDGSFF LYSKLTVDKS RWQEGNVFSC  420
SVMHEALHNH YTQKSLSLSP GKGGGGSGGG GSGGGGSEIV LTQSPGTLSL SPGERATLSC  480
RASQSVRGRY LAWYQQKPGQ APRLLIYGAS SRATGIPDRF SGSGSGTDFT LTISRLEPED  540
FAVFYCQQYG SSPRTFGCGT KVEIKGGGGS GGGGSGGGGS GGGGSEVQLL ESGGGLVQPG  600
GSLRLSCAAS GFTFSSYAMS WVRQAPGKCL EWVSGITGSG GSTYYADSVK GRFTISRDNS  660
KNTLYLQMNS LRAEDTAVYY CAKDPGTTVI MSWFDPWGQG TLVTVSA                707

SEQ ID NO: 178          moltype = AA  length = 707
FEATURE                 Location/Qualifiers
REGION                  1..707
                        note = Synthetic Construct
source                  1..707
                        mol_type = protein
                        organism = synthetic construct
SEQUENCE: 178
EVQLVQSGAE VKKPGASVKV SCKASGYTFT DYEIHWVRQA PGKGLEWMGA IDPETGGTAY  60
NQKFKGRVTM TTDTSTSTAY MELRSLRSDD TAVYYCYSYD YVTYWGQGTT VTVSSASTKG  120
PSVFPLAPCS RSTSESTAAL GCLVKDYFPE PVTVSWNSGA LTSGVHTFPA VLQSSGLYSL  180
SSVVTVPSSS LGTKTYTCNV DHKPSNTKVD KRVESKYGPP CPPCPAPEAA GGPSVFLFPP  240
KPKDTLMISR TPEVTCVVVD VSQEDPEVQF NWYVDGVEVH NAKTKPREEQ FNSTYRVVSV  300
LTVLHQDWLN GKEYKCKVSN KGLPSSIEKT ISKAKGQPRE PQVYTLPPSQ EEMTKNQVSL  360
```

```
TCLVKGFYPS DIAVEWESNG QPENNYKTTP PVLDSDGSFF LYSKLTVDKS RWQEGNVFSC  420
SVMHEALHNH YTQKSLSLSP GKGGGGSGGG GSGGGGSEVQ LLESGGGLVQ PGGSLRLSCA  480
ASGFTFSSYA MSWVRQAPGK CLEWVSGITG SGGSTYYADS VKGRFTISRD NSKNTLYLQM  540
NSLRAEDTAV YYCAKDPGTT VIMSWFDPWG QGTLVTVSSG GGGSGGGGSG GGGSGGGGSE  600
IVLTQSPGTL SLSPGERATL SCRASQSVRG RYLAWYQQKP GQAPRLLIYG ASSRATGIPD  660
RFSGSGSGTD FTLTISRLEP EDFAVFYCQQ YGSSPRTFGC GTKVEIK                707

SEQ ID NO: 179         moltype = AA  length = 706
FEATURE                Location/Qualifiers
REGION                 1..706
                       note = Synthetic Construct
source                 1..706
                       mol_type = protein
                       organism = synthetic construct
SEQUENCE: 179
EVQLVQSGAE VKKPGASVKV SCKASGYTFT DYEIHWVRQA PGKGLEWMGA IDPETGGTAY  60
NQKFKGRVTM TTDTSTSTAY MELRSLRSDD TAVYYCYSYD YVTYWGQGTT VTVSSASTKG  120
PSVFPLAPCS RSTSESTAAL GCLVKDYFPE PVTVSWNSGA LTSGVHTFPA VLQSSGLYSL  180
SSVVTVPSSN FGTQTYTCNV DHKPSNTKVD KTVERKCCVE CPPCPAPPVA GPSVFLFPPK  240
PKDTLMISRT PEVTCVVVDV SHEDPEVQFN WYVDGVEVHN AKTKPREEQF NSTFRVVSVL  300
TVVHQDWLNG KEYKCKVSNK GLPAPIEKTI SKTKGQPREP QVYTLPPSRE EMTKNQVSLT  360
CLVKGFYPSD IAVEWESNGQ PENNYKTTPP MLDSDGSFFL YSKLTVDKSR WQQGNVFSCS  420
VMHEALHNHY TQKSLSLSPG KGGGGSGGGG SGGGGSEVQL LESGGGLVQP GGSLRLSCAA  480
SGFTFSSYAM SWVRQAPGKC LEWVSGITGS GGSTYYADSV KGRFTISRDN SKNTLYLQMN  540
SLRAEDTAVY YCAKDPGTTV IMSWFDPWGQ GTLVTVSSGG GGSGGGGSGG GGSGGGGSEI  600
VLTQSPGTLS LSPGERATLS CRASQSVRGR YLAWYQQKPG QAPRLLIYGA SSRATGIPDR  660
FSGSGSGTDF TLTISRLEPE DFAVFYCQQY GSSPRTFGCG TKVEIK                 706

SEQ ID NO: 180         moltype = AA  length = 710
FEATURE                Location/Qualifiers
REGION                 1..710
                       note = Synthetic Construct
source                 1..710
                       mol_type = protein
                       organism = synthetic construct
SEQUENCE: 180
EVQLVQSGAE VKKPGASVKV SCKASGYTFT DYEIHWVRQA PGKGLEWMGA IDPETGGTAY  60
NQKFKGRVTM TTDTSTSTAY MELRSLRSDD TAVYYCYSYD YVTYWGQGTT VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP EAAGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKGGGGS GGGGSGGGGS EVQLLESGGG LVQPGGSLRL  480
SCAASGFTFS SYAMSWVRQA PGKCLEWVSG ITGSGGSTYY ADSVKGRFTI SRDNSKNTLY  540
LQMNSLRAED TAVYYCAKDP GTTVIMSWFD PWGQGTLVTV SSGGGGSGGG GSGGGGSGGG  600
GSEIVLTQSP GTLSLSPGER ATLSCRASQS VRGRYLAWYQ QKPGQAPRLL IYGASSRATG  660
IPDRFSGSGS GTDFTLTISR LEPEDFAVFY CQQYGSSPRT FGCGTKVEIK             710

SEQ ID NO: 181         moltype =   length =
SEQUENCE: 181
000

SEQ ID NO: 182         moltype =   length =
SEQUENCE: 182
000

SEQ ID NO: 183         moltype = AA  length = 190
FEATURE                Location/Qualifiers
REGION                 1..190
                       note = Synthetic Construct
source                 1..190
                       mol_type = protein
                       organism = synthetic construct
SEQUENCE: 183
QGWQAFKNDA TEIIPELGEY PEPPPELENN KTMNRAENGG RPPHHPFETK DVSEYSCREL  60
HFTRYVTDGP CRSAKPVTEL VCSGQCGPAR LLPNAIGRGK WWRPSGPDFR CIPDRYRAQR  120
VQLLCPGGEA PRARKVRLVA SCKCKRLTRF HNQSELKDFG TEAARPQKGR KPRPRARSAK  180
ANQAELENAY                                                         190

SEQ ID NO: 184         moltype = AA  length = 190
FEATURE                Location/Qualifiers
REGION                 1..190
                       note = Synthetic Construct
source                 1..190
                       mol_type = protein
                       organism = synthetic construct
```

```
SEQUENCE: 184
QGWQAFKNDA TEIIPELGEY PEPPPDLENN KTMNRAENGG RPPHHPFETK DVSEYSCREL  60
HFTRYVTDGQ CRSAKPVTEL VCSGQCGPAR LLPNAIGRGK WWRPSGPDFR CIPDRYRAQR  120
VQLLCPGGAA PRARKVRLVA SCKCKRLTRF HNQSELKDFG PEAARPQKGR KPRPRARGAK  180
ANQAELENAY                                                        190

SEQ ID NO: 185         moltype = AA  length = 24
FEATURE                Location/Qualifiers
REGION                 1..24
                       note = Synthetic Construct
source                 1..24
                       mol_type = protein
                       organism = synthetic construct
SEQUENCE: 185
GPARLLPNAI GRGKWWRPSG PDFR                                        24

SEQ ID NO: 186         moltype = AA  length = 8
FEATURE                Location/Qualifiers
REGION                 1..8
                       note = Synthetic Construct
source                 1..8
                       mol_type = protein
                       organism = synthetic construct
SEQUENCE: 186
IGRGKWWR                                                          8

SEQ ID NO: 187         moltype = AA  length = 11
FEATURE                Location/Qualifiers
REGION                 1..11
                       note = Synthetic Construct
source                 1..11
                       mol_type = protein
                       organism = synthetic construct
SEQUENCE: 187
PNAIGRGKWW R                                                      11

SEQ ID NO: 188         moltype = AA  length = 12
FEATURE                Location/Qualifiers
REGION                 1..12
                       note = Synthetic Construct
source                 1..12
                       mol_type = protein
                       organism = synthetic construct
SEQUENCE: 188
IGRGKWWRPS GP                                                     12

SEQ ID NO: 189         moltype = AA  length = 190
FEATURE                Location/Qualifiers
REGION                 1..190
                       note = Synthetic Construct
source                 1..190
                       mol_type = protein
                       organism = synthetic construct
SEQUENCE: 189
QGWQAFKNDA TEIIPELGEY PEPPPELENN KTMNRAENGG RPPHHPFETK DVSEYSCREL  60
HFTRYVTDGQ CRSAKPVTEL VCSGQCGPAR LLPNAIGRGK WWRPSGPDFR CIPDRYRAQR  120
VQLLCPGGAA PRARKVRLVA SCKCKRLTRF HNQSELKDFG PEAARPQKGR KPRPRARGAK  180
ANQAELENAY                                                        190

SEQ ID NO: 190         moltype = AA  length = 188
FEATURE                Location/Qualifiers
REGION                 1..188
                       note = Synthetic Construct
source                 1..188
                       mol_type = protein
                       organism = synthetic construct
SEQUENCE: 190
QGWQAFRNDA TEVIPGLGEY PEPPPENNQT MNRAENGGRP PHHPYDAKDV SEYSCRELHY  60
TRFLTDGPCR SAKPVTELVC SGQCGPARLL PNAIGRVKWW RPNGPDFRCI PDRYRAQRVQ  120
LLCPGGAAPR SRKVRLVASC KCKRLTRFHN QSELKDFGPE TARPQKGRKP RPGARGAKAN  180
QAELENAY                                                          188

SEQ ID NO: 191         moltype = AA  length = 190
FEATURE                Location/Qualifiers
REGION                 1..190
                       note = Synthetic Construct
source                 1..190
                       mol_type = protein
                       organism = synthetic construct
```

```
SEQUENCE: 191
QGWQAFKNDA TEIIPGLREY PEPPQELENN QTMNRAENGG RPPHHPYDTK DVSEYSCREL  60
HYTRFVTDGP CRSAKPVTEL VCSGQCGPAR LLPNAIGRVK WWRPNGPDFR CIPDRYRAQR  120
VQLLCPGGAA PRSRKVRLVA SCKCKRLTRF HNQSELKDFG PETARPQKGR KPRPRARGAK  180
ANQAELENAY                                                         190

SEQ ID NO: 192         moltype = AA  length = 24
FEATURE                Location/Qualifiers
REGION                 1..24
                       note = Synthetic Construct
source                 1..24
                       mol_type = protein
                       organism = synthetic construct
SEQUENCE: 192
GPARLLPNAI GRVKWWRPNG PDFR                                         24

SEQ ID NO: 193         moltype = AA  length = 12
FEATURE                Location/Qualifiers
REGION                 1..12
                       note = Synthetic Construct
source                 1..12
                       mol_type = protein
                       organism = synthetic construct
SEQUENCE: 193
GPARLLPNAI GR                                                      12

SEQ ID NO: 194         moltype = AA  length = 11
FEATURE                Location/Qualifiers
REGION                 1..11
                       note = Synthetic Construct
source                 1..11
                       mol_type = protein
                       organism = synthetic construct
SEQUENCE: 194
RLLPNAIGRG K                                                       11

SEQ ID NO: 195         moltype = AA  length = 11
FEATURE                Location/Qualifiers
REGION                 1..11
                       note = Synthetic Construct
source                 1..11
                       mol_type = protein
                       organism = synthetic construct
SEQUENCE: 195
KWWRPSGPDF R                                                       11

SEQ ID NO: 196         moltype = AA  length = 11
FEATURE                Location/Qualifiers
REGION                 1..11
                       note = Synthetic Construct
source                 1..11
                       mol_type = protein
                       organism = synthetic construct
SEQUENCE: 196
PNAIGRVKWW R                                                       11

SEQ ID NO: 197         moltype = AA  length = 12
FEATURE                Location/Qualifiers
REGION                 1..12
                       note = Synthetic Construct
source                 1..12
                       mol_type = protein
                       organism = synthetic construct
SEQUENCE: 197
IGRVKWWRPN GP                                                      12

SEQ ID NO: 198         moltype = AA  length = 11
FEATURE                Location/Qualifiers
REGION                 1..11
                       note = Synthetic Construct
source                 1..11
                       mol_type = protein
                       organism = synthetic construct
SEQUENCE: 198
KWWRPNGPDF R                                                       11
```

```
SEQ ID NO: 199          moltype = AA  length = 5
FEATURE                 Location/Qualifiers
REGION                  1..5
                        note = Synthetic Construct
source                  1..5
                        mol_type = protein
                        organism = synthetic construct
SEQUENCE: 199
DFEIH                                                           5

SEQ ID NO: 200          moltype = AA  length = 17
FEATURE                 Location/Qualifiers
REGION                  1..17
                        note = Synthetic Construct
source                  1..17
                        mol_type = protein
                        organism = synthetic construct
SEQUENCE: 200
AIDPETGGSA NNQKFKA                                              17
```

ANTI-SCLEROSTIN CONSTRUCTS AND USES THEREOF

CROSS-REFERENCE TO RELATED APPLICATIONS

This application is a continuation of U.S. Application No. 17,982,481, filed on Nov. 7, 2022, now U.S. Pat. No. 12,630,651, issued on May 19, 2026, which is a continuation of International Application No. PCT/CN2021/120612, filed on Sep. 26, 2021, which claims priority to International Application No. PCT/CN2020/118387, filed on Sep. 28, 2020, the contents of each of which are incorporated herein by reference in their entirety for all purposes.

TECHNICAL FIELD

The present disclosure relates to anti-Sclerostin constructs (such as anti-Sclerostin antibodies) and the uses thereof.

REFERENCE TO AN ELECTRONIC SEQUENCE LISTING

The content of the electronic sequence listing (210912000202SeqList.xml; Size: 406,570 bytes; and Date of Creation: Jan. 16, 2026) is herein incorporated by reference in its entirety.

BACKGROUND OF THE APPLICATION

The function of the SOST gene product, Sclerostin, as an inhibitor of bone formation in humans was discovered by genetic mapping studies that pinpointed loss-of-function mutations in the SOST gene as causative in the high bone mass (HBM) disorder sclerosteosis (Balemans et al., 2001 Hum. Mol. Genet. 10, 537-543; Brunkow et al., 2001 *Am. J. Hum. Genet.* 68, 577-589). In mice, deletion of the SOST gene causes an increase in bone mass and strength due to increased bone formation, while overexpression of a human Sclerostin transgene result in low bone mass and decreased bone strength (Ke et al., 2012 *Endocr. Rev.* 33, 747-783.).

The disclosures of all publications, patents, patent applications and published patent applications referred to herein are hereby incorporated herein by reference in their entirety.

BRIEF SUMMARY OF THE APPLICATION

The following summary is illustrative only and is not intended to be limiting in any way. That is, the following summary is provided to introduce highlights, benefits and advantages of the novel molecules and the uses thereof. Thus, the following summary is not intended to identify essential features of the claimed subject matter, nor is it intended for use in determining the scope of the claimed subject matter.

The present application in one aspect provides anti-Sclerostin constructs comprising an antibody moiety that specifically recognizes Sclerostin (such as human Sclerostin) comprising a heavy chain variable region ($V_H$) and a light chain variable region ($V_L$), such as any of the anti-Sclerostin constructs described herein. In some embodiments, the antibody moiety is an antibody or antigen-binding fragment thereof selected from the group consisting of a full-length antibody, a bispecific antibody, a single-chain Fv (scFv) fragment, a Fab fragment, a Fab' fragment, a $F(ab')_2$, an Fv fragment, a disulfide stabilized Fv fragment (dsFv), a dsscFv, a $(dsFv)_2$, a Fv-Fc fusion, a scFv-Fc fusion, a scFv-Fv fusion, a diabody, a tribody, and a tetrabody. In some embodiments, the construct is a full-length antibody comprising an Fc fragment. In some embodiments, the antibody moiety is a scFv fragment.

The present application in another aspect provides anti-Sclerostin constructs comprising an antibody moiety that specifically recognizes Sclerostin (such as human Sclerostin), and a second moiety. In some embodiments, the second moiety comprises a half-life extending moiety (such as an Fc fragment). In some embodiments, the second moiety comprises an agent selected from the group consisting of a parathyroid hormone (PTH), a selective estrogen receptor modulator (SERM), a bisphosphonate, prostaglandin E (PGE) receptor agonists, Vascular endothelial growth factor (VEGF), transforming growth factor-β (TGFβ), growth factor (myostatin) and calcitonin.

In some embodiments, the second moiety comprises a second antibody moiety that specifically recognizes an antigen. In some embodiments, there is provided anti-Sclerostin constructs comprising a first antibody moiety that specifically recognizes Sclerostin (including but not limited to anti-Sclerostin antibody moieties described herein), and a second antibody moiety that specifically recognizes Dickkopf-1 (DKK1) or receptor activator of nuclear factor kappa beta ligand (RANKL). Antibody moieties that recognize DKK1 or RANKL can be any anti-DKK1 antibody moiety or anti-RANKL antibody moiety (including but not limited to those described herein). In some embodiments, the second antibody moiety is a full-length antibody, a Fab, a Fab', a $(Fab')_2$, an Fv, a single chain Fv (scFv) fragment, a scFv-scFv, a minibody, a diabody, or an sdAb. In some embodiments, the second antibody moiety is a full-length antibody comprising an Fc fragment, and wherein the anti-Sclerostin antibody moiety is a single chain Fv (scFv) fragment. In some embodiments, the second antibody moiety is a scFv fragment, and wherein the anti-Sclerostin antibody moiety is a full-length antibody comprising an Fc fragment. In some embodiments, the scFv fragment is fused to (e.g., N-terminus and/or C-terminus of) both of the heavy chains and/or light chains of the full-length antibody (via a linker or without a linker). In some embodiments, the construct comprises: a) a first polypeptide comprising a first light chain comprising, from N-terminus to C-terminus, i) the $V_L$, ii) a first light chain constant domain ("first CL domain"); b) a second polypeptide comprising a first heavy chain comprising, from N-terminus to C-terminus, i) the $V_H$, ii) a first heavy chain constant domain ("first CH1 domain"), and iii) a first Fc domain; c) a third polypeptide comprising a second heavy chain comprising, from N-terminus to C-terminus, i) the $V_{H-2}$, ii) a second heavy chain constant domain ("second CH1 domain"), and iii) a second Fc domain; and d) a fourth polypeptide comprising a second light chain comprising, from N-terminus to C-terminus, i) the $V_{L-2}$, ii) ii) a second light chain constant domain ("second CL domain"), wherein the first and the second Fc domains form an Fc fragment. The first or second CH1 and/or the first or second Fc domain may have various modifications as described herein.

The present application in another aspect provides anti-Sclerostin constructs that specifically bind to Sclerostin competitively with any of the anti-Sclerostin constructs described herein.

The present application in another aspect provides pharmaceutical compositions comprising any of the anti-Sclerostin constructs described herein and a pharmaceutically acceptable carrier. In some embodiments, the composition further comprises an agent selected from the group consisting of a parathyroid hormone (PTH), a selective estrogen receptor modulator (SERM), VEGF, TGFβ, growth factor (myostatin) and calcitonin.

The present application in another aspect provides isolated nucleic acids encoding any of the anti-Sclerostin constructs described herein or a portion thereof (e.g., one or more polypeptides thereof).

The present application in another aspect provides vectors comprising any of the isolated nucleic acids described herein.

The present application in another aspect provides isolated host cells comprising any of the isolated nucleic acids and/or any of the vectors described herein.

The present application in another aspect provides methods of producing an anti-Sclerostin construct comprising: a) culturing any of the isolated host cells described herein under conditions effective to express the anti-Sclerostin construct or a portion thereof (e.g., one or more polypeptides thereof); and b) obtaining the expressed anti-Sclerostin construct or a portion thereof from the host cells.

The present application in another aspect provides methods of treating a disease or condition in an individual, comprising administering to the individual an effective mount of an anti-Sclerostin construct such as any of the anti-Sclerostin constructs described herein, or any of the pharmaceutical compositions described herein. In some embodiments, the disease or condition is a bone-related disorder. In some embodiments, the bone-related disorder is osteogenesis imperfecta, osteopetrosis, osteoporosis (in men and/or women), senile osteoporosis, delay bone healing, delayed or non-union bone fractures, Paget's disease, immobilization-induced bone loss, glucocorticoid-induced bone loss, inflammation-induced bone loss including arthritis-induced bone loss or other disease or condition associated with a) bone loss of either quantity or quality or both and/or b) abnormality of bone structure and quality. In some embodiments, the anti-Sclerostin construct or the pharmaceutical composition is administered parenterally into the individual. In some embodiments, the method further comprises administering a second agent or therapy (e.g., an anti-DKK1 antibody or an anti-RANKL antibody). In some embodiments, the second agent or therapy comprises an agent selected from the group consisting of a parathyroid hormone (PTH), a selective estrogen receptor modulator (SERM), a bisphosphonate, a prostaglandin E (PGE) receptor agonist, VEGF, and TGFβ, growth factor (myostatin) and calcitonin. In some embodiments, the individual is a human.

DETAILED DESCRIPTION OF THE APPLICATION

Figure 1:
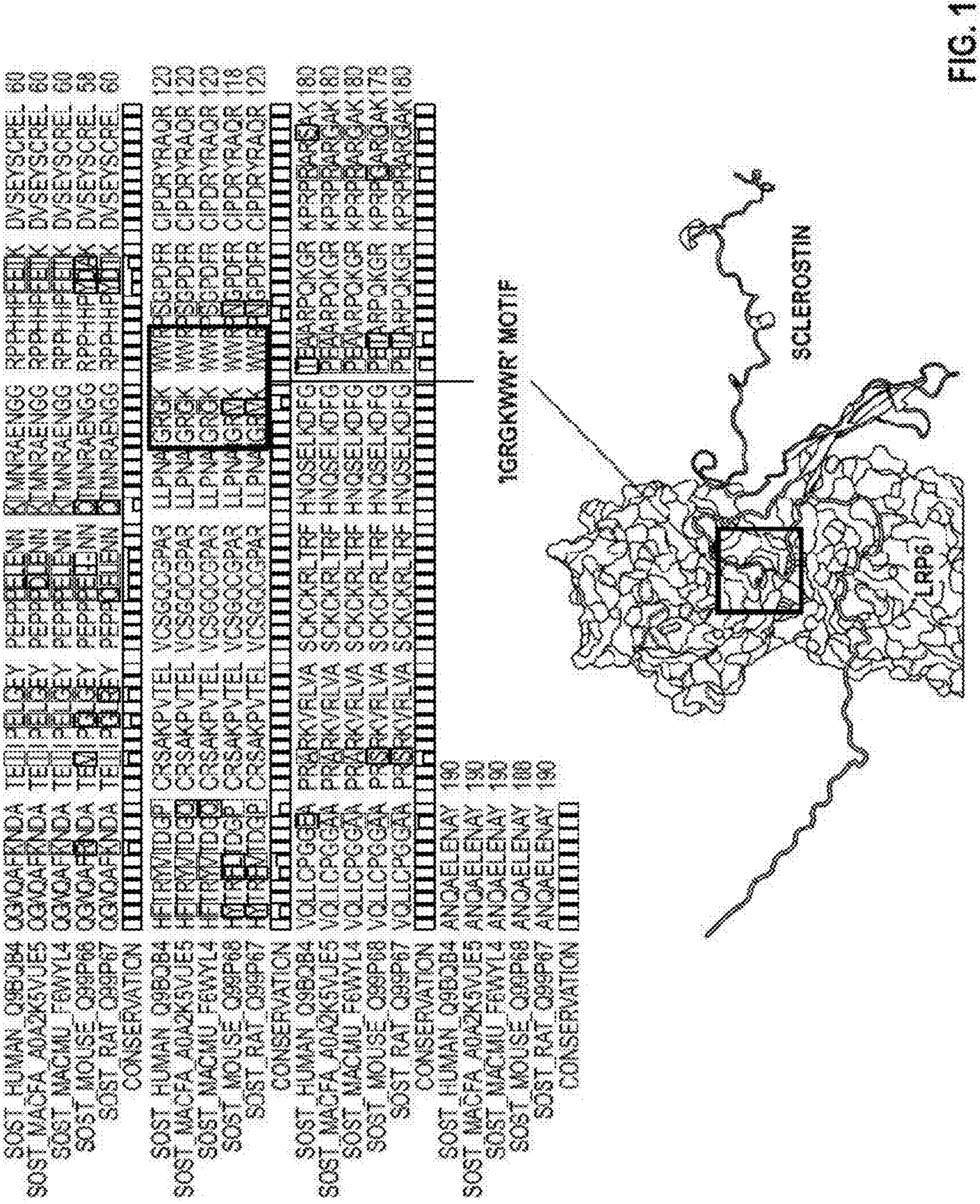
FIG. 1 shows the sequences (SOST_HUMAN_Q9BQB4: _SEQ ID NO: 183; SOST_MACFA_A0A2K5VUE5: SEQ ID NO: 184; SOST_MACMU_F6WYL4: SEQ ID NO: 189; SOST_MOUSE_Q99P68: SEQ ID NO: 190; and SOST_RAT_Q99P67: SEQ ID NO: 191) and conformation 'IGRGKWWR' motif (SEQ ID NO: 186) on the second loop of Sclerostin to illustrate the interaction between Sclerostin and LDL Receptor Related Protein 6 (LRP6).

The present application provides novel anti-Sclerostin constructs that specifically bind to Sclerostin (such as anti-Sclerostin monoclonal antibodies or multispecific antibodies), methods of preparing the anti-Sclerostin constructs, methods of using the constructs (e.g., methods of treating a disease or condition). The exemplary anti-Sclerostin constructs described herein achieved advantageous effects. For examples, exemplary anti-Sclerostin constructs exhibited higher binding affinity to Sclerostin as compared to Romosozumab. See Examples 3, 5, and 6 (Tables 5, 7, and 8).

I. Definitions

The term "antibody" is used in its broadest sense and encompasses various antibody structures, including but not limited to monoclonal antibodies, polyclonal antibodies, multispecific antibodies (e.g., bispecific antibodies), full-length antibodies and antigen-binding fragments thereof, so long as they exhibit the desired antigen-binding activity. The term "antibody moiety" refers to a full-length antibody or an antigen-binding fragment thereof.

A full-length antibody comprises two heavy chains and two light chains. The variable regions of the light and heavy chains are responsible for antigen binding. The variable domains of the heavy chain and light chain may be referred to as "$V_H$" and "$V_L$", respectively. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "antigen-binding fragment" as used herein refers to an antibody fragment including, for example, a diabody, a Fab, a Fab', a $F(ab')_2$, an Fv fragment, a disulfide stabilized Fv fragment (dsFv), a $(dsFv)_2$, a bispecific dsFv (dsFv-dsFv'), a disulfide stabilized diabody (ds diabody), a single-chain Fv (scFv), a dsscFv, an scFv dimer (bivalent diabody), a multispecific antibody formed from a portion of an antibody comprising one or more CDRs, a camelized single domain antibody, a Nanobody®, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

"Fv" is the minimum antibody fragment, which contains a complete antigen-recognition and -binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$ domains which enables the scFv to form the desired structure for antigen binding. For a review of scFv, see Plückthun in *The Pharmacology of Monoclonal Antibodies*, vol. 113, Rosenburg and Moore eds., Springer-Verlag, New York, pp. 269-315 (1994).

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., *J. Mol. Biol.,* 273: 927-948 (1997); MacCallum et al., J. Mol. Biol. 262:732-745 (1996); Abhinandan and Martin, *Mol. Immunol.,* 45:3832-3839 (2008); Lefranc M. P. et al., *Dev. Comp. Immunol.,* 27:55-77 (2003); and Honegger and Plückthun, *J. Mol. Biol.,* 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above-cited references are set forth below in Table 1 as a comparison. CDR prediction algorithms and interfaces are known in the art, including, for example, Abhinandan and Martin, *Mol. Immunol.,* 45:3832-3839 (2008); Ehrenmann F. et al., *Nucleic Acids Res.,* 38: D301-D307 (2010); and Adolf-Bryfogle J. et al., *Nucleic Acids Res.,* 43: D432-D438 (2015). The contents of the references cited in this paragraph are incorporated herein by reference in their entireties for use in the present application and for possible inclusion in one or more claims herein. In some embodiments, the CDR sequences provided herein are based on IMGT definition. For example, the CDR sequences may be determined by the VBASE2 tool (see also Retter I, Althaus H H, Münch R, Müller W: VBASE2, an integrative V gene database. Nucleic Acids Res. 2005 Jan. 1; 33 (Database issue): D671-4, which is incorporated herein by reference in its entirety).

The term "osteoporosis" as used herein refers to premenopausal idiopathic osteoporosis, postmenopausal osteoporosis, menopausal osteoporosis, postoophorectomy osteoporosis, osteoporosis of disuse, drug-induced osteoporosis, osteoporosis due to malabsorption, post-surgical malabsorption osteoporosis and/or senile osteoporosis.

The term "osteopenia" as used herein refers to premenopausal idiopathic osteopenia, postmenopausal osteopenia, senile osteopenia, drug-induced osteopenia, osteopenia of disuse, neonatal osteopenia and/or spaceflight osteopenia caused by reduced gravity.

The term "metabolic bone diseases" as used herein includes but not limit to renal osteodystrophy, primary and secondary hyperparathyroidism, familial hyperparathyroidism syndromes, parathyroid disorders, osteodystrophy, osteochondrosis, hyperphosphatasia.

The term "osteonecrosis" as used herein refers to avascular necrosis of bone, avascular necrosis secondary to diving, osteonecrosis of jaw.

The term "bone loss" as used herein refers to postmenopausal bone loss, Immobilization-induced bone loss, Weightlessness induced bone loss, Disease associated facial bone loss, Disease associated cranial bone loss, Disease associated bone loss of the jaw, Disease associated bone loss of the skull, bone loss associated with space travel, glucocorticoid-induced bone loss, Drug-induced bone loss, Organ transplant related bone loss, Kidney transplant related bone loss, HIV associated bone loss, bone loss associated with loss of growth hormone, bone loss associated with cystic fibrosis, Chemotherapy associated bone loss, Tumor induced bone loss, Cancer-related bone loss, Hormone ablative bone loss, Oral bone loss, Heparin-induced bone loss, Inflammation-induced bone loss including arthritis-induced bone loss or other disease or condition associated with a) bone loss of either quantity or quality or both and/or b) abnormality of bone structure and quality. bone loss caused by reduced gravity.

The term "nonunion" or "delay bone healing" as used herein refers to delayed or non-union bone fractures, hip fracture, pseudoarthritis after fusion or arthrodesis, osteolysis, postsurgical osteolysis, nonunion after spinal arthrodesis, enhancement/acceleration of spinal fusion, chronic pain after arthroplasty.

The term "osteomalacia" as used herein refers to Vitamin-D-resistant osteomalacia, calcium deficiency, sarcopenia, cancer sarcopenia, tumor-induced osteomalacia.

The term "fracture" as used herein includes but not limited to compression fracture, fragility fracture, pathologic fracture, stress fracture, hip fracture, fracture of femoral neck, atypical hip fracture, femoral intertrochanter fracture, fracture of bone in neoplastic disease.

The term "hypercalcemia" as used herein includes hypercalcemia of malignancy, myopathy due to hypercalcemia, hypercalcemia in chronic kidney disease.

The term "multiple myeloma related bone disorders" as used herein refers to multiple myeloma bone disease and ore osteoporosis in multiple myelomatosis.

The term "primary bone tumor" as used herein includes osteosarcoma, osteochondroma, osteoblastoma, osteochondromyxoma, osteoclastoma, osteoma, osteoid osteoma, chondrosarcoma, chondroblastoma, chondromyxoid fibroma, myxoid chondrosarcoma, sarcoma, ewing sarcoma, kaposi sarcoma, periosteal sarcoma, glomangiosarcoma, giant cell tumor, giant cell sarcoma, giant cell angiofibroma, haemangioendothelial sarcoma, undifferentiated sarcoma, fibrosarcoma, bone cyst, aneurysmal bone cyst, multiple endocrine neoplasia.

The term "malignancies" for "bone metastasis of malignancies" includes breast cancer, lung cancer, hepatic cancer, ovarian cancer, pancreatic cancer, colorectal cancer, gastric cancer, prostate cancer, thyroid cancer, thymus cancer.

The term "inflammatory or infectious bone disease" as used herein refers to osteomyelitis, pyogenic osteomyelitis, ankylosing spondylitis.

The term "bone marrow or haemotological disorders diseases" as used herein refers to leukemia, malignant lymphoma, haematological malignancy, haematologic disease, bone marrow disease.

The term "musculoskeletal rare disease" as used herein includes Osteogenesis imperfecta, Albers-Schonberg disease, congenital pseudarthrosis of the tibia, enchondromatosis, fibrous dysplasia, Gaucher's Disease, Marfan's syndrome, multiple hereditary exotoses, neurofibromatosis, osteogenesis imperfecta, osteopetrosis, osteopoikilosis, sclerotic lesions, pseudoarthrosis, melorheostosis, Juvenile arthritides, thalassemia, mucopolysaccharidoses, turner syndrome, Pown Syndrome, Klinefelter Syndrome, leprosy, Perthes' Disease, adolescent idiopathic scoliosis, Winchester Syndrome, Menkes Disease, ischemic bone disease (such as Legg-Calve-Perthes disease, regional migratory osteoporosis), Idiopathic infantile hypercalcemia, Acromegaly, Hypogonadism, Albright-McCune-Sternberg syndrome, Aluminium bone disease, Camurati-Engelmann disease, Osteopetrosis and infantile neuroaxonal dystrophy, Dysosteosclerosis, Pycnodysostosis, Gorham-Stout syndrome, Cystic angiomatosis, Paget's disease, Juvenile Paget's disease, Osteoporosis-oculocutaneous-hypopigmentation syndrome, Osteoporosis in classical or atypical cystic fibrosis, Bowed tibiae-radial anomalies-osteopenia-fractures, X-linked hypophosphatemic osteomalacia, Familial expansile osteolysis, Osteopoikilosis, Melorheostosis, Craniometaphyseal dysplasia, Osteoporosis-pseudoglioma syndrome, Cleidocranial dysplasia, Hajdu-Cheney syndrome, Winchester-Torg syndrome, Cole-Carpenter syndrome, Hypophosphatasia, Hereditary hyperphosphatasia, Fibrodysplasia ossificans progressive, Familial hypocalciuric hypercalcemia, Pseudohypoparathyroidism, Acrodysostosis, Eiken syndrome, Multiple enchondromatosis, Vitamin D hydroxylation-deficient rickets, Hypophosphatemic rickets.

The term "cartilage-related disorder" as used herein includes but not limited to Chondromatosis, Chondrodysplasia, Chondrodystrophic myotonia, Juxtacortical chondroma, Tear of cartilage of knee, Osteoarthritis, Osteochondrodystrophy.

The term "muscle-related disorder" as used herein includes sarcopenia and cancer sarcopenia.

The term "surgeries" as used in "facilitation of heal after bone or joint surgeries" refers to orthopedic procedures, dental procedures, implant surgery, joint replacement, joint-preserving surgery, distraction osteogenesis, bone lengthening, bone grafting, bone cosmetic surgery and bone repair such as fracture healing, nonunion healing, delayed union healing and facial reconstruction.

TABLE 1

| CDR DEFINITIONS | | | | | |
|---|---|---|---|---|---|
| | Kabat[1] | Chothia[2] | MacCallum[3] | IMGT[4] | AHo[5] |
| $V_H$ CDR1 | 31-35 | 26-32 | 30-35 | 27-38 | 25-40 |
| $V_H$ CDR2 | 50-65 | 53-55 | 47-58 | 56-65 | 58-77 |
| $V_H$ CDR3 | 95-102 | 96-101 | 93-101 | 105-117 | 109-137 |
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or hypervariable region (HVR) of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the CDR residues as herein defined.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, See Jones et al., *Nature* 321:522-525 (1986);

Riechmann et al., *Nature* 332:323-329 (1988); and Presta, *Curr. Op. Struct. Biol.* 2:593-596 (1992).

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al., *J. Mol. Biol.,* 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.,* 147(1):86-95 (1991). See also van Dijk and van de Winkel, *Curr. Opin. Pharmacol.,* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, MegAlign® (DNASTAR®), or MUSCLE™ software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE™ (Edgar, R. C., *Nucleic Acids Research* 32(5):1792-1797, 2004; Edgar, R. C., *BMC Bioinformatics* 5(1):113, 2004).

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "constant domain" refers to the portion of an immunoglobulin molecule having a more conserved amino acid sequence relative to the other portion of the immunoglobulin, the variable domain, which contains the antigen-binding site. The constant domain contains the $C_H1$, $C_H2$ and $C_H3$ domains (collectively, $C_H$) of the heavy chain and the CHL (or $C_L$) domain of the light chain.

The "light chains" of antibodies (immunoglobulins) from any mammalian species can be assigned to one of two clearly distinct types, called kappa ("κ") and lambda ("λ"), based on the amino acid sequences of their constant domains.

The "$C_H1$ domain" (also referred to as "C1" of "H1" domain) usually extends from about amino acid 118 to about amino acid 215 (EU numbering system).

"Hinge region" is generally defined as a region in IgG corresponding to Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "$C_H2$ domain" of a human IgG Fc region (also referred to as "C2" domain) usually extends from about amino acid 231 to about amino acid 340. The $C_H2$ domain is unique in that it is not closely paired with another domain. Rather, two N-linked branched carbohydrate chains are interposed between the two $C_H2$ domains of an intact native IgG molecule. It has been speculated that the carbohydrate may provide a substitute for the domain-domain pairing and help stabilize the CH2 domain. Burton, *Molec Immunol.* 22:161-206 (1985).

The "$C_H3$ domain" (also referred to as "C3" domain) comprises the stretch of residues C-terminal to a $C_H2$ domain in an Fc region (i.e. from about amino acid residue 341 to the C-terminal end of an antibody sequence, typically at amino acid residue 446 or 447 of an IgG).

The term "Fc region" or "fragment crystallizable region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Fc receptor" or "FcR" describes a receptor that binds the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See M. Daëron, *Annu. Rev. Immunol.* 15:203-234 (1997). FcRs are reviewed in Ravetch and Kinet, *Annu. Rev. Immunol.* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "epitope" as used herein refers to the specific group of atoms or amino acids on an antigen to which an antibody or antibody moiety binds. Two antibodies or antibody moieties may bind the same epitope within an antigen if they exhibit competitive binding for the antigen.

As used herein, a first antibody or fragment thereof "competes" for binding to a target antigen with a second antibody or fragment thereof when the first antibody or fragment thereof inhibits the target antigen binding of the second antibody of fragment thereof by at least about 50% (such as at least about any one of 55%, 60%, 65%, 70%, 75%, 80%, 85%, 90%, 95%, 98% or 99%) in the presence of an equimolar concentration of the first antibody or fragment thereof, or vice versa. A high throughput process for "binning" antibodies based upon their cross-competition is described in PCT Publication No. WO 03/48731.

As use herein, the terms "specifically binds," "specifically recognizing," and "is specific for" refer to measurable and reproducible interactions, such as binding between a target and an antibody or antibody moiety, which is determinative of the presence of the target in the presence of a heterogeneous population of molecules, including biological molecules. For example, an antibody or antibody moiety that specifically recognizes a target (which can be an epitope) is an antibody or antibody moiety that binds this target with greater affinity, avidity, more readily, and/or with greater duration than its bindings to other targets. In some embodiments, the extent of binding of an antibody to an unrelated target is less than about 10% of the binding of the antibody to the target as measured, e.g., by a radioimmunoassay (RIA). In some embodiments, an antibody that specifically binds a target has a dissociation constant ($K_D$) of $\leq 10^{-5}$ M, $\leq 10^{-6}$ M, $\leq 10^{-7}$ M, ≤10-8 M, $\leq 10^{-9}$ M, $\leq 10^{-10}$ M, $\leq 10^{-11}$ M, or $\leq 10^{-12}$ M. In some embodiments, an antibody specifically binds an epitope on a protein that is conserved among the protein from different species. In some embodiments, specific binding can include, but does not require exclusive binding. Binding specificity of the antibody or antigen-binding domain can be determined experimentally by methods known in the art. Such methods comprise, but are not limited to Western blots, ELISA-, RIA-, ECL-, IRMA™-, EIA-, BLI-, BIACORE™-tests and peptide scans.

An "isolated" antibody (or construct) is one that has been identified, separated and/or recovered from a component of its production environment (e.g., natural or recombinant). Preferably, the isolated polypeptide is free of association with all other components from its production environment.

An "isolated" nucleic acid molecule encoding a construct, antibody, or antigen-binding fragment thereof described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, and may contain mutations. Mutant progeny that has the same function or biological activity as screened or selected for in the originally transformed cell are included herein.

As used herein, "treatment" or "treating" is an approach for obtaining beneficial or desired results, including clinical results. For purposes of this application, beneficial or desired clinical results include, but are not limited to, one or more of the following: alleviating one or more symptoms resulting from the disease, diminishing the extent of the disease, stabilizing the disease, preventing or delaying the spread of the disease, preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. The methods of the application contemplate any one or more of these aspects of treatment.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to that of a reference. In certain embodiments, by "reduce" or "inhibit" is meant the ability to cause an overall decrease of 20% or greater. In another embodiment, by "reduce" or "inhibit" is meant the ability to cause an overall decrease of 50% or greater. In yet another embodiment, by "reduce" or "inhibit" is meant the ability to cause an overall decrease of 75%, 85%, 90%, 95%, or greater.

A "reference" as used herein, refers to any sample, standard, or level that is used for comparison purposes. A reference may be obtained from a healthy and/or non-diseased sample. In some examples, a reference may be obtained from an untreated sample. In some examples, a reference is obtained from a non-diseased or non-treated sample of an individual. In some examples, a reference is obtained from one or more healthy individuals who are not the individual or patient.

As used herein, "delaying development of a disease" means to defer, hinder, slow, retard, stabilize, suppress and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease.

"Preventing" as used herein, includes providing prophylaxis with respect to the occurrence or recurrence of a disease in an individual that may be predisposed to the disease but has not yet been diagnosed with the disease.

As used herein, to "suppress" a function or activity is to reduce the function or activity when compared to otherwise same conditions except for a condition or parameter of interest, or alternatively, as compared to another condition. For example, an antibody which suppresses tumor growth reduces the rate of growth of the tumor compared to the rate of growth of the tumor in the absence of the antibody.

The terms "subject," "individual," and "patient" are used interchangeably herein to refer to a mammal, including, but not limited to, human, bovine, horse, feline, canine, rodent, or primate. In some embodiments, the individual is a human.

An "effective amount" of an agent refers to an amount effective, at dosages and for periods of time necessary, to achieve the desired therapeutic or prophylactic result. The specific dose may vary depending on one or more of: the particular agent chosen, the dosing regimen to be followed, whether it is administered in combination with other compounds, timing of administration, the tissue to be imaged, and the physical delivery system in which it is carried.

The terms "pharmaceutical formulation" and "pharmaceutical composition" refer to a preparation which is in such form as to permit the biological activity of the active ingredient(s) to be effective, and which contains no additional components which are unacceptably toxic to an individual to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to an individual. A pharmaceutically acceptable carrier is non-toxic to recipients at the dosages and concentrations employed and is compatible with other ingredients of the formulation. The pharmaceutically acceptable carrier is appropriate for the formulation employed. Pharmaceutically acceptable carriers or excipients have preferably met the required standards of toxicological and manufacturing testing and/or are included on the Inactive Ingredient Guide prepared by the U.S. Food and Drug administration.

A "sterile" formulation is aseptic or essentially free from living microorganisms and their spores.

Administration "in combination with" one or more further therapeutic agents includes simultaneous (concurrent) and consecutive or sequential administration in any order.

The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about 60 minutes, such as no more than about any of 30, 15, 10, 5, or 1 minutes.

The term "sequentially" is used herein to refer to administration of two or more therapeutic agents where the administration of one or more agent(s) continues after discontinuing the administration of one or more other agent(s). For example, administration of the two or more therapeutic agents are administered with a time separation of more than about 15 minutes, such as about any of 20, 30, 40, 50, or 60 minutes, 1 day, 2 days, 3 days, 1 week, 2 weeks, or 1 month, or longer.

As used herein, "in conjunction with" refers to administration of one treatment modality in addition to another treatment modality. As such, "in conjunction with" refers to administration of one treatment modality before, during or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (e.g., a package or container) or kit comprising at least one reagent, e.g., a medicament for treatment of a disease or disorder, or a probe for specifically detecting a biomarker described herein. In certain embodiments, the manufacture or kit is promoted, distributed, or sold as a unit for performing the methods described herein.

It is understood that embodiments of the application described herein include "consisting" and/or "consisting essentially of" embodiments.

Reference to "about" a value or parameter herein includes (and describes) variations that are directed to that value or parameter per se. For example, description referring to "about X" includes description of "X".

The term "about X-Y" used herein has the same meaning as "about X to about Y."

As used herein and in the appended claims, the singular forms "a," "or," and "the" include plural referents unless the context clearly dictates otherwise.

II. Anti-Sclerostin Constructs

The present application provides anti-Sclerostin constructs comprising an anti-Sclerostin antibody moiety that specifically binds to Sclerostin (product of SOST) as described herein.

Sclerostin is a secreted glycoprotein with a C-terminal cysteine knot-like (CTCK) domain and sequence similarity to the DAN (differential screening-selected gene aberrative in neuroblastoma) family of bone morphogenetic protein (BMP) antagonists. Loss-of-function mutations in this gene are associated with an autosomal-recessive disorder, sclerosteosis, which causes progressive bone overgrowth. A deletion downstream of this gene, which causes reduced Sclerostin expression, is associated with a milder form of the disorder called van Buchem disease.

In some embodiments, there is provided an anti-Sclerostin construct comprising an antibody moiety that specifically recognizes Sclerostin, wherein the antibody moiety binds to an epitope on Sclerostin, wherein the epitope comprises the amino acid sequence set forth in SEQ ID NO: 186.

In some embodiments, the anti-Sclerostin construct comprises an antibody moiety comprising a heavy chain variable region ($V_H$) and a light chain variable region ($V_L$), wherein the antibody moiety competes for a binding epitope of Sclerostin with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9, and the $V_{L-2}$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of SEQ ID NO: 20.

In some embodiments, the anti-Sclerostin construct comprises an antibody moiety comprising a heavy chain variable region ($V_H$) and a light chain variable region ($V_L$), wherein the antibody moiety competes for a binding epitope of Sclerostin with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 1, the HC-CDR2 comprising the amino acid sequence of SEQ ID NO: 6, and the HC-CDR3 comprising the amino acid sequence of SEQ ID NO: 10, and the $V_{L-2}$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of SEQ ID NO: 20.

In some embodiments, the anti-Sclerostin construct comprises an antibody moiety comprising a heavy chain variable region ($V_H$) and a light chain variable region ($V_L$), wherein the antibody moiety competes for a binding epitope of Sclerostin with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 2, the HC-CDR2 comprising the amino acid sequence of SEQ ID NO: 7, and the HC-CDR3 comprising the amino acid sequence of SEQ ID NO: 10, and the $V_{L-2}$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of SEQ ID NO: 20.

In some embodiments, the anti-Sclerostin construct comprises an antibody moiety comprising a heavy chain variable region ($V_H$) and a light chain variable region ($V_L$), wherein the antibody moiety competes for a binding epitope of Sclerostin with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 2, the HC-CDR2 comprising the amino acid sequence of SEQ ID NO: 6, and the HC-CDR3 comprising the amino acid sequence of SEQ ID NO: 10, and the $V_{L-2}$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of SEQ ID NO: 20.

In some embodiments, the anti-Sclerostin construct comprises an antibody moiety comprising a heavy chain variable region ($V_H$) and a light chain variable region ($V_L$), wherein the antibody moiety competes for a binding epitope of Sclerostin with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 10, and the $V_{L-2}$ comprises the LC-CDR1 comprising the amino acid sequence of SEQ ID NO: 16, the LC-CDR2 comprising the amino acid sequence of SEQ ID NO: 18, and the LC-CDR3 comprising the amino acid sequence of SEQ ID NO: 20.

In some embodiments, the anti-Sclerostin construct comprises an antibody moiety comprising a heavy chain variable region ($V_H$) and a light chain variable region ($V_L$), wherein the antibody moiety competes for a binding epitope of Sclerostin with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 3, the HC-CDR2 comprising the amino acid sequence of SEQ ID NO: 7, and the HC-CDR3 comprising the amino acid sequence of SEQ ID NO: 10, and the $V_{L-2}$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of SEQ ID NO: 20.

In some embodiments, the anti-Sclerostin construct comprises an antibody moiety comprising a heavy chain variable region ($V_H$) and a light chain variable region ($V_L$), wherein the antibody moiety competes for a binding epitope of Sclerostin with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 10, and the $V_{L-2}$ comprises the LC-CDR1 comprising the amino acid sequence of SEQ ID NO: 16, the LC-CDR2 comprising the amino acid sequence of SEQ ID NO: 18, and the LC-CDR3 comprising the amino acid sequence of SEQ ID NO: 20.

In some embodiments, the anti-Sclerostin construct comprises an antibody moiety comprising a heavy chain variable region ($V_H$) and a light chain variable region ($V_L$), wherein the antibody moiety competes for a binding epitope of Sclerostin with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 4, the HC-CDR2 comprising the amino acid sequence of SEQ ID NO: 8, and the HC-CDR3 comprising the amino acid sequence of SEQ ID NO: 11, and the $V_{L-2}$ comprises the LC-CDR1 comprising the amino acid sequence of SEQ ID NO: 17, the LC-CDR2 comprising the amino acid sequence of SEQ ID NO: 19, and the LC-CDR3 comprising the amino acid sequence of SEQ ID NO: 21.

In some embodiments, the anti-Sclerostin construct comprises an antibody moiety comprising a heavy chain variable region ($V_H$) and a light chain variable region ($V_L$), wherein the antibody moiety competes for a binding epitope of Sclerostin with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 2, the HC-CDR2 comprising the amino acid sequence of SEQ ID NO: 6, and the HC-CDR3 comprising the amino acid sequence of SEQ ID NO: 10, and the $V_{L-2}$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of SEQ ID NO: 20.

In some embodiments, the anti-Sclerostin construct comprises an antibody moiety comprising a heavy chain variable region ($V_H$) and a light chain variable region ($V_L$), wherein the antibody moiety competes for a binding epitope of Sclerostin with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9, and the $V_{L-2}$ comprises the LC-CDR1 comprising the amino acid sequence of SEQ ID NO: 85, the LC-CDR2 comprising the amino acid sequence of SEQ ID NO: 18, and the LC-CDR3 comprising the amino acid sequence of SEQ ID NO: 20.

In some embodiments, the anti-Sclerostin construct comprises an antibody moiety comprising a heavy chain variable region ($V_H$) and a light chain variable region ($V_L$), wherein the antibody moiety competes for a binding epitope of Sclerostin with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9, and the $V_{L-2}$ comprises the LC-CDR1 comprising the amino acid sequence of SEQ ID NO: 86, the LC-CDR2 comprising the amino acid sequence of SEQ ID NO: 18, and the LC-CDR3 comprising the amino acid sequence of SEQ ID NO: 20.

In some embodiments, the $V_H$ comprises i) the HC-CDR1 comprising the amino acid sequence of any one of SEQ ID NOs: 1-4 and 12, ii) the HC-CDR2 comprising the amino acid sequence of any one of SEQ ID NOs: 5-8 and 13, and iii) the HC-CDR3 comprising the amino acid sequence any one of SEQ ID NOs: 9-11 and 14, or a variant thereof comprising up to 5, 4, 3, 2, or 1 amino acid substitutions in the HC-CDRs, and the $V_L$ comprises i) the LC-CDR1 comprising the amino acid sequence of any one of SEQ ID NOs: 15-17, ii) the LC-CDR2 comprising the amino acid sequence of any one of SEQ ID NOs: 18 and 19, and iii) the LC-CDR3 comprising the amino acid sequence of any one of SEQ ID NOs: 20 and 21, or a variant thereof comprising up to 5, 4, 3, 2, or 1 amino acid substitutions in the LC-CDRs.

In some embodiments, the anti-Sclerostin construct comprises an antibody moiety comprising a heavy chain variable region ($V_H$) and a light chain variable region ($V_L$), wherein the $V_H$ comprises the HC-CDR1 comprising the amino acid sequence of SEQ ID NO: 12, the HC-CDR2 comprising the amino acid sequence of SEQ ID NO: 13, and the HC-CDR3 comprising the amino acid sequence of SEQ ID NO: 14; and the $V_L$ comprises the LC-CDR1 comprising the amino acid sequence of SEQ ID NO: 15 or 16, the LC-CDR2 comprising the amino acid sequence of SEQ ID NO: 18, and the LC-CDR3 comprising the amino acid sequence of any one of SEQ ID NOs: 20.

In some embodiments, the anti-Sclerostin construct comprises an antibody moiety comprising a heavy chain variable region ($V_H$) and a light chain variable region ($V_L$), wherein the $V_H$ comprises i) the HC-CDR1 comprising the amino acid sequence of SEQ ID NO: 1, ii) the HC-CDR2 comprising the amino acid sequence of SEQ ID NO: 5, and iii) the HC-CDR3 comprising the amino acid sequence of SEQ ID NO: 9, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 15, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application. In some embodiments, the $V_H$ comprises i) the HC-CDR1 comprising the amino acid sequence of SEQ ID NO: 1, ii) the HC-CDR2 comprising the amino acid sequence of SEQ ID NO: 5, and iii) the HC-CDR3 comprising the amino acid sequence of SEQ ID NO: 9, and the $V_L$ comprises i) the LC-CDR1 comprising the amino acid sequence of SEQ ID NO: 15, ii) the LC-CDR2 comprising the amino acid sequence of SEQ ID NO: 18, and iii) the LC-CDR3 comprising the amino acid sequence of SEQ ID NO: 20. In some embodiments, the $V_H$ comprises an amino acid sequence of SEQ ID NO: 87, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 88, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 22, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 23, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 26, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 27, or a variant comprising an amino acid sequence having at least about 80% (such as at least about any one of 80%, 85%, 90%, 95%, 96%, 97%, 98%, or 99%) sequence identity.

In some embodiments, the anti-Sclerostin construct comprises an antibody moiety comprising a heavy chain variable region ($V_H$) and a light chain variable region ($V_L$), wherein the $V_H$ comprises i) the HC-CDR1 comprising the amino acid sequence of SEQ ID NO: 1, ii) the HC-CDR2 comprising the amino acid sequence of SEQ ID NO: 6, and iii) the HC-CDR3 comprising the amino acid sequence of SEQ ID NO: 10, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 15, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application. In some embodiments, the $V_H$ comprises an amino acid sequence of SEQ ID NO: 24, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 25, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 36, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 37, or a variant comprising an amino acid sequence having at least about 80% (such as at least about any one of 80%, 85%, 90%, 95%, 96%, 97%, 98%, or 99%) sequence identity.

In some embodiments, the anti-Sclerostin construct comprises an antibody moiety comprising a heavy chain variable region ($V_H$) and a light chain variable region ($V_L$), wherein the $V_H$ comprises i) the HC-CDR1 comprising the amino acid sequence of SEQ ID NO: 2, ii) the HC-CDR2 comprising the amino acid sequence of SEQ ID NO: 7, and iii) the HC-CDR3 comprising the amino acid sequence of SEQ ID NO: 10, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 15, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application. In some embodiments, the $V_H$ comprises an amino acid sequence of SEQ ID NO: 28, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 29, or a variant comprising an amino acid sequence having at least about 80% (such as at least about any one of 80%, 85%, 90%, 95%, 96%, 97%, 98%, or 99%) sequence identity.

In some embodiments, the anti-Sclerostin construct comprises an antibody moiety comprising a heavy chain variable region ($V_H$) and a light chain variable region ($V_L$), wherein the $V_H$ comprises i) the HC-CDR1 comprising the amino acid sequence of SEQ ID NO: 2, ii) the HC-CDR2 comprising the amino acid sequence of SEQ ID NO: 6, and iii) the HC-CDR3 comprising the amino acid sequence of SEQ ID NO: 10, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 15, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application. In some embodiments, the $V_H$ comprises an amino acid sequence of SEQ ID NO: 30, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 31, or a variant comprising an amino acid sequence having at least about 80% (such as at least about any one of 80%, 85%, 90%, 95%, 96%, 97%, 98%, or 99%) sequence identity.

In some embodiments, the anti-Sclerostin construct comprises an antibody moiety comprising a heavy chain variable region ($V_H$) and a light chain variable region ($V_L$), wherein the $V_H$ comprises i) the HC-CDR1 comprising the amino acid sequence of SEQ ID NO: 1, ii) the HC-CDR2 comprising the amino acid sequence of SEQ ID NO: 5, and iii) the HC-CDR3 comprising the amino acid sequence of SEQ ID NO: 10, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 16, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application. In some embodiments, the $V_H$ comprises an amino acid sequence of SEQ ID NO: 32, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 33, or a variant comprising an amino acid sequence having at least about 80% (such as at least about any one of 80%, 85%, 90%, 95%, 96%, 97%, 98%, or 99%) sequence identity.

In some embodiments, the anti-Sclerostin construct comprises an antibody moiety comprising a heavy chain variable region ($V_H$) and a light chain variable region ($V_L$), wherein the $V_H$ comprises i) the HC-CDR1 comprising the amino acid sequence of SEQ ID NO: 3, ii) the HC-CDR2 comprising the amino acid sequence of SEQ ID NO: 7, and iii) the HC-CDR3 comprising the amino acid sequence of SEQ ID NO: 10, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 15, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application. In some embodiments, the $V_H$ comprises an amino acid sequence of SEQ ID NO: 34, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 35, or a variant comprising an amino acid sequence having at least about 80% (such as at least about any one of 80%, 85%, 90%, 95%, 96%, 97%, 98%, or 99%) sequence identity.

In some embodiments, the anti-Sclerostin construct comprises an antibody moiety comprising a heavy chain variable region ($V_H$) and a light chain variable region ($V_L$), wherein the $V_H$ comprises i) the HC-CDR1 comprising the amino acid sequence of SEQ ID NO: 1, ii) the HC-CDR2 comprising the amino acid sequence of SEQ ID NO: 5, and iii) the HC-CDR3 comprising the amino acid sequence of SEQ ID NO: 10, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 16, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application. In some embodiments, the $V_H$ comprises an amino acid sequence of SEQ ID NO: 38, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 39, or a variant comprising an amino acid sequence having at least about 80% (such as at least about any one of 80%, 85%, 90%, 95%, 96%, 97%, 98%, or 99%) sequence identity.

In some embodiments, the anti-Sclerostin construct comprises an antibody moiety comprising a heavy chain variable region ($V_H$) and a light chain variable region ($V_L$), wherein the $V_H$ comprises i) the HC-CDR1 comprising the amino acid sequence of SEQ ID NO: 4, ii) the HC-CDR2 comprising the amino acid sequence of SEQ ID NO: 8, and iii) the HC-CDR3 comprising the amino acid sequence of SEQ ID NO: 11, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 17, ii) the LC-CDR2 comprising the amino acid sequence of SEQ ID NO: 19, and iii) the LC-CDR3 comprising the amino acid sequence of SEQ ID NO: 21, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application. In some embodiments, the $V_H$ comprises an amino acid sequence of SEQ ID NO: 40, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 41, or a variant comprising an amino acid sequence having at least about 80% (such as at least about any one of 80%, 85%, 90%, 95%, 96%, 97%, 98%, or 99%) sequence identity.

In some embodiments, the anti-Sclerostin construct comprises an antibody moiety comprising a heavy chain variable region ($V_H$) and a light chain variable region ($V_L$), wherein the $V_H$ comprises i) the HC-CDR1 comprising the amino acid sequence of SEQ ID NO: 1, ii) the HC-CDR2 comprising the amino acid sequence of SEQ ID NO: 5, and iii) the HC-CDR3 comprising the amino acid sequence of SEQ ID NO: 9, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 85, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application. In some embodiments, the $V_H$ comprises i) the HC-CDR1 comprising the amino acid sequence of SEQ ID NO: 1, ii) the HC-CDR2 comprising the amino acid sequence of SEQ ID NO: 5, and iii) the HC-CDR3 comprising the amino acid sequence of SEQ ID NO: 9, and the $V_L$ comprises i) the LC-CDR1 comprising the amino acid sequence of SEQ ID NO: 85, ii) the LC-CDR2 comprising the amino acid sequence of SEQ ID NO: 18, and iii) the LC-CDR3 comprising the amino acid sequence of SEQ ID NO: 20. In some embodiments, the $V_H$ comprises an amino acid sequence of SEQ ID NO: 87, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 89, or a variant comprising an amino acid sequence having at least about 80% (such as at least about any one of 80%, 85%, 90%, 95%, 96%, 97%, 98%, or 99%) sequence identity.

In some embodiments, the anti-Sclerostin construct comprises an antibody moiety comprising a heavy chain variable region ($V_H$) and a light chain variable region ($V_L$), wherein the $V_H$ comprises i) the HC-CDR1 comprising the amino acid sequence of SEQ ID NO: 1, ii) the HC-CDR2 comprising the amino acid sequence of SEQ ID NO: 5, and iii) the HC-CDR3 comprising the amino acid sequence of SEQ ID NO: 9, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 86, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application. In some embodiments, the $V_H$ comprises i) the HC-CDR1 comprising the amino acid sequence of SEQ ID NO: 1, ii) the HC-CDR2 comprising the amino acid sequence of SEQ ID NO: 5, and iii) the HC-CDR3 comprising the amino acid sequence of SEQ ID NO: 9, and the $V_L$ comprises i) the LC-CDR1 comprising the amino acid sequence of SEQ ID NO: 86, ii) the LC-CDR2 comprising the amino acid sequence of SEQ ID NO: 18, and iii) the LC-CDR3 comprising the amino acid sequence of SEQ ID NO: 20. In some embodiments, the $V_H$ comprises an amino acid sequence of SEQ ID NO: 87, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 90, or a variant comprising an amino acid sequence having at least about 80% (such as at least about any one of 80%, 85%, 90%, 95%, 96%, 97%, 98%, or 99%) sequence identity.

In some embodiments, there is provided an anti-Sclerostin construct comprising an antibody moiety that specifically recognizes Sclerostin, wherein the antibody moiety comprises a heavy chain variable region ($V_H$) and a light chain variable region ($V_L$), wherein:

a) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 22, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 23;

b) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 24, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 25;

c) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 26, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 27;

d) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 28, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 29;

e) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 30, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 31;

f) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 32, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 33;

g) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 34, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 35;

h) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 36, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 37;

i) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 38, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 39;

j) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 40, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 41;

k) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 87, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 88;

l) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 87, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 89; or m) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 87, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 90.

In some embodiments, the construct comprises or is an antibody or antigen-binding fragment thereof selected from the group consisting of a full-length antibody, a bispecific antibody, a single-chain Fv (scFv) fragment, a Fab fragment, a Fab' fragment, a $F(ab')_2$, an Fv fragment, a disulfide stabilized Fv fragment (dsFv), a dsscFv, a $(dsFv)_2$, a $V_HH$, a Fv-Fc fusion, a scFv-Fc fusion, a scFv-Fv fusion, a diabody, a tribody, and a tetrabody.

In some embodiments, the anti-Sclerostin antibody moiety is a full-length antibody.

In some embodiments, the anti-Sclerostin antibody moiety is a scFv or dsscFv.

In some embodiments, the anti-Sclerostin antibody moiety described above comprises an Fc fragment of an immunoglobulin selected from the group consisting of IgG, IgA, IgD, IgE, IgM, and combinations and hybrids thereof. In some embodiments, the anti-Sclerostin antibody moiety or the full-length antibody described above comprises an Fc fragment of an immunoglobulin selected from the group consisting of IgG1, IgG2, IgG3, IgG4, and combinations and hybrids thereof. In some embodiments, the Fc fragment has a reduced effector function as compared to the corresponding wildtype Fc fragment. In some embodiments, the Fc fragment has an enhanced effector function as compared to the corresponding wildtype Fc fragment.

In some embodiments, the antibody moiety comprises a humanized antibody of any of the antibody moiety described herein.

In some embodiments, the anti-Sclerostin construct comprises or is an anti-Sclerostin fusion protein.

In some embodiments, the anti-Sclerostin construct comprises or is a multispecific anti-Sclerostin construct (such as a bispecific antibody).

In some embodiments, the Sclerostin is a human Sclerostin.

a) Antibody Affinity

Binding specificity of the antibody moieties can be determined experimentally by methods known in the art. Such methods comprise, but are not limited to Western blots, ELISA-, RIA-, ECL-, IRMA™-, EIA-, BLI-, BIACORE™-tests and peptide scans.

In some embodiments, the $K_D$ of the binding between the antibody moiety and Sclerostin is about $10^{-7}$ M to about $10^{-12}$ M, about $10^{-7}$ M to about $10^{-8}$ M, about $10^{-8}$ M to about $10^{-9}$ M, about $10^{-9}$ M to about $10^{-10}$ M, about $10^{-10}$ M to about $10^{-11}$ M, about $10^{-11}$ M to about $10^{-12}$ M, about 10-7 M to about $10^{-12}$ M, about $10^{-8}$ M to about $10^{-12}$ M, about $10^{-9}$ M to about $10^{-12}$ M, about $10^{-10}$ M to about $10^{-12}$ M, about $10^{-7}$ M to about $10^{-11}$ M, about $10^{-8}$ M to about $10^{-11}$ M, about $10^{-9}$ M to about $10^{-11}$ M, about $10^{-7}$ M to about $10^{-10}$ M, about $10^{-8}$ M to about $10^{-10}$ M, or about $10^{-7}$ M to about $10^{-9}$ M. In some embodiments, the $K_D$ of the binding between the antibody moiety and Sclerostin is stronger than about any one of $10^{-7}$ M, $10^{-8}$ M, $10^{-9}$ M, $10^{-10}$ M, $10^{-11}$ M, or $10^{-12}$ M. In some embodiments, the Sclerostin is a human Sclerostin. In some embodiments, Sclerostin is cynomolgus Sclerostin.

In some embodiments, the Kon of the binding between the antibody moiety and Sclerostin is about $10^3$ $M^{-1}$ $s^{-1}$ to about $10^8$ $M^{-1}$ $s^{-1}$, about $10^3$ $M^{-1}$ $s^{-1}$ to about $10^4$ $M^{-1}$ $s^{-1}$, about $10^4$ $M^{-1}$ $s^{-1}$ to about $10^5$ $M^{-1}$ $s^{-1}$, about $10^5$ $M^{-1}$ $s^{-1}$ to about $10^6$ $M^{-1}$ $s^{-1}$, about $10^6$ $M^{-1}$ $s^{-1}$ to about $10^7$ $M^{-1}$ $s^{-1}$, or about $10^7$ $M^{-1}$ $s^{-1}$ to about $10^8$ $M^{-1}$ $s^{-1}$. In some embodiments, the Kon of the binding between the antibody moiety and Sclerostin is about $10^3$ $M^{-1}$ $s^{-1}$ to about $10^5$ $M^{-1}$ $s^{-1}$, about $10^4$ $M^{-1}$ $s^{-1}$ to about $10^6$ $M^{-1}$ $s^{-1}$, about $10^5$ $M^{-1}$ $s^{-1}$ to about $10^7$ $M^{-1}$ $s^{-1}$, about $10^6$ $M^{-1}$ $s^{-1}$ to about $10^8$ $M^{-1}$ $s^{-1}$, about $10^4$ $M^{-1}$ $s^{-1}$ to about $10^7$ $M^{-1}$ $s^{-1}$, or about $10^5$ $M^{-1}$ $s^{-1}$ to about $10^8$ $M^{-1}$ $s^{-1}$. In some embodiments, the Kon of the binding between the antibody moiety and Sclerostin is no more than about any one of $10^3$ $M^{-1}$ $s^{-1}$, $10^4$ $M^{-1}$ $s^{-1}$, $10^5$ $M^{-1}$ $s^{-1}$, $10^6$ $M^{-1}$ $s^{-1}$, $10^7$ $M^{-1}$ $s^{-1}$ or $10^8$ $M^{-1}$ $s^{-1}$. In some embodiments, Sclerostin is human Sclerostin. In some embodiments, Sclerostin is cynomolgus Sclerostin.

In some embodiments, the $K_{off}$ of the binding between the antibody moiety and Sclerostin is about 1 $s^{-1}$ to about $10^{-6}$ $s^{-1}$, about 1 $s^{-1}$ to about $10^{-2}$ $s^{-1}$, about $10^{-2}$ $s^{-1}$ to about $10^{-3}$ $s^{-1}$, about 10-3 $s^{-1}$ to about $10^{-4}$ $s^{-1}$, about $10^{-4}$ $s^{-1}$ to about $10^{-5}$ $s^{-1}$, about $10^{-5}$ $s^{-1}$ to about $10^{-6}$ $s^{-1}$, about 1 $s^{-1}$ to about $10^{-5}$ $s^{-1}$, about $10^{-2}$ $s^{-1}$ to about $10^{-6}$ $s^{-1}$, about $10^{-3}$ $s^{-1}$ to about $10^{-6}$ $s^{-1}$, about $10^{-4}$ $s^{-1}$ to about $10^{-6}$ $s^{-1}$, about $10^{-2}$ $s^{-1}$ to about $10^{-5}$ $s^{-1}$, or about $10^{-3}$ $s^{-1}$ to about $10^{-5}$ $s^{-1}$. In some embodiments, the $K_{off}$ of the binding between the antibody moiety and Sclerostin is at least about any one of 1 $s^{-1}$, $10^{-2}$ $s^{-1}$, $10^{-3}$ $s^{-1}$, $10^{-4}$ $s^{-1}$, $10^{-5}$ $s^{-1}$ or $10^{-6}$ $s^{-1}$. In some embodiments, Sclerostin is human Sclerostin. In some embodiments, Sclerostin is cynomolgus Sclerostin.

In some embodiments, the binding affinity of the anti-Sclerostin antibody moiety or anti-Sclerostin construct are higher (for example, has a smaller $K_D$ value) than an existing anti-Sclerostin antibody (e.g., Romosozumab).

b) Chimeric or Humanized Antibodies

In some embodiments, the anti-Sclerostin construct (e.g., the anti-Sclerostin antibody moiety) is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In some embodiments, a chimeric antibody comprises a non-human variable region (e.g., a variable region derived from mouse) and a human constant region. In some embodiments, a chimeric antibody is a "class switched" antibody in which the class or subclass has been changed from that of the parent antibody. Chimeric antibodies include antigen-binding fragments thereof.

In some embodiments, the anti-Sclerostin construct (e.g., the anti-Sclerostin antibody moiety) is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); Framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

It is understood that the humanization of mouse derived antibodies is a common and routinely used art. It is therefore understood that a humanized format of any and all of the anti-Sclerostin antibodies disclosed in Sequence Table can be used in a preclinical or clinical setting. In cases where a humanized format of any of the referenced anti-Sclerostin antibodies or their antigen-binding regions thereof is used in such a preclinical or clinical setting, the then humanized format is expected to bear the same or similar biological activities and profiles as the original non-humanized format.

c) Human Antibodies

In some embodiments, the anti-Sclerostin construct (e.g., the anti-Sclerostin antibody moiety) is a human antibody (known as human domain antibody, or human dAb). Human antibodies can be produced using various techniques known in the art. Human antibodies are described generally in van Dijk and van de Winkel, *Curr. Opin. Pharmacol.* 5:368-74 (2001), Lonberg, *Curr. Opin. Immunol.* 20:450-459 (2008), and Chen, *Mol. Immunol.* 47(4):912-21 (2010). Transgenic mice or rats capable of producing fully human single-domain antibodies (or sdAb) are known in the art. See, e.g., US20090307787A1, U.S. Pat. No. 8,754,287, US20150289489A1, US20100122358A1, and WO2004049794.

Human antibodies (e.g., human dAbs) may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies (e.g., human dAbs) can also be made by hybridoma-based methods. Human myeloma and mouse-human heteromyeloma cell lines for the production of human monoclonal antibodies have been described (See, e.g., Kozbor *J. Immunol.,* 133:3001 (1984); Brodeur et al., *Monoclonal Antibody Production Techniques and Applications*, pp. 51-63 (Marcel Dekker, Inc., New York, 1987); and Boerner et al., *J. Immunol.,* 147:86 (1991)). Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4): 265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies (e.g., human dAbs) may also be generated by isolating Fv clone variable domain sequences selected from human-derived phage display libraries. Such variable domain sequences may then be combined with a desired human constant domain. Techniques for selecting human antibodies from antibody libraries are described below.

d) Library-Derived Antibodies

The anti-Sclerostin antibody moieties described herein may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, NJ, 2001) and further described, e.g., in the McCafferty et al., *Nature* 348:552-554; Clackson et al., *Nature* 352:624-628 (1991); Marks et al., *J. Mol. Biol.* 222:581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004). Methods for constructing single-domain antibody libraries have been described, for example, See U.S. Pat. No. 7,371,849.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12:433-455 (1994). Phage typically displays antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J,* 12:725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227:381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

e) Substitution, Insertion, Deletion and Variants

In some embodiments, antibody variants having one or more amino acid substitutions are provided. Sites of interest for substitutional mutagenesis include the HVRs (or CDRs) and FRs. Conservative substitutions are shown in Table 2 under the heading of "Preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

| Amino acid substitutions | | |
|---|---|---|
| Original Residue | Exemplary Substitutions | Preferred Substitutions |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or CDRs.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

f) Glycosylation Variants

In some embodiments, the anti-Sclerostin construct (e.g., the anti-Sclerostin antibody moiety) is altered to increase or decrease the extent to which the construct is glycosylated. Addition or deletion of glycosylation sites to an antibody may be conveniently accomplished by altering the amino acid sequence such that one or more glycosylation sites is created or removed.

Where the antibody moiety comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the antibody moiety may be made in order to create antibody variants with certain improved properties.

In some embodiments, the anti-Sclerostin construct (e.g., the anti-Sclerostin antibody moiety) has a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87:614 (2004); Kanda, Y. et al., *Biotechnol. Bioeng.,* 94(4):680-688 (2006); and WO2003/085107).

In some embodiments, the anti-Sclerostin construct (e.g., the anti-Sclerostin antibody moiety) has bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

g) Fc Region Variants and Light Chain Constant Region Variants

In some embodiments, the anti-Sclerostin construct (e.g., the anti-Sclerostin antibody moiety) comprises an Fc fragment.

The term "Fc region," "Fc domain," "Fc fragment" or "Fc" refers to a C-terminal non-antigen binding region of an immunoglobulin heavy chain that contains at least a portion of the constant region. The term includes native Fc regions and variant Fc regions. In some embodiments, a human IgG heavy chain Fc region extends from Cys226 to the carboxyl-terminus of the heavy chain. However, the C-terminal lysine (Lys447) of the Fc region may or may not be present, without affecting the structure or stability of the Fc region. Unless otherwise specified herein, numbering of amino acid residues in the IgG or Fc region is according to the EU numbering system for antibodies, also called the EU index, as described in Kabat et al., Sequences of Proteins of Immunological Interest, 5th Ed. Public Health Service, National Institutes of Health, Bethesda, MD, 1991.

In some embodiments, the Fc fragment is from an immunoglobulin selected from the group consisting of IgG, IgA, IgD, IgE, IgM, and combinations and hybrids thereof. In some embodiments, the Fc fragment is from an immunoglobulin selected from the group consisting of IgG1, IgG2, IgG3, IgG4, and combinations and hybrids thereof.

In some embodiments, the Fc fragment has a reduced effector function as compared to corresponding wildtype Fc fragment (such as at least about 30%, 40%, 50%, 60%, 70%, 80%, 85%, 90%, or 95% reduced effector function as measured by the level of antibody-dependent cellular cytotoxicity (ADCC)).

In some embodiments, the Fc fragment is an IgG1 Fc fragment. In some embodiments, the IgG1 Fc fragment comprises a L234A mutation and/or a L235A mutation. In some embodiments, the Fc fragment is an IgG2 or IgG4 Fc fragment. In some embodiments, the Fc fragment is an IgG4 Fc fragment comprising a S228P, F234A, and/or a L235A mutation. In some embodiments, the Fc fragment comprises a N297A mutation. In some embodiments, the Fc fragment comprises a N297G mutation.

In some embodiments, one or more amino acid modifications may be introduced into the Fc region of the antibody moiety, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions. In some embodiments, the Fc fragment is derived from a rat Fc region sequence (e.g., a rat IgG2 Fc) or a mouse Fc region sequence (e.g., a mouse IgG1 Fc).

In some embodiments, the Fc fragment comprises a human IgG2 Fc region.

In some embodiments, the Fc fragment comprises a human IgG4 Fc region. In some embodiments, the Fc fragment comprises a modified human IgG4 heavy chain Fc region comprising one or more (such as two, three, or four) substitutions selected from the group consisting of S228P, T366W, and optional H435R, and optional Y436F. The numberings of the modifications described herein are according to the EU index unless otherwise noted. In some embodiments, the Fc fragment comprises a modified human IgG4 heavy chain Fc region comprising S228P, T366W, and optional H435R, and optional Y436F. In some embodiments, the Fc fragment comprises a modified human IgG4 heavy chain Fc region comprising one or more (such as two, three, four, five or six) substitutions selected from the group consisting of F126C, L128C, C131S, F170C, P161C, V173C, S228P, T366S, L368A, and Y407V, and optional H435R, and optional Y436F. In some embodiments, the Fc fragment comprises a modified human IgG4 heavy chain Fc region comprising a) C131S, S228P, T366S, L368A, and Y407V, and b) one of the substitutions selected from the group consisting of F126C, L128C, F170C, P161C, and V173C, and c) optional H435R, and optional Y436F. In some embodiments, the Fc fragment comprises a modified human IgG4 heavy chain Fc region comprising one or more (such as two, three, four, five or six) substitutions selected from the group consisting of F126C, C131S, S228P, T366S, L368A, and Y407V, and optional H435R, and optional Y436F. In some embodiments, the Fc fragment comprises a modified human IgG4 heavy chain Fc region comprising F126C, C131S, S228P, T366S, L368A, and Y407V, and optional H435R, and optional Y436F. In some embodiments, the Fc fragment comprises a modified human IgG4 heavy chain Fc region comprising L128C, C131S, S228P, T366S, L368A, and Y407V, and optional H435R, and optional Y436F. In some embodiments, the Fc fragment comprises a modified human IgG4 heavy chain Fc region comprising C131S, F170C, S228P, T366S, L368A, and Y407V, and optional H435R, and optional Y436F. In some embodiments, the Fc fragment comprises a modified human IgG4 heavy chain Fc region comprising C131S, V173C, S228P, T366S, L368A, and Y407V, and optional H435R, and optional Y436F. In some embodiments, the Fc fragment comprises a modified human IgG4 heavy chain Fc region comprising C131S, P171C, S228P, T366S, L368A, and Y407V, and optional H435R, and optional Y436F.

In some embodiments, the anti-Sclerostin construct comprises a Fc fragment comprising a) a first modified human IgG4 heavy chain Fc region comprising S228P, T366W, and b) a second modified human IgG4 heavy chain Fc region comprising a) C131S, S228P, T366S, L368A, and Y407V, and optional H435R, and optional Y436F, and b) one of the substitutions selected from the group consisting of F126C, L128C, F170C, P161C, and V173C.

In some embodiments, the anti-Sclerostin construct comprises a Fc fragment comprising a) a first modified human IgG4 heavy chain Fc region comprising S228P, T366W, and b) a second modified human IgG4 heavy chain Fc region comprising F126C, C131S, S228P, T366S, L368A, Y407V, H435R, and Y436F.

In some embodiments, the anti-Sclerostin construct comprises a Fc fragment comprising a) a first modified human IgG4 heavy chain Fc region comprising S228P, T366W, and b) a second modified human IgG4 heavy chain Fc region comprising L128C, C131S, S228P, T366S, L368A, Y407V, H435R, and Y436F.

In some embodiments, the anti-Sclerostin construct comprises a Fc fragment comprising a) a first modified human IgG4 heavy chain Fc region comprising S228P, T366W, and b) a second modified human IgG4 heavy chain Fc region comprising C131S, F170C, S228P, T366S, L368A, Y407V, H435R, and Y436F.

In some embodiments, the anti-Sclerostin construct comprises a Fc fragment comprising a) a first modified human IgG4 heavy chain Fc region comprising S228P, T366W, and b) a second modified human IgG4 heavy chain Fc region comprising C131S, V173C, S228P, T366S, L368A, Y407V, H435R, and Y436F.

In some embodiments, the anti-Sclerostin construct comprises a Fc fragment comprising a) a first modified human IgG4 heavy chain Fc region comprising S228P, T366W, and b) a second modified human IgG4 heavy chain Fc region comprising C131S, P171C, S228P, T366S, L368A, Y407V, H435R, and Y436F.

In some embodiments, the anti-Sclerostin construct comprises a human Ig kappa light chain constant region. In some embodiments, the anti-Sclerostin construct comprises a modified human Ig kappa light chain constant region comprising F118C, S121C, Q160C, S162C, S176C, and/or C214S. In some embodiments, the anti-Sclerostin construct comprises a modified human Ig kappa light chain constant region comprising S121C and C214S. In some embodiments, the anti-Sclerostin construct comprises a modified human Ig kappa light chain constant region comprising F118C and C214S. In some embodiments, the anti-Sclerostin construct comprises a modified human Ig kappa light chain constant region comprising S176C and C214S. In some embodiments, the anti-Sclerostin construct comprises a modified human Ig kappa light chain constant region comprising Q160C and C214S. In some embodiments, the anti-Sclerostin construct comprises a modified human Ig kappa light chain constant region comprising S162C and C214S.

In some embodiments, the Fc fragment possesses some but not all effector functions, which make it a desirable candidate for applications in which the half-life of the antibody moiety in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 2 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (See Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581). In some embodiments, the Fc fragment comprises a N297A mutation. In some embodiments, the Fc fragment comprises a N297G mutation.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, the Fc fragment is an IgG1 Fc fragment. In some embodiments, the IgG1 Fc fragment comprises a L234A mutation and/or a L235A mutation. In some embodiments, the Fc fragment is an IgG2 or IgG4 Fc fragment. In some embodiments, the Fc fragment is an IgG4 Fc fragment comprising a S228P, F234A, and/or a L235A mutation.

In some embodiments, the antibody moiety comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164:4178-4184 (2000).

In some embodiments, the antibody moiety variant comprising a variant Fc region comprising one or more amino acid substitutions which alters half-life and/or changes binding to the neonatal Fc receptor (FcRn). Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which alters binding of the Fc region to FcRn. Such Fc variants include those with substitutions at one or more of Fc region residues at positions 250, 252, 254, 256, 307, 308, 428, 434 (U.S. Pat. No. 7,371,826), including the so-called "LS" Fc mutant comprising M428L and N434S (WO 2009/086320), and so-called "YTE" Fc mutant comprising M252Y, S254T and T256E (WO 2002/060919).

See also Duncan & Winter, *Nature* 322:738-40 (1988); U.S. Pat. Nos. 5,648,260; 5,624,821; and WO 94/29351 concerning other examples of Fc region variants.

h) Cysteine Engineered Antibody Variants

In some embodiments, it may be desirable to create cysteine engineered antibody moieties, e.g., "thioMAbs™," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an antibody-drug conjugate, as described further herein. In some embodiments, any one or more of the following residues may be substituted with cysteine: A118 (EU numbering) of the heavy chain; and S400 (EU numbering) of the heavy chain Fc region. Cysteine engineered antibody moieties may be generated as described, e.g., in U.S. Pat. No. 7,521,541.

i) Antibody Derivatives

In some embodiments, the antibody moiety described herein may be further modified to comprise additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in diagnosis under defined conditions, etc.

In some embodiments, the antibody moiety may be further modified to comprise one or more biologically active protein, polypeptides or fragments thereof. "Bioactive" or "biologically active", as used herein interchangeably, means showing biological activity in the body to carry out a specific function. For example, it may mean the combination with a particular biomolecule such as protein, DNA, etc., and then promotion or inhibition of the activity of such biomolecule. In some embodiments, the bioactive protein or fragments thereof include proteins and polypeptides that are administered to patients as the active drug substance for prevention of or treatment of a disease or condition, as well as proteins and polypeptides that are used for diagnostic purposes, such as enzymes used in diagnostic tests or in vitro assays, as well as proteins and polypeptides that are administered to a patient to prevent a disease such as a vaccine.

Multispecific Anti-Sclerostin Constructs

The anti-Sclerostin constructs in some embodiments comprise a multispecific (e.g., bispecific) anti-Sclerostin construct comprising an anti-Sclerostin antibody moiety according to any one of the anti-Sclerostin antibody moieties described herein, and a second binding moiety (such as a second antibody moiety) specifically recognizing a second antigen. In some embodiments, the multispecific anti-Sclerostin molecule comprises an anti-Sclerostin antibody moiety and a second antibody moiety specifically recognizing a second antigen. In some embodiments, the second antigen is an immune checkpoint molecule. In some embodiments, the second antigen is DKK1 (Dickkopf WNT Signaling Pathway Inhibitor 1) or RANKL (Receptor Activator of NF-κB Ligand).

Multispecific Constructs Targeting Both Sclerostin and RANKL

The present application provides multispecific constructs targeting both Sclerostin and RANKL. In some embodiments, there is provided a multispecific construct comprising a first antibody moiety that specifically recognizes Sclerostin and a second antibody moiety that specifically recognizes RANKL. In some embodiments, the Sclerostin is a human Sclerostin. In some embodiments, the RANKL is a human RANKL.

RANKL (Receptor activator of nuclear factor kappa-B ligand), also known as tumor necrosis factor ligand superfamily member 11 (TNFSF11), is a ligand for osteoprotegerin and functions as a key factor for osteoclast differentiation and activation. This protein was shown to be a dendritic cell survival factor and is involved in the regulation of T cell-dependent immune response. T cell activation was reported to induce expression of this gene and lead to an increase of osteoclastogenesis and bone loss. This protein was shown to activate antiapoptotic kinase AKT/PKB through a signaling complex involving SRC kinase and tumor necrosis factor receptor-associated factor (TRAF6), which indicated this protein may have a role in the regulation of cell apoptosis. Targeted disruption of the related gene in mice led to severe osteopetrosis and a lack of osteoclasts. The deficient mice exhibited defects in early differentiation of T and B lymphocytes, and failed to form lobulo-alveolar mammary structures during pregnancy.

Exemplary Anti-RANKL Antibody Moieties

In some embodiments, the anti-RANKL antibody moiety (such as an scFv) used in multispecific anti-Sclerostin constructs described herein comprises an antibody moiety comprising a heavy chain variable region ($V_H$) and a light chain variable region ($V_L$), wherein the antibody moiety competes for a binding epitope of RANKL with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 66, the HC-CDR2 comprising the amino acid sequence of SEQ ID NO: 67, and the HC-CDR3 comprising the amino acid sequence of SEQ ID NO: 68, and the $V_{L-2}$ comprises the LC-CDR1 comprising the amino acid sequence of SEQ ID NO: 69, the LC-CDR2 comprising the amino acid sequence of SEQ ID NO: 70, and the LC-CDR3 comprising the amino acid sequence of SEQ ID NO: 71.

In some embodiments, the anti-RANKL antibody moiety (such as an scFv) used in multispecific anti-Sclerostin constructs comprises an antibody moiety comprising a heavy chain variable region ($V_H$) and a light chain variable region ($V_L$), wherein the $V_H$ comprises the HC-CDR1 comprising the amino acid sequence of SEQ ID NO: 66, the HC-CDR2 comprising the amino acid sequence of SEQ ID NO: 67, and the HC-CDR3 comprising the amino acid sequence of SEQ ID NO: 68, and the $V_L$ comprises the LC-CDR1 comprising the amino acid sequence of SEQ ID NO: 69, the LC-CDR2 comprising the amino acid sequence of SEQ ID NO: 70, and the LC-CDR3 comprising the amino acid sequence of SEQ ID NO: 71. In some embodiments, the $V_H$ comprises an amino acid sequence of SEQ ID NO: 72, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 73, or a variant comprising an amino acid sequence having at least about 80% (such as at least about any one of 80%, 85%, 90%, 95%, 96%, 97%, 98%, or 99%) sequence identity.

In some embodiments, the anti-RANKL moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 72; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 73.

In some embodiments, there is provided a multispecific construct comprising a first antibody moiety that specifically recognizes RANKL and a second antibody moiety that specifically recognizes Sclerostin, wherein the first antibody moiety comprises an anti-RANKL single domain antibody (sdAb) moiety, and wherein the second antibody moiety comprises a full-length antibody comprising a heavy chain variable region ($V_H$) and a second light chain variable region ($V_L$) and an Fc fragment. In some embodiments, the anti-RANKL sdAb is fused to both of the heavy chains of the full-length antibody comprising an Fc fragment. In some embodiments, the anti-RANKL sdAb is fused to both of the light chains of the full-length antibody. In some embodiments, the anti-RANKL sdAb is fused to N-terminus of both heavy or light chains of the full-length antibody. In some embodiments, the anti-RANKL sdAb is fused to C-terminus of both heavy or light chains of the full-length antibody. In some embodiments, the anti-RANKL sdAb is fused to the full-length antibody via a linker (such as any of the linkers described herein). In some embodiments, the anti-RANKL sdAb is fused to the full-length antibody without a linker.

In some embodiments, there is provided a multispecific construct comprising a first antibody moiety that specifically recognizes RANKL and a second antibody moiety that specifically recognizes Sclerostin, wherein the first antibody moiety comprises an anti-RANKL single domain antibody (sdAb) moiety, wherein the second antibody moiety comprises a heavy chain variable region ($V_H$) and a second light chain variable region ($V_L$), wherein the construct comprises: a) two chimeric heavy chains each comprising, from N-terminus to C-terminus, the i) the $V_H$, ii) a first heavy chain constant domain ("$C_H1$ domain"), iii) the anti-RANKL sdAb, and iv) an Fc domain, wherein the two Fc domains form an Fc fragment; b) two light chains comprising the $V_L$ and a light chain constant domain ("$C_L$ domain"). In some embodiments, the anti-RANKL sdAb is fused to the Fc domain via a first linker. In some embodiments, the anti-RANKL sdAb is fused to the $V_H$ via a second linker.

In some embodiments, there is provided a multispecific construct comprising a first antibody moiety that specifically recognizes RANKL and a second antibody moiety that specifically recognizes Sclerostin, wherein the first antibody moiety comprises an anti-RANKL single domain antibody (sdAb) moiety, wherein the second antibody moiety comprises a heavy chain variable region ($V_H$) and a second light chain variable region ($V_L$), and wherein the construct comprises: a) a first heavy chain comprising, from N-terminus to C-terminus, i) the anti-RANKL sdAb, and ii) a first Fc domain; b) a second heavy chain comprising, from N-terminus to C-terminus, i) the $V_H$, ii) a first heavy chain constant domain ("CH1 domain"), and iii) a second Fc domain; and c) a light chain comprising the $V_L$ and a light chain constant domain ("$C_L$ domain"), wherein the first and the second Fc domains form an Fc fragment.

In some embodiments, one of the first and the second Fc domains comprises a T366W mutation, and optionally a S354C mutation, and wherein the other Fc domain comprises a T366S mutation, a L368A mutation, a Y407V mutation, and optionally a Y349C mutation.

In some embodiments, wherein the second antibody moiety competes for a binding epitope of RANKL with a third antibody moiety comprising a second heavy chain variable region ($V_{H-2}$) and a second light chain variable region ($V_{L-2}$), wherein the $V_{H-2}$ comprises the HC-CDR1 comprising the amino acid sequence of SEQ ID NO: 66, the HC-CDR2 comprising the amino acid sequence of SEQ ID NO: 67, and the HC-CDR3 comprising the amino acid sequence of SEQ ID NO: 68, and the $V_{L-2}$ comprises the LC-CDR1 comprising the amino acid sequence of SEQ ID NO: 69, the LC-CDR2 comprising the amino acid sequence of SEQ ID NO: 70, and the LC-CDR3 comprising the amino acid sequence of SEQ ID NO: 71. In some embodiments, the $V_H$ comprises a HC-CDR1 comprising the amino acid sequence of SEQ ID NO: 66, a HC-CDR2 comprising the amino acid sequence of SEQ ID NO: 67, and a HC-CDR3 comprising the amino acid sequence of SEQ ID NO: 68, and the $V_L$ comprises a LC-CDR1 comprising the amino acid sequence of SEQ ID NO: 69, a LC-CDR2 comprising the amino acid sequence of SEQ ID NO: 70, and a LC-CDR3 comprising the amino acid sequence of SEQ ID NO: 71.

In some embodiments, the anti-Sclerostin construct is a multispecific (e.g., bispecific) anti-Sclerostin construct comprising a) an anti-Sclerostin antibody moiety according to any one of the anti-Sclerostin antibody moieties described herein; b) a second antibody moiety specifically recognizing RANKL (an anti-RANKL antibody moiety such as any of the anti-RANKL antibody moieties described herein). In some embodiments, the anti-Sclerostin $V_H$ comprises i) the HC-CDR1 comprising the amino acid sequence of SEQ ID NO: 1, ii) the HC-CDR2 comprising the amino acid sequence of SEQ ID NO: 5, and iii) the HC-CDR3 comprising the amino acid sequence of SEQ ID NO: 9, or a variant thereof comprising up to 5, 4, 3, 2, or 1 amino acid substitutions in the HC-CDRs, and the anti-Sclerostin $V_L$ comprises i) the LC-CDR1 comprising the amino acid sequence of SEQ ID NO: 15, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs.

In some embodiments, the anti-Sclerostin $V_H$ comprises i) the HC-CDR1 comprising the amino acid sequence of SEQ ID NO: 1, ii) the HC-CDR2 comprising the amino acid sequence of SEQ ID NO: 5, and iii) the HC-CDR3 comprising the amino acid sequence of SEQ ID NO: 9, or a variant thereof comprising up to 5, 4, 3, 2, or 1 amino acid substitutions in the HC-CDRs, and the anti-Sclerostin $V_L$ comprises i) the LC-CDR1 comprising the amino acid sequence of SEQ ID NO: 85, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs.

In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-Sclerostin construct is a multispecific (e.g., bispecific) anti-Sclerostin construct comprising a) an anti-Sclerostin full-length antibody comprising two heavy chains and two light chains, wherein the two heavy chains each comprises a heavy chain variable region ($V_H$) and the two light chains each comprises a light chain variable region ($V_L$), b) an anti-RANKL antibody moiety (such as any of the antibody moiety described herein) fused to at least both of the heavy chains of the anti-Sclerostin full-length antibody. In some embodiments, the anti-RANKL antibody moiety is fused to N-terminus of both heavy chains. In some embodiments, the anti-RANKL antibody moiety is fused to C-terminus of both heavy chains.

In some embodiments, the anti-Sclerostin construct is a multispecific (e.g., bispecific) anti-Sclerostin construct comprising a) an anti-RANKL antibody moiety comprising a full-length antibody comprising two heavy chains and two light chains, wherein the two heavy chains each comprises a heavy chain variable region ($V_H$) and the two light chains each comprises a light chain variable region ($V_L$), b) an anti-Sclerostin antibody moiety (such as any of the anti-Sclerostin antibody moiety described herein) fused to at least one or both of the heavy chains of the anti-RANKL full-length antibody. In some embodiments, the anti-Sclerostin antibody moiety is fused to N-terminus of both heavy chains. In some embodiments, the anti-Sclerostin antibody moiety is fused to C-terminus of both heavy chains.

In some embodiments, the anti-Sclerostin construct is a multispecific (e.g., bispecific) anti-Sclerostin construct comprising a) an anti-Sclerostin full-length antibody comprising two heavy chains and two light chains, wherein the two heavy chains each comprises a heavy chain variable region ($V_H$) and the two light chains each comprises a light chain variable region ($V_L$), b) an anti-RANKL antibody moiety (such as any of the antibody moiety described herein) fused to at least both of the light chains of the anti-Sclerostin full-length antibody. In some embodiments, the anti-RANKL antibody moiety is fused to N-terminus of both light chains. In some embodiments, the anti-RANKL antibody moiety is fused to C-terminus of both light chains.

In some embodiments, the anti-Sclerostin construct is a multispecific (e.g., bispecific) anti-Sclerostin construct comprising a) an anti-RANKL antibody moiety comprising a full-length antibody comprising two heavy chains and two light chains, wherein the two heavy chains each comprises a heavy chain variable region ($V_H$) and the two light chains each comprises a light chain variable region ($V_L$), b) an anti-Sclerostin antibody moiety (such as any of the antibody moiety described herein) fused to at least both of the light chains of the anti-RANKL full-length antibody. In some embodiments, the anti-Sclerostin antibody moiety is fused to N-terminus of both light chains. In some embodiments, the anti-Sclerostin antibody moiety is fused to C-terminus of both light chains.

In some embodiments, there is provided a multispecific construct comprising a first antibody moiety that specifically recognizes Sclerostin and a second antibody moiety that specifically recognizes RANKL, wherein the first antibody moiety comprises single chain Fv fragment (scFv) comprising a first heavy chain variable region ($V_{H-1}$) and a first light chain variable region ($V_{L-1}$), and wherein the second antibody moiety is a full-length antibody comprising a second heavy chain variable region ($V_{H-2}$), a second light chain variable region ($V_{L-2}$) and an Fc fragment. In some embodiments, the first antibody moiety is fused to one or both of the heavy chains of the full-length antibody. In some embodiments, the first antibody moiety is fused to one or both of the light chains of the full-length antibody. In some embodiments, the first antibody moiety is fused to N-terminus of the one or both of the heavy chains or light chains of the full-length antibody. In some embodiments, the first antibody moiety is fused to C-terminus of the one or both of the heavy chains or light chains of the full-length antibody. In some embodiments, the first antibody moiety is fused to the full-length antibody via a first linker (such as any of the linkers described herein). In some embodiments, the first antibody moiety is fused to the full-length antibody without a linker. In some embodiments, the $V_{H-1}$ is fused with the $V_{L-1}$ via a second linker (such as any of the linkers described herein).

In some embodiments, there is provided a multispecific construct comprising a first antibody moiety that specifically recognizes Sclerostin and a second antibody moiety that specifically recognizes RANKL, wherein the first antibody moiety is a full-length antibody comprising a first heavy chain variable region ($V_{H-1}$), a first light chain variable region ($V_{L-1}$) and an Fc fragment, and wherein the second antibody moiety comprises single chain Fv fragment (scFv) comprising a second heavy chain variable region ($V_{H-2}$) and a second light chain variable region ($V_{L-2}$). In some embodiments, the second antibody moiety is fused to both of the heavy chains of the full-length antibody. In some embodiments, the second antibody moiety is fused to both of the light chains of the full-length antibody. In some embodiments, the second antibody moiety is fused to N-terminus of both of the heavy chains or light chains of the full-length antibody. In some embodiments, the second antibody moiety is fused to C-terminus of the both of the heavy chains or light chains of the full-length antibody. In some embodiments, the second antibody moiety is fused to the full-length antibody via a first linker (such as any of the linkers described herein). In some embodiments, the second antibody moiety is fused to the full-length antibody without a linker. In some embodiments, the $V_{H-2}$ is fused with the $V_{L-2}$ via a second linker (such as any of the linkers described herein), to enable correct scFv assembling. In some embodiments, the $V_{H-2}$ is fused with the $V_{L-2}$ without a linker.

In some embodiments, there is provided a multispecific construct specifically recognizing Sclerostin and RANKL, comprising a first antibody moiety and a second antibody, wherein the first antibody moiety comprises a first heavy chain variable region ($V_{H-1}$) and a first light chain variable region ($V_{L-1}$), and wherein the second antibody moiety comprises a second heavy chain variable region ($V_{H-2}$) and a second light chain variable region ($V_{L-2}$), wherein the construct comprises: a) a first polypeptide comprising a first light chain comprising, from N-terminus to C-terminus, i) the $V_{L-1}$, ii) a first light chain constant domain ("first CL domain"); b) a second polypeptide comprising a first heavy chain, from N-terminus to C-terminus, i) the $V_{H-1}$, ii) a first heavy chain constant domain ("first CH1 domain"), and iii) a first Fc domain; c) a third polypeptide comprising a second heavy chain comprising, from N-terminus to C-terminus, i) the $V_{H-2}$, ii) a second heavy chain constant domain ("second CH1 domain"), and iii) a second Fc domain; and d) a fourth polypeptide comprising a second light chain, from N-terminus to C-terminus, i) the $V_{L-2}$, ii) ii) a first light chain constant domain ("the second CL domain"), wherein the first and the second Fc domains form a Fc fragment. In some embodiments, the first antibody moiety specifically recognizes Sclerostin, and the second antibody moiety specifically recognizes RANKL. In some embodiments, the first antibody moiety specifically recognizes RANKL, and the second antibody moiety specifically recognizes Sclerostin.

In some embodiments, one of the first and the second Fc domains comprises a T366W mutation, and optionally a S354C mutation, and wherein the other Fc domain comprises a T366S mutation, a L368A mutation, a Y407V mutation, and optionally a Y349C mutation, wherein numbering is according to the EU index.

In some embodiments, either i) the first CH1 domain and the first CL domain or ii) the second CH1 domain and the second CL domain are selected from the group consisting of: a) a CH1 domain wherein the amino acid at position 141 is substituted for cysteine and the cysteine at position 131 (e.g., in IgG2 or IgG4) or 220 (e.g., in IgG1) is substituted for a non-cysteine amino acid; and a CL domain wherein the amino acid at position 116 is substituted for cysteine and the cysteine at position 214 is substituted for a non-cysteine amino acid; b) a CH1 domain wherein the amino acid at position 168 is substituted for cysteine and the cysteine position 131 (e.g., in IgG2 or IgG4) or 220 (e.g., in IgG1) is substituted for a non-cysteine amino acid; and a CL domain wherein the amino acid at position 164 is substituted for cysteine and the cysteine at position 214 is substituted for a non-cysteine amino acid; c) a CH1 domain wherein the amino acid at position 126 is substituted for cysteine and the cysteine at position 131 (e.g., in IgG2 or IgG4) or 220 (e.g., in IgG1) is substituted for a non-cysteine amino acid; and a CL domain wherein the amino acid at position 121 is substituted for cysteine and the cysteine at position 214 is substituted for a non-cysteine amino acid; d) a CH1 domain wherein the amino acid at position 128 is substituted for cysteine and the cysteine at position 131 (e.g., in IgG2 or IgG4) or 220 (e.g., in IgG1) is substituted for a non-cysteine amino acid; and a CL domain wherein the amino acid at position 118 is substituted for cysteine and the cysteine at position 214 is substituted for a non-cysteine amino acid; e) a CH1 domain wherein the amino acid at position 170 is substituted for cysteine and the cysteine at position 131 (e.g., in IgG2 or IgG4) or 220 (e.g., in IgG1) is substituted for a non-cysteine amino acid; and a CL domain wherein the amino acid at position 176 is substituted for cysteine and the cysteine at position 214 is substituted for a non-cysteine amino acid; f) a CH1 domain wherein the amino acid at position 171 is substituted for cysteine and the cysteine at position 131 (e.g., in IgG2 or IgG4) or 220 (e.g., in IgG1) is substituted for a non-cysteine amino acid; and a CL domain wherein the amino acid at position 162 is substituted for cysteine and the cysteine at position 214 is substituted for a non-cysteine amino acid; g) a CH1 domain wherein the amino acid at position 173 is substituted for cysteine and the cysteine at position 131 (e.g., in IgG2 or IgG4) or 220 (e.g., in IgG1) is substituted for a non-cysteine amino acid; and a CL domain wherein the amino acid at position 160 is substituted for cysteine and the cysteine at position 214 is substituted for a non-cysteine amino acid; wherein numbering is according to the EU index.

In some embodiments, there is provided a multispecific construct comprising a first antibody moiety that specifically recognizes Sclerostin and a second antibody moiety that specifically recognizes RANKL, wherein the first antibody moiety is an anti-Sclerostin full-length antibody comprising two heavy chains and two light chains, wherein the two heavy chains each comprises a first heavy chain variable region ($V_{H-1}$), wherein the two light chains each comprises a first light chain variable region ($V_{L-1}$), and wherein the second antibody moiety comprises an anti-RANKL single chain Fv fragment (scFv) comprising a second heavy chain variable region ($V_{H-2}$) and a second light chain variable region ($V_{L-2}$), wherein the second antibody moiety is fused to C-terminus of both heavy chains of the anti-Sclerostin full-length antibody. In some embodiments, the $V_{H-1}$ comprises an amino acid sequence of SEQ ID NO: 22, or a variant comprising an amino acid sequence having at least about 80% (such as at least about any one of 80%, 85%, 90%, 95%, 96%, 97%, 98%, or 99%) sequence identity; and the $V_{L-1}$ comprises an amino acid sequence of SEQ ID NO: 23, or a variant comprising an amino acid sequence having at least about 80% (such as at least about any one of 80%, 85%, 90%, 95%, 96%, 97%, 98%, or 99%) sequence identity. In some embodiments, the $V_{H-2}$ comprises the HC-CDR1 comprising the amino acid sequence of SEQ ID NO: 66, the HC-CDR2 comprising the amino acid sequence of SEQ ID NO: 67, and the HC-CDR3 comprising the amino acid sequence of SEQ ID NO: 68, and the $V_{L-2}$ comprises the LC-CDR1 comprising the amino acid sequence of SEQ ID NO: 69, the LC-CDR2 comprising the amino acid sequence of SEQ ID NO: 70, and the LC-CDR3 comprising the amino acid sequence of SEQ ID NO: 71. In some embodiments, the $V_{H-2}$ comprises an amino acid sequence of SEQ ID NO: 72, or a variant comprising an amino acid sequence having at least about 80% (such as at least about any one of 80%, 85%, 90%, 95%, 96%, 97%, 98%, or 99%) sequence identity; and the $V_{L-1}$ comprises an amino acid sequence of SEQ ID NO: 73, or a variant comprising an amino acid sequence having at least about 80% (such as at least about any one of 80%, 85%, 90%, 95%, 96%, 97%, 98%, or 99%) sequence identity.

In some embodiments, there is provided a multispecific construct specifically recognizing Sclerostin and RANKL, comprising a first antibody moiety and a second antibody, wherein the first antibody moiety comprises a first heavy chain variable region ($V_{H-1}$) and a first light chain variable region ($V_{L-1}$), and wherein the second antibody moiety comprises a second heavy chain variable region ($V_{H-2}$) and a second light chain variable region ($V_{L-2}$), wherein the construct comprises: a) a first polypeptide comprising a first light chain comprising, from N-terminus to C-terminus, i) the $V_{L-1}$, ii) a first light chain constant domain ("first CL domain"); b) a second polypeptide comprising a first heavy chain, from N-terminus to C-terminus, i) the $V_{H-1}$, ii) a first heavy chain constant domain ("first CH1 domain"), and iii) a first Fc domain; c) a third polypeptide comprising a second heavy chain comprising, from N-terminus to C-terminus, i) the $V_{H-2}$, ii) a second heavy chain constant domain ("second CH1 domain"), and iii) a second Fc domain; and d) a fourth polypeptide comprising a second light chain, from N-terminus to C-terminus, i) the $V_{L-2}$, ii) ii) a first light chain constant domain ("the second CL domain"), wherein the first and the second Fc domains form a Fc fragment, wherein the first antibody moiety specifically recognizes Sclerostin, and wherein the second antibody moiety specifically recognizes RANKL. In some embodiments, the $V_{H-1}$ comprises an amino acid sequence of SEQ ID NO: 22, or a variant comprising an amino acid sequence having at least about 80% (such as at least about any one of 80%, 85%, 90%, 95%, 96%, 97%, 98%, or 99%) sequence identity; and the $V_{L-1}$ comprises an amino acid sequence of SEQ ID NO: 23, or a variant comprising an amino acid sequence having at least about 80% (such as at least about any one of 80%, 85%, 90%, 95%, 96%, 97%, 98%, or 99%) sequence identity. In some embodiments, the $V_{H-2}$ comprises the HC-CDR1 comprising the amino acid sequence of SEQ ID NO: 66, the HC-CDR2 comprising the amino acid sequence of SEQ ID NO: 67, and the HC-CDR3 comprising the amino acid sequence of SEQ ID NO: 68, and the $V_{L-2}$ comprises the LC-CDR1 comprising the amino acid sequence of SEQ ID NO: 69, the LC-CDR2 comprising the amino acid sequence of SEQ ID NO: 70, and the LC-CDR3 comprising the amino acid sequence of SEQ ID NO: 71. In some embodiments, the $V_{H-2}$ comprises an amino acid sequence of SEQ ID NO: 72, or a variant comprising an amino acid sequence having at least about 80% (such as at least about any one of 80%, 85%, 90%, 95%, 96%, 97%, 98%, or 99%) sequence identity; and the $V_{L-1}$ comprises an amino acid sequence of SEQ ID NO: 73, or a variant comprising an amino acid sequence having at least about 80% (such as at least about any one of 80%, 85%, 90%, 95%, 96%, 97%, 98%, or 99%) sequence identity.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 134; b) a first light chain comprising a first light chain variable region ($V_{L-1}$) and a first light chain constant region, wherein the first light chain comprises an amino acid sequence of SEQ ID NO: 135; c) a second heavy chain comprising a second variable heavy chain variable region ($V_{H-2}$) and a second heavy chain constant region, wherein the second heavy chain comprises the amino acid sequence of SEQ ID NO: 156; and d) a second light chain comprising a second light chain variable region ($V_{L-2}$) and a second light chain constant region, wherein the second light chain comprises the amino acid sequence of SEQ ID NO: 157, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing RANKL.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 134; b) a first light chain comprising a first light chain variable region ($V_{L-1}$) and a first light chain constant region, wherein the first light chain comprises an amino acid sequence of SEQ ID NO: 135; c) a second heavy chain comprising a second variable heavy chain variable region ($V_{H-2}$) and a second heavy chain constant region, wherein the second heavy chain comprises the amino acid sequence of SEQ ID NO: 158; and d) a second light chain comprising a second light chain variable region ($V_{L-2}$) and a second light chain constant region, wherein the second light chain comprises the amino acid sequence of SEQ ID NO: 159, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing RANKL. In some embodiments, the $V_{H-1}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9; and the $V_{L-1}$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of any one of SEQ ID NOs: 20. In some embodiments, In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 134; b) a first light chain comprising a first light chain variable region ($V_{L-1}$) and a first light chain constant region, wherein the first light chain comprises an amino acid sequence of SEQ ID NO: 135; c) a second heavy chain comprising a second variable heavy chain variable region ($V_{H-2}$) and a second heavy chain constant region, wherein the second heavy chain comprises the amino acid sequence of SEQ ID NO: 160; and d) a second light chain comprising a second light chain variable region ($V_{L-2}$) and a second light chain constant region, wherein the second light chain comprises the amino acid sequence of SEQ ID NO: 161, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing RANKL.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 134; b) a first light chain comprising a first light chain variable region ($V_{L-1}$) and a first light chain constant region, wherein the first light chain comprises an amino acid sequence of SEQ ID NO: 135; c) a second heavy chain comprising a second variable heavy chain variable region ($V_{H-2}$) and a second heavy chain constant region, wherein the second heavy chain comprises the amino acid sequence of SEQ ID NO: 162; and d) a second light chain comprising a second light chain variable region ($V_{L-2}$) and a second light chain constant region, wherein the second light chain comprises the amino acid sequence of SEQ ID NO: 163, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing RANKL.

In some embodiments, there is provided a multispecific (e.g., bispecific) anti-Sclerostin construct comprising a) a first antibody moiety that specifically recognizes Sclerostin comprising a first heavy chain variable region ($V_{H-1}$) and a first light chain variable region ($V_{L-1}$), wherein the $V_{H-1}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9, and the $V_{L-1}$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of SEQ ID NO: 20, and b) a second antibody moiety that specifically recognizes RANKL comprising a second heavy chain variable region ($V_{H-2}$) and a second light chain variable region ($V_{L-2}$), wherein the $V_{H-2}$ comprises the HC-CDR1 comprising the amino acid sequence of SEQ ID NO: 66, the HC-CDR2 comprising the amino acid sequence of SEQ ID NO: 67, and the HC-CDR3 comprising the amino acid sequence of SEQ ID NO: 68, and the $V_{L-2}$ comprises the LC-CDR1 comprising the amino acid sequence of SEQ ID NO: 69, the LC-CDR2 comprising the amino acid sequence of SEQ ID NO: 70, and the LC-CDR3 comprising the amino acid sequence of SEQ ID NO: 71. In some embodiments, the $V_{H-1}$ comprises an amino acid sequence of SEQ ID NO: 22, and the $V_{L-1}$ comprises an amino acid sequence of SEQ ID NO: 23. In some embodiments, the $V_{H-1}$ comprises an amino acid sequence of SEQ ID NO: 87 or 168, and the $V_{L-1}$ comprises an amino acid sequence of SEQ ID NO: 88 or 169. In some embodiments, the $V_{H-1}$ comprises an amino acid sequence of SEQ ID NO: 87, and the $V_{L-1}$ comprises an amino acid sequence of SEQ ID NO: 88. In some embodiments, the $V_{H-1}$ comprises an amino acid sequence of SEQ ID NO: 168, and the $V_{L-1}$ comprises an amino acid sequence of SEQ ID NO: 169. In some embodiments, the $V_{H-2}$ comprises an amino acid sequence of SEQ ID NO: 72, and the $V_{L-2}$ comprises an amino acid sequence of SEQ ID NO: 73. In some embodiments, the first antibody moiety is a full-length antibody comprising two heavy chains and two light chains, and the second antibody moiety is a scFv comprising the $V_{H-2}$ and $V_{L-2}$. In some embodiments, the $V_{H-2}$ is fused to the N-terminus of the $V_{L-2}$. In some embodiments, the $V_{H-2}$ is fused to the C-terminus of the $V_{L-2}$ optionally with a single alanine amino acid appended to the C-terminus of $V_{H-2}$. In some embodiments, the $V_{H-2}$ and the $V_{L-2}$ are fused via a linker (e.g., a GS linker, e.g., $(GGGGS)_4$ (SEQ ID NO: 77)). In some embodiments, the $V_{H-1}$ and the $V_{L-1}$ are fused without a linker. In some embodiments, the scFv is a dsscFv optionally comprising a) a G44C mutation in the $V_H$ or $V_{H-2}$ according to the numbering of SEQ ID NO: 60, and b) a G100C mutation in the $V_L$ or $V_{L-2}$ according to the numbering of SEQ ID NO: 61. In some embodiments, the second antibody moiety is fused to N-terminus of two heavy chains of the full-length antibody. In some embodiments, the second antibody moiety is fused to C-terminus of two heavy chains of the full-length antibody. In some embodiments, the second antibody moiety is fused to N-terminus of two light chains of the full-length antibody. In some embodiments, the second antibody moiety is fused to C-terminus of two light chains of the full-length antibody. In some embodiments, the second antibody moiety is a full-length antibody comprising two heavy chains and two light chains, and the first antibody moiety is a scFv comprising the $V_{H-1}$ and the $V_{L-1}$. In some embodiments, the $V_{H-1}$ is fused to the N-terminus of the $V_{L-1}$. In some embodiments, the $V_{H-1}$ is fused to the C-terminus of the $V_{L-1}$ optionally with a single alanine amino acid appended to the C-terminus of $V_{H-1}$. In some embodiments, the $V_{H-1}$ and the $V_{L-1}$ are fused via a linker (e.g., a GS linker, e.g., $(GGGGS)_4$ (SEQ ID NO: 77)). In some embodiments, the scFv is a dsscFv optionally comprising a) a G44C mutation in the $V_H$ or $V_{H-2}$ according to the numbering of SEQ ID NO: 60, and b) a G100C mutation in the $V_L$ or $V_{L-2}$ according to the numbering of SEQ ID NO: 61. In some embodiments, the first antibody moiety is fused to N-terminus of one or two heavy chains of the full-length antibody. In some embodiments, the first antibody moiety is fused to C-terminus of one or two heavy chains of the full-length antibody. In some embodiments, the first antibody moiety is fused to N-terminus of one or two light chains of the full-length antibody. In some embodiments, the first antibody moiety is fused to C-terminus of one or two light chains of the full-length antibody. In some embodiments, the first antibody moiety and the second antibody moiety are fused via a linker (e.g., a GS linker, e.g., $(GGGGS)_3$ (SEQ ID NO: 76)). In some embodiments, the first antibody moiety and the second antibody moiety are fused without a linker.

In some embodiments, there is provided a multispecific (e.g., bispecific) construct comprising a first antibody moiety that specifically recognizes Sclerostin and a second antibody moiety that specifically recognizes RANKL, wherein the multispecific construct comprises two heavy chains and two light chains, wherein the two heavy chains each comprises an amino acid sequence of SEQ ID NO: 126, wherein the two light chains each comprises an amino acid sequence of SEQ ID NO: 129.

In some embodiments, there is provided a multispecific (e.g., bispecific) construct comprising a first antibody moiety that specifically recognizes Sclerostin and a second antibody moiety that specifically recognizes RANKL, wherein the multispecific construct comprises two heavy chains and two light chains, wherein the two heavy chains each comprises an amino acid sequence of SEQ ID NO: 127, wherein the two light chains each comprises an amino acid sequence of SEQ ID NO: 129.

In some embodiments, there is provided a multispecific (e.g., bispecific) construct comprising a first antibody moiety that specifically recognizes Sclerostin and a second antibody moiety that specifically recognizes RANKL, wherein the multispecific construct comprises two heavy chains and two light chains, wherein the two heavy chains each comprises an amino acid sequence of SEQ ID NO: 128, wherein the two light chains each comprises an amino acid sequence of SEQ ID NO: 129.

In some embodiments, there is provided a multispecific (e.g., bispecific) construct comprising a first antibody moiety that specifically recognizes Sclerostin and a second antibody moiety that specifically recognizes RANKL, wherein the multispecific construct comprises two heavy chains and two light chains, wherein the two heavy chains each comprises an amino acid sequence of SEQ ID NO: 133 wherein the two light chains each comprises an amino acid sequence of SEQ ID NO: 130.

In some embodiments, there is provided a multispecific (e.g., bispecific) construct comprising a first antibody moiety that specifically recognizes Sclerostin and a second antibody moiety that specifically recognizes RANKL, wherein the multispecific construct comprises two heavy chains and two light chains, wherein the two heavy chains each comprises an amino acid sequence of SEQ ID NO: 133, wherein the two light chains each comprises an amino acid sequence of SEQ ID NO: 131.

In some embodiments, there is provided a multispecific (e.g., bispecific) construct comprising a first antibody moiety that specifically recognizes Sclerostin and a second antibody moiety that specifically recognizes RANKL, wherein the multispecific construct comprises two heavy chains and two light chains, wherein the two heavy chains each comprises an amino acid sequence of SEQ ID NO: 133, wherein the two light chains each comprises an amino acid sequence of SEQ ID NO: 132.

In some embodiments, there is provided a multispecific (e.g., bispecific) anti-Sclerostin construct comprising a) a first antibody moiety that specifically recognizes Sclerostin comprising a first heavy chain variable region ($V_{H-1}$) and a first light chain variable region ($V_{L-1}$), wherein the $V_{H-1}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9, and the $V_{L-1}$ comprises the LC-CDR1 comprising the amino acid sequence of SEQ ID NO: 85, the LC-CDR2 comprising the amino acid sequence of SEQ ID NO: 18, and the LC-CDR3 comprising the amino acid sequence of SEQ ID NO: 20, and b) a second antibody moiety that specifically recognizes RANKL comprising a second heavy chain variable region ($V_{H-2}$) and a second light chain variable region ($V_{L-2}$), wherein the $V_{H-2}$ comprises the HC-CDR1 comprising the amino acid sequence of SEQ ID NO: 66, the HC-CDR2 comprising the amino acid sequence of SEQ ID NO: 67, and the HC-CDR3 comprising the amino acid sequence of SEQ ID NO: 68, and the $V_{L-2}$ comprises the LC-CDR1 comprising the amino acid sequence of SEQ ID NO: 69, the LC-CDR2 comprising the amino acid sequence of SEQ ID NO: 70, and the LC-CDR3 comprising the amino acid sequence of SEQ ID NO: 71. In some embodiments, the $V_{H-1}$ comprises an amino acid sequence of SEQ ID NO: 87 or 168, and the $V_{L-1}$ comprises an amino acid sequence of SEQ ID NO: 89 or 170. In some embodiments, the $V_{H-1}$ comprises an amino acid sequence of SEQ ID NO: 87, and the $V_{L-1}$ comprises an amino acid sequence of SEQ ID NO: 89. In some embodiments, the $V_{H-1}$ comprises an amino acid sequence of SEQ ID NO: 168, and the $V_{L-1}$ comprises an amino acid sequence of SEQ ID NO: 170. In some embodiments, the $V_{H-2}$ comprises an amino acid sequence of SEQ ID NO: 72, and the $V_{L-2}$ comprises an amino acid sequence of SEQ ID NO: 73. In some embodiments, the first antibody moiety is a full-length antibody comprising two heavy chains and two light chains, and the second antibody moiety is a scFv comprising the $V_{H-2}$ and $V_{L-2}$. In some embodiments, the $V_{H-2}$ is fused to the N-terminus of the $V_{L-2}$. In some embodiments, the $V_{H-2}$ is fused to the C-terminus of the $V_{L-2}$ optionally with a single alanine amino acid appended to the C-terminus of $V_{H-2}$. In some embodiments, the $V_{H-2}$ and the $V_{L-2}$ are fused via a linker (e.g., a GS linker, e.g., $(GGGGS)_4$ (SEQ ID NO: 77)). In some embodiments, the $V_{H-1}$ and the $V_{L-1}$ are fused without a linker. In some embodiments, the scFv is converted to a dsscFv with H44-L100 disulfide bond formed by G44C mutation on $V_{H-2}$ and G100C mutation on $V_{L-2}$. In some embodiments, the second antibody moiety is fused to N-terminus of two heavy chains of the full-length antibody. In some embodiments, the second antibody moiety is fused to C-terminus of two heavy chains of the full-length antibody. In some embodiments, the second antibody moiety is fused to N-terminus of two light chains of the full-length antibody. In some embodiments, the second antibody moiety is fused to C-terminus of two light chains of the full-length antibody. In some embodiments, the second antibody moiety is a full-length antibody comprising two heavy chains and two light chains, and the first antibody moiety is a scFv comprising the $V_{H-1}$ and the $V_{L-1}$. In some embodiments, the $V_{H-1}$ is fused to the N-terminus of the $V_{L-1}$. In some embodiments, the $V_{H-1}$ is fused to the C-terminus of the $V_{L-1}$ optionally with a single alanine amino acid appended to the C-terminus of $V_{H-1}$. In some embodiments, the $V_{H-1}$ and the $V_{L-1}$ are fused via a linker (e.g., a GS linker, e.g., $(GGGGS)_4$ (SEQ ID NO: 77)). In some embodiments, the $V_{H-1}$ and the $V_{L-1}$ are fused via a linker without a linker. In some embodiments, the scFv is a dsscFv optionally comprising a) a G44C mutation in the $V_H$ or $V_{H-2}$ according to the numbering of SEQ ID NO: 60, and b) a G100C mutation in the $V_L$ or $V_{L-2}$ according to the numbering of SEQ ID NO: 61. In some embodiments, the first antibody moiety is fused to N-terminus of one or two heavy chains of the full-length antibody. In some embodiments, the first antibody moiety is fused to C-terminus of one or two heavy chains of the full-length antibody. In some embodiments, the first antibody moiety is fused to N-terminus of one or two light chains of the full-length antibody. In some embodiments, the first antibody moiety is fused to C-terminus of one or two light chains of the full-length antibody. In some embodiments, the first antibody moiety and the second antibody moiety are fused via a linker (e.g., a GS linker, e.g., $(GGGGS)_3$ (SEQ ID NO: 76)). In some embodiments, the first antibody moiety and the second antibody moiety are fused without a linker.

In some embodiments, the anti-RANKL antibody moiety and the anti-Sclerostin antibody moiety are fused with each other via a linker such as any of the linkers described herein with any operable form that allows the proper function of the binding moieties.

Multispecific Constructs Targeting Both Sclerostin and DKK1

In some embodiments, the anti-Sclerostin construct is a multispecific (e.g., bispecific) anti-Sclerostin construct comprising a) an anti-Sclerostin antibody moiety according to any one of the anti-Sclerostin antibody moieties described herein; b) a second antibody moiety specifically recognizing DKK1 (an anti-DKK1 antibody moiety).

DKK1 (Dickkopf-related protein 1) is a member of the dickkopf family of proteins. Members of this family are secreted proteins characterized by two cysteine-rich domains that mediate protein-protein interactions. DKK1 binds to the LRP6 co-receptor and inhibits beta-catenin-dependent Wnt signaling. This gene plays a role in embryonic development and may be important in bone formation in adults.

Exemplary Anti-DKK1 Antibody Moieties

In some embodiments, the anti-DKK1 antibody moiety (such as an scFv) used in multispecific anti-Sclerostin constructs comprises an antibody moiety comprising a heavy chain variable region ($V_H$) and a light chain variable region ($V_L$), wherein the antibody moiety competes for a binding epitope of DKK1 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 42, the HC-CDR2 comprising the amino acid sequence of SEQ ID NO: 43, and the HC-CDR3 comprising the amino acid sequence of SEQ ID NO: 44, and the $V_{L-2}$ comprises the LC-CDR1 comprising the amino acid sequence of SEQ ID NO: 45, the LC-CDR2 comprising the amino acid sequence of SEQ ID NO: 46, and the LC-CDR3 comprising the amino acid sequence of SEQ ID NO: 47.

In some embodiments, the anti-DKK1 antibody moiety (such as an scFv) used in multispecific anti-Sclerostin constructs comprises an antibody moiety comprising a heavy chain variable region ($V_H$) and a light chain variable region ($V_L$), wherein the antibody moiety competes for a binding epitope of DKK1 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 48, the HC-CDR2 comprising the amino acid sequence of SEQ ID NO: 49, and the HC-CDR3 comprising the amino acid sequence of SEQ ID NO: 50, and the $V_{L-2}$ comprises the LC-CDR1 comprising the amino acid sequence of SEQ ID NO: 51, the LC-CDR2 comprising the amino acid sequence of SEQ ID NO: 52, and the LC-CDR3 comprising the amino acid sequence of SEQ ID NO: 58.

In some embodiments, the anti-DKK1 antibody moiety (such as an scFv) used in multispecific anti-Sclerostin constructs comprises an antibody moiety comprising a heavy chain variable region ($V_H$) and a light chain variable region ($V_L$), wherein the antibody moiety competes for a binding epitope of DKK1 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 54, the HC-CDR2 comprising the amino acid sequence of SEQ ID NO: 55, and the HC-CDR3 comprising the amino acid sequence of SEQ ID NO: 56, and the $V_{L-2}$ comprises the LC-CDR1 comprising the amino acid sequence of SEQ ID NO: 57, the LC-CDR2 comprising the amino acid sequence of SEQ ID NO: 58, and the LC-CDR3 comprising the amino acid sequence of SEQ ID NO: 59.

In some embodiments, the anti-DKK1 antibody moiety (such as an scFv) used in multispecific anti-Sclerostin constructs comprises an antibody moiety comprising a heavy chain variable region ($V_H$) and a light chain variable region ($V_L$), wherein the $V_H$ comprises the HC-CDR1 comprising the amino acid sequence of SEQ ID NO: 42, the HC-CDR2 comprising the amino acid sequence of SEQ ID NO: 43, and the HC-CDR3 comprising the amino acid sequence of SEQ ID NO: 44, and the $V_L$ comprises the LC-CDR1 comprising the amino acid sequence of SEQ ID NO: 45, the LC-CDR2 comprising the amino acid sequence of SEQ ID NO: 46, and the LC-CDR3 comprising the amino acid sequence of SEQ ID NO: 47. In some embodiments, the $V_H$ comprises an amino acid sequence of SEQ ID NO: 60, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 61, or a variant comprising an amino acid sequence having at least about 80% (such as at least about any one of 80%, 85%, 90%, 95%, 96%, 97%, 98%, or 99%) sequence identity.

In some embodiments, the anti-DKK1 antibody moiety (such as an scFv) used in multispecific anti-Sclerostin constructs comprises an antibody moiety comprising a heavy chain variable region ($V_H$) and a light chain variable region ($V_L$), wherein the $V_H$ comprises the HC-CDR1 comprising the amino acid sequence of SEQ ID NO: 48, the HC-CDR2 comprising the amino acid sequence of SEQ ID NO: 49, and the HC-CDR3 comprising the amino acid sequence of SEQ ID NO: 50, and the $V_L$ comprises the LC-CDR1 comprising the amino acid sequence of SEQ ID NO: 51, the LC-CDR2 comprising the amino acid sequence of SEQ ID NO: 52, and the LC-CDR3 comprising the amino acid sequence of SEQ ID NO: 58. In some embodiments, the $V_H$ comprises an amino acid sequence of SEQ ID NO: 62, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 63, or a variant comprising an amino acid sequence having at least about 80% (such as at least about any one of 80%, 85%, 90%, 95%, 96%, 97%, 98%, or 99%) sequence identity.

In some embodiments, the anti-DKK1 antibody moiety (such as an scFv) used in multispecific anti-Sclerostin constructs comprises an antibody moiety comprising a heavy chain variable region ($V_H$) and a light chain variable region ($V_L$), wherein the $V_H$ comprises the HC-CDR1 comprising the amino acid sequence of SEQ ID NO: 54, the HC-CDR2 comprising the amino acid sequence of SEQ ID NO: 55, and the HC-CDR3 comprising the amino acid sequence of SEQ ID NO: 56, and the $V_L$ comprises the LC-CDR1 comprising the amino acid sequence of SEQ ID NO: 57, the LC-CDR2 comprising the amino acid sequence of SEQ ID NO: 58, and the LC-CDR3 comprising the amino acid sequence of SEQ ID NO: 59. In some embodiments, the $V_H$ comprises an amino acid sequence of SEQ ID NO: 64, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 65, or a variant comprising an amino acid sequence having at least about 80% (such as at least about any one of 80%, 85%, 90%, 95%, 96%, 97%, 98%, or 99%) sequence identity.

In some embodiments, the anti-DKK1 moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 60, 62, or 64; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 61, 63, or 65.

In some embodiments, there is provided a multispecific (e.g., bispecific) anti-Sclerostin construct comprising a) an anti-Sclerostin full-length antibody comprising two heavy chains and two light chains, wherein the two heavy chains each comprises a heavy chain variable region ($V_H$) and the two light chains each comprises a light chain variable region ($V_L$), b) an anti-DKK1 antibody moiety (such as any of the antibody moiety described herein) fused to at least both of the heavy chains of the anti-Sclerostin full-length antibody. In some embodiments, the anti-DKK1 antibody moiety is fused to N-terminus of both heavy chains. In some embodiments, the anti-DKK1 antibody moiety is fused to C-terminus of both heavy chains.

In some embodiments, there is provided a multispecific (e.g., bispecific) anti-Sclerostin construct comprising a) an anti-DKK1 antibody moiety comprising a full-length antibody comprising two heavy chains and two light chains, wherein the two heavy chains each comprises a heavy chain variable region ($V_H$) and the two light chains each comprises a light chain variable region ($V_L$), b) an anti-Sclerostin antibody moiety (such as any of the anti-Sclerostin antibody moiety described herein) fused to at least one or both of the heavy chains of the anti-DKK1 full-length antibody. In some embodiments, the anti-Sclerostin antibody moiety is fused to N-terminus of both heavy chains. In some embodiments, the anti-Sclerostin antibody moiety is fused to C-terminus of both heavy chains.

In some embodiments, there is provided a multispecific (e.g., bispecific) anti-Sclerostin construct comprising a) an anti-Sclerostin full-length antibody comprising two heavy chains and two light chains, wherein the two heavy chains each comprises a heavy chain variable region ($V_H$) and the two light chains each comprises a light chain variable region ($V_L$), b) an anti-DKK1 antibody moiety (such as any of the antibody moiety described herein) fused to at least both of the light chains of the anti-Sclerostin full-length antibody. In some embodiments, the anti-DKK1 antibody moiety is fused to N-terminus of both light chains. In some embodiments, the anti-DKK1 antibody moiety is fused to C-terminus of both light chains.

In some embodiments, there is provided a multispecific (e.g., bispecific) anti-Sclerostin construct comprising a) an anti-DKK1 antibody moiety comprising a full-length antibody comprising two heavy chains and two light chains, wherein the two heavy chains each comprises a heavy chain variable region ($V_H$) and the two light chains each comprises a light chain variable region ($V_L$), b) an anti-Sclerostin antibody moiety (such as any of the antibody moiety described herein) fused to at least one or both of the light chains of the anti-DKK1 full-length antibody. In some embodiments, the anti-Sclerostin antibody moiety is fused to N-terminus of both light chains. In some embodiments, the anti-Sclerostin antibody moiety is fused to C-terminus of both light chains.

In some embodiments, the anti-Sclerostin antibody moiety and the anti-DKK1 antibody moiety are fused with each other via a linker such as any of the linkers described herein with any operable form that allows the proper function of the binding moieties. In some embodiments, the anti-Sclerostin antibody moiety and the anti-DKK1 antibody moiety are fused without a linker.

In some embodiments, there is provided a multispecific (e.g., bispecific) anti-Sclerostin construct comprising a) a first antibody moiety that specifically recognizes Sclerostin comprising a first heavy chain variable region ($V_{H-1}$) and a first light chain variable region ($V_{L-1}$), wherein the $V_{H-1}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9, and the $V_{L-1}$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of SEQ ID NO: 20, and b) a second antibody moiety that specifically recognizes DKK1 comprising a second heavy chain variable region ($V_{H-2}$) and a second light chain variable region ($V_{L-2}$), wherein the $V_{H-2}$ comprises the HC-CDR1 comprising the amino acid sequence of SEQ ID NO: 42, the HC-CDR2 comprising the amino acid sequence of SEQ ID NO: 43, and the HC-CDR3 comprising the amino acid sequence of SEQ ID NO: 44, and the $V_{L-2}$ comprises the LC-CDR1 comprising the amino acid sequence of SEQ ID NO: 45, the LC-CDR2 comprising the amino acid sequence of SEQ ID NO: 46, and the LC-CDR3 comprising the amino acid sequence of SEQ ID NO: 47. In some embodiments, the $V_{H-1}$ comprises an amino acid sequence of SEQ ID NO: 22, and the $V_{L-1}$ comprises an amino acid sequence of SEQ ID NO: 23. In some embodiments, the $V_{H-1}$ comprises an amino acid sequence of SEQ ID NO: 87 or 168, and the $V_{L-1}$ comprises an amino acid sequence of SEQ ID NO: 88 or 169. In some embodiments, the $V_{H-1}$ comprises an amino acid sequence of SEQ ID NO: 87, and the $V_{L-1}$ comprises an amino acid sequence of SEQ ID NO: 88. In some embodiments, the $V_{H-1}$ comprises an amino acid sequence of SEQ ID NO: 168, and the $V_{L-1}$ comprises an amino acid sequence of SEQ ID NO: 169. In some embodiments, the $V_{H-2}$ comprises an amino acid sequence of SEQ ID NO: 60, 164, or 166, and the $V_{L-2}$ comprises an amino acid sequence of SEQ ID NO: 61, 165, or 167. In some embodiments, the $V_{H-2}$ comprises an amino acid sequence of SEQ ID NO: 164, and the $V_{L-2}$ comprises an amino acid sequence of SEQ ID NO: 165. In some embodiments, the $V_{H-2}$ comprises an amino acid sequence of SEQ ID NO: 166, and the $V_{L-2}$ comprises an amino acid sequence of SEQ ID NO: 167. In some embodiments, the $V_{H-2}$ comprises an amino acid sequence of SEQ ID NO: 61, and the $V_{L-2}$ comprises an amino acid sequence of SEQ ID NO: 167. In some embodiments, the first antibody moiety is a full-length antibody comprising two heavy chains and two light chains, and the second antibody moiety is a scFv comprising the $V_{H-2}$ and $V_{L-2}$. In some embodiments, the $V_{H-2}$ is fused to the N-terminus of the $V_{L-2}$ optionally with a single alanine amino acid appended to the C-terminus of $V_{H-2}$. In some embodiments, the $V_{H-2}$ is fused to the C-terminus of the $V_{L-2}$. In some embodiments, the $V_{H-2}$ and the $V_{L-2}$ are fused via a linker (e.g., a GS linker, e.g., $(GGGGS)_4$ (SEQ ID NO: 77)). In some embodiments, the $V_{H-1}$ and the $V_{L-1}$ are fused without a linker. In some embodiments, the scFv is a dsscFv optionally comprising a) a G44C mutation in the $V_H$ or $V_{H-2}$ according to the numbering of SEQ ID NO: 60, and b) a G100C mutation in the $V_L$ or $V_{L-2}$ according to the numbering of SEQ ID NO: 61. In some embodiments, the second antibody moiety is fused to N-terminus of two heavy chains of the full-length antibody. In some embodiments, the second antibody moiety is fused to C-terminus of two heavy chains of the full-length antibody. In some embodiments, the second antibody moiety is fused to N-terminus of two light chains of the full-length antibody. In some embodiments, the second antibody moiety is fused to C-terminus of two light chains of the full-length antibody. In some embodiments, the second antibody moiety is a full-length antibody comprising two heavy chains and two light chains, and the first antibody moiety is a scFv comprising the $V_{H-1}$ and the $V_{L-1}$. In some embodiments, the $V_{H-1}$ is fused to the N-terminus of the $V_{L-1}$. In some embodiments, the $V_{H-1}$ is fused to the C-terminus of the $V_{L-1}$ optionally with a single alanine amino acid appended to the C-terminus of $V_{H-1}$. In some embodiments, the $V_{H-1}$ and the $V_{L-1}$ are fused via a linker (e.g., a GS linker, e.g., $(GGGGS)_4$ (SEQ ID NO: 77)). In some embodiments, the $V_{H-1}$ and the $V_{L-1}$ are fused without a linker. In some embodiments, the scFv is a dsscFv optionally comprising a) a G44C mutation in the $V_H$ or $V_{H-2}$ according to the numbering of SEQ ID NO: 60, and b) a G100C mutation in the $V_L$ or $V_{L-2}$ according to the numbering of SEQ ID NO: 61. In some embodiments, the first antibody moiety is fused to N-terminus of one or two heavy chains of the full-length antibody. In some embodiments, the first antibody moiety is fused to C-terminus of one or two heavy chains of the full-length antibody. In some embodiments, the first antibody moiety is fused to N-terminus of one or two light chains of the full-length antibody. In some embodiments, the first antibody moiety is fused to C-terminus of one or two light chains of the full-length antibody. In some embodiments, the first antibody moiety and the second antibody moiety are fused via a linker (e.g., a GS linker, e.g., $(GGGGS)_3$ (SEQ ID NO: 76)). In some embodiments, the first antibody moiety and the second antibody moiety are fused without a linker.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 91, wherein the two light chains each comprises an amino acid sequence of SEQ ID NO: 93.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 92, wherein the two light chains each comprises an amino acid sequence of SEQ ID NO: 93.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 94, wherein the two light chains each comprises an amino acid sequence of SEQ ID NO: 96.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 95, wherein the two light chains each comprises an amino acid sequence of SEQ ID NO: 96.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 97, wherein the two light chains each comprises an amino acid sequence of SEQ ID NO: 99.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 98, wherein the two light chains each comprises an amino acid sequence of SEQ ID NO: 99.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 100, wherein the two light chains each comprises an amino acid sequence of SEQ ID NO: 102.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 101, wherein the two light chains each comprises an amino acid sequence of SEQ ID NO: 102.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 103, wherein the two light chains each comprises an amino acid sequence of SEQ ID NO: 104.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 103, wherein the two light chains each comprises an amino acid sequence of SEQ ID NO: 105.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 106, wherein the two light chains each comprises an amino acid sequence of SEQ ID NO: 107.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 106, wherein the two light chains each comprises an amino acid sequence of SEQ ID NO: 108.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 109, wherein the two light chains each comprises an amino acid sequence of SEQ ID NO: 110.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 109, wherein the two light chains each comprises an amino acid sequence of SEQ ID NO: 111.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 112, wherein the two light chains each comprises an amino acid sequence of SEQ ID NO: 113.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 112, wherein the two light chains each comprises an amino acid sequence of SEQ ID NO: 114.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 117, wherein the two light chains each comprises an amino acid sequence of SEQ ID NO: 119.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 118, wherein the two light chains each comprises an amino acid sequence of SEQ ID NO: 119.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 123, wherein the two light chains each comprises an amino acid sequence of SEQ ID NO: 125.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 124, wherein the two light chains each comprises an amino acid sequence of SEQ ID NO: 125.

In some embodiments, there is provided a multispecific (e.g., bispecific) anti-Sclerostin construct comprising a) a first antibody moiety that specifically recognizes Sclerostin comprising a first heavy chain variable region ($V_{H\text{-}1}$) and a first light chain variable region ($V_{L\text{-}1}$), wherein the $V_{H\text{-}1}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9, and the $V_{L\text{-}1}$ comprises the LC-CDR1 comprising the amino acid sequence of SEQ ID NO: 85, the LC-CDR2 comprising the amino acid sequence of SEQ ID NO: 18, and the LC-CDR3 comprising the amino acid sequence of SEQ ID NO: 20, and b) a second antibody moiety that specifically recognizes DKK1 comprising a second heavy chain variable region ($V_{H\text{-}2}$) and a second light chain variable region ($V_{L\text{-}2}$), wherein the $V_{H\text{-}2}$ comprises the HC-CDR1 comprising the amino acid sequence of SEQ ID NO: 42, the HC-CDR2 comprising the amino acid sequence of SEQ ID NO: 43, and the HC-CDR3 comprising the amino acid sequence of SEQ ID NO: 44, and the $V_{L\text{-}2}$ comprises the LC-CDR1 comprising the amino acid sequence of SEQ ID NO: 45, the LC-CDR2 comprising the amino acid sequence of SEQ ID NO: 46, and the LC-CDR3 comprising the amino acid sequence of SEQ ID NO: 47. In some embodiments, the $V_{H\text{-}1}$ comprises an amino acid sequence of SEQ ID NO: 87 or 168, and the $V_{L\text{-}1}$ comprises an amino acid sequence of SEQ ID NO: 89 or 170. In some embodiments, the $V_{H\text{-}1}$ comprises an amino acid sequence of SEQ ID NO: 87, and the $V_{L\text{-}1}$ comprises an amino acid sequence of SEQ ID NO: 89. In some embodiments, the $V_{H\text{-}1}$ comprises an amino acid sequence of SEQ ID NO: 168, and the $V_{L\text{-}1}$ comprises an amino acid sequence of SEQ ID NO: 170. In some embodiments, the $V_{H\text{-}2}$ comprises an amino acid sequence of SEQ ID NO: 60, 164, or 166, and the $V_{L\text{-}2}$ comprises an amino acid sequence of SEQ ID NO: 61, 165, or 167. In some embodiments, the $V_{H\text{-}2}$ comprises an amino acid sequence of SEQ ID NO: 164, and the $V_{L\text{-}2}$ comprises an amino acid sequence of SEQ ID NO: 165. In some embodiments, the $V_{H\text{-}2}$ comprises an amino acid sequence of SEQ ID NO: 166, and the $V_{L\text{-}2}$ comprises an amino acid sequence of SEQ ID NO: 167. In some embodiments, the $V_{H\text{-}2}$ comprises an amino acid sequence of SEQ ID NO: 61, and the $V_{L\text{-}2}$ comprises an amino acid sequence of SEQ ID NO: 167. In some embodiments, the first antibody moiety is a full-length antibody comprising two heavy chains and two light chains, and the second antibody moiety is a scFv comprising the $V_{H\text{-}2}$ and $V_{L\text{-}2}$. In some embodiments, the $V_{H\text{-}2}$ is fused to the N-terminus of the $V_{L\text{-}2}$. In some embodiments, the $V_{H\text{-}2}$ is fused to the C-terminus of the $V_{L\text{-}2}$ optionally with a single alanine amino acid appended to the C-terminus of $V_{H\text{-}2}$. In some embodiments, the $V_{H\text{-}2}$ and the $V_{L\text{-}2}$ are fused via a linker (e.g., a GS linker, e.g., $(GGGGS)_4$ (SEQ ID NO: 77)). In some embodiments, the $V_{H\text{-}1}$ and the $V_{L\text{-}1}$ are fused without a linker. In some embodiments, the scFv is a dsscFv optionally comprising a) a G44C mutation in the $V_H$ or $V_{H\text{-}2}$ according to the numbering of SEQ ID NO: 60, and b) a G100C mutation in the $V_L$ or $V_{L\text{-}2}$ according to the numbering of SEQ ID NO: 61. In some embodiments, the second antibody moiety is fused to N-terminus of two heavy chains of the full-length antibody. In some embodiments, the second antibody moiety is fused to C-terminus of two heavy chains of the full-length antibody. In some embodiments, the second antibody moiety is fused to N-terminus of two light chains of the full-length antibody. In some embodiments, the second antibody moiety is fused to C-terminus of two light chains of the full-length antibody. In some embodiments, the second antibody moiety is a full-length antibody comprising two heavy chains and two light chains, and the first antibody moiety is a scFv comprising the $V_{H\text{-}1}$ and the $V_{L\text{-}1}$. In some embodiments, the $V_{H\text{-}1}$ is fused to the N-terminus of the $V_{L\text{-}1}$. In some embodiments, the $V_{H\text{-}1}$ is fused to the C-terminus of the $V_{L\text{-}1}$ optionally with a single alanine amino acid appended to the C-terminus of $V_{H\text{-}1}$. In some embodiments, the $V_{H\text{-}1}$ and the $V_{L\text{-}1}$ are fused via a linker (e.g., a GS linker, e.g., $(GGGGS)_4$ (SEQ ID NO: 77)). In some embodiments, the $V_{H\text{-}1}$ and the $V_{L\text{-}1}$ are fused without a linker. In some embodiments, the scFv is converted to a dsscFv with H44-L100 disulfide bond formed by G44C mutation on $V_{H\text{-}1}$ and G100C mutation on $V_{L\text{-}1}$. In some embodiments, the first antibody moiety is fused to N-terminus of one or two heavy chains of the full-length antibody. In some embodiments, the first antibody moiety is fused to C-terminus of one or two heavy chains of the full-length antibody. In some embodiments, the first antibody moiety is fused to N-terminus of one or two light chains of the full-length antibody. In some embodiments, the first antibody moiety is fused to C-terminus of one or two light chains of the full-length antibody. In some embodiments, the first antibody moiety and the second antibody moiety are fused via a linker (e.g., a GS linker, e.g., $(GGGGS)_3$ (SEQ ID NO: 76)). In some embodiments, the first antibody moiety and the second antibody moiety are fused without a linker.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 115, wherein the two light chains each comprises an amino acid sequence of SEQ ID NO: 119.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 116, wherein the two light chains each comprises an amino acid sequence of SEQ ID NO: 119.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 120, wherein the two light chains each comprises an amino acid sequence of SEQ ID NO: 122.

In some embodiments, there is provided a multispecific (e.g., bispecific) construct comprising a first antibody moiety that specifically recognizes Sclerostin and a second antibody moiety that specifically recognizes DKK1, wherein the multispecific construct comprises two heavy chains and two light chains, wherein the two heavy chains each comprises an amino acid sequence of SEQ ID NO: 121, wherein the two light chains each comprises an amino acid sequence of SEQ ID NO: 122.

In some embodiments, there is provided a multispecific (e.g., bispecific) anti-Sclerostin construct comprising a) a first antibody moiety that specifically recognizes Sclerostin comprising a first heavy chain variable region ($V_{H-1}$) and a first light chain variable region ($V_{L-1}$), wherein the $V_{H-1}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9, and the $V_{L-1}$ comprises the LC-CDR1 comprising the amino acid sequence of SEQ ID NO: 85, the LC-CDR2 comprising the amino acid sequence of SEQ ID NO: 18, and the LC-CDR3 comprising the amino acid sequence of SEQ ID NO: 20, and b) a second antibody moiety that specifically recognizes DKK1 comprising a second heavy chain variable region ($V_{H-2}$) and a second light chain variable region ($V_{L-2}$), wherein the $V_{H-2}$ comprises the HC-CDR1 comprising the amino acid sequence of SEQ ID NO: 48, the HC-CDR2 comprising the amino acid sequence of SEQ ID NO: 49, and the HC-CDR3 comprising the amino acid sequence of SEQ ID NO: 50, and the $V_{L-2}$ comprises the LC-CDR1 comprising the amino acid sequence of SEQ ID NO: 51, the LC-CDR2 comprising the amino acid sequence of SEQ ID NO: 52, and the LC-CDR3 comprising the amino acid sequence of SEQ ID NO: 58. In some embodiments, the $V_{H-1}$ comprises an amino acid sequence of SEQ ID NO: 87 or 168, and the $V_{L-1}$ comprises an amino acid sequence of SEQ ID NO: 89 or 170. In some embodiments, the $V_{H-1}$ comprises an amino acid sequence of SEQ ID NO: 87, and the $V_{L-1}$ comprises an amino acid sequence of SEQ ID NO: 89. In some embodiments, the $V_{H-1}$ comprises an amino acid sequence of SEQ ID NO: 168, and the $V_{L-1}$ comprises an amino acid sequence of SEQ ID NO: 170. In some embodiments, the $V_{H-2}$ comprises an amino acid sequence of SEQ ID NO: 62, and the $V_{L-2}$ comprises an amino acid sequence of SEQ ID NO: 63. In some embodiments, the first antibody moiety is a full-length antibody comprising two heavy chains and two light chains, and the second antibody moiety is a scFv comprising the $V_{H-2}$ and $V_{L-2}$. In some embodiments, the $V_{H-2}$ is fused to the N-terminus of the $V_{L-2}$ optionally with a single alanine amino acid appended to the C-terminus of $V_{H-2}$. In some embodiments, the $V_{H-2}$ is fused to the C-terminus of the $V_{L-2}$. In some embodiments, the $V_{H-2}$ and the $V_{L-2}$ are fused via a linker (e.g., a GS linker, e.g., $(GGGGS)_4$ (SEQ ID NO: 77)). In some embodiments, the $V_{H-1}$ and the $V_{L-1}$ are fused without a linker. In some embodiments, the scFv is a dsscFv optionally comprising a) a G44C mutation in the $V_H$ or $V_{H-2}$ according to the numbering of SEQ ID NO: 60, and b) a G100C mutation in the $V_L$ or $V_{L-2}$ according to the numbering of SEQ ID NO: 61. In some embodiments, the second antibody moiety is fused to N-terminus of two heavy chains of the full-length antibody. In some embodiments, the second antibody moiety is fused to C-terminus of two heavy chains of the full-length antibody. In some embodiments, the second antibody moiety is fused to N-terminus of two light chains of the full-length antibody. In some embodiments, the second antibody moiety is fused to C-terminus of two light chains of the full-length antibody. In some embodiments, the second antibody moiety is a full-length antibody comprising two heavy chains and two light chains, and the first antibody moiety is a scFv comprising the $V_{H-1}$ and the $V_{L-1}$. In some embodiments, the $V_{H-1}$ is fused to the N-terminus of the $V_{L-1}$. In some embodiments, the $V_{H-1}$ is fused to the C-terminus of the $V_{L-1}$ optionally with a single alanine amino acid appended to the C-terminus of $V_{H-1}$. In some embodiments, the $V_{H-1}$ and the $V_{L-1}$ are fused via a linker (e.g., a GS linker, e.g., $(GGGGS)_4$ (SEQ ID NO: 77)). In some embodiments, the $V_{H-1}$ and the $V_{L-1}$ are fused without a linker. In some embodiments, the scFv is a dsscFv optionally comprising a) a G44C mutation in the $V_H$ or $V_{H-2}$ according to the numbering of SEQ ID NO: 60, and b) a G100C mutation in the $V_L$ or $V_{L-2}$ according to the numbering of SEQ ID NO: 61. In some embodiments, the first antibody moiety is fused to N-terminus of one or two heavy chains of the full-length antibody. In some embodiments, the first antibody moiety is fused to C-terminus of one or two heavy chains of the full-length antibody. In some embodiments, the first antibody moiety is fused to N-terminus of one or two light chains of the full-length antibody. In some embodiments, the first antibody moiety is fused to C-terminus of one or two light chains of the full-length antibody. In some embodiments, the first antibody moiety and the second antibody moiety are fused via a linker (e.g., a GS linker, e.g., $(GGGGS)_3$ (SEQ ID NO: 76)). In some embodiments, the first antibody moiety and the second antibody moiety are fused without a linker.

In some embodiments, there is provided a multispecific (e.g., bispecific) anti-Sclerostin construct comprising a) a first antibody moiety that specifically recognizes Sclerostin comprising a first heavy chain variable region ($V_{H-1}$) and a first light chain variable region ($V_{L-1}$), wherein the $V_{H-1}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9, and the $V_{L-1}$ comprises the LC-CDR1 comprising the amino acid sequence of SEQ ID NO: 85, the LC-CDR2 comprising the amino acid sequence of SEQ ID NO: 18, and the LC-CDR3 comprising the amino acid sequence of SEQ ID NO: 20, and b) a second antibody moiety that specifically recognizes DKK1 comprising a second heavy chain variable region ($V_{H-2}$) and a second light chain variable region ($V_{L-2}$), wherein the $V_{H-2}$ comprises the HC-CDR1 comprising the amino acid sequence of SEQ ID NO: 54, the HC-CDR2 comprising the amino acid sequence of SEQ ID NO: 55, and the HC-CDR3 comprising the amino acid sequence of SEQ ID NO: 56, and the $V_{L-2}$ comprises the LC-CDR1 comprising the amino acid sequence of SEQ ID NO: 57, the LC-CDR2 comprising the amino acid sequence of SEQ ID NO: 58, and the LC-CDR3 comprising the amino acid sequence of SEQ ID NO: 59. In some embodiments, the $V_{H-1}$ comprises an amino acid sequence of SEQ ID NO: 87 or 168, and the $V_{L-1}$ comprises an amino acid sequence of SEQ ID NO: 89 or 170. In some embodiments, the $V_{H-1}$ comprises an amino acid sequence of SEQ ID NO: 87, and the $V_{L-1}$ comprises an amino acid sequence of SEQ ID NO: 89. In some embodiments, the $V_{H-1}$ comprises an amino acid sequence of SEQ ID NO: 168, and the $V_{L-1}$ comprises an amino acid sequence of SEQ ID NO: 170. In some embodiments, the $V_{H-2}$ comprises an amino acid sequence of SEQ ID NO: 64, and the $V_{L-2}$ comprises an amino acid sequence of SEQ ID NO: 65. In some embodiments, the first antibody moiety is a full-length antibody comprising two heavy chains and two light chains, and the second antibody moiety is a scFv comprising the $V_{H-2}$ and $V_{L-2}$. In some embodiments, the $V_{H-2}$ is fused to the N-terminus of the $V_{L-2}$. In some embodiments, the $V_{H-2}$ is fused to the C-terminus of the $V_{L-2}$ optionally with a single alanine amino acid appended to the C-terminus of $V_{H-2}$. In some embodiments, the $V_{H-2}$ and the $V_{L-2}$ are fused via a linker (e.g., a GS linker, e.g., $(GGGGS)_4$ (SEQ ID NO: 77)). In some embodiments, the $V_{H-1}$ and the $V_{L-1}$ are fused without a linker. In some embodiments, the scFv is a dsscFv optionally comprising a) a G44C mutation in the $V_H$ or $V_{H-2}$ according to the numbering of SEQ ID NO: 60, and b) a G100C mutation in the $V_L$ or $V_{L-2}$ according to the numbering of SEQ ID NO: 61. In some embodiments, the second antibody moiety is fused to N-terminus of two heavy chains of the full-length antibody. In some embodiments, the second antibody moiety is fused to C-terminus of two heavy chains of the full-length antibody. In some embodiments, the second antibody moiety is fused to N-terminus of two light chains of the full-length antibody. In some embodiments, the second antibody moiety is fused to C-terminus of two light chains of the full-length antibody. In some embodiments, the second antibody moiety is a full-length antibody comprising two heavy chains and two light chains, and the first antibody moiety is a scFv comprising the $V_{H-1}$ and the $V_{L-1}$. In some embodiments, the $V_{H-1}$ is fused to the N-terminus of the $V_{L-1}$. In some embodiments, the $V_{H-1}$ is fused to the C-terminus of the $V_{L-1}$ optionally with a single alanine amino acid appended to the C-terminus of $V_{H-2}$. In some embodiments, the $V_{H-1}$ and the $V_{L-1}$ are fused via a linker (e.g., a GS linker, e.g., $(GGGGS)_4$ (SEQ ID NO: 77)). In some embodiments, the $V_{H-1}$ and the $V_{L-1}$ are fused without a linker. In some embodiments, the scFv is a dsscFv optionally comprising a) a G44C mutation in the $V_H$ or $V_{H-2}$ according to the numbering of SEQ ID NO: 60, and b) a G100C mutation in the $V_L$ or $V_{L-2}$ according to the numbering of SEQ ID NO: 61. In some embodiments, the first antibody moiety is fused to N-terminus of one or two heavy chains of the full-length antibody. In some embodiments, the first antibody moiety is fused to C-terminus of one or two heavy chains of the full-length antibody. In some embodiments, the first antibody moiety is fused to N-terminus of one or two light chains of the full-length antibody. In some embodiments, the first antibody moiety is fused to C-terminus of one or two light chains of the full-length antibody. In some embodiments, the first antibody moiety and the second antibody moiety are fused via a linker (e.g., a GS linker, e.g., $(GGGGS)_3$ (SEQ ID NO: 76)). In some embodiments, the first antibody moiety and the second antibody moiety are fused without a linker.

In some embodiments, there is provided a multispecific (e.g., bispecific) anti-Sclerostin construct comprising a) a first antibody moiety that specifically recognizes Sclerostin comprising a first heavy chain variable region ($V_{H-1}$) and a first light chain variable region ($V_{L-1}$), wherein the $V_{H-1}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9, and the $V_{L-1}$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of SEQ ID NO: 20, and b) a second antibody moiety that specifically recognizes DKK1 comprising a second heavy chain variable region ($V_{H-2}$) and a second light chain variable region ($V_{L-2}$), wherein the $V_{H-2}$ comprises the HC-CDR1 comprising the amino acid sequence of SEQ ID NO: 48, the HC-CDR2 comprising the amino acid sequence of SEQ ID NO: 49, and the HC-CDR3 comprising the amino acid sequence of SEQ ID NO: 50, and the $V_{L-2}$ comprises the LC-CDR1 comprising the amino acid sequence of SEQ ID NO: 51, the LC-CDR2 comprising the amino acid sequence of SEQ ID NO: 52, and the LC-CDR3 comprising the amino acid sequence of SEQ ID NO: 58. In some embodiments, the $V_{H-1}$ comprises an amino acid sequence of SEQ ID NO: 22, and the $V_{L-1}$ comprises an amino acid sequence of SEQ ID NO: 23. In some embodiments, the $V_{H-1}$ comprises an amino acid sequence of SEQ ID NO: 87 or 168, and the $V_{L-1}$ comprises an amino acid sequence of SEQ ID NO: 88 or 169. In some embodiments, the $V_{H-1}$ comprises an amino acid sequence of SEQ ID NO: 87, and the $V_{L-1}$ comprises an amino acid sequence of SEQ ID NO: 88. In some embodiments, the $V_{H-1}$ comprises an amino acid sequence of SEQ ID NO: 168, and the $V_{L-1}$ comprises an amino acid sequence of SEQ ID NO: 169. In some embodiments, the $V_{H-2}$ comprises an amino acid sequence of SEQ ID NO: 62, and the $V_{L-2}$ comprises an amino acid sequence of SEQ ID NO: 63. In some embodiments, the first antibody moiety is a full-length antibody comprising two heavy chains and two light chains, and the second antibody moiety is a scFv comprising the $V_{H-2}$ and $V_{L-2}$. In some embodiments, the $V_{H-2}$ is fused to the N-terminus of the $V_{L-2}$. In some embodiments, the $V_{H-2}$ is fused to the C-terminus of the $V_{L-2}$ optionally with a single alanine amino acid appended to the C-terminus of $V_{H-2}$. In some embodiments, the $V_{H-2}$ and the $V_{L-2}$ are fused via a linker (e.g., a GS linker, e.g., $(GGGGS)_4$ (SEQ ID NO: 77)). In some embodiments, the $V_{H-1}$ and the $V_{L-1}$ are fused without a linker. In some embodiments, the scFv is a dsscFv optionally comprising a) a G44C mutation in the $V_H$ or $V_{H-2}$ according to the numbering of SEQ ID NO: 60, and b) a G100C mutation in the $V_L$ or $V_{L-2}$ according to the numbering of SEQ ID NO: 61. In some embodiments, the second antibody moiety is fused to N-terminus of two heavy chains of the full-length antibody. In some embodiments, the second antibody moiety is fused to C-terminus of two heavy chains of the full-length antibody. In some embodiments, the second antibody moiety is fused to N-terminus of two light chains of the full-length antibody. In some embodiments, the second antibody moiety is fused to C-terminus of two light chains of the full-length antibody. In some embodiments, the second antibody moiety is a full-length antibody comprising two heavy chains and two light chains, and the first antibody moiety is a scFv comprising the $V_{H-1}$ and the $V_{L-1}$. In some embodiments, the $V_{H-1}$ is fused to the N-terminus of the $V_{L-1}$. In some embodiments, the $V_{H-1}$ is fused to the C-terminus of the $V_{L-1}$ optionally with a single alanine amino acid appended to the C-terminus of $V_{H-1}$. In some embodiments, the $V_{H-1}$ and the $V_{L-1}$ are fused via a linker (e.g., a GS linker, e.g., $(GGGGS)_4$ (SEQ ID NO: 77)). In some embodiments, the $V_{H-1}$ and the $V_{L-1}$ are fused without a linker. In some embodiments, the scFv is a dsscFv optionally comprising a) a G44C mutation in the $V_H$ or $V_{H-2}$ according to the numbering of SEQ ID NO: 60, and b) a G100C mutation in the $V_L$ or $V_{L-2}$ according to the numbering of SEQ ID NO: 61. In some embodiments, the first antibody moiety is fused to N-terminus of one or two heavy chains of the full-length antibody. In some embodiments, the first antibody moiety is fused to C-terminus of one or two heavy chains of the full-length antibody. In some embodiments, the first antibody moiety is fused to N-terminus of one or two light chains of the full-length antibody. In some embodiments, the first antibody moiety is fused to C-terminus of one or two light chains of the full-length antibody. In some embodiments, the first antibody moiety and the second antibody moiety are fused via a linker (e.g., a GS linker, e.g., $(GGGGS)_3$ (SEQ ID NO: 76)). In some embodiments, the first antibody moiety and the second antibody moiety are fused without a linker.

In some embodiments, there is provided a multispecific (e.g., bispecific) anti-Sclerostin construct comprising a) a first antibody moiety that specifically recognizes Sclerostin comprising a first heavy chain variable region ($V_{H-1}$) and a first light chain variable region ($V_{L-1}$), wherein the $V_{H-1}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9, and the $V_{L-1}$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of SEQ ID NO: 20, and b) a second antibody moiety that specifically recognizes DKK1 comprising a second heavy chain variable region ($V_{H-2}$) and a second light chain variable region ($V_{L-2}$), wherein the $V_{H-2}$ comprises the HC-CDR1 comprising the amino acid sequence of SEQ ID NO: 54, the HC-CDR2 comprising the amino acid sequence of SEQ ID NO: 55, and the HC-CDR3 comprising the amino acid sequence of SEQ ID NO: 56, and the $V_{L-2}$ comprises the LC-CDR1 comprising the amino acid sequence of SEQ ID NO: 57, the LC-CDR2 comprising the amino acid sequence of SEQ ID NO: 58, and the LC-CDR3 comprising the amino acid sequence of SEQ ID NO: 59. In some embodiments, the $V_{H-1}$ comprises an amino acid sequence of SEQ ID NO: 22, and the $V_{L-1}$ comprises an amino acid sequence of SEQ ID NO: 23. In some embodiments, the $V_{H-1}$ comprises an amino acid sequence of SEQ ID NO: 87 or 168, and the $V_{L-1}$ comprises an amino acid sequence of SEQ ID NO: 88 or 169. In some embodiments, the $V_{H-1}$ comprises an amino acid sequence of SEQ ID NO: 87, and the $V_{L-1}$ comprises an amino acid sequence of SEQ ID NO: 88. In some embodiments, the $V_{H-1}$ comprises an amino acid sequence of SEQ ID NO: 168, and the $V_{L-1}$ comprises an amino acid sequence of SEQ ID NO: 169. In some embodiments, the $V_{H-2}$ comprises an amino acid sequence of SEQ ID NO: 64, and the $V_{L-2}$ comprises an amino acid sequence of SEQ ID NO: 65. In some embodiments, the first antibody moiety is a full-length antibody comprising two heavy chains and two light chains, and the second antibody moiety is a scFv comprising the $V_{H-2}$ and $V_{L-2}$. In some embodiments, the $V_{H-2}$ is fused to the N-terminus of the $V_{L-2}$. In some embodiments, the $V_{H-2}$ is fused to the C-terminus of the $V_{L-2}$ optionally with a single alanine amino acid appended to the C-terminus of $V_{H-2}$. In some embodiments, the $V_{H-2}$ and the $V_{L-2}$ are fused via a linker (e.g., a GS linker, e.g., $(GGGGS)_4$ (SEQ ID NO: 77)). In some embodiments, the $V_{H-1}$ and the $V_{L-1}$ are fused without a linker. In some embodiments, the scFv is a dsscFv optionally comprising a) a G44C mutation in the $V_H$ or $V_{H-2}$ according to the numbering of SEQ ID NO: 60, and b) a G100C mutation in the $V_L$ or $V_{L-2}$ according to the numbering of SEQ ID NO: 61. In some embodiments, the second antibody moiety is fused to N-terminus of two heavy chains of the full-length antibody. In some embodiments, the second antibody moiety is fused to C-terminus of two heavy chains of the full-length antibody. In some embodiments, the second antibody moiety is fused to N-terminus of two light chains of the full-length antibody. In some embodiments, the second antibody moiety is fused to C-terminus of two light chains of the full-length antibody. In some embodiments, the second antibody moiety is a full-length antibody comprising two heavy chains and two light chains, and the first antibody moiety is a scFv comprising the $V_{H-1}$ and the $V_{L-1}$. In some embodiments, the $V_{H-1}$ is fused to the N-terminus of the $V_{L-1}$. In some embodiments, the $V_{H-1}$ is fused to the C-terminus of the $V_{L-1}$ optionally with a single alanine amino acid appended to the C-terminus of $V_{H-1}$. In some embodiments, the $V_{H-1}$ and the $V_{L-1}$ are fused via a linker (e.g., a GS linker, e.g., $(GGGGS)_4$ (SEQ ID NO: 77)). In some embodiments, the $V_{H-1}$ and the $V_{L-1}$ are fused without a linker. In some embodiments, the scFv is a dsscFv optionally comprising a) a G44C mutation in the $V_H$ or $V_{H-2}$ according to the numbering of SEQ ID NO: 60, and b) a G100C mutation in the $V_L$ or $V_{L-2}$ according to the numbering of SEQ ID NO: 61. In some embodiments, the first antibody moiety is fused to N-terminus of one or two heavy chains of the full-length antibody. In some embodiments, the first antibody moiety is fused to C-terminus of one or two heavy chains of the full-length antibody. In some embodiments, the first antibody moiety is fused to N-terminus of one or two light chains of the full-length antibody. In some embodiments, the first antibody moiety is fused to C-terminus of one or two light chains of the full-length antibody. In some embodiments, the first antibody moiety and the second antibody moiety are fused via a linker (e.g., a GS linker, e.g., $(GGGGS)_3$ (SEQ ID NO: 76)). In some embodiments, the first antibody moiety and the second antibody moiety are fused without a linker.

In some embodiments, there is provided a multispecific construct specifically recognizing Sclerostin and DKK1, comprising a first antibody moiety and a second antibody, wherein the first antibody moiety comprises a first heavy chain variable region ($V_{H-1}$) and a first light chain variable region ($V_{L-1}$), and wherein the second antibody moiety comprises a second heavy chain variable region ($V_{H-2}$) and a second light chain variable region ($V_{L-2}$), wherein the construct comprises: a) a first polypeptide comprising a first light chain comprising, from N-terminus to C-terminus, i) the $V_{L-1}$, ii) a first light chain constant domain ("first CL domain"); b) a second polypeptide comprising a first heavy chain, from N-terminus to C-terminus, i) the $V_{H-1}$, ii) a first heavy chain constant domain ("first CH1 domain"), and iii) a first Fc domain; c) a third polypeptide comprising a second heavy chain comprising, from N-terminus to C-terminus, i) the $V_{H-2}$, ii) a second heavy chain constant domain ("second CH1 domain"), and iii) a second Fc domain; and d) a fourth polypeptide comprising a second light chain, from N-terminus to C-terminus, i) the $V_{L-2}$, ii) ii) a first light chain constant domain ("the second CL domain"), wherein the first and the second Fc domains form a Fc fragment. In some embodiments, the first antibody moiety specifically recognizes Sclerostin, and the second antibody moiety specifically recognizes DKK1. In some embodiments, the first antibody moiety specifically recognizes DKK1, and the second antibody moiety specifically recognizes Sclerostin.

In some embodiments, one of the first and the second Fc domains comprises a T366W mutation, and optionally a S354C mutation, and wherein the other Fc domain comprises a T366S mutation, a L368A mutation, a Y407V mutation, and optionally a Y349C mutation, wherein numbering is according to the EU index.

In some embodiments, either i) the first CH1 domain and the first CL domain or ii) the second CH1 domain and the second CL domain are selected from the group consisting of: a) a CH1 domain wherein the amino acid at position 141 is substituted for cysteine and the cysteine at position 131 (e.g., in IgG2 or IgG4) or 220 (e.g., in IgG1) is substituted for a non-cysteine amino acid; and a CL domain wherein the amino acid at position 116 is substituted for cysteine and the cysteine at position 214 is substituted for a non-cysteine amino acid; b) a CH1 domain wherein the amino acid at position 168 is substituted for cysteine and the cysteine at position 131 (e.g., in IgG2 or IgG4) or 220 (e.g., in IgG1) is substituted for a non-cysteine amino acid; and a CL domain wherein the amino acid at position 164 is substituted for cysteine and the cysteine at position 214 is substituted for a non-cysteine amino acid; c) a CH1 domain wherein the amino acid at position 126 is 131 or substituted for cysteine and the cysteine at position 220 is substituted for a non-cysteine amino acid; and a CL domain wherein the amino acid at position 121 is substituted for cysteine and the cysteine at position 214 is substituted for a non-cysteine amino acid; d) a CH1 domain wherein the amino acid at position 128 is substituted for cysteine and the cysteine at position 131 (e.g., in IgG2 or IgG4) or 220 (e.g., in IgG1) is substituted for a non-cysteine amino acid; and a CL domain wherein the amino acid at position 118 is substituted for cysteine and the cysteine at position 214 is substituted for a non-cysteine amino acid; e) a CH1 domain wherein the amino acid at position 170 is substituted for cysteine and the cysteine at position 131 (e.g., in IgG2 or IgG4) or 220 (e.g., in IgG1) is substituted for a non-cysteine amino acid; and a CL domain wherein the amino acid at position 176 is substituted for cysteine and the cysteine at position 214 is substituted for a non-cysteine amino acid; f) a CH1 domain wherein the amino acid at position 171 is substituted for cysteine and the cysteine at position 131 (e.g., in IgG2 or IgG4) or 220 (e.g., in IgG1) is substituted for a non-cysteine amino acid; and a CL domain wherein the amino acid at position 162 is substituted for cysteine and the cysteine at position 214 is substituted for a non-cysteine amino acid; g) a CH1 domain wherein the amino acid at position 173 is substituted for cysteine and the cysteine at position 131 (e.g., in IgG2 or IgG4) or 220 (e.g., in IgG1) is substituted for a non-cysteine amino acid; and a CL domain wherein the amino acid at position 160 is substituted for cysteine and the cysteine at position 214 is substituted for a non-cysteine amino acid; wherein numbering is according to the EU index.

In some embodiments, the first heavy chain comprises a modified human IgG4 heavy chain Fc region comprising S228P, T366W, H435R, and Y436F; the second heavy chain comprises a modified human IgG4 heavy chain Fc region comprising F126C, C131S, S228P, T366S, L368A, and Y407V; and the second light chain comprises a modified human Ig kappa light chain constant region comprising S121C and C214S.

In some embodiments, the first heavy chain comprises a modified human IgG4 heavy chain Fc region comprising S228P, T366S, L368A, and Y407V; the second heavy chain comprises a modified human IgG4 heavy chain Fc region comprising F126C, C131S, S228P, T366W, H435R, and Y436F; and the second light chain comprises a modified human Ig kappa light chain constant region comprising S121C and C214S.

In some embodiments, the first heavy chain comprises a modified human IgG4 heavy chain Fc region comprising S228P, T366W, H435R, and Y436F; the second heavy chain comprises a modified human IgG4 heavy chain Fc region comprising L128C, C131S, S228P, T366S, L368A, and Y407V; and the second light chain comprises a modified human Ig kappa light chain constant region comprising F118C and C214S.

In some embodiments, the first heavy chain comprises a modified human IgG4 heavy chain Fc region comprising S228P, T366S, L368A, and Y407V; the second heavy chain comprises a modified human IgG4 heavy chain Fc region comprising L128C, C131S, S228P, T366W, H435R, and Y436F; and the second light chain comprises a modified human Ig kappa light chain constant region comprising F118C and C214S.

In some embodiments, the first heavy chain comprises a modified human IgG4 heavy chain Fc region comprising S228P, T366S, L368A, and Y407V; the second heavy chain comprises a modified human IgG4 heavy chain Fc region comprising F170C, C131S, S228P, T366W, H435R, and Y436F; and the second light chain comprises a modified human Ig kappa light chain constant region comprising S176C and C214S.

In some embodiments, the first heavy chain comprises a modified human IgG4 heavy chain Fc region comprising S228P, T366S, L368A, and Y407V; the second heavy chain comprises a modified human IgG4 heavy chain Fc region comprising V173C, C131S, S228P, T366W, H435R, and Y436F; and the second light chain comprises a modified human Ig kappa light chain constant region comprising Q160C and C214S.

In some embodiments, the first antibody moiety specifically recognizing Sclerostin, and the second antibody moiety specifically recognizing DKK1. In some embodiments, the $V_{H-1}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9, and the $V_{L-1}$ comprises the LC-CDR1 comprising the amino acid sequence of SEQ ID NO: 15 or 85, the LC-CDR2 comprising the amino acid sequence of SEQ ID NO: 18, and the LC-CDR3 comprising the amino acid sequence of SEQ ID NO: 20. In some embodiments, the $V_{H-1}$ comprises an amino acid sequence of SEQ ID NO: 22, and the $V_{L-1}$ comprises an amino acid sequence of SEQ ID NO: 23. In some embodiments, the $V_{H-1}$ comprises an amino acid sequence of SEQ ID NO: 87 or 168, and the $V_{L-1}$ comprises an amino acid sequence of SEQ ID NO: 88 or 169. In some embodiments, the $V_{H-1}$ comprises an amino acid sequence of SEQ ID NO: 87, and the $V_{L-1}$ comprises an amino acid sequence of SEQ ID NO: 88. In some embodiments, the $V_{H-1}$ comprises an amino acid sequence of SEQ ID NO: 168, and the $V_{L-1}$ comprises an amino acid sequence of SEQ ID NO: 169. In some embodiments, the $V_{H-1}$ comprises an amino acid sequence of SEQ ID NO: 87 or 168, and the $V_{L-1}$ comprises an amino acid sequence of SEQ ID NO: 89 or 160. In some embodiments, the $V_{H-1}$ comprises an amino acid sequence of SEQ ID NO: 87, and the $V_{L-1}$ comprises an amino acid sequence of SEQ ID NO: 89. In some embodiments, the $V_{H-1}$ comprises an amino acid sequence of SEQ ID NO: 168, and the $V_{L-1}$ comprises an amino acid sequence of SEQ ID NO: 170. In some embodiments, a) the $V_{H-2}$ comprises the HC-CDR1 comprising the amino acid sequence of SEQ ID NO: 42, the HC-CDR2 comprising the amino acid sequence of SEQ ID NO: 43, and the HC-CDR3 comprising the amino acid sequence of SEQ ID NO: 44, and the $V_{L-2}$ comprises the LC-CDR1 comprising the amino acid sequence of SEQ ID NO: 45, the LC-CDR2 comprising the amino acid sequence of SEQ ID NO: 46, and the LC-CDR3 comprising the amino acid sequence of SEQ ID NO: 47; b) the $V_{H-2}$ comprises the HC-CDR1 comprising the amino acid sequence of SEQ ID NO: 48, the HC-CDR2 comprising the amino acid sequence of SEQ ID NO: 49, and the HC-CDR3 comprising the amino acid sequence of SEQ ID NO: 50, and the $V_{L-2}$ comprises the LC-CDR1 comprising the amino acid sequence of SEQ ID NO: 51, the LC-CDR2 comprising the amino acid sequence of SEQ ID NO: 52, and the LC-CDR3 comprising the amino acid sequence of SEQ ID NO: 58; or c) the $V_{H-2}$ comprises the HC-CDR1 comprising the amino acid sequence of SEQ ID NO: 54, the HC-CDR2 comprising the amino acid sequence of SEQ ID NO: 55, and the HC-CDR3 comprising the amino acid sequence of SEQ ID NO: 56, and the $V_{L-2}$ comprises the LC-CDR1 comprising the amino acid sequence of SEQ ID NO: 57, the LC-CDR2 comprising the amino acid sequence of SEQ ID NO: 58, and the LC-CDR3 comprising the amino acid sequence of SEQ ID NO: 59.

In some embodiments, the first antibody moiety specifically recognizing DKK1, and the second antibody moiety specifically recognizing Sclerostin. In some embodiments, the $V_{H-2}$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9, and the $V_{L-2}$ comprises the LC-CDR1 comprising the amino acid sequence of SEQ ID NO: 15 or 85, the LC-CDR2 comprising the amino acid sequence of SEQ ID NO: 18, and the LC-CDR3 comprising the amino acid sequence of SEQ ID NO: 20. In some embodiments, the $V_{H-2}$ comprises an amino acid sequence of SEQ ID NO: 22, and the $V_{L-2}$ comprises an amino acid sequence of SEQ ID NO: 23. In some embodiments, the $V_{H-2}$ comprises an amino acid sequence of SEQ ID NO: 87 or 168, and the $V_{L-2}$ comprises an amino acid sequence of SEQ ID NO: 88 or 169. In some embodiments, the $V_{H-2}$ comprises an amino acid sequence of SEQ ID NO: 87, and the $V_{L-2}$ comprises an amino acid sequence of SEQ ID NO: 88. In some embodiments, the $V_{H-2}$ comprises an amino acid sequence of SEQ ID NO: 168, and the $V_{L-2}$ comprises an amino acid sequence of SEQ ID NO: 169. In some embodiments, the $V_{H-2}$ comprises an amino acid sequence of SEQ ID NO: 87 or 169, and the $V_{L-2}$ comprises an amino acid sequence of SEQ ID NO: 89 or 170. In some embodiments, the $V_{H-2}$ comprises an amino acid sequence of SEQ ID NO: 87, and the $V_{L-2}$ comprises an amino acid sequence of SEQ ID NO: 89. In some embodiments, the $V_{H-2}$ comprises an amino acid sequence of SEQ ID NO: 168, and the $V_{L-2}$ comprises an amino acid sequence of SEQ ID NO: 170. In some embodiments, a) the $V_{H-1}$ comprises the HC-CDR1 comprising the amino acid sequence of SEQ ID NO: 42, the HC-CDR2 comprising the amino acid sequence of SEQ ID NO: 43, and the HC-CDR3 comprising the amino acid sequence of SEQ ID NO: 44, and the $V_{L-1}$ comprises the LC-CDR1 comprising the amino acid sequence of SEQ ID NO: 45, the LC-CDR2 comprising the amino acid sequence of SEQ ID NO: 46, and the LC-CDR3 comprising the amino acid sequence of SEQ ID NO: 47; b) the $V_{H-1}$ comprises the HC-CDR1 comprising the amino acid sequence of SEQ ID NO: 48, the HC-CDR2 comprising the amino acid sequence of SEQ ID NO: 49, and the HC-CDR3 comprising the amino acid sequence of SEQ ID NO: 50, and the $V_{L-1}$ comprises the LC-CDR1 comprising the amino acid sequence of SEQ ID NO: 51, the LC-CDR2 comprising the amino acid sequence of SEQ ID NO: 52, and the LC-CDR3 comprising the amino acid sequence of SEQ ID NO: 58; or c) the $V_{H-1}$ comprises the HC-CDR1 comprising the amino acid sequence of SEQ ID NO: 54, the HC-CDR2 comprising the amino acid sequence of SEQ ID NO: 55, and the HC-CDR3 comprising the amino acid sequence of SEQ ID NO: 56, and the $V_{L-1}$ comprises the LC-CDR1 comprising the amino acid sequence of SEQ ID NO: 57, the LC-CDR2 comprising the amino acid sequence of SEQ ID NO: 58, and the LC-CDR3 comprising the amino acid sequence of SEQ ID NO: 59.

In some embodiments, there is provided a multispecific construct comprising a first antibody moiety that specifically recognizes Sclerostin and a second antibody moiety that specifically recognizes DKK1, wherein the first antibody moiety is an anti-Sclerostin full-length antibody comprising two heavy chains and two light chains, wherein the two heavy chains each comprises a first heavy chain variable region ($V_{H-1}$), wherein the two light chains each comprises a first light chain variable region ($V_{L-1}$), and wherein the second antibody moiety comprises an anti-DKK1 single chain Fv fragment (scFv) comprising a second heavy chain variable region ($V_{H-2}$) and a second light chain variable region ($V_{L-2}$), wherein the second antibody moiety is fused to C-terminus of both heavy chains of the anti-Sclerostin full-length antibody. In some embodiments, the $V_{H-1}$ comprises an amino acid sequence of SEQ ID NO: 22, or a variant comprising an amino acid sequence having at least about 80% (such as at least about any one of 80%, 85%, 90%, 95%, 96%, 97%, 98%, or 99%) sequence identity; and the $V_{L-1}$ comprises an amino acid sequence of SEQ ID NO: 23, or a variant comprising an amino acid sequence having at least about 80% (such as at least about any one of 80%, 85%, 90%, 95%, 96%, 97%, 98%, or 99%) sequence identity. In some embodiments, the $V_{H-2}$ comprises the HC-CDR1 comprising the amino acid sequence of SEQ ID NO: 42, the HC-CDR2 comprising the amino acid sequence of SEQ ID NO: 43, and the HC-CDR3 comprising the amino acid sequence of SEQ ID NO: 44, and the $V_{L-2}$ comprises the LC-CDR1 comprising the amino acid sequence of SEQ ID NO: 45, the LC-CDR2 comprising the amino acid sequence of SEQ ID NO: 46, and the LC-CDR3 comprising the amino acid sequence of SEQ ID NO: 47. In some embodiments, the $V_{H-2}$ comprises an amino acid sequence of SEQ ID NO: 60, or a variant comprising an amino acid sequence having at least about 80% (such as at least about any one of 80%, 85%, 90%, 95%, 96%, 97%, 98%, or 99%) sequence identity; and the $V_{L-1}$ comprises an amino acid sequence of SEQ ID NO: 61, or a variant comprising an amino acid sequence having at least about 80% (such as at least about any one of 80%, 85%, 90%, 95%, 96%, 97%, 98%, or 99%) sequence identity.

In some embodiments, there is provided a multispecific construct specifically recognizing Sclerostin and DKK1, comprising a first antibody moiety and a second antibody, wherein the first antibody moiety comprises a first heavy chain variable region ($V_{H-1}$) and a first light chain variable region ($V_{L-1}$), and wherein the second antibody moiety comprises a second heavy chain variable region ($V_{H-2}$) and a second light chain variable region ($V_{L-2}$), wherein the construct comprises: a) a first polypeptide comprising a first light chain comprising, from N-terminus to C-terminus, i) the $V_{L-1}$, ii) a first light chain constant domain ("first CL domain"); b) a second polypeptide comprising a first heavy chain, from N-terminus to C-terminus, i) the $V_{H-1}$, ii) a first heavy chain constant domain ("first CH1 domain"), and iii) a first Fc domain; c) a third polypeptide comprising a second heavy chain comprising, from N-terminus to C-terminus, i) the $V_{H-2}$, ii) a second heavy chain constant domain ("second CH1 domain"), and iii) a second Fc domain; and d) a fourth polypeptide comprising a second light chain, from N-terminus to C-terminus, i) the $V_{L-2}$, ii) ii) a first light chain constant domain ("the second CL domain"), wherein the first and the second Fc domains form a Fc fragment, wherein the first antibody moiety specifically recognizes Sclerostin, and wherein the second antibody moiety specifically recognizes DKK1. In some embodiments, the $V_{H-1}$ comprises an amino acid sequence of SEQ ID NO: 22, or a variant comprising an amino acid sequence having at least about 80% (such as at least about any one of 80%, 85%, 90%, 95%, 96%, 97%, 98%, or 99%) sequence identity; and the $V_{L-1}$ comprises an amino acid sequence of SEQ ID NO: 23, or a variant comprising an amino acid sequence having at least about 80% (such as at least about any one of 80%, 85%, 90%, 95%, 96%, 97%, 98%, or 99%) sequence identity. In some embodiments, the $V_{H-2}$ comprises the HC-CDR1 comprising the amino acid sequence of SEQ ID NO: 42, the HC-CDR2 comprising the amino acid sequence of SEQ ID NO: 43, and the HC-CDR3 comprising the amino acid sequence of SEQ ID NO: 44, and the $V_{L-2}$ comprises the LC-CDR1 comprising the amino acid sequence of SEQ ID NO: 45, the LC-CDR2 comprising the amino acid sequence of SEQ ID NO: 46, and the LC-CDR3 comprising the amino acid sequence of SEQ ID NO: 47. In some embodiments, the $V_{H-2}$ comprises an amino acid sequence of SEQ ID NO: 60, or a variant comprising an amino acid sequence having at least about 80% (such as at least about any one of 80%, 85%, 90%, 95%, 96%, 97%, 98%, or 99%) sequence identity; and the $V_{L-1}$ comprises an amino acid sequence of SEQ ID NO: 61, or a variant comprising an amino acid sequence having at least about 80% (such as at least about any one of 80%, 85%, 90%, 95%, 96%, 97%, 98%, or 99%) sequence identity.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 134; b) a first light chain comprising a first light chain variable region ($V_{L-1}$) and a first light chain constant region, wherein the first light chain comprises an amino acid sequence of SEQ ID NO: 135; c) a second heavy chain comprising a second variable heavy chain variable region ($V_{H-2}$) and a second heavy chain constant region, wherein the second heavy chain comprises the amino acid sequence of SEQ ID NO: 136; and d) a second light chain comprising a second light chain variable region ($V_{L-2}$) and a second light chain constant region, wherein the second light chain comprises the amino acid sequence of SEQ ID NO: 137, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing DKK1.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 134; b) a first light chain comprising a first light chain variable region ($V_{L-1}$) and a first light chain constant region, wherein the first light chain comprises an amino acid sequence of SEQ ID NO: 135; c) a second heavy chain comprising a second variable heavy chain variable region ($V_{H-2}$) and a second heavy chain constant region, wherein the second heavy chain comprises the amino acid sequence of SEQ ID NO: 138; and d) a second light chain comprising a second light chain variable region ($V_{L-2}$) and a second light chain constant region, wherein the second light chain comprises the amino acid sequence of SEQ ID NO: 139, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing DKK1.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 134; b) a first light chain comprising a first light chain variable region ($V_{L-1}$) and a first light chain constant region, wherein the first light chain comprises an amino acid sequence of SEQ ID NO: 135; c) a second heavy chain comprising a second variable heavy chain variable region ($V_{H-2}$) and a second heavy chain constant region, wherein the second heavy chain comprises the amino acid sequence of SEQ ID NO: 140; and d) a second light chain comprising a second light chain variable region ($V_{L-2}$) and a second light chain constant region, wherein the second light chain comprises the amino acid sequence of SEQ ID NO: 141, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing DKK1.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 134; b) a first light chain comprising a first light chain variable region ($V_{L-1}$) and a first light chain constant region, wherein the first light chain comprises an amino acid sequence of SEQ ID NO: 135; c) a second heavy chain comprising a second variable heavy chain variable region ($V_{H-2}$) and a second heavy chain constant region, wherein the second heavy chain comprises the amino acid sequence of SEQ ID NO: 142; and d) a second light chain comprising a second light chain variable region ($V_{L-2}$) and a second light chain constant region, wherein the second light chain comprises the amino acid sequence of SEQ ID NO: 143, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing DKK1.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 134; b) a first light chain comprising a first light chain variable region ($V_{L-1}$) and a first light chain constant region, wherein the first light chain comprises an amino acid sequence of SEQ ID NO: 135; c) a second heavy chain comprising a second variable heavy chain variable region ($V_{H-2}$) and a second heavy chain constant region, wherein the second heavy chain comprises the amino acid sequence of SEQ ID NO: 144; and d) a second light chain comprising a second light chain variable region ($V_{L-2}$) and a second light chain constant region, wherein the second light chain comprises the amino acid sequence of SEQ ID NO: 145, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing DKK1.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 146; b) a first light chain comprising a first light chain variable region ($V_{L-1}$) and a first light chain constant region, wherein the first light chain comprises an amino acid sequence of SEQ ID NO: 147; c) a second heavy chain comprising a second variable heavy chain variable region ($V_{H-2}$) and a second heavy chain constant region, wherein the second heavy chain comprises the amino acid sequence of SEQ ID NO: 148; and d) a second light chain comprising a second light chain variable region ($V_{L-2}$) and a second light chain constant region, wherein the second light chain comprises the amino acid sequence of SEQ ID NO: 149, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing DKK1.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 146; b) a first light chain comprising a first light chain variable region ($V_{L-1}$) and a first light chain constant region, wherein the first light chain comprises an amino acid sequence of SEQ ID NO: 147; c) a second heavy chain comprising a second variable heavy chain variable region ($V_{H-2}$) and a second heavy chain constant region, wherein the second heavy chain comprises the amino acid sequence of SEQ ID NO: 150; and d) a second light chain comprising a second light chain variable region ($V_{L-2}$) and a second light chain constant region, wherein the second light chain comprises the amino acid sequence of SEQ ID NO: 151, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing DKK1.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 146; b) a first light chain comprising a first light chain variable region ($V_{L-1}$) and a first light chain constant region, wherein the first light chain comprises an amino acid sequence of SEQ ID NO: 147; c) a second heavy chain comprising a second variable heavy chain variable region ($V_{H-2}$) and a second heavy chain constant region, wherein the second heavy chain comprises the amino acid sequence of SEQ ID NO: 152; and d) a second light chain comprising a second light chain variable region ($V_{L-2}$) and a second light chain constant region, wherein the second light chain comprises the amino acid sequence of SEQ ID NO: 153, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing DKK1.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 146; b) a first light chain comprising a first light chain variable region ($V_{L-1}$) and a first light chain constant region, wherein the first light chain comprises an amino acid sequence of SEQ ID NO: 147; c) a second heavy chain comprising a second variable heavy chain variable region ($V_{H-2}$) and a second heavy chain constant region, wherein the second heavy chain comprises the amino acid sequence of SEQ ID NO: 154; and d) a second light chain comprising a second light chain variable region ($V_{L-2}$) and a second light chain constant region, wherein the second light chain comprises the amino acid sequence of SEQ ID NO: 155, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing DKK1.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 146; b) a first light chain comprising a first light chain variable region ($V_{L-1}$) and a first light chain constant region, wherein the first light chain comprises an amino acid sequence of SEQ ID NO: 147; c) a second heavy chain comprising a second variable heavy chain variable region ($V_{H-2}$) and a second heavy chain constant region, wherein the second heavy chain comprises the amino acid sequence of SEQ ID NO: 156; and d) a second light chain comprising a second light chain variable region ($V_{L-2}$) and a second light chain constant region, wherein the second light chain comprises the amino acid sequence of SEQ ID NO: 157, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing RANKL.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 146; b) a first light chain comprising a first light chain variable region ($V_{L-1}$) and a first light chain constant region, wherein the first light chain comprises an amino acid sequence of SEQ ID NO: 147; c) a second heavy chain comprising a second variable heavy chain variable region ($V_{H-2}$) and a second heavy chain constant region, wherein the second heavy chain comprises the amino acid sequence of SEQ ID NO: 158; and d) a second light chain comprising a second light chain variable region ($V_{L-2}$) and a second light chain constant region, wherein the second light chain comprises the amino acid sequence of SEQ ID NO: 159, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing RANKL.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 146; b) a first light chain comprising a first light chain variable region ($V_{L-1}$) and a first light chain constant region, wherein the first light chain comprises an amino acid sequence of SEQ ID NO: 147; c) a second heavy chain comprising a second variable heavy chain variable region ($V_{H-2}$) and a second heavy chain constant region, wherein the second heavy chain comprises the amino acid sequence of SEQ ID NO: 160; and d) a second light chain comprising a second light chain variable region ($V_{L-2}$) and a second light chain constant region, wherein the second light chain comprises the amino acid sequence of SEQ ID NO: 161, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing RANKL.

In some embodiments, there is provided a multispecific (e.g., bispecific) construct, comprising a) a first heavy chain comprising a first variable heavy chain variable region ($V_{H-1}$) and a first heavy chain constant region, wherein the first heavy chain comprises an amino acid sequence of SEQ ID NO: 146; b) a first light chain comprising a first light chain variable region ($V_{L-1}$) and a first light chain constant region, wherein the first light chain comprises an amino acid sequence of SEQ ID NO: 147; c) a second heavy chain comprising a second variable heavy chain variable region ($V_{H-2}$) and a second heavy chain constant region, wherein the second heavy chain comprises the amino acid sequence of SEQ ID NO: 162; and d) a second light chain comprising a second light chain variable region ($V_{L-2}$) and a second light chain constant region, wherein the second light chain comprises the amino acid sequence of SEQ ID NO: 163, wherein the $V_{H-1}$ and the $V_{L-1}$ comprises a first antibody moiety specifically recognizing Sclerostin, wherein the $V_{H-2}$ and the $V_{L-2}$ comprises a second antibody moiety specifically recognizing RANKL.

Anti-Sclerostin Fusion Proteins or Antibody-Drug Conjugate

The anti-Sclerostin constructs in some embodiments is a fusion protein or an antibody-drug conjugate that comprises an anti-Sclerostin antibody moiety (e.g., an anti-Sclerostin scFv) and a second moiety.

In some embodiments, the second moiety comprises a half-life extending moiety. In some embodiments, the half-life extending moiety is an albumin binding moiety (e.g., an albumin binding antibody moiety).

In some embodiments, the second moiety comprises an agent selected from the group consisting of a parathyroid hormone (PTH), a selective estrogen receptor modulator (SERM), a bisphosphonate, a prostaglandin E (PGE) receptor agonist, VEGF, TGFβ, growth factor (myostatin) and calcitonin.

In some embodiments, the anti-Sclerostin antibody moiety and the second moiety are fused via a linker (such as any of the linkers described in the "Linkers" section). In some embodiments, the anti-Sclerostin antibody moiety and the second moiety are fused without a linker.

Linkers

In some embodiments, the anti-Sclerostin constructs described herein comprise one or more linkers between two moieties (e.g., the anti-Sclerostin antibody moiety and the half-life extending moiety, the anti-Sclerostin antibody moiety and the second binding moiety in the multispecific constructs described above). The length, the degree of flexibility and/or other properties of the linker(s) used in the anti-Sclerostin constructs may have some influence on properties, including but not limited to the affinity, specificity or avidity for one or more particular antigens or epitopes. For example, longer linkers may be selected to ensure that two adjacent domains do not sterically interfere with one another. In some embodiment, a linker (such as peptide linker) comprises flexible residues (such as glycine and serine) so that the adjacent domains are free to move relative to each other. For example, a glycine-serine doublet can be a suitable peptide linker. In some embodiments, the linker is a non-peptide linker. In some embodiments, the linker is a peptide linker. In some embodiments, the linker is a non-cleavable linker. In some embodiments, the linker is a cleavable linker.

Other linker considerations include the effect on physical or pharmacokinetic properties of the resulting compound, such as solubility, lipophilicity, hydrophilicity, hydrophobicity, stability (more or less stable as well as planned degradation), rigidity, flexibility, immunogenicity, modulation of antibody binding, the ability to be incorporated into a micelle or liposome, and the like.

Peptide Linkers

The peptide linker may have a naturally occurring sequence, or a non-naturally occurring sequence. For example, a sequence derived from the hinge region of heavy chain only antibodies may be used as the linker. See, for example, WO1996/34103.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acid to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

An essential technical feature of such peptide linker is that said peptide linker does not comprise any polymerization activity. The characteristics of a peptide linker, which comprise the absence of the promotion of secondary structures, are known in the art and described, e.g., in Dall'Acqua et al. (Biochem. (1998) 37, 9266-9273), Cheadle et al. (Mol Immunol (1992) 29, 21-30) and Raag and Whitlow (FASEB (1995) 9(1), 73-80). A particularly preferred amino acid in context of the "peptide linker" is Gly. Furthermore, peptide linkers that also do not promote any secondary structures are preferred. The linkage of the domains to each other can be provided by, e.g., genetic engineering. Methods for preparing fused and operatively linked bispecific single chain constructs and expressing them in mammalian cells or bacteria are well-known in the art (e.g. WO 99/54440, Ausubel, Current Protocols in Molecular Biology, Green Publishing Associates and Wiley Interscience, N. Y. 1989 and 1994 or Sambrook et al., Molecular Cloning: A Laboratory Manual, Cold Spring Harbor Laboratory Press, Cold Spring Harbor, N. Y., 2001).

The peptide linker can be a stable linker, which is not cleavable by proteases, especially by Matrix metalloproteinases (MMPs).

The linker can also be a flexible linker. Exemplary flexible linkers include glycine polymers $(G)_n$ (SEQ ID NO: 78), glycine-serine polymers (including, for example, $(GS)_n$ (SEQ ID NO: 79), $(GSGGS)_n$ (SEQ ID NO: 80), $(GGGGS)_n$ (SEQ ID NO: 81), and $(GGGS)_n$ (SEQ ID NO: 82), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (See Scheraga, Rev. Computational Chem. 11 173-142 (1992)). The ordinarily skilled artisan will recognize that design of an antibody fusion protein can include linkers that are all or partially flexible, such that the linker can include a flexible linker portion as well as one or more portions that confer less flexible structure to provide a desired antibody fusion protein structure.

Furthermore, exemplary linkers also include the amino acid sequence of such as $(GGGGS)_n$ (SEQ ID NO: 81), wherein n is an integer between 1 and 8, e.g. $(GGGGS)_3$ (SEQ ID NO: 76), $(GGGGS)_4$ (SEQ ID NO: 77), or $(GGGGS)_6$ (SEQ ID NO: 83). In some embodiments, the peptide linker comprises the amino acid sequence of $(GSTSGSGKPGSGEGS)_n$ (SEQ ID NO: 84), wherein n is an integer between 1 and 3.

Non-Peptide Linkers

Coupling of two moieties may be accomplished by any chemical reaction that will bind the two molecules so long as both components retain their respective activities, e.g., binding to Sclerostin and a second agent in an anti-Sclerostin multispecific antibody, respectively. This linkage can include many chemical mechanisms, for instance covalent binding, affinity binding, intercalation, coordinate binding and complexation. In some embodiments, the binding is covalent binding. Covalent binding can be achieved either by direct condensation of existing side chains or by the incorporation of external bridging molecules. Many bivalent or polyvalent linking agents may be useful in coupling protein molecules in this context. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents (See Killen and Lindstrom, Jour. Immun. 133:1335-2549 (1984); Jansen et al., Immunological Reviews 62:185-216 (1982); and Vitetta et al., Science 238:1098 (1987)).

Linkers that can be applied in the present application are described in the literature (see, for example, Ramakrishnan, S. et al., Cancer Res. 44:201-208 (1984) describing use of MBS (M-maleimidobenzoyl-N-hydroxysuccinimide ester). In some embodiments, non-peptide linkers used herein include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus may lead to bispecific antibodies with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form antibody fusion protein with increased stability. Disulfide linkages, are in general, less stable than other linkages because the disulfide linkage is cleaved in vitro, resulting in less antibody fusion protein available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

III. Methods of Preparation

In some embodiments, there is provided a method of preparing an anti-Sclerostin construct or antibody moiety that specifically binds to Sclerostin and a composition such as polynucleotide, nucleic acid construct, vector, host cell, or culture medium that is produced during the preparation of the anti-Sclerostin construct or antibody moiety. The anti-Sclerostin construct or antibody moiety or composition described herein may be prepared by a number of processes as generally described below and more specifically in the Examples.

Antibody Expression and Production

The antibodies (including anti-Sclerostin monoclonal antibodies, anti-Sclerostin bispecific antibodies, and anti-Sclerostin antibody moieties) described herein can be prepared using any known methods in the art, including those described below and in the Examples.

Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies. For example, the monoclonal antibodies may be made using the hybridoma method first described by Kohler et al., *Nature,* 256:495 (1975), or may be made by recombinant DNA methods (U.S. Pat. No. 4,816,567). In the hybridoma method, a mouse or other appropriate host animal, such as a hamster or a llama, is immunized as hereinabove described to elicit lymphocytes that produce or are capable of producing antibodies that will specifically bind the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986). Also See Example 1 for immunization in Camels.

The immunizing agent will typically include the antigenic protein or a fusion variant thereof. An immunizing agent may be comprised of purified full-length or truncated Sclerostin polypeptides, or variants or fragments (i.e., peptides)

thereof. Such peptides may be generated by proteolytic cleavage of a larger polypeptide, by recombinant molecular methodologies, or may be chemically synthesized by methods as described herein and known in the art. Based on crystallographic structure of human Sclerostin in complex with LRP6 (Kim, J. 2020, *Nat Commun* 11:5357-5357), the loop tip containing the 'IGRGKWWR' motif (SEQ ID NO: 186) was found to be the main binding determinant for binding of Sclerostin to the first propeller of LRP6. Peptides useful as immunizing agent typically may have an amino acid sequence of at least 7 consecutive amino acids from a Sclerostin amino acid sequence covering the 'IGRGKWWR' motif (SEQ ID NO: 186) on the second loop such as those described herein, and preferably have at least 8, 9, 10, 11, 12, 14, 15, 16, 18, 19, 20, 21, 22, 23, or 24 consecutive amino acids comprising the 'IGRGKWWR' motif (SEQ ID NO: 186). Certain other preferred peptide agents comprise at least 8 but no more than 12 or more consecutive amino acids of the Sclerostin sequence covering the 'IGRGKWWR' motif (SEQ ID NO: 186), and other preferred peptide agent comprises 24 consecutive amino acids of the second loop of Sclerostin polypeptide. Other preferred peptide agents comprise any whole integer number of amino acids between and including 8 and 24 consecutive amino acids covering 'IGRGKWWR' motif (SEQ ID NO: 186) in the second loop thereof, or polypeptide comprising full-length Sclerostin sequence. Within one embodiment the immunizing agent is full-length human Sclerostin, or preferably a portion of the second loop thereof, e.g., synthesized peptides within the second loop as described herein covering amino acids 110-133, or more preferably 119-130, or more preferably 116-126, or more preferably 118-125, to generated antibodies that specifically recognize the 'IGRGKWWR' motif (SEQ ID NO: 186) of the second loop on Sclerostin. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., X63-Ag8-653) available from the American Type Culture Collection, Manassas, Va. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen. Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.*, 107:220 (1980). To select the monoclonal antibodies that specifically neutralize Sclerostin's ability to inhibit Wnt activity, the resulting hybridomas can be screened in order to determine the presence of antibodies which are reactive with both full-length human Sclerostin and peptides from the second loop containing the 'IGRGKWWR' motif (SEQ ID NO: 186) using ELISA or BLI approach. Hybridomas that produce monoclonal antibodies that specifically bind to both full-length Sclerostin and the peptides containing the 'IGRGKWWR' motif (SEQ ID NO: 186) thereof are preferred as described in Example 3 and 4. And monoclonal antibodies that were able to block, impair, or inhibit the binding of full-length human Sclerostin to a low-density lipoprotein receptor-related protein family member, e.g., LRP5 or LRP6, are selected using HEK293/TCF/LEF/Wnt1 reporter gene assay (Hannoush R N., 2008, *PLoS ONE*, 3: e3498) as described in Example 7.

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose™, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130:151-188 (1992).

In a further embodiment, antibodies can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nucl. Acids Res.,* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide. Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

Nucleic Acid Molecules Encoding Antibody Moieties

In some embodiments, there is provided a polynucleotide encoding any one of the anti-Sclerostin constructs or antibody moieties described herein. In some embodiments, there is provided a polynucleotide prepared using any one of the methods as described herein. In some embodiments, a nucleic acid molecule comprises a polynucleotide that encodes a heavy chain or a light chain of an antibody moiety (e.g., anti-Sclerostin antibody moiety). In some embodiments, a nucleic acid molecule comprises both a polynucleotide that encodes a heavy chain and a polynucleotide that encodes a light chain, of an antibody moiety (e.g., anti-Sclerostin antibody moiety). In some embodiments, a first nucleic acid molecule comprises a first polynucleotide that encodes a heavy chain and a second nucleic acid molecule comprises a second polynucleotide that encodes a light chain.

In some such embodiments, the heavy chain and the light chain are expressed from one nucleic acid molecule, or from two separate nucleic acid molecules, as two separate polypeptides. In some embodiments, such as when an antibody is a scFv, a single polynucleotide encodes a single polypeptide comprising both a heavy chain and a light chain linked together.

In some embodiments, a polynucleotide encoding a heavy chain or light chain of an antibody moiety (e.g., anti-Sclerostin antibody moiety) comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

In some embodiments, the polynucleotide is a DNA. In some embodiments, the polynucleotide is an RNA. In some embodiments, the RNA is an mRNA.

Nucleic acid molecules may be constructed using recombinant DNA techniques conventional in the art. In some embodiments, a nucleic acid molecule is an expression vector that is suitable for expression in a selected host cell.

Nucleic Acid Construct

In some embodiments, there is provided a nucleic acid construct comprising any one of the polynucleotides described herein. In some embodiments, there is provided a nucleic acid construct prepared using any method described herein.

In some embodiments, the nucleic acid construct further comprises a promoter operably linked to the polynucleotide. In some embodiments, the polynucleotide corresponds to a gene, wherein the promoter is a wild-type promoter for the gene.

Vectors

In some embodiments, there is provided a vector comprising any polynucleotides that encode the heavy chains and/or light chains of any one of the antibody moieties described herein (e.g., anti-Sclerostin antibody moieties) or nucleic acid construct described herein. In some embodiments, there is provided a vector prepared using any method described herein. Vectors comprising polynucleotides that encode any of anti-Sclerostin constructs such as antibodies, scFvs, fusion proteins or other forms of constructs described herein (e.g., anti-Sclerostin scFv) are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is a scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NSO cells. Exemplary such vectors are described, e.g., in Running Deer et al., *Biotechnol. Prog.* 20:880-889 (2004).

Host Cells

In some embodiments, there is provided a host cell comprising any polypeptide, nucleic acid construct and/or vector described herein. In some embodiments, there is provided a host cell prepared using any method described herein. In some embodiments, the host cell is capable of producing any of antibody moieties described herein under a fermentation condition.

In some embodiments, the antibody moieties described herein (e.g., anti-Sclerostin antibody moieties) may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, the antibody moieties described herein (e.g., anti-Sclerostin antibody moieties) may be expressed in yeast. See, e.g., U.S. Publication No. US 2006/0270045 A1. In some embodiments, a particular eukaryotic host cell is selected based on its ability to make desired post-translational modifications to the heavy chains and/or light chains of the antibody moiety. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Non-limiting exemplary methods are described, e.g., in Sambrook et al., Molecular Cloning, A Laboratory Manual, $3^{rd}$ ed. Cold Spring Harbor Laboratory Press (2001). Nucleic acids may be transiently or stably transfected in the desired host cells, according to any suitable method.

The present application also provides host cells comprising any of the polynucleotides or vectors described herein. In some embodiments, the invention provides a host cell comprising an anti-Sclerostin antibody. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*).

In some embodiments, the antibody moiety is produced in a cell-free system. Non-limiting exemplary cell-free systems are described, e.g., in Sitaraman et al., *Methods Mol. Biol.* 498:229-44 (2009); Spirin, *Trends Biotechnol.* 22:538-45 (2004); Endo et al., *Biotechnol. Adv.* 21:695-713 (2003).

Culture Medium

In some embodiments, there is provided a culture medium comprising any antibody moiety, polynucleotide, nucleic acid construct, vector, and/or host cell described herein. In some embodiments, there is provided a culture medium prepared using any method described herein.

In some embodiments, the medium comprises hypoxanthine, aminopterin, and/or thymidine (e.g., HAT medium). In some embodiments, the medium does not comprise serum. In some embodiments, the medium comprises serum. In some embodiments, the medium is a D-MEM or RPMI-1640 medium.

Purification of Antibody Moieties

The anti-Sclerostin constructs (e.g., anti-Sclerostin monoclonal antibodies or multispecific antibodies) may be purified by any suitable method. Such methods include, but are not limited to, the use of affinity matrices or hydrophobic interaction chromatography. Suitable affinity ligands include the ROR1 ECD and ligands that bind antibody constant regions. For example, a Protein A, Protein G, Protein A/G, or an antibody affinity column may be used to bind the constant region and to purify an anti-Sclerostin construct comprising an Fc fragment. Hydrophobic interactive chromatography, for example, a butyl or phenyl column, may also suitable for purifying some polypeptides such as antibodies. Ion exchange chromatography (e.g. anion exchange chromatography and/or cation exchange chromatography) may also suitable for purifying some polypeptides such as antibodies. Mixed-mode chromatography (e.g. reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

IV. Methods of Treatments

In some embodiments, there is provided a method of treating a disease or condition in an individual, comprising administering to the individual an effective mount of the anti-Sclerostin construct or pharmaceutical composition described herein. In some embodiments, the disease or condition is a bone-related disorder or cartilage related disorder, a bone marrow or haemotological disorder, a musculoskeletal rare disease, a muscle-related disorder, or a cancer.

The methods described herein are applicable to any bone-related disease or condition. In some embodiments, the bone-related disorder is osteogenesis imperfecta, osteoporosis or osteopenia (in men and/or women), osteonecrosis, delay bone healing, non-union bone fractures, multiple myeloma, multiple myeloma related bone disorders, primary bone tumor, bone metastasis of malignancies, inflammatory or infectious bone disease, osteomalacia, hypercalcemia, Paget's disease, immobilization-induced bone loss, glucocorticoid-induced bone loss, inflammation-induced bone loss including arthritis-induced bone loss, spaceflight osteoporosis/osteopenia and bone loss caused by reduced gravity or other disease or condition associated with a) bone loss of either quantity or quality or both and/or b) abnormality of bone structure and quality. In some embodiments, the bone-related disorder is osteoporosis or osteopenia. In some embodiments, the bone-related disorder is osteogenesis imperfecta. In some embodiments, the bone-related disorder is multiple myeloma and multiple myeloma related bone disorders.

In some embodiments, the disease or condition is a cartilage disorder. In some embodiments, the cartilage disorder is chondromatosis, chondrodysplasia, achondroplasia, epiphyseal dysplasia, chondrodystrophic myotonia, juxtacortical chondroma, tear of cartilage of knee, osteofibrous dysplasia, osteoarthritis, osteogenesis imperfecta, hypophosphatemic rickets or osteochondrodystrophy.

In some embodiments, the disease or condition is a muscle-related disorder. In some embodiments, the muscle-related disorder is sarcopenia and cancer sarcopenia.

In some embodiments, the disease or condition is a cancer (e.g., a hematological malignancy, e.g., multiple myeloma).

In some embodiments, there is provided a method of facilitation of heal after bone or joint surgeries in an individual, comprising administering to the individual an effective mount of the anti-Sclerostin construct (such as any of the anti-Sclerostin constructs described herein).

In some embodiments, there is provided a method of treating a disease or condition (e.g., a bone-related disease) in an individual, comprising administering to the individual an effective mount of an anti-Sclerostin construct comprising an antibody moiety comprising a heavy chain variable region ($V_H$) and a light chain variable region ($V_L$), wherein the $V_H$ comprises i) the HC-CDR1 comprising the amino acid sequence of SEQ ID NO: 1, ii) the HC-CDR2 comprising the amino acid sequence of SEQ ID NO: 5, and iii) the HC-CDR3 comprising the amino acid sequence of SEQ ID NO: 9, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 15 or 85, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs.

In some embodiments, there is provided a method of treating a disease or condition (e.g., a bone-related disease) in an individual, comprising administering to the individual an effective mount of an multispecific construct comprising a first antibody moiety that specifically recognizes Sclerostin and a second antibody moiety specifically recognizes RANKL. In some embodiments, the first antibody moiety comprises a first heavy chain variable region ($V_{H-1}$) and a first light chain variable region ($V_{L-1}$), wherein the $V_{H-1}$ comprises i) the HC-CDR1 comprising the amino acid sequence of SEQ ID NO: 1, ii) the HC-CDR2 comprising the amino acid sequence of SEQ ID NO: 5, and iii) the HC-CDR3 comprising the amino acid sequence of SEQ ID NO: 9, or a variant thereof comprising up to 5, 4, 3, 2, or 1 amino acid substitutions in the HC-CDRs, and the $V_{L-1}$ comprises i) the LC-CDR1 comprising the amino acid sequence of SEQ ID NO: 15 or 85, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs. In some embodiments, the second antibody moiety comprising a second heavy chain variable region ($V_{H-2}$) and a second light chain variable region ($V_{L-2}$), wherein the $V_{H-2}$ comprises the HC-CDR1 comprising the amino acid sequence of SEQ ID NO: 66, the HC-CDR2 comprising the amino acid sequence of SEQ ID NO: 67, and the HC-CDR3 comprising the amino acid sequence of SEQ ID NO: 68, and the $V_{L-2}$ comprises the LC-CDR1 comprising the amino acid sequence of SEQ ID NO: 69, the LC-CDR2 comprising the amino acid sequence of SEQ ID NO: 70, and the LC-CDR3 comprising the amino acid sequence of SEQ ID NO: 71.

In some embodiments, there is provided a method of treating a disease or condition (e.g., a bone-related disease) in an individual, comprising administering to the individual an effective mount of an multispecific construct comprising a first antibody moiety that specifically recognizes Sclerostin and a second antibody moiety specifically recognizes DKK1. In some embodiments, the first antibody moiety comprises a first heavy chain variable region ($V_{H-1}$) and a first light chain variable region ($V_{L-1}$), wherein the $V_{H-1}$ comprises i) the HC-CDR1 comprising the amino acid sequence of SEQ ID NO: 1, ii) the HC-CDR2 comprising the amino acid sequence of SEQ ID NO: 5, and iii) the HC-CDR3 comprising the amino acid sequence of SEQ ID NO: 9, or a variant thereof comprising up to 5, 4, 3, 2, or 1 amino acid substitutions in the HC-CDRs, and the $V_{L-1}$ comprises i) the LC-CDR1 comprising the amino acid sequence of SEQ ID NO: 15 or 85, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs. In some embodiments, the second antibody moiety comprising a second heavy chain variable region ($V_{H-2}$) and a second light chain variable region ($V_{L-2}$), wherein: a) the $V_{H-2}$ comprises the HC-CDR1 comprising the amino acid sequence of SEQ ID NO: 42, the HC-CDR2 comprising the amino acid sequence of SEQ ID NO: 43, and the HC-CDR3 comprising the amino acid sequence of SEQ ID NO: 44, and the $V_{L-2}$ comprises the LC-CDR1 comprising the amino acid sequence of SEQ ID NO: 45, the LC-CDR2 comprising the amino acid sequence of SEQ ID NO: 46, and the LC-CDR3 comprising the amino acid sequence of SEQ ID NO: 47; b) the $V_{H-2}$ comprises the HC-CDR1 comprising the amino acid sequence of SEQ ID NO: 48, the HC-CDR2 comprising the amino acid sequence of SEQ ID NO: 49, and the HC-CDR3 comprising the amino acid sequence of SEQ ID NO: 50, and the $V_{L-2}$ comprises the LC-CDR1 comprising the amino acid sequence of SEQ ID NO: 51, the LC-CDR2 comprising the amino acid sequence of SEQ ID NO: 52, and the LC-CDR3 comprising the amino acid sequence of SEQ ID NO: 58; or c) the $V_{H-2}$ comprises the HC-CDR1 comprising the amino acid sequence of SEQ ID NO: 54, the HC-CDR2 comprising the amino acid sequence of SEQ ID NO: 55, and the HC-CDR3 comprising the amino acid sequence of SEQ ID NO: 56, and the $V_{L-2}$ comprises the LC-CDR1 comprising the amino acid sequence of SEQ ID NO: 57, the LC-CDR2 comprising the amino acid sequence of SEQ ID NO: 58, and the LC-CDR3 comprising the amino acid sequence of SEQ ID NO: 59.

In some embodiments, the subject is a mammal (such as a human).

Dosing and Method of Administering the Anti-Sclerostin Construct

The dosing regimen of the anti-Sclerostin construct (such as the specific dosages and frequencies) used for treating a disease or disorder as described herein administered into the individual may vary with the particular anti-Sclerostin construct (such as anti-Sclerostin monoclonal or multispecific antibodies, such as anti-Sclerostin fusion proteins), the mode of administration, and the type of disease or condition being treated.

In some embodiments of any of the above aspects, the effective amount of an anti-Sclerostin construct (such as anti-Sclerostin monoclonal or multispecific antibodies) is in the range of about 0.001 μg/kg to about 500 mg/kg of total body weight, for example, about 0.005 μg/kg to about 100 mg/kg, about 0.01 μg/kg to about 50 mg/kg, or about 0.01 μg/kg to about 5 mg/kg.

In some embodiments, the treatment comprises more than one administration of the anti-Sclerostin constructs (such as about two, three, four, five, six, seven, eight, night, or ten administrations of anti-Sclerostin constructs). In some embodiments, the anti-Sclerostin construct is administered at a frequency of about daily, weekly, two times per week, once a month, once every three months, once every six months, or once a year.

The anti-Sclerostin construct can be administered to an individual (such as human) via various routes, including, for example, intravenous, intra-articular, intra-arterial, intraperitoneal, intrapulmonary, oral, inhalation, intravesicular, intramuscular, intra-tracheal, subcutaneous, intraocular, intrathecal, transmucosal, and transdermal. In some embodiments, the anti-Sclerostin construct is included in a pharmaceutical composition while administered into the individual. In some embodiments, sustained continuous release formulation of the composition may be used. In some embodiments, the composition is administered intravenously. In some embodiments, the composition is administered intraperitoneally. In some embodiments, the composition is administered intravenously. In some embodiments, the composition is administered intraperitoneally. In some embodiments, the composition is administered intramuscularly. In some embodiments, the composition is administered subcutaneously. In some embodiments, the composition is administered intravenously. In some embodiments, the composition is administered orally.

Combination Therapy

This application also provides methods of administering an anti-Sclerostin construct into an individual for treating a disease or condition (such as a bone-related disease), wherein the method further comprises administering a second agent or therapy. In some embodiments, the second agent or therapy is a standard or commonly used agent or therapy for treating the disease or condition.

In some embodiments, there is provided a method of treating a disease or condition (e.g., a bone-related disease) in an individual, comprising administering to the individual a) an effective mount of an anti-Sclerostin construct (such as any of the anti-Sclerostin constructs described herein); and b) a second therapy or agent. In some embodiments, the second therapy or agent is an anti-DKK1 antibody or an anti-RANKL antibody. In some embodiments, the second agent or therapy comprises an agent selected from the group consisting of a parathyroid hormone (PTH), a selective estrogen receptor modulator (SERM), a bisphosphonate, a prostaglandin E (PGE) receptor agonist, VEGF, and TGFβ, growth factor (myostatin) and calcitonin.

In some embodiments, there is provided a method of treating a disease or condition (e.g., a bone-related disease) in an individual, comprising administering to the individual a) an effective mount of an anti-Sclerostin construct (such as any of the anti-Sclerostin constructs described herein); and b) an anti-DKK1 antibody. In some embodiments, the anti-Sclerostin construct comprises an antibody moiety comprising a heavy chain variable region ($V_H$) and a light chain variable region ($V_L$), wherein the $V_H$ comprises i) the HC-CDR1 comprising the amino acid sequence of SEQ ID NO: 1, ii) the HC-CDR2 comprising the amino acid sequence of SEQ ID NO: 5, and iii) the HC-CDR3 comprising the amino acid sequence of SEQ ID NO: 9, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 15 or 85, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs. In some embodiments, the anti-DKK1 antibody comprises a second heavy chain variable region ($V_{H-2}$) and a second light chain variable region ($V_{L-2}$), wherein the $V_{H-2}$ comprises the HC-CDR1 comprising the amino acid sequence of SEQ ID NO: 66, the HC-CDR2 comprising the amino acid sequence of SEQ ID NO: 67, and the HC-CDR3 comprising the amino acid sequence of SEQ ID NO: 68, and the $V_{L-2}$ comprises the LC-CDR1 comprising the amino acid sequence of SEQ ID NO: 69, the LC-CDR2 comprising the amino acid sequence of SEQ ID NO: 70, and the LC-CDR3 comprising the amino acid sequence of SEQ ID NO: 71.

In some embodiments, there is provided a method of treating a disease or condition (e.g., a bone-related disease) in an individual, comprising administering to the individual a) an effective mount of an anti-Sclerostin construct (such as any of the anti-Sclerostin constructs described herein); and b) an anti-RANKL antibody. In some embodiments, the anti-Sclerostin construct comprises an antibody moiety comprising a heavy chain variable region ($V_H$) and a light chain variable region ($V_L$), wherein the $V_H$ comprises i) the HC-CDR1 comprising the amino acid sequence of SEQ ID NO: 1, ii) the HC-CDR2 comprising the amino acid sequence of SEQ ID NO: 5, and iii) the HC-CDR3 comprising the amino acid sequence of SEQ ID NO: 9, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 15 or 85, ii) the LC-CDR2 comprising the amino acid sequence of SEQ ID NO: 18, and iii) the LC-CDR3 comprising the amino acid sequence of SEQ ID NO: 20, or a variant thereof comprising up to 5, 4, 3, 2, or 1 amino acid substitutions in the LC-CDRs. In some embodiments, the anti-RANKL antibody comprises a second heavy chain variable region ($V_{H-2}$) and a second light chain variable region ($V_{L-2}$), wherein: a) the $V_{H-2}$ comprises the HC-CDR1 comprising the amino acid sequence of SEQ ID NO: 42, the HC-CDR2 comprising the amino acid sequence of SEQ ID NO: 43, and the HC-CDR3 comprising the amino acid sequence of SEQ ID NO: 44, and the $V_{L-2}$ comprises the LC-CDR1 comprising the amino acid sequence of SEQ ID NO: 45, the LC-CDR2 comprising the amino acid sequence of SEQ ID NO: 46, and the LC-CDR3 comprising the amino acid sequence of SEQ ID NO: 47; b) the $V_{H-2}$ comprises the HC-CDR1 comprising the amino acid sequence of SEQ ID NO: 48, the HC-CDR2 comprising the amino acid sequence of SEQ ID NO: 49, and the HC-CDR3 comprising the amino acid sequence of SEQ ID NO: 50, and the $V_{L-2}$ comprises the LC-CDR1 comprising the amino acid sequence of SEQ ID NO: 51, the LC-CDR2 comprising the amino acid sequence of SEQ ID NO: 52, and the LC-CDR3 comprising the amino acid sequence of SEQ ID NO: 58; or c) the $V_{H-2}$ comprises the HC-CDR1 comprising the amino acid sequence of SEQ ID NO: 54, the HC-CDR2 comprising the amino acid sequence of SEQ ID NO: 55, and the HC-CDR3 comprising the amino acid sequence of SEQ ID NO: 56, and the $V_{L-2}$ comprises the LC-CDR1 comprising the amino acid sequence of SEQ ID NO: 57, the LC-CDR2 comprising the amino acid sequence of SEQ ID NO: 58, and the LC-CDR3 comprising the amino acid sequence of SEQ ID NO: 59.

In some embodiments, the anti-Sclerostin construct and the second agent or therapy are administered simultaneously. In some embodiments, the anti-Sclerostin construct and the second agent or therapy are administered concurrently. In some embodiments, the anti-Sclerostin construct and the second agent or therapy are administered sequentially.

V. Compositions, Kits and Articles of Manufacture

Also provided herein are compositions (such as formulations, such as pharmaceutical compositions) comprising any one of the anti-Sclerostin construct or anti-Sclerostin antibody moiety described herein, nucleic acid encoding the antibody moieties, vector comprising the nucleic acid encoding the antibody moieties, or host cells comprising the nucleic acid or vector.

In some embodiments, there is provided a pharmaceutical composition comprising an anti-Sclerostin construct (such as any of the anti-Sclerostin constructs described herein) and a pharmaceutically acceptable carrier. In some embodiments, the composition further comprises an agent selected from the group consisting of a parathyroid hormone (PTH), a selective estrogen receptor modulator (SERM), VEGF, TGFβ, growth factor (myostatin) and calcitonin.

Suitable formulations of the anti-Sclerostin construct described herein can be obtained by mixing the anti-Sclerostin construct or anti-Sclerostin antibody moiety having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be imaged, diagnosed, or treated herein.

The formulations to be used for in vivo administration must be sterile. This is readily accomplished by, e.g., filtration through sterile filtration membranes.

Also provided are kits comprising any one of the anti-Sclerostin construct or anti-Sclerostin antibody moiety described herein. The kits may be useful for any of the methods of modulating cell composition or treatment described herein.

In some embodiments, there is provided a kit comprising an anti-Sclerostin construct specifically binding to Sclerostin.

In some embodiments, the kit further comprises a device capable of delivering the anti-Sclerostin construct into an individual. One type of device, for applications such as parenteral delivery, is a syringe that is used to inject the composition into the body of a subject. Inhalation devices may also be used for certain applications.

In some embodiments, the kit further comprises a therapeutic agent for treating a disease or condition, e.g., a bone-related disease, e.g., osteogenesis imperfecta, osteopetrosis, or a disease or condition associated with bone loss.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information.

The present application thus also provides articles of manufacture. The article of manufacture can comprise a container and a label or package insert on or associated with the container. Suitable containers include vials (such as sealed vials), bottles, jars, flexible packaging, and the like. Generally, the container holds a composition, and may have a sterile access port (for example the container may be an intravenous solution bag or a vial having a stopper pierceable by a hypodermic injection needle). The label or package insert indicates that the composition is used for imaging, diagnosing, or treating a particular condition in an individual. The label or package insert will further comprise instructions for administering the composition to the individual and for imaging the individual. The label may indicate directions for reconstitution and/or use. The container holding the composition may be a multi-use vial, which allows for repeat administrations (e.g. from 2-6 administrations) of the reconstituted formulation. Package insert refers to instructions customarily included in commercial packages of diagnostic products that contain information about the indications, usage, dosage, administration, contraindications and/or warnings concerning the use of such diagnostic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the compositions and instructions for use, packaged in quantities sufficient for storage and use in pharmacies, for example, hospital pharmacies and compounding pharmacies.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXEMPLARY EMBODIMENTS

Embodiment 1. An anti-Sclerostin construct comprising an antibody moiety that specifically recognizes Sclerostin, wherein the antibody moiety binds to an epitope on Sclerostin, wherein the epitope comprises the amino acid sequence set forth in SEQ ID NO: 186.

Embodiment 2. An anti-Sclerostin construct comprising an antibody moiety that specifically recognizes Sclerostin, wherein the antibody moiety comprises a heavy chain variable region ($V_H$) and a light chain variable region ($V_L$), wherein:

the $V_H$ comprises a HC-CDR1 comprising the amino acid sequence of any one of SEQ ID NOs: 1-4 and 12, a HC-CDR2 comprising the amino acid sequence of any one of SEQ ID NOs: 5-8 and 13, and a HC-CDR3 comprising the amino acid sequence of any one of SEQ ID NOs: 9-11 and 14, or a variant thereof comprising up to 5, 4, 3, 2, or 1 amino acid substitutions in the HC-CDRs; and the $V_L$ comprises a LC-CDR1 comprising the amino acid sequence of any one of SEQ ID NOs: 15-17, 85, and 86, a LC-CDR2 comprising the amino acid sequence of any one of SEQ ID NOs: 18 and 19, and a LC-CDR3 comprising the amino acid sequence of any one of SEQ ID NOs: 20 and 21, or a variant thereof comprising up to 5, 4, 3, 2, or 1 amino acid substitutions in the LC-CDRs.

Embodiment 3. The anti-Sclerostin construct of embodiment 1 or embodiment 2, wherein:

a) the $V_H$ comprises the HC-CDR1 comprising the amino acid sequence of SEQ ID NO: 12, the HC-CDR2 comprising the amino acid sequence of SEQ ID NO: 13, and the HC-CDR3 comprising the amino acid sequence of SEQ ID NO: 14; and the $V_L$ comprises the LC-CDR1 comprising the amino acid sequence of SEQ ID NO: 15 or 16, the LC-CDR2 comprising the amino acid sequence of SEQ ID NO: 18, and the LC-CDR3 comprising the amino acid sequence of any one of SEQ ID NOs: 20, or b) the $V_H$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9; and the $V_L$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of any one of SEQ ID NOs: 20.

Embodiment 4. The anti-Sclerostin construct of embodiment 1 or embodiment 2, wherein the $V_H$ comprises the HC-CDR1 comprising the amino acid sequence of SEQ ID NO: 1, the HC-CDR2 comprising the amino acid sequence of SEQ ID NO: 6, and the HC-CDR3 comprising the amino acid sequence of SEQ ID NO: 10; and the $V_L$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of any one of SEQ ID NOs: 20.

Embodiment 5. The anti-Sclerostin construct of embodiment 1 or embodiment 2, wherein the $V_H$ comprises the HC-CDR1 comprising the amino acid sequence of SEQ ID NO: 2, the HC-CDR2 comprising the amino acid sequence of SEQ ID NO: 7, and the HC-CDR3 comprising the amino acid sequence of SEQ ID NO: 10; and the $V_L$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of any one of SEQ ID NOs: 20.

Embodiment 6. The anti-Sclerostin construct of embodiment 1 or embodiment 2, wherein the $V_H$ comprises the HC-CDR1 comprising the amino acid sequence of SEQ ID NO: 2, the HC-CDR2 comprising the amino acid sequence of SEQ ID NO: 6, and the HC-CDR3 comprising the amino acid sequence of SEQ ID NO: 10; and the $V_L$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of any one of SEQ ID NOs: 20.

Embodiment 7. The anti-Sclerostin construct of embodiment 1 or embodiment 2, wherein the $V_H$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 10; and the $V_L$ comprises the LC-CDR1 comprising the amino acid sequence of SEQ ID NO: 16, the LC-CDR2 comprising the amino acid sequence of SEQ ID NO: 18, and the LC-CDR3 comprising the amino acid sequence of any one of SEQ ID NOs: 20.

Embodiment 8. The anti-Sclerostin construct of embodiment 1 or embodiment 2, wherein the $V_H$ comprises the HC-CDR1 comprising the amino acid sequence of SEQ ID NO: 3, the HC-CDR2 comprising the amino acid sequence of SEQ ID NO: 7, and the HC-CDR3 comprising the amino acid sequence of SEQ ID NO: 10; and the $V_L$ comprises the LC-CDR1 comprising the amino acid sequence of SEQ ID NO: 15, the LC-CDR2 comprising the amino acid sequence of SEQ ID NO: 18, and the LC-CDR3 comprising the amino acid sequence of any one of SEQ ID NOs: 20.

Embodiment 9. The anti-Sclerostin construct of embodiment 1 or embodiment 2, wherein the $V_H$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 10; and the $V_L$ comprises the LC-CDR1 comprising the amino acid sequence of SEQ ID NO: 16, the LC-CDR2 comprising the amino acid sequence of SEQ ID NO: 18, and the LC-CDR3 comprising the amino acid sequence of any one of SEQ ID NOs: 20.

Embodiment 10. The anti-Sclerostin construct of embodiment 1 or embodiment 2, wherein the $V_H$ comprises the HC-CDR1 comprising the amino acid sequence of SEQ ID NO: 4, the HC-CDR2 comprising the amino acid sequence of SEQ ID NO: 8, and the HC-CDR3 comprising the amino acid sequence of SEQ ID NO: 11; and the $V_L$ comprises the LC-CDR1 comprising the amino acid sequence of SEQ ID NO: 17, the LC-CDR2 comprising the amino acid sequence of SEQ ID NO: 19, and the LC-CDR3 comprising the amino acid sequence of any one of SEQ ID NOs: 21.

Embodiment 11. The anti-Sclerostin construct of embodiment 1 or embodiment 2, wherein the $V_H$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9; and the $V_L$ comprises the LC-CDR1 comprising the amino acid sequence of SEQ ID NO: 85, the LC-CDR2 comprising the amino acid sequence of SEQ ID NO: 18, and the LC-CDR3 comprising the amino acid sequence of any one of SEQ ID NOs: 20.

Embodiment 12. The anti-Sclerostin construct of embodiment 1 or embodiment 2, wherein the $V_H$ comprises the HC-CDR1 comprising the amino acid sequence of SEQ ID NO: 1, the HC-CDR2 comprising the amino acid sequence of SEQ ID NO: 5, and the HC-CDR3 comprising the amino acid sequence of SEQ ID NO: 9; and the $V_L$ comprises the LC-CDR1 comprising the amino acid sequence of SEQ ID NO: 86, the LC-CDR2 comprising the amino acid sequence of SEQ ID NO: 18, and the LC-CDR3 comprising the amino acid sequence of any one of SEQ ID NOs: 20.

Embodiment 13. An anti-Sclerostin construct comprising an antibody moiety that specifically recognizes Sclerostin, wherein the antibody moiety comprises a heavy chain variable region ($V_H$) and a light chain variable region ($V_L$), wherein:

a) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 22, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 23;

b) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 24, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 25;

c) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 26, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 27;

d) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 28, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 29;

e) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 30, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 31;

f) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 32, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 33;

g) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 34, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 35;

h) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 36, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 37;

i) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 38, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 39;

j) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 40, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 41;

k) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 87, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 88;

l) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 87, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 89; or m) a HC-CDR1, a HC-CDR2, and a HC-CDR3, respectively comprising the amino acid sequences of a CDR1, a CDR2, and a CDR3 within the $V_H$ having the sequence set forth in SEQ ID NO: 87, and a LC-CDR1, a LC-CDR2, and a LC-CDR3, respectively comprising the amino acid sequences of a CDR1, a CDR2, and a CDR3 within the $V_L$ having the sequence set forth in SEQ ID NO: 90.

Embodiment 14. The anti-Sclerostin construct of any one of embodiments 1-13, wherein the $V_H$ comprises an amino acid sequence of any one of SEQ ID NOs: 22, 24, 26, 28, 30, 32, 34, 36, 38, 40, and 87, or a variant comprising an amino acid sequence having at least about 80% sequence identity; and/or wherein the $V_L$ comprises an amino acid sequence of any one of SEQ ID NOs: 23, 25, 27, 29, 31, 33, 35, 37, 39, 41, and 88-90 or a variant comprising an amino acid sequence having at least about 80% sequence identity.

Embodiment 15. The anti-Sclerostin construct of embodiment 14, wherein:

a) the $V_H$ comprises an amino acid sequence of SEQ ID NO: 22, or a variant comprising an amino acid sequence having at least about 80% sequence identity; and the $V_L$ comprises an amino acid sequence of SEQ ID NO: 23, or a variant comprising an amino acid sequence having at least about 80% sequence identity, b) the $V_H$ comprises an amino acid sequence of SEQ ID NO: 24, or a variant comprising an amino acid sequence having at least about 80% sequence identity; and the $V_L$ comprises an amino acid sequence of SEQ ID NO: 25, or a variant comprising an amino acid sequence having at least about 80% sequence identity, c) the $V_H$ comprises an amino acid sequence of SEQ ID NO: 26, or a variant comprising an amino acid sequence having at least about 80% sequence identity; and the $V_L$ comprises an amino acid sequence of SEQ ID NO: 27, or a variant comprising an amino acid sequence having at least about 80% sequence identity, d) the $V_H$ comprises an amino acid sequence of SEQ ID NO: 28, or a variant comprising an amino acid sequence having at least about 80% sequence identity; and the $V_L$ comprises an amino acid sequence of SEQ ID NO: 29, or a variant comprising an amino acid sequence having at least about 80% sequence identity, e) the $V_H$ comprises an amino acid sequence of SEQ ID NO: 30, or a variant comprising an amino acid sequence having at least about 80% sequence identity; and the $V_L$ comprises an amino acid sequence of SEQ ID NO: 31, or a variant comprising an amino acid sequence having at least about 80% sequence identity, f) the $V_H$ comprises an amino acid sequence of SEQ ID NO: 32, or a variant comprising an amino acid sequence having at least about 80% sequence identity; and the $V_L$ comprises an amino acid sequence of SEQ ID NO: 33, or a variant comprising an amino acid sequence having at least about 80% sequence identity, g) the $V_H$ comprises an amino acid sequence of SEQ ID NO: 34, or a variant comprising an amino acid sequence having at least about 80% sequence identity; and the $V_L$ comprises an amino acid sequence of SEQ ID NO: 35, or a variant comprising an amino acid sequence having at least about 80% sequence identity, h) the $V_H$ comprises an amino acid sequence of SEQ ID NO: 36, or a variant comprising an amino acid sequence having at least about 80% sequence identity; and the $V_L$ comprises an amino acid sequence of SEQ ID NO: 37, or a variant comprising an amino acid sequence having at least about 80% sequence identity, i) the $V_H$ comprises an amino acid sequence of SEQ ID NO: 38, or a variant comprising an amino acid sequence having at least about 80% sequence identity; and the $V_L$ comprises an amino acid sequence of SEQ ID NO: 39, or a variant comprising an amino acid sequence having at least about 80% sequence identity, j) the $V_H$ comprises an amino acid sequence of SEQ ID NO: 40, or a variant comprising an amino acid sequence having at least about 80% sequence identity; and the $V_L$ comprises an amino acid sequence of SEQ ID NO: 41, or a variant comprising an amino acid sequence having at least about 80% sequence identity, k) the $V_H$ comprises an amino acid sequence of SEQ ID NO: 87, or a variant comprising an amino acid sequence having at least about 80% sequence identity; and the $V_L$ comprises an amino acid sequence of SEQ ID NO: 88, or a variant comprising an amino acid sequence having at least about 80% sequence identity, l) the $V_H$ comprises an amino acid sequence of SEQ ID NO: 87, or a variant comprising an amino acid sequence having at least about 80% sequence identity; and the $V_L$ comprises an amino acid sequence of SEQ ID NO: 89, or a variant comprising an amino acid sequence having at least about 80% sequence identity, or m) the $V_H$ comprises an amino acid sequence of SEQ ID NO: 87, or a variant comprising an amino acid sequence having at least about 80% sequence identity; and the $V_L$ comprises an amino acid sequence of SEQ ID NO: 90, or a variant comprising an amino acid sequence having at least about 80% sequence identity.

Embodiment 16. An anti-Sclerostin construct comprising an antibody moiety that specifically recognizes Sclerostin, wherein the antibody moiety is a humanized antibody moiety derived from an anti-Sclerostin antibody comprising a heavy chain variable region ($V_H$) and a second light chain variable region ($V_L$), wherein:

a) the $V_H$ comprises a HC-CDR1 comprising the amino acid sequence of SEQ ID NO: 1, a HC-CDR2 comprising the amino acid sequence of SEQ ID NO: 5, and a HC-CDR3 comprising the amino acid sequence of SEQ ID NO: 9, or a variant thereof comprising up to 5, 4, 3, 2, or 1 amino acid substitutions in the HC-CDRs; and the $V_L$ comprises a LC-CDR1 comprising the amino acid sequence of SEQ ID NO: 15, a LC-CDR2 comprising the amino acid sequence of SEQ ID NO: 18, and a LC-CDR3 comprising the amino acid sequence of any one of SEQ ID NOs: 20, or a variant thereof comprising up to 5, 4, 3, 2, or 1 amino acid substitutions in the LC-CDRs;

b) the $V_H$ comprises a HC-CDR1 comprising the amino acid sequence of SEQ ID NO: 1, a HC-CDR2 comprising the amino acid sequence of SEQ ID NO: 6, and a HC-CDR3 comprising the amino acid sequence of SEQ ID NO: 10, or a variant thereof comprising up to 5, 4, 3, 2, or 1 amino acid substitutions in the HC-CDRs; and the $V_L$ comprises a LC-CDR1 comprising the amino acid sequence of SEQ ID NO: 15, a LC-CDR2 comprising the amino acid sequence of SEQ ID NO: 18, and a LC-CDR3 comprising the amino acid sequence of any one of SEQ ID NOs: 20, or a variant thereof comprising up to 5, 4, 3, 2, or 1 amino acid substitutions in the LC-CDRs;

c) the $V_H$ comprises a HC-CDR1 comprising the amino acid sequence of SEQ ID NO: 2, a HC-CDR2 comprising the amino acid sequence of SEQ ID NO: 7, and a HC-CDR3 comprising the amino acid sequence of SEQ ID NO: 10, or a variant thereof comprising up to 5, 4, 3, 2, or 1 amino acid substitutions in the HC-CDRs; and the $V_L$ comprises a LC-CDR1 comprising the amino acid sequence of SEQ ID NO: 15, a LC-CDR2 comprising the amino acid sequence of SEQ ID NO: 18, and a LC-CDR3 comprising the amino acid sequence of any one of SEQ ID NOs: 20, or a variant thereof comprising up to 5, 4, 3, 2, or 1 amino acid substitutions in the LC-CDRs;

d) the $V_H$ comprises a HC-CDR1 comprising the amino acid sequence of SEQ ID NO: 3, a HC-CDR2 comprising the amino acid sequence of SEQ ID NO: 6, and a HC-CDR3 comprising the amino acid sequence of SEQ ID NO: 10, or a variant thereof comprising up to 5, 4, 3, 2, or 1 amino acid substitutions in the HC-CDRs; and the $V_L$ comprises a LC-CDR1 comprising the amino acid sequence of SEQ ID NO: 15, a LC-CDR2 comprising the amino acid sequence of SEQ ID NO: 18, and a LC-CDR3 comprising the amino acid sequence of any one of SEQ ID NOs: 20, or a variant thereof comprising up to 5, 4, 3, 2, or 1 amino acid substitutions in the LC-CDRs;

e) the $V_H$ comprises a HC-CDR1 comprising the amino acid sequence of SEQ ID NO: 199, a HC-CDR2 comprising the amino acid sequence of SEQ ID NO: 5, and a HC-CDR3 comprising the amino acid sequence of SEQ ID NO: 10, or a variant thereof comprising up to 5, 4, 3, 2, or 1 amino acid substitutions in the HC-CDRs; and the $V_L$ comprises a LC-CDR1 comprising the amino acid sequence of SEQ ID NO: 16, a LC-CDR2 comprising the amino acid sequence of SEQ ID NO: 18, and a LC-CDR3 comprising the amino acid sequence of any one of SEQ ID NOs: 20, or a variant thereof comprising up to 5, 4, 3, 2, or 1 amino acid substitutions in the LC-CDRs;

f) the $V_H$ comprises a HC-CDR1 comprising the amino acid sequence of SEQ ID NO: 3, a HC-CDR2 comprising the amino acid sequence of SEQ ID NO: 200, and a HC-CDR3 comprising the amino acid sequence of SEQ ID NO: 10, or a variant thereof comprising up to 5, 4, 3, 2, or 1 amino acid substitutions in the HC-CDRs; and the $V_L$ comprises a LC-CDR1 comprising the amino acid sequence of SEQ ID NO: 15, a LC-CDR2 comprising the amino acid sequence of SEQ ID NO: 18, and a LC-CDR3 comprising the amino acid sequence of any one of SEQ ID NOs: 20, or a variant thereof comprising up to 5, 4, 3, 2, or 1 amino acid substitutions in the LC-CDRs;

g) the $V_H$ comprises a HC-CDR1 comprising the amino acid sequence of SEQ ID NO: 199, a HC-CDR2 comprising the amino acid sequence of SEQ ID NO: 5, and a HC-CDR3 comprising the amino acid sequence of SEQ ID NO: 10, or a variant thereof comprising up to 5, 4, 3, 2, or 1 amino acid substitutions in the HC-CDRs; and the $V_L$ comprises a LC-CDR1 comprising the amino acid sequence of SEQ ID NO: 16, a LC-CDR2 comprising the amino acid sequence of SEQ ID NO: 18, and a LC-CDR3 comprising the amino acid sequence of any one of SEQ ID NOs: 20, or a variant thereof comprising up to 5, 4, 3, 2, or 1 amino acid substitutions in the LC-CDRs; or h) the $V_H$ comprises a HC-CDR1 comprising the amino acid sequence of SEQ ID NO: 4, a HC-CDR2 comprising the amino acid sequence of SEQ ID NO: 8, and a HC-CDR3 comprising the amino acid sequence of SEQ ID NO: 11, or a variant thereof comprising up to 5, 4, 3, 2, or 1 amino acid substitutions in the HC-CDRs; and the $V_L$ comprises a LC-CDR1 comprising the amino acid sequence of SEQ ID NO: 17, a LC-CDR2 comprising the amino acid sequence of SEQ ID NO: 19, and a LC-CDR3 comprising the amino acid sequence of any one of SEQ ID NOs: 21, or a variant thereof comprising up to 5, 4, 3, 2, or 1 amino acid substitutions in the LC-CDRs.

Embodiment 17. The anti-Sclerostin construct of any one of embodiments 1-16, wherein the antibody moiety is an antibody or antigen-binding fragment thereof selected from the group consisting of a full-length antibody, a bispecific antibody, a single-chain Fv (scFv) fragment, a Fab fragment, a Fab' fragment, a $F(ab')_2$, an Fv fragment, a disulfide stabilized Fv fragment (dsFv), a disulfide stabilized scFv (dsscFv), a $(dsFv)_2$, a Fv-Fc fusion, a scFv-Fc fusion, a scFv-Fv fusion, a diabody, a tribody, and a tetrabody.

Embodiment 18. The anti-Sclerostin construct of any one of embodiments 1-17, wherein the construct is a full-length antibody comprising an Fc fragment.

Embodiment 19. The anti-Sclerostin construct of embodiment 17, wherein the antibody moiety is a scFv fragment.

Embodiment 20. The anti-Sclerostin construct of any one of embodiments 1-19, wherein the Sclerostin is a human Sclerostin.

Embodiment 21. The anti-Sclerostin construct of any one of embodiments 1-17 and 19-20, wherein the anti-Sclerostin construct further comprises a second moiety.

Embodiment 22. The anti-Sclerostin construct of embodiment 21, wherein the second moiety comprises a second antibody moiety that specifically recognizes an antigen.

Embodiment 23. The anti-Sclerostin construct of embodiment 22, wherein the second antibody moiety comprises a second heavy chain variable region ($V_{H-2}$) and a light chain variable region ($V_{L-2}$).

Embodiment 24. The anti-Sclerostin construct of embodiment 22 or embodiment 23, wherein the antigen is DKK1.

Embodiment 25. The anti-Sclerostin construct of embodiment 24, wherein the DKK1 is a human DKK1.

Embodiment 26. The anti-Sclerostin construct of embodiment 24 or embodiment 25, wherein the second antibody moiety competes for a binding epitope of DKK1 with a third antibody moiety comprising a third heavy chain variable region ($V_{H-3}$) and a third light chain variable region ($V_{L-3}$), wherein:

a) the $V_{H-3}$ comprising a HC-CDR1 comprising the amino acid sequence of SEQ ID NO: 42, a HC-CDR2 comprising the amino acid sequence of SEQ ID NO: 43, and a HC-CDR3 comprising the amino acid sequence of SEQ ID NO: 44, and the $V_{L-3}$ comprises a LC-CDR1 comprising the amino acid sequence of SEQ ID NO: 45, a LC-CDR2 comprising the amino acid sequence of SEQ ID NO: 46, and a LC-CDR3 comprising the amino acid sequence of SEQ ID NO: 47;

b) the $V_{H-3}$ comprises a HC-CDR1 comprising the amino acid sequence of SEQ ID NO: 48, a HC-CDR2 comprising the amino acid sequence of SEQ ID NO: 49, and a HC-CDR3 comprising the amino acid sequence of SEQ ID NO: 50, and the $V_{L-3}$ comprises a LC-CDR1 comprising the amino acid sequence of SEQ ID NO: 51, a LC-CDR2 comprising the amino acid sequence of SEQ ID NO: 52, and a LC-CDR3 comprising the amino acid sequence of SEQ ID NO: 58; or c) the $V_{H-3}$ comprises a HC-CDR1 comprising the amino acid sequence of SEQ ID NO: 54, a HC-CDR2 comprising the amino acid sequence of SEQ ID NO: 55, and a HC-CDR3 comprising the amino acid sequence of SEQ ID NO: 56, and the $V_{L-3}$ comprises a LC-CDR1 comprising the amino acid sequence of SEQ ID NO: 57, a LC-CDR2 comprising the amino acid sequence of SEQ ID NO: 58, and a LC-CDR3 comprising the amino acid sequence of SEQ ID NO: 59.

Embodiment 27. The anti-Sclerostin construct of embodiment 26, wherein $V_{H-2}$ comprises the HC-CDR1 comprising the amino acid sequence of SEQ ID NO: 42, the HC-CDR2 comprising the amino acid sequence of SEQ ID NO: 43, and the HC-CDR3 comprising the amino acid sequence of SEQ ID NO: 44, and the $V_{L-2}$ comprises the LC-CDR1 comprising the amino acid sequence of SEQ ID NO: 45, the LC-CDR2 comprising the amino acid sequence of SEQ ID NO: 46, and the LC-CDR3 comprising the amino acid sequence of SEQ ID NO: 47.

Embodiment 28. The anti-Sclerostin construct of embodiment 26, wherein the $V_{H-2}$ comprises the HC-CDR1 comprising the amino acid sequence of SEQ ID NO: 48, the HC-CDR2 comprising the amino acid sequence of SEQ ID NO: 49, and the HC-CDR3 comprising the amino acid sequence of SEQ ID NO: 50, and the $V_{L-2}$ comprises the LC-CDR1 comprising the amino acid sequence of SEQ ID NO: 51, the LC-CDR2 comprising the amino acid sequence of SEQ ID NO: 52, and the LC-CDR3 comprising the amino acid sequence of SEQ ID NO: 58.

Embodiment 29. The anti-Sclerostin construct of embodiment 26, wherein the $V_{H-2}$ comprising the HC-CDR1 comprising the amino acid sequence of SEQ ID NO: 54, the HC-CDR2 comprising the amino acid sequence of SEQ ID NO: 55, and the HC-CDR3 comprising the amino acid sequence of SEQ ID NO: 56, and the $V_{L-2}$ comprises the LC-CDR1 comprising the amino acid sequence of SEQ ID NO: 57, the LC-CDR2 comprising the amino acid sequence of SEQ ID NO: 58, and the LC-CDR3 comprising the amino acid sequence of SEQ ID NO: 59.

Embodiment 30. The anti-Sclerostin construct of embodiment 22 or embodiment 23, wherein the antigen is RANKL.

Embodiment 31. The anti-Sclerostin construct of embodiment 30, wherein the antigen is human RANKL.

Embodiment 32. The anti-Sclerostin construct of embodiment 30 or embodiment 31, wherein the second antibody moiety competes for a binding epitope of RANKL with a third antibody moiety comprising a third heavy chain variable region ($V_{H-3}$) and a third light chain variable region ($V_{L-3}$), wherein the $V_{H-3}$ comprising a HC-CDR1 comprising the amino acid sequence of SEQ ID NO: 66, a HC-CDR2 comprising the amino acid sequence of SEQ ID NO: 67, and a HC-CDR3 comprising the amino acid sequence of SEQ ID NO: 68, and the $V_{L-3}$ comprises a LC-CDR1 comprising the amino acid sequence of SEQ ID NO: 69, a LC-CDR2 comprising the amino acid sequence of SEQ ID NO: 70, and a LC-CDR3 comprising the amino acid sequence of SEQ ID NO: 71.

Embodiment 33. The anti-Sclerostin construct of embodiment 31, wherein the $V_{H-2}$ comprises the HC-CDR1 comprising the amino acid sequence of SEQ ID NO: 66, the HC-CDR2 comprising the amino acid sequence of SEQ ID NO: 67, and the HC-CDR3 comprising the amino acid sequence of SEQ ID NO: 68, and the $V_{L-2}$ comprises the LC-CDR1 comprising the amino acid sequence of SEQ ID NO: 69, the LC-CDR2 comprising the amino acid sequence of SEQ ID NO: 70, and the LC-CDR3 comprising the amino acid sequence of SEQ ID NO: 71.

Embodiment 34. The anti-Sclerostin construct of any one of embodiments 22-33, wherein the second antibody moiety is a full-length antibody, a Fab, a Fab', a (Fab')2, an Fv, a single chain Fv (scFv) fragment, an scFv-scFv, a minibody, a diabody, or an sdAb.

Embodiment 35. The anti-Sclerostin construct of embodiment 34, wherein the second antibody moiety is a full-length antibody comprising two heavy chains, two light chains and a Fc fragment, and wherein the anti-Sclerostin antibody moiety is a single chain Fv (scFv) fragment comprising the $V_H$ fused with the $V_L$.

Embodiment 36. The anti-Sclerostin construct of embodiment 35, wherein the anti-Sclerostin antibody moiety is fused to one or both of the heavy chains of the full-length antibody.

Embodiment 37. The anti-Sclerostin construct of any one of embodiments 34-36, wherein the anti-Sclerostin antibody moiety is fused to one or both of the light chains of the full-length antibody.

Embodiment 38. The anti-Sclerostin construct of embodiment 36 or 37, wherein the anti-Sclerostin antibody moiety is fused to N-terminus of the one or both of the heavy chains or light chains of the full-length antibody.

Embodiment 39. The anti-Sclerostin construct of any one of embodiments 36-38, wherein the anti-Sclerostin antibody moiety is fused to C-terminus of the one or both of the heavy chains or light chains of the full-length antibody.

Embodiment 40. The anti-Sclerostin construct of any one of embodiments 36-39, wherein the anti-Sclerostin antibody moiety is fused to the full-length antibody via a first linker.

Embodiment 41. The anti-Sclerostin construct of any one of embodiments 36-39, wherein the anti-Sclerostin antibody moiety is fused to the full-length antibody without a linker.

Embodiment 42. The anti-Sclerostin construct of embodiment 40, wherein the first linker is a GS linker selected from the group consisting of SEQ ID NOs: 74-84.

Embodiment 43. The anti-Sclerostin construct of any one of embodiments 35-42, wherein the $V_H$ is fused with the $V_L$ via a second linker.

Embodiment 44. The anti-Sclerostin construct of embodiment 43, wherein the scFv fragment comprises, from N-terminus to C-terminus, the $V_H$, the second linker, and the $V_L$.

Embodiment 45. The anti-Sclerostin construct of embodiment 43, wherein the scFv fragment comprises, from N-terminus to C-terminus, the $V_L$, the second linker, and the $V_H$, and optionally a C-terminal alanine residue.

Embodiment 46. The anti-Sclerostin construct of any one of embodiments 43-45, wherein the second linker comprises an amino acid sequence of SEQ ID NO: 76 or 77.

Embodiment 47. The anti-Sclerostin construct of any one of embodiments 23-33, wherein the second antibody moiety is a scFv fragment comprising the $V_{H-2}$ and the $V_{L-2}$, and wherein the anti-Sclerostin antibody moiety is a full-length antibody comprising two heavy chains, two light chains and a Fc fragment.

Embodiment 48. The anti-Sclerostin construct of embodiment 46, wherein the second antibody moiety is fused to both of the heavy chains of the full-length antibody.

Embodiment 49. The anti-Sclerostin construct of embodiment 47 or 48, wherein the second antibody moiety is fused to both of the light chains of the full-length antibody.

Embodiment 50. The anti-Sclerostin construct of embodiment 48 or 49, wherein the antibody moiety is fused to N-terminus of both of the heavy chains or light chains of the full-length antibody.

Embodiment 51. The anti-Sclerostin construct of any one of embodiments 47-50, wherein the antibody moiety is fused to C-terminus of both of the heavy chains or light chains of the full-length antibody.

Embodiment 52. The anti-Sclerostin construct of any one of embodiments 47-51, wherein the antibody moiety is fused to the full-length antibody via a first linker.

Embodiment 53. The anti-Sclerostin construct of any one of embodiments 47-51, wherein the antibody moiety is fused to the full-length antibody without a linker.

Embodiment 54. The anti-Sclerostin construct of embodiment 52, wherein the first linker is a GS first linker selected from the group consisting of SEQ ID NOs: 74-84.

Embodiment 55. The anti-Sclerostin construct of any one of embodiments 47-54, wherein the $V_{H-2}$ is fused with the $V_{L-2}$ via a second linker.

Embodiment 56. The anti-Sclerostin construct of any one of embodiments 47-54, wherein the $V_{H-2}$ is fused with the $V_{L-2}$ without a linker.

Embodiment 57. The anti-Sclerostin construct of embodiment 55, wherein the scFv fragment comprises, from N-terminus to C-terminus, the $V_{H-2}$, the second linker, and the $V_{L-2}$.

Embodiment 58. The anti-Sclerostin construct of embodiment 55, wherein the scFv fragment comprises, from N-terminus to C-terminus, the $V_{L-2}$, the second linker, and the $V_{H-2}$, and optionally a C-terminal alanine residue.

Embodiment 59. The anti-Sclerostin construct of any one of embodiments 55 and 57-58, wherein the second linker comprises an amino acid sequence of SEQ ID NO: 76 or 77.

Embodiment 60. The anti-Sclerostin construct of any one of embodiments 35-59, wherein the scFv is a disulfide stabilized scFv ("dsscFv").

Embodiment 61. The anti-Sclerostin construct of embodiment 60, wherein the dsscFv comprises a) a G44C mutation in the $V_H$ or $V_{H-2}$ according to the numbering of SEQ ID NO: 60, and b) a G100C mutation in the $V_L$ or $V_{L-2}$ according to the numbering of SEQ ID NO: 61.

Embodiment 62. The anti-Sclerostin construct of any one of embodiments 35-61, wherein the construct comprises:

1) two heavy chains fused with the anti-Sclerostin or second antibody moiety each comprising the amino acid sequence of SEQ ID NO: 91, and two light chains each comprising the amino acid sequence of SEQ ID NO: 93;
2) two heavy chains fused with the anti-Sclerostin or second antibody moiety each comprising the amino acid sequence of SEQ ID NO: 92, and two light chains each comprising the amino acid sequence of SEQ ID NO: 93;

3) two heavy chains fused with the anti-Sclerostin or second antibody moiety each comprising the amino acid sequence of SEQ ID NO: 94, and two light chains each comprising the amino acid sequence of SEQ ID NO: 96;

4) two heavy chains fused with the anti-Sclerostin or second antibody moiety each comprising the amino acid sequence of SEQ ID NO: 95, and two light chains each comprising the amino acid sequence of SEQ ID NO: 96;

5) two heavy chains fused with the anti-Sclerostin or second antibody moiety each comprising the amino acid sequence of SEQ ID NO: 97, and two light chains each comprising the amino acid sequence of SEQ ID NO: 99;

6) two heavy chains fused with the anti-Sclerostin or second antibody moiety each comprising the amino acid sequence of SEQ ID NO: 98, and two light chains each comprising the amino acid sequence of SEQ ID NO: 99;

7) two heavy chains fused with the anti-Sclerostin or second antibody moiety each comprising the amino acid sequence of SEQ ID NO: 100, and two light chains each comprising the amino acid sequence of SEQ ID NO: 102;

8) two heavy chains fused with the anti-Sclerostin or second antibody moiety each comprising the amino acid sequence of SEQ ID NO: 101, and two light chains each comprising the amino acid sequence of SEQ ID NO: 102;

9) two heavy chains each comprising the amino acid sequence of SEQ ID NO:103, and two light chains fused with the anti-Sclerostin or second antibody moiety each comprising the amino acid sequence of SEQ ID NO: 104;

10) two heavy chains each comprising the amino acid sequence of SEQ ID NO: 103, and two light chains fused with the anti-Sclerostin or second antibody moiety each comprising the amino acid sequence of SEQ ID NO: 105;

11) two heavy chains each comprising the amino acid sequence of SEQ ID NO: 106, and two light chains fused with the anti-Sclerostin or second antibody moiety each comprising the amino acid sequence of SEQ ID NO: 107;

12) two heavy chains each comprising the amino acid sequence of SEQ ID NO: 106, and two light chains fused with the anti-Sclerostin or second antibody moiety each comprising the amino acid sequence of SEQ ID NO: 108;

13) two heavy chains each comprising the amino acid sequence of SEQ ID NO: 109, and two light chains fused with the anti-Sclerostin or second antibody moiety each comprising the amino acid sequence of SEQ ID NO: 110;

14) two heavy chains each comprising the amino acid sequence of SEQ ID NO: 109, and two light chains fused with the anti-Sclerostin or second antibody moiety each comprising the amino acid sequence of SEQ ID NO: 111;

15) two heavy chains each comprising the amino acid sequence of SEQ ID NO: 112, and two light chains fused with the anti-Sclerostin or second antibody moiety each comprising the amino acid sequence of SEQ ID NO: 113;

16) two heavy chains each comprising the amino acid sequence of SEQ ID NO: 112, and two light chains fused with the anti-Sclerostin or second antibody moiety each comprising the amino acid sequence of SEQ ID NO: 114;

17) two heavy chains fused with the anti-Sclerostin or second antibody moiety each comprising the amino acid sequence of SEQ ID NO: 115, and two light chains each comprising the amino acid sequence of SEQ ID NO: 119;

18) two heavy chains fused with the anti-Sclerostin or second antibody moiety each comprising the amino acid sequence of SEQ ID NO: 116, and two light chains each comprising the amino acid sequence of SEQ ID NO: 119;

19) two heavy chains fused with the anti-Sclerostin or second antibody moiety each comprising the amino acid sequence of SEQ ID NO: 117, and two light chains each comprising the amino acid sequence of SEQ ID NO: 119;

20) two heavy chains fused with the anti-Sclerostin or second antibody moiety each comprising the amino acid sequence of SEQ ID NO: 118, and two light chains each comprising the amino acid sequence of SEQ ID NO: 119;

21) two heavy chains fused with the anti-Sclerostin or second antibody moiety each comprising the amino acid sequence of SEQ ID NO: 120, and two light chains each comprising the amino acid sequence of SEQ ID NO: 122;

22) two heavy chains fused with the anti-Sclerostin or second antibody moiety each comprising the amino acid sequence of SEQ ID NO: 121, and two light chains each comprising the amino acid sequence of SEQ ID NO: 122;

23) two heavy chains fused with the anti-Sclerostin or second antibody moiety each comprising the amino acid sequence of SEQ ID NO: 123, and two light chains each comprising the amino acid sequence of SEQ ID NO: 125;

24) two heavy chains fused with the anti-Sclerostin or second antibody moiety each comprising the amino acid sequence of SEQ ID NO: 124, and two light chains each comprising the amino acid sequence of SEQ ID NO: 125;

25) two heavy chains fused with the anti-Sclerostin or second antibody moiety each comprising the amino acid sequence of SEQ ID NO: 126, and two light chains each comprising the amino acid sequence of SEQ ID NO: 129;

26) two heavy chains fused with the anti-Sclerostin or second antibody moiety each comprising the amino acid sequence of SEQ ID NO: 127, and two light chains each comprising the amino acid sequence of SEQ ID NO: 129;

27) two heavy chains fused with the anti-Sclerostin or second antibody moiety each comprising the amino acid sequence of SEQ ID NO: 128, and two light chains each comprising the amino acid sequence of SEQ ID NO: 129;

28) two heavy chains each comprising the amino acid sequence of SEQ ID NO: 133, and two light chains fused with the anti-Sclerostin or second antibody moiety each comprising the amino acid sequence of SEQ ID NO: 130;

29) two heavy chains each comprising the amino acid sequence of SEQ ID NO: 133, and two light chains fused with the anti-Sclerostin or second antibody moiety each comprising the amino acid sequence of SEQ ID NO: 131;

30) two heavy chains each comprising the amino acid sequence of SEQ ID NO: 133, and two light chains fused with the anti-Sclerostin or second antibody moiety each comprising the amino acid sequence of SEQ ID NO: 132;

31) two heavy chains fused with the anti-Sclerostin or second antibody moiety each comprising the amino acid sequence of SEQ ID NO: 177, and two light chains each comprising the amino acid sequence of SEQ ID NO: 125;

32) two heavy chains fused with the anti-Sclerostin or second antibody moiety each comprising the amino acid sequence of SEQ ID NO: 178, and two light chains each comprising the amino acid sequence of SEQ ID NO: 125;

33) two heavy chains fused with the anti-Sclerostin or second antibody moiety each comprising the amino acid sequence of SEQ ID NO: 178, and two light chains each comprising the amino acid sequence of SEQ ID NO: 122;

34) two heavy chains fused with the anti-Sclerostin or second antibody moiety each comprising the amino acid sequence of SEQ ID NO: 179, and two light chains each comprising the amino acid sequence of SEQ ID NO: 122; or 35) two heavy chains fused with the anti-Sclerostin or second antibody moiety each comprising the amino acid sequence of SEQ ID NO: 180, and two light chains each comprising the amino acid sequence of SEQ ID NO: 122.

Embodiment 63. The anti-Sclerostin construct of any one of embodiments 23-33, wherein the construct comprises:

a) a first polypeptide comprising a first light chain comprising, from N-terminus to C-terminus, i) the $V_L$, ii) a first light chain constant domain ("first CL domain");

b) a second polypeptide comprising a first heavy chain comprising, from N-terminus to C-terminus, i) the $V_H$, ii) a first heavy chain constant domain ("first CH1 domain"), and iii) a first Fc domain;

c) a third polypeptide comprising a second heavy chain comprising, from N-terminus to C-terminus, i) the $V_{H-2}$, ii) a second heavy chain constant domain ("second CH1 domain"), and iii) a second Fc domain; and d) a fourth polypeptide comprising a second light chain comprising, from N-terminus to C-terminus, i) the $V_{L-2}$, ii) ii) a second light chain constant domain ("second CL domain"), wherein the first and the second Fc domains form an Fc fragment.

Embodiment 64. The anti-Sclerostin construct of embodiment 63, wherein one of the first and the second Fc domains comprises a T366W mutation, and optionally a S354C mutation, and wherein the other Fc domain comprises a T366S mutation, a L368A mutation, a Y407V mutation, and optionally a Y349C mutation, wherein numbering is according to the EU index.

Embodiment 65. The anti-Sclerostin construct of embodiment 63 or embodiment 64, wherein either i) the first CH1 domain and the first CL domain or ii) the second CH1 domain and the second CL domain are selected from the group consisting of:

a) a CH1 domain wherein the amino acid at position 141 is substituted for cysteine and the cysteine at position 131 (e.g., in IgG2 or IgG4) or 220 (e.g., in IgG1) is substituted for a non-cysteine amino acid; and a CL domain wherein the amino acid at position 116 is substituted for cysteine and the cysteine at position 214 is substituted for a non-cysteine amino acid;

b) a CH1 domain wherein the amino acid at position 168 is substituted for cysteine and the cysteine at position 131 (e.g., in IgG2 or IgG4) or 220 (e.g., in IgG1) is substituted for a non-cysteine amino acid; and a CL domain wherein the amino acid at position 164 is substituted for cysteine and the cysteine at position 214 is substituted for a non-cysteine amino acid;

c) a CH1 domain wherein the amino acid at position 126 is substituted for cysteine and the cysteine at position 131 (e.g., in IgG2 or IgG4) or 220 (e.g., in IgG1) is substituted for a non-cysteine amino acid; and a CL domain wherein the amino acid at position 121 is substituted for cysteine and the cysteine at position 214 is substituted for a non-cysteine amino acid;

d) a CH1 domain wherein the amino acid at position 128 is substituted for cysteine and the cysteine at position 131 (e.g., in IgG2 or IgG4) or 220 (e.g., in IgG1) is substituted for a non-cysteine amino acid; and a CL domain wherein the amino acid at position 118 is substituted for cysteine and the cysteine at position 214 is substituted for a non-cysteine amino acid;

e) a CH1 domain wherein the amino acid at position 170 is substituted for cysteine and the cysteine at position 131 (e.g., in IgG2 or IgG4) or 220 (e.g., in IgG1) is substituted for a non-cysteine amino acid; and a CL domain wherein the amino acid at position 176 is substituted for cysteine and the cysteine at position 214 is substituted for a non-cysteine amino acid;

f) a CH1 domain wherein the amino acid at position 171 is substituted for cysteine and the cysteine at position 131 (e.g., in IgG2 or IgG4) or 220 (e.g., in IgG1) is substituted for a non-cysteine amino acid; and a CL domain wherein the amino acid at position 162 is substituted for cysteine and the cysteine at position 214 is substituted for a non-cysteine amino acid;

g) a CH1 domain wherein the amino acid at position 173 is substituted for cysteine and the cysteine at position 131 (e.g., in IgG2 or IgG4) or 220 (e.g., in IgG1) is substituted for a non-cysteine amino acid; and a CL domain wherein the amino acid at position 160 is substituted for cysteine and the cysteine at position 214 is substituted for a non-cysteine amino acid;

wherein numbering is according to the EU index.

Embodiment 66. The anti-Sclerostin construct of any of embodiments 63-65, comprising:

1) the first polypeptide comprises the amino acid sequence of SEQ ID NO: 135, the second polypeptide comprises the amino acid sequence of SEQ ID NO: 134, the third polypeptide comprises the amino acid sequence of SEQ ID NO: 136, and the fourth polypeptide comprises the amino acid sequence of SEQ ID NO: 137;

2) the first polypeptide comprises the amino acid sequence of SEQ ID NO: 135, the second polypeptide comprises the amino acid sequence of SEQ ID NO: 134, the third polypeptide comprises the amino acid sequence of SEQ ID NO: 138, and the fourth polypeptide comprises the amino acid sequence of SEQ ID NO: 139;

3) the first polypeptide comprises the amino acid sequence of SEQ ID NO: 135, the second polypeptide comprises the amino acid sequence of SEQ ID NO: 134, the third polypeptide comprises the amino acid sequence of SEQ ID NO: 140, and the fourth polypeptide comprises the amino acid sequence of SEQ ID NO: 141;

4) the first polypeptide comprises the amino acid sequence of SEQ ID NO: 135, the second polypeptide comprises the amino acid sequence of SEQ ID NO: 134, the third polypeptide comprises the amino acid sequence of SEQ ID NO: 142, and the fourth polypeptide comprises the amino acid sequence of SEQ ID NO: 143;

5) the first polypeptide comprises the amino acid sequence of SEQ ID NO: 135, the second polypeptide comprises the amino acid sequence of SEQ ID NO: 134, the third polypeptide comprises the amino acid sequence of SEQ ID NO: 144, and the fourth polypeptide comprises the amino acid sequence of SEQ ID NO: 145;

6) the first polypeptide comprises the amino acid sequence of SEQ ID NO: 147, the second polypeptide comprises the amino acid sequence of SEQ ID NO: 146, the third polypeptide comprises the amino acid sequence of SEQ ID NO: 148, and the fourth polypeptide comprises the amino acid sequence of SEQ ID NO: 149;

7) the first polypeptide comprises the amino acid sequence of SEQ ID NO: 147, the second polypeptide comprises the amino acid sequence of SEQ ID NO: 146, the third polypeptide comprises the amino acid sequence of SEQ ID NO: 150, and the fourth polypeptide comprises the amino acid sequence of SEQ ID NO: 151;

8) the first polypeptide comprises the amino acid sequence of SEQ ID NO: 147, the second polypeptide comprises the amino acid sequence of SEQ ID NO: 146, the third polypeptide comprises the amino acid sequence of SEQ ID NO: 152, and the fourth polypeptide comprises the amino acid sequence of SEQ ID NO: 153;

9) the first polypeptide comprises the amino acid sequence of SEQ ID NO: 147, the second polypeptide comprises the amino acid sequence of SEQ ID NO: 146, the third polypeptide comprises the amino acid sequence of SEQ ID NO: 154, and the fourth polypeptide comprises the amino acid sequence of SEQ ID NO: 155;

10) the first polypeptide comprises the amino acid sequence of SEQ ID NO: 147, the second polypeptide comprises the amino acid sequence of SEQ ID NO: 146, the third polypeptide comprises the amino acid sequence of SEQ ID NO: 156, and the fourth polypeptide comprises the amino acid sequence of SEQ ID NO: 157;

11) the first polypeptide comprises the amino acid sequence of SEQ ID NO: 147, the second polypeptide comprises the amino acid sequence of SEQ ID NO: 146, the third polypeptide comprises the amino acid sequence of SEQ ID NO: 158, and the fourth polypeptide comprises the amino acid sequence of SEQ ID NO: 159;

12) the first polypeptide comprises the amino acid sequence of SEQ ID NO: 147, the second polypeptide comprises the amino acid sequence of SEQ ID NO: 146, the third polypeptide comprises the amino acid sequence of SEQ ID NO: 160, and the fourth polypeptide comprises the amino acid sequence of SEQ ID NO: 161;

13) the first polypeptide comprises the amino acid sequence of SEQ ID NO: 147, the second polypeptide comprises the amino acid sequence of SEQ ID NO: 146, the third polypeptide comprises the amino acid sequence of SEQ ID NO: 162, and the fourth polypeptide comprises the amino acid sequence of SEQ ID NO: 163;

14) the first polypeptide comprises the amino acid sequence of SEQ ID NO: 147, the second polypeptide comprises the amino acid sequence of SEQ ID NO: 171, the third polypeptide comprises the amino acid sequence of SEQ ID NO: 172, and the fourth polypeptide comprises the amino acid sequence of SEQ ID NO: 163.

15) the first polypeptide comprises the amino acid sequence of SEQ ID NO: 147, the second polypeptide comprises the amino acid sequence of SEQ ID NO: 173, the third polypeptide comprises the amino acid sequence of SEQ ID NO: 174, and the fourth polypeptide comprises the amino acid sequence of SEQ ID NO: 163.

16) the first polypeptide comprises the amino acid sequence of SEQ ID NO: 147, the second polypeptide comprises the amino acid sequence of SEQ ID NO: 175, the third polypeptide comprises the amino acid sequence of SEQ ID NO: 176, and the fourth polypeptide comprises the amino acid sequence of SEQ ID NO: 163. Embodiment 67. The anti-Sclerostin construct of embodiment 21, wherein the second moiety comprises a half-life extending moiety.

Embodiment 68. The anti-Sclerostin construct of embodiment 67, wherein the half-life extending moiety is an Fc fragment.

Embodiment 69. The anti-Sclerostin construct of any one of embodiments 18, and 35-66 and 68, wherein the Fc fragment is selected from the group consisting of Fc fragments form IgG, IgA, IgD, IgE, IgM, and combinations and hybrids thereof.

Embodiment 70. The anti-Sclerostin construct of embodiment 69, wherein the Fc fragment is selected from the group consisting of Fc fragments from IgG1, IgG2, IgG3, IgG4, and combinations and hybrids thereof.

Embodiment 71. The anti-Sclerostin construct of embodiment 69 or embodiment 70, wherein the Fc fragment comprises a H435R mutation and a Y436F mutation.

Embodiment 72. The anti-Sclerostin construct of any of embodiments 69-71, wherein the Fc fragment has a reduced effector function as compared to the corresponding wildtype Fc fragment.

Embodiment 73. The anti-Sclerostin construct of any of embodiments 69-71, wherein the Fc fragment has: a) an enhanced effector function as compared to the corresponding wildtype Fc fragment, and/or b) an enhanced FcRn binding affinity as compared to the corresponding wildtype Fc fragment.

Embodiment 74. The anti-Sclerostin construct of embodiment 21, wherein the construct is an antibody-drug conjugate or antibody fusion protein.

Embodiment 75. The anti-Sclerostin construct of embodiment 74, wherein the second moiety comprises an agent or agents selected from the group consisting of a parathyroid hormone (PTH), a selective estrogen receptor modulator (SERM), a bisphosphonate, a prostaglandin E (PGE) receptor agonist, VEGF, TGFβ, growth factor (myostatin), calcitonin and combinations thereof.

Embodiment 76. An anti-Sclerostin construct that specifically binds to Sclerostin competitively with the anti-Sclerostin construct of any one of embodiments 1-75.

Embodiment 77. A pharmaceutical composition comprising the anti-Sclerostin construct of any one of embodiments 1-76 and a pharmaceutically acceptable carrier.

Embodiment 78. The pharmaceutical composition of embodiment 77, wherein the composition further comprises an agent or agents selected from the group consisting of a parathyroid hormone (PTH), a selective estrogen receptor modulator (SERM), VEGF, and TGFβ, growth factor (myostatin), calcitonin and combinations thereof.

Embodiment 79. An isolated nucleic acid encoding the anti-Sclerostin construct of any one of embodiments 1-76.

Embodiment 80. A vector comprising the isolated nucleic acid of embodiment 79.

Embodiment 81. An isolated host cell comprising the isolated nucleic acid of embodiment 79, or the vector of embodiment 80.

Embodiment 82. A method of producing an anti-Sclerostin construct comprising:

a) culturing the isolated host cell of embodiment 81 under conditions effective to express the anti-Sclerostin construct or a portion thereof; and
b) obtaining the expressed anti-Sclerostin construct or a portion thereof from the host cell.

Embodiment 83. A method of treating and/or preventing a disease or condition in an individual, comprising administering to the individual an effective mount of the anti-Sclerostin construct of any one of embodiments 1-76, or the pharmaceutical composition of embodiment 77 or embodiment 78.

Embodiment 84. The method of embodiment 83, wherein the disease or condition is a bone-related disorder or cartilage-related disorder, a bone marrow or haemotological disorder, a musculoskeletal rare disease, a muscle-related disorder, or a cancer.

Embodiment 85. The method of embodiment 84, wherein the bone-related disorder is osteogenesis imperfecta, osteoporosis or osteopenia (in men and women), osteonecrosis, delay bone healing, non-union bone fractures, multiple myeloma, multiple myeloma related bone disorders, primary bone tumor, bone metastasis of malignancies, inflammatory or infectious bone disease, osteomalacia, hypercalcemia, Paget's disease, immobilization-induced bone loss, glucocorticoid-induced bone loss, inflammation-induced bone loss including arthritis-induced bone loss, spaceflight osteoporosis/osteopenia and bone loss caused by reduced gravity or other disease or condition associated with a) bone loss of either quantity or quality or both and/or b) abnormality of bone structure and quality.

Embodiment 86. The method of embodiment 85, wherein the bone-related disorder is osteoporosis or osteopenia.

Embodiment 87. The method of embodiment 85, wherein the bone-related disorder is osteogenesis imperfecta.

Embodiment 88. The method of embodiment 85, wherein the bone-related disorder is multiple myeloma and multiple myeloma related bone disorders.

Embodiment 89. The method of embodiment 84, wherein the cartilage disorder is chondromatosis, chondrodysplasia, achondroplasia, epiphyseal dysplasia, chondrodystrophic myotonia, juxtacortical chondroma, tear of cartilage of knee, osteofibrous dysplasia, osteoarthritis, osteogenesis imperfecta, hypophosphatemic rickets or osteochondrodystrophy.

Embodiment 90. The method of embodiment 84, wherein the muscle-related disorder is sarcopenia and cancer sarcopenia.

Embodiment 91. A method of facilitation of heal after bone or joint surgeries in an individual, comprising administering to the individual an effective mount of the anti-Sclerostin construct of any one of embodiments 1-76, and/or the pharmaceutical composition of embodiment 77 or embodiment 78.

Embodiment 92. The method of any one of embodiments 83-91, wherein the anti-Sclerostin construct is administered by subcutaneous injection, intravenous injection, intramuscular injection or administered orally or parenterally into the individual.

Embodiment 93. The method of any one of embodiments 83-92, wherein the method further comprises administering a second agent or therapy.

Embodiment 94. The method of embodiment 93, wherein the second agent or therapy comprises an anti-DKK1 antibody.

Embodiment 95. The method of embodiment 93, wherein the second agent or therapy comprises an anti-RANKL antibody.

Embodiment 96. The method of embodiment 93, wherein the second agent or therapy comprises an agent selected from the group consisting of a parathyroid hormone (PTH), a selective estrogen receptor modulator (SERM), a bisphosphonate, a prostaglandin E (PGE) receptor agonist, VEGF, TGFβ, growth factor (myostatin) and calcitonin.

Embodiment 97. The method of any one of embodiments 83-96, wherein the individual is a human.

EXAMPLES

The examples below are intended to be purely exemplary of the application and should therefore not be considered to limit the application in any way. The following examples and detailed description are offered by way of illustration and not by way of limitation.

Example 1. Generation of Anti-Sclerostin Monoclonal Antibodies

The anti-human Sclerostin monoclonal antibody was produced by immunizing mice. Experimental BALB/c mice (18-20 g, 7-8 weeks of age, Beijing Vital River Laboratory Animal Technology Co., Ltd.) and C57 mice (18-20 g, 7-8 weeks of age, Beijing Vital River Laboratory Animal Technology Co., Ltd.) were used. The animals were kept in the SPF level laboratory for 1 week, with 12/12 hours light/dark cycle, at a temperature of 20-25° C., and humidity of 40-60%. Human SOST recombinant protein with a His tag (HST-H5245, Acro Biosystems) was used as an immunogen. A proprietary adjuvant (Lot No 20200120) was used for emulsification, and the antigen was added with equal volume of adjuvant to reach total volume of 300 ul. The antigen/adjuvant solution was emulsified with electro blender and mixed with multi-dimension rotator. After sanitation with 75% alcohol, the antigen/adjuvant solution was injected subcutaneously. The antigen was emulsified and inoculated on days 0, 14, 28. A booster immunization was performed by intraperitoneal (IP) injection of antigen solution formulated with saline at 50 μg/mouse 3 days prior to splenocyte fusion. A blood titer test was performed on days 22, 36, and 45. After the third immunization, two mice with highest blood titer tending to platform were selected for splenocyte fusion. Hybridoma cells were obtained by fusing splenocyte with myeloma Sp2/0 cells by using a conventional fusion procedure with Electro Cell Manipulator (BTX, ECM2001). The binding activity of mouse serum to human Sclerostin was measured by the ELISA method of Example 3, and the monoclonal hybridoma cell strains with good binding activities in vitro were selected. The results are shown in Table 5.

Example 2. Cloning and Sequencing of Anti-Sclerostin Monoclonal Antibodies

The process of hybridoma sequencing was performed as follows. Total RNA was isolated from the hybridoma cells following the technical manual of TRIzol® Reagent. Total RNA was then reverse-transcribed into cDNA using either isotype-specific anti-sense primers or universal primers following the technical manual of PrimeScript™ 1st Strand cDNA Synthesis Kit. Antibody fragments of heavy chain and light chain were amplified according to the standard operating procedure (SOP) of rapid amplification of cDNA ends (RACE). Amplified antibody fragments were cloned into a standard cloning vector separately. Colony PCR was performed to screen for clones with inserts of correct sizes. The consensus sequence was provided.

Sequence Analysis

DNA sequence data from all constructs were analyzed and consensus sequences for heavy and light chain were determined. Tables 3 and 4 list $V_H$ and $V_L$ CDRs of various antibodies and consensus sequences.

TABLE 3

$V_H$ CDRs of various antibodies and consensus sequences.

| | HC-CDR1 | HC-CDR2 | HC-CDR3 |
|---|---|---|---|
| 93B1B7 | DYEIH (SEQ ID NO: 1) | AIDPETGGTAYNQKFKG (SEQ ID NO: 5) | YDYVTY (SEQ ID NO: 9) |
| 94B12D3 | DYEIH (SEQ ID NO: 1) | AIDPETGGTAYNQKFKA (SEQ ID NO: 6) | YDYVSY (SEQ ID NO: 10) |
| 71G6G8 | DYEIH (SEQ ID NO: 1) | AIDPETGGTAYNQKFKG (SEQ ID NO: 5) | YDYVTY (SEQ ID NO: 9) |
| 56E5C10 | DFEMH (SEQ ID NO: 2) | AIDPETGGTAYNQKFTA (SEQ ID NO: 7) | YDYVSY (SEQ ID NO: 10) |
| 91F6D10 | DYEMH (SEQ ID NO: 3) | AIDPETGGTAYNQKFKA (SEQ ID NO: 6) | YDYVSY (SEQ ID NO: 10) |
| 51E8D4 | DFEIH (SEQ ID NO: 199) | AIDPETGGTAYNQKFKG (SEQ ID NO: 5) | YDYVSY (SEQ ID NO: 10) |
| 97C11D7 | DYEMH (SEQ ID NO: 3) | AIDPETGGSANNQKFKA (SEQ ID NO: 200) | YDYVSY (SEQ ID NO: 10) |
| 81B2B6 | DYEMH (SEQ ID NO: 3) | AIDPETGGTAYNQKFKA (SEQ ID NO: 6) | YDYVSY (SEQ ID NO: 10) |
| 84F2D5 | DFEIH (SEQ ID NO: 199) | AIDPETGGTAYNQKFKG (SEQ ID NO: 5) | YDYVSY (SEQ ID NO: 10) |
| 65B12C9 | SYWMH (SEQ ID NO: 4) | MIHPNSGSSNYNEKFKS (SEQ ID NO: 8) | DYDDEGFAY (SEQ ID NO: 11) |
| Consensus sequence | $DX_1EX_2H$ $X_1$ = Y or F, $X_2$ = M or I. (SEQ ID NO: 12) | $AIDPETGGX_3AX_4NQKFX_5X_6$ $X_3$ = T or S, $X_4$ = Y or N, $X_5$ = K or T, $X_6$ = A, G, or S. (SEQ ID NO: 13) | $YDYVX_7Y$ $X_7$ = T or S (SEQ ID NO: 14) |

TABLE 4

$V_L$ CDRs of various antibodies.

| | LC-CDR1 | LC-CDR2 | LC-CDR3 |
|---|---|---|---|
| 93B1B7 | KSSQSLLYSDGRTYLN (SEQ ID NO: 15) | LVSKLDS (SEQ ID NO: 18) | WQGTHLPHT (SEQ ID NO: 20) |
| 94B12D3 | KSSQSLLYSDGRTYLN (SEQ ID NO: 15) | LVSKLDS (SEQ ID NO: 18) | WQGTHLPHT (SEQ ID NO: 20) |
| 71G6G8 | KSSQSLLYSDGRTYLN (SEQ ID NO: 15) | LVSKLDS (SEQ ID NO: 18) | WQGTHLPHT (SEQ ID NO: 20) |

TABLE 4-continued

| $V_L$ CDRs of various antibodies. | | | |
|---|---|---|---|
| | LC-CDR1 | LC-CDR2 | LC-CDR3 |
| 56E5C10 | KSSQSLLYSDGRTYLN (SEQ ID NO: 15) | LVSKLDS (SEQ ID NO: 18) | WQGTHLPHT (SEQ ID NO: 20) |
| 91F6D10 | KSSQSLLYSDGRTYLN (SEQ ID NO: 15) | LVSKLDS (SEQ ID NO: 18) | WQGTHLPHT (SEQ ID NO: 20) |
| 51E8D4 | KSSQSLLYSDGKTYLN (SEQ ID NO: 16) | LVSKLDS (SEQ ID NO: 18) | WQGTHLPHT (SEQ ID NO: 20) |
| 97C11D7 | KSSQSLLYSDGRTYLN (SEQ ID NO: 15) | LVSKLDS (SEQ ID NO: 18) | WQGTHLPHT (SEQ ID NO: 20) |
| 81B2B6 | KSSQSLLYSDGRTYLN (SEQ ID NO: 15) | LVSKLDS (SEQ ID NO: 18) | WQGTHLPHT (SEQ ID NO: 20) |
| 84F2D5 | KSSQSLLYSDGKTYLN (SEQ ID NO: 16) | LVSKLDS (SEQ ID NO: 18) | WQGTHLPHT (SEQ ID NO: 20) |
| 65B12C9 | KASQSVSNDVA (SEQ ID NO: 17) | YASNRCT (SEQ ID NO: 19) | QQDYSSPWT (SEQ ID NO: 21) |

Example 3. Binding of Anti-Sclerostin Antibodies to Sclerostin as Measured by ELISA The ability of antibodies to specifically bind Sclerostin was determined by an ELISA capture assay. Plates were coated, in a 96-well half-area, with 100 μl/well of mouse His-tagged human Sclerostin (NCBI® reference No. is NP_079513.1) [0.5 μg/mg], in coating buffer (PBS, pH 7.4), and incubated at RT for one hour, or 4° C. overnight. The plates were washed once with 100 μl/well of washing solution (PBS containing 0.2% Tween™20, BIO-RAD). Plates were then incubated in blocking solution (PBS containing 1% BSA, 1% goat serum and 0.5% Tween™20; 100 μl/well) for one hour at room temperature (RT). Anti-Sclerostin antibodies at various concentrations (1000, 333.3, 111.1, 37.0, 12.3, 4.1, 1.4, 0.5, 0.15, 0.05 ng/ml), a positive control antibody Romosozumab or non-Sclerostin related IgG (human or rat IgG, negative control), were then added to each well in 20 μl/well of blocking solution, and plates were incubated at RT for one hour. NeutrAvidin™ HRP (Pierce, Catalog #31001) diluted in blocking solution (1:50, 000 dilution) was added at to each well (20 ml/well), and the plates were incubated at RT for one hour prior to three washes with 100 ml/well of washing solution. SuperSignal™ ELISA Femto (ThermoFisher Scientific, Catalog #37074) working solution was added to the plates (20 ml/well), and the signal was read using a luminometer at 425 nm.

As shown in Table 5 below, the tested anti-Sclerostin antibodies exhibited comparable or more advantageous $EC_{50}$ value as compared to that of Romosozumab. Specifically, 93B1B7 exhibited more advantageous $EC_{50}$ value as compared to that of Romosozumab.

TABLE 5

| The ELISA activity of anti-Sclerostin murine antibodies. | |
|---|---|
| Antibodies | $EC_{50}$ (nM) |
| 93B1B7 | 0.04 |
| 94B12D3 | 0.04 |

TABLE 5-continued

| The ELISA activity of anti-Sclerostin murine antibodies. | |
|---|---|
| Antibodies | $EC_{50}$ (nM) |
| 71G6G8 | 0.04 |
| 56E5C10 | 0.09 |
| 91F6D10 | 0.06 |
| 51E8D4 | 0.07 |
| 97C11D7 | 0.04 |
| 81B2B6 | 0.01 |
| 84F2D5 | 0.02 |
| 65B12C9 | 0.04 |
| Romosozumab | 0.11 |

Example 4. Binding Epitopes Identification for Anti-Sclerostin Antibody

Targeting the correct epitope is a critical step in selection of a monoclonal antibody to achieve the desired mechanism of action (Wilson, P C, 2012, *Nat. Rev. Immunol.* 12, 709-719). The synthetic peptide-based antibody production against B cell epitopes has been used broadly in developing therapeutic antibodies and vaccines for various diseases in the known art (Ben-Yedidia T., 1997, *Curr Opin Bio technol* 8:442-448; Bijker M S, 2007, *Expert Rev Vaccines* 6:591-603), with the specificity advantage of obtained antibodies being restricted to defined epitopes. The second loop on Sclerostin has been proven by NMR and crystallographic structures to interact directly with low-density lipoprotein receptor-related protein family member, e.g., LRP5 or LRP6, and blocks the interaction between LRPs and Wnt family members. Based on crystallographic structure of human Sclerostin in complex with LRP6 (Kim, J. 2020, *Nat. Commun.* 11:5357-5357), the loop tip containing the 'IGRGKWWR' motif (SEQ ID NO: 186) as shown in FIG. 1 was found to be the main binding determinant for binding of Sclerostin to the first propeller of LRP6.

Figure 2:
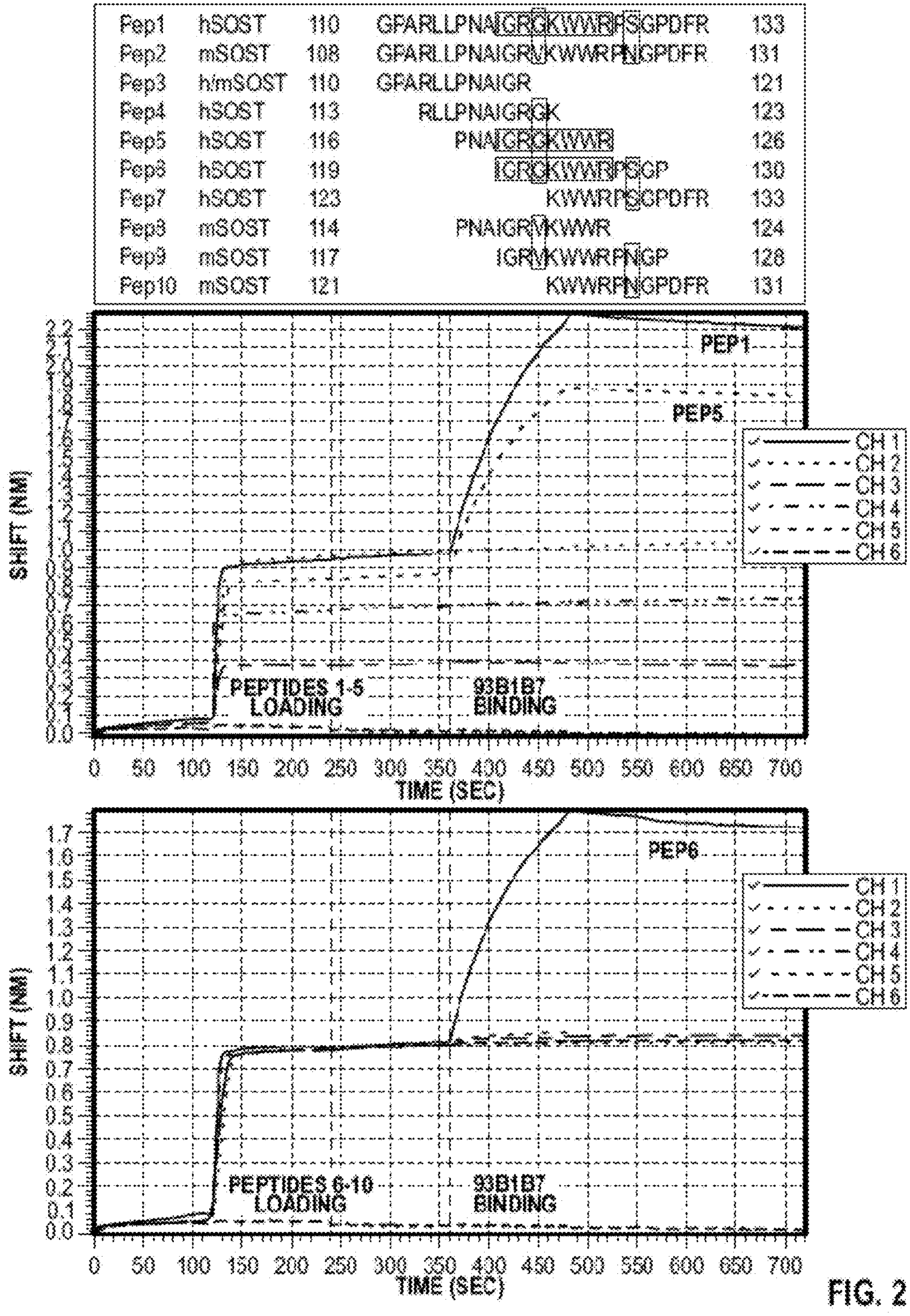
FIG. 2 shows Sclerostin epitope mapping of monoclonal Ab (mAb) 93B1B7 using synthetic peptide fragments (Pep1: SEQ ID NO: 185; Pep2: SEQ ID NO: 192; Pep3: SEQ ID NO: 193; Pep4: SEQ ID NO: 194; Pep5: SEQ ID NO: 187; Pep6: SEQ ID NO: 188; Pep7: SEQ ID NO: 195; Pep8: SEQ ID NO: 196; Pep9: SEQ ID NO: 197; Pep10: SEQ ID NO: 198) on the second loop of Sclerostin.
Figure 3:
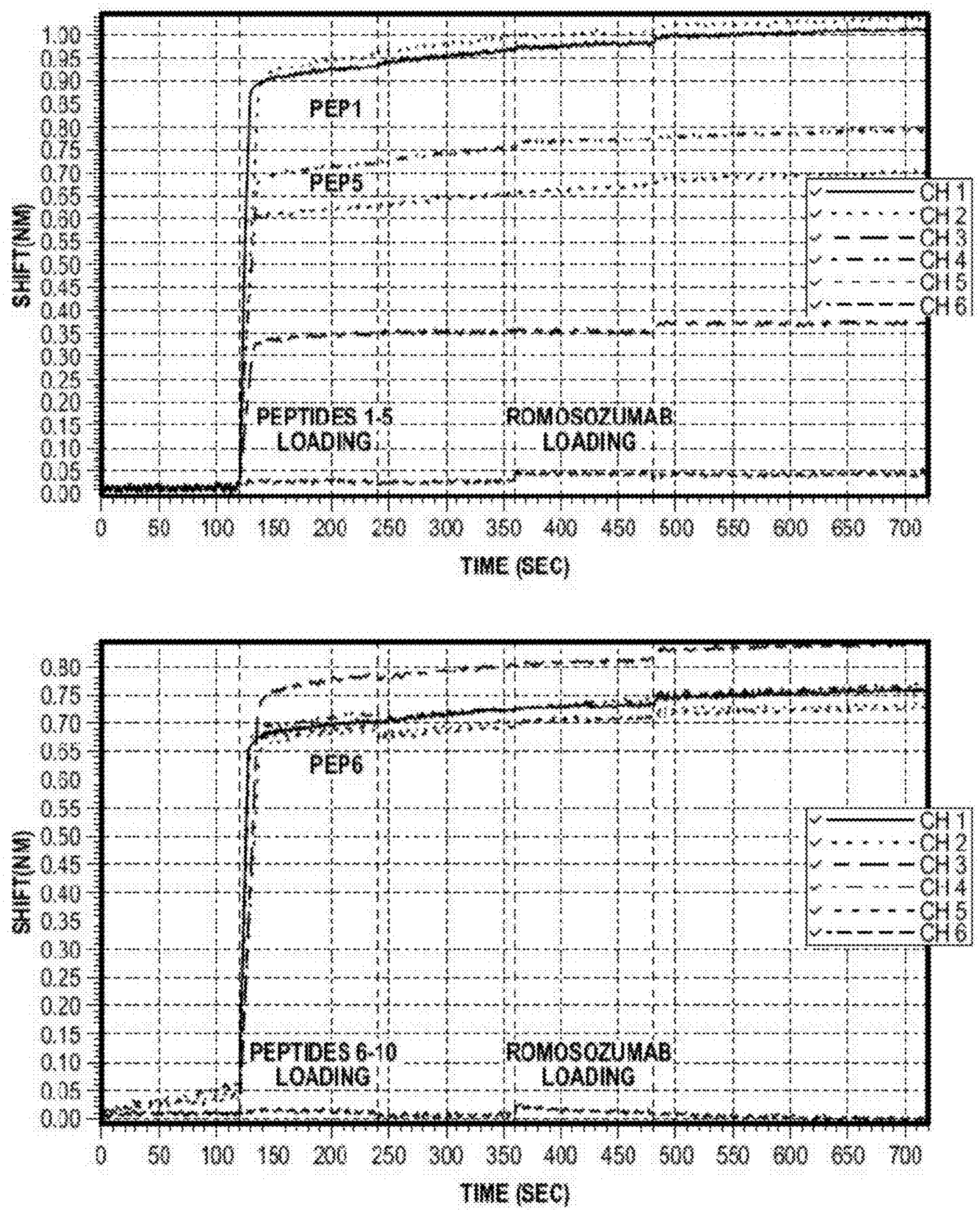
FIG. 3 shows that Romosozumab does not recognize peptides from the second loop of human Sclerostin bound by mAb 93B1B7.

Antibody 93B1B7's binding to chemically synthesized peptides comprising the sequences listed in FIG. 2 from the second loop of human and mouse sclerostin was tested with bio-layer interferometry approach (Gator®, Probe Life). The peptides were biotinylated (NHS-Biotin Reagents, Thermo, #21343) and immobilized on Streptavidin biosensor, using a 0.5 μg/ml solution. 5 μg/ml mAb 93B1B7 in kinetics buffer (PBS, pH 7.4, 0.05% Tween™-20, 0.2% BSA) was used as the analytes and binding sensorgrams are shown in FIG. 1. Pep1 (SEQ ID NO: 185), pep5 (SEQ ID NO:187) and (pep6 SEQ ID NO:188) that have the same 'IGRGKWWR' (SEQ ID NO: 186) motif on human Sclerostin were recognized by 93B1B7 with high affinity. In contrast, these peptides cannot be recognized by Romosozumab as show in FIG. 3.

Figure 4:
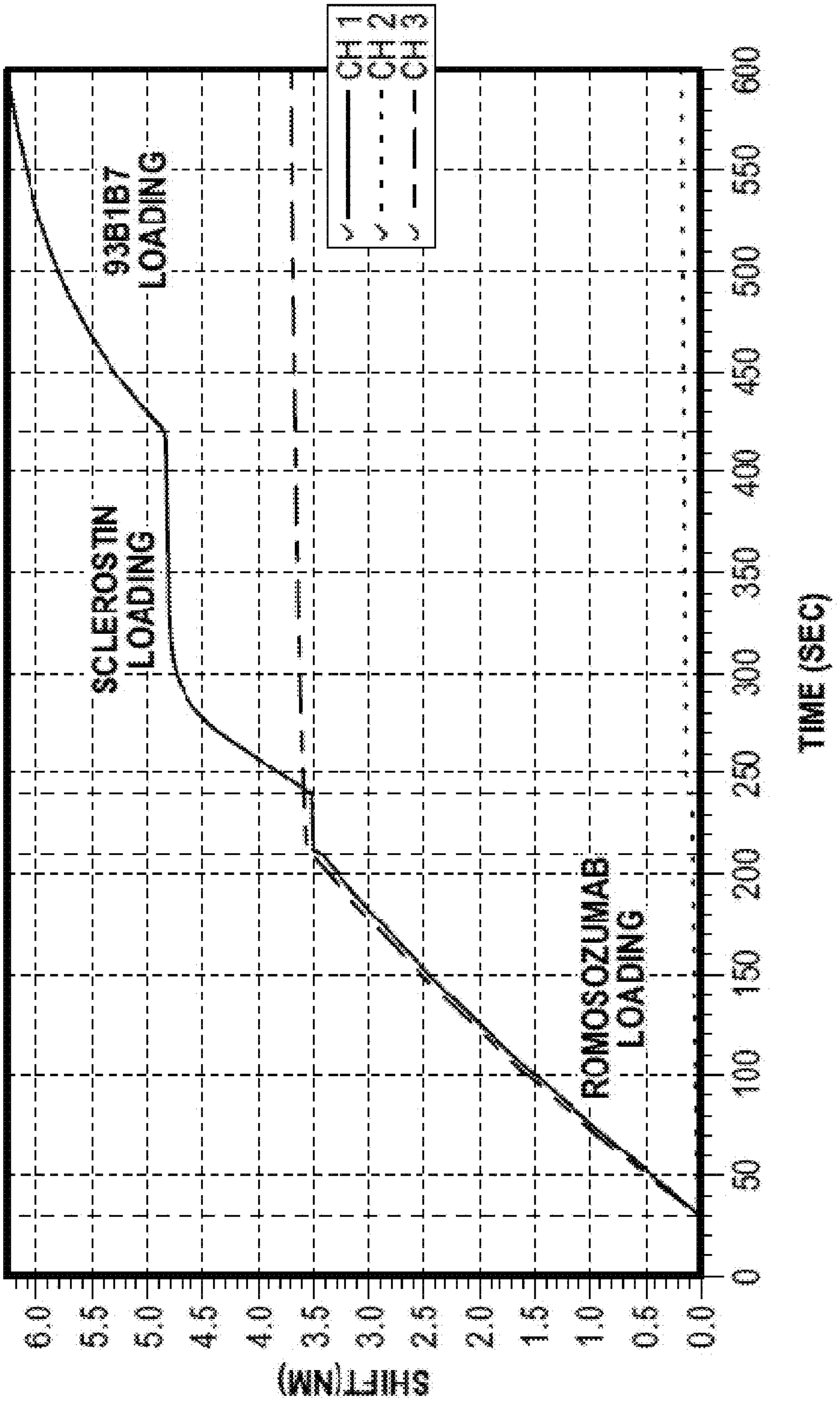
FIG. 4 shows that 93B1B7 and Romosozumab occupy different Sclerostin epitopes and do not cross-block each other's binding to sclerostin.

To further demonstrate that the binding epitope of 93B1B7 is completely different from that of Romosozumab, 5 g/ml Romosozumab was immobilized on anti-hFc probe, and 2 μg/ml human sclerostin and 5 μg/ml 93B1B7 in kinetics buffer (PBS, pH 7.4, 0.05% Tween™-20, 0.2% BSA) were sequentially added as analytes. The binding sensorgram is shown in FIG. 4 which indicating Romosozumab and 93B1B7 can bind sclerostin simultaneously by occupying different binding sites and thus do not cross-block each other. Therefore, the binding epitope ('IGRGKWWR' motif, SEQ ID NO: 186) are unique to the antibodies herein and do not overlap with that of Romosozumab.

The majority of anti-sclerostin antibodies discovered here antibodies have very similar binding activities and CDR sequences (see Tables 3 and 4), so we believe that they share the same specificity and binding epitopes. Thus, these antibodies discovered herein were further confirmed that they bind to a specific epitope on Sclerostin that has the 'IGRGKWWR' motif (SEQ ID NO: 186). This enables them to completely prevent the binding between Sclerostin and LRP6, thereby resulting in stronger Sclerostin neutralization than other anti-Sclerostin antibodies such as Romosozumab. This is consistent with the observation that the antibodies disclosed herein are more advantageous over Romosozumab in sclerostin binding and neutralizing activities as disclosed in the examples below.

Example 5. Humanization of Anti-Sclerostin Antibodies

Antibody 93B1B7 was humanized by grafting the complementarity determining regions (CDRs) onto human germline frameworks. The light chain germline acceptor sequence chosen was the human VK2 A19 V-region and VK1 O12 V-region plus JK4 J-region (V-BASE). The heavy chain germline acceptor sequence chosen was the human VH1 1-18 V-region plus JH4 J-region (V BASE). The CDR's grafted from the donor to the acceptor sequence are as defined by Kabat (Kabat et al. 1987), with the exception of CDR-H1 and H2 where the combined Chothia/Kabat definition is used. Genes encoding a full-length IgG4P antibody encompassing initial V-region sequences were constructed by an automated synthesis approach (Vanzyme Inc.), and modified to generate the final grafted versions by oligonucleotide directed mutagenesis. In order to retain full activity and maintain high thermostability, donor residues at positions 93 (Tyrosine) and 94 (Serine) of the humanized heavy chain (Kabat numbering) were retained, and acceptor residue at position 43 (Glutamine) was changed to Lysine which is more populated at this position. Similarly, donor residues at position 46 (Arginine) of the humanized light chains (Kabat numbering) were retained. In addition, one potential aspartate isomerization site in the light chain CDR L1 was removed by mutating Glycerin residue at position 30 to Serine. Humanized anti-Sclerostin antibodies hAb-1, hAb-2 and hAb-3 were generated. See Table 6 for their CDR, $V_H$ and $V_L$ sequences.

TABLE 6

CDR, $V_H$ and $V_L$ sequences of exemplary humanized anti-Sclerostin antibodies

| | hAb-1 | hAb-2 | hAb-3 |
|---|---|---|---|
| HC-CDR1 | DYEIH (SEQ ID NO: 1) | DYEIH (SEQ ID NO: 1) | DYEIH (SEQ ID NO: 1) |
| HC-CDR2 | AIDPETGGT AYNQKFKG (SEQ ID NO: 5) | AIDPETGGT AYNQKFKG (SEQ ID NO: 5) | AIDPETGGT AYNQKFKG (SEQ ID NO: 5) |
| HC-CDR3 | YDYVTY (SEQ ID NO: 9) | YDYVTY (SEQ ID NO: 9) | YDYVTY (SEQ ID NO: 9) |
| LC-CDR1 | KSSQSLLYS DGRTYLN (SEQ ID NO: 15) | RSSQSLLYSD GRTYLN (SEQ ID NO: 85) | RSSQSLLYSDSRTYLN (SEQ ID NO: 86) |
| LC-CDR2 | LVSKLDS (SEQ ID NO: 18) | LVSKLDS (SEQ ID NO: 18) | LVSKLDS (SEQ ID NO: 18) |
| LC-CDR3 | WQGTHLPHT (SEQ ID NO: 20) | WQGTHLPHT (SEQ ID NO: 20) | WQGTHLPHT (SEQ ID NO: 20) |
| $V_H$ | SEQ ID NO: 87 | SEQ ID NO: 87 | SEQ ID NO: 87 |
| $V_L$ | SEQ ID NO: 88 | SEQ ID NO: 89 | SEQ ID NO: 90 |

Example 6. Binding Kinetics of Humanized Anti-Sclerostin Antibodies for Human and Cynomolgus Monkey Sclerostin Measured by Bio-Layer Interferometry (BLI) Assay The binding affinity of humanized anti-Sclerostin antibodies to human and cynomolgus monkey Sclerostin were determined with bio-layer interferometry using a Gator® instrument (Probe Life). Antibodies were immobilized on an anti-hFc biosensor, using a 5 μg solution. Serial dilutions of human Sclerostin and cynomolgus monkey Sclerostin from 4 μg/ml by two folds in kinetics buffer (PBS, pH 7.4, 0.05% Tween™-20, 0.2% BSA, 10 μM biotin) were used as the analytes. Affinity ($K_D$) and kinetic parameters ($K_{on}$ and $K_{off}$) were calculated from a global fit (1:1) of the data using the Gator® software.

The results were shown in Table 7 as below. The humanized antibodies hAb-1 and hAb-2 show higher affinities for human and Cynomolgus monkey Sclerostins as compared to reference Romosozumab.

TABLE 7

The binding kinetics of humanized antibody against Sclerostin of different species.

| | Human | | | Cynomolgus Monkey | | |
|---|---|---|---|---|---|---|
| Antibodies | $K_{on}$ (1/Ms) | $K_{off}$ (1/s) | $K_D$ (M) | $K_{on}$ (1/Ms) | $K_{off}$ (1/s) | $K_D$ (M) |
| 93B1B7 | $1.0 \times 10^{6}$ | $8.4 \times 10^{-5}$ | $5.1 \times 10^{-11}$ | $2.2 \times 10^{6}$ | $6.5 \times 10^{-5}$ | $1.8 \times 10^{-11}$ |
| hAb-1 | $7.3 \times 10^{5}$ | $3.0 \times 10^{-4}$ | $4.1 \times 10^{-10}$ | $1.28 \times 10^{6}$ | $2.29 \times 10^{-4}$ | $1.8 \times 10^{-10}$ |
| hAb-2 | $7.8 \times 10^{5}$ | $2.0 \times 10^{-4}$ | $2.4 \times 10^{-10}$ | $1.54 \times 10^{6}$ | $8.06 \times 10^{-5}$ | $5.5 \times 10^{-11}$ |
| Romosozumab | $1.4 \times 10^{6}$ | $2.8 \times 10^{-4}$ | $7.8 \times 10^{-10}$ | $7.55 \times 10^{5}$ | $2.39 \times 10^{-4}$ | $3.5 \times 10^{-10}$ |

Example 7. Sclerostin-Neutralization Activity of Anti-Sclerostin Antibodies in HEK293/TCF/LEF/Wnt1 Cells The antibodies were capable of neutralizing Sclerostin and blocking Wnt1 induced TCF/LEF luciferase activity, as determined in an HEK293 based assay.

The Wnt proteins are a family of secreted glycoproteins that are critical regulators of osteoblast differentiation and activity in both mice and humans. Wnt signals are transduced by a family of seven-pass transmembrane G-protein coupled receptors of the frizzled (Fzd) family, and a coreceptor of the arrow/LRP family, such as LRP5 and LRP6, or a RYK or ROR transmembrane tyrosine kinase. The binding of a given Wnt to a Fzd receptor and coreceptor activates multiple distinct intracellular signaling cascades, historically divided into the canonical β-catenin-dependent pathway and noncanonical β-catenin-independent pathways. β-catenin is an important transcriptional coactivator that regulates gene transcription in response to Wnt signaling. The binding of Wnt to a Fzd receptor complex results in phosphorylation of the LRP5/6 complex, and subsequently stabilizes β-catenin in cytoplasm. Stabilized β-catenin is then translocated into the nucleus and interacts with the Lymphoid-enhancing factor/T-cell factor (LEF/TCF) family of high mobility group (HMG)-type transcription factors, to stimulate expression of target genes.

In the study of Wnt signaling pathway antagonists and its antibody blockades, the cell line, HEK293/TCF/LEF/Wnt1, was obtained from Askgene (Askgene, CA). The inhibitory activities of Wnt signaling antagonists, such as Sclerostin and DKK1, were analyzed using this HEK293 cell line expressing a TCF/LEF firefly luciferase reporter gene. Addition of Sclerostin or DKK1 antagonizes the Wnt1 signal, resulting in diminished luciferase activity. Conversely, addition of Sclerostin or DKK1 antibody will block the diminished signal and restore the luciferase activities. Upon arrival, cells were cultured in RPMI1640 culture medium with L-glutamine (Life Technologies, CA), containing 10% fetal bovine serum (FBS), non-essential amino acids, sodium pyruvate, 2-merceptoethanol, 1% penicillin/streptomycin, 400 μg/ml G418, and 2 μg/ml puromycin. Cells were harvested and plated into a white 96-well plate, at a concentration of 30,000 cells/well.

When testing the inhibitory effect of the antagonist, the culture medium was removed and 50 μl of assay medium (culture medium without G418 and puromycin) containing 10 mM LiCl, was added into each well. The tested Sclerostin and DKK1 proteins were serial diluted, and equal amount of antagonist was added into the assay plate and incubated for 6 hours at 37° C. with 5% $CO_2$. Then, 100 μl/well of One-Step firefly luciferase (Pierce, CA) reagent was added, and the luciferase activity was measured using a BioTek® Gen5 luminescence microplate reader (Winooski, VT). When testing the neutralization activities of the antibodies, a serial dilution of the test antibodies and control antibodies was made in assay medium. A fixed amount of either Sclerostin or DKK1 protein was added and incubated for 15 minutes. Then, 50 μl of the medium was transferred into assay plate, incubated for 6 hours at 37° C. with 5% $CO_2$, and analyzed using BioTek® Gen5 luminescence microplate reader.

Results were shown in Table 8 below. As shown, all murine anti-Sclerostin antibodies except 65B12C9 exhibited comparable or more advantageous $EC_{50}$ value as compared to that of Romosozumab. The three humanized antibodies, hAb-1, hAb-2 and hAb-3 exhibited more advantageous $EC_{50}$ value than that of Romosozumab.

TABLE 8

The Sclerostin-neutralisation activity for murine and humanized antibodies in HEK293/TCF/LEF/Wnt1 cells

| Antibodies | $EC_{50}$ (nM) |
|---|---|
| 93B1B7 | 57.9 |
| 94B12D3 | 62.8 |
| 71G6G8 | 67.41 |
| 56E5C10 | 64.2 |
| 91F6D10 | 60.58 |
| 51E8D4 | 63.35 |
| 97C11D7 | 55.36 |
| 81B2B6 | 59.61 |
| 84F2D5 | 59.42 |
| 65B12C9 | 152.5 |
| hAb-1 | 13.89 |
| hAb-2 | 14.9 |

TABLE 8-continued

| The Sclerostin-neutralisation activity for murine and humanized antibodies in HEK293/TCF/LEF/Wnt1 cells | |
|---|---|
| Antibodies | $EC_{50}$ (nM) |
| hAb-3 | 15.13 |
| Romosozumab | 42.31 |

Example 8: Solubility and Stability of Humanized Anti-Sclerostin Antibodies

The humanized anti-human Sclerostin_antibody hAb-1 and hAb-2 described in this invention and the reference antibody Romosozumab were accessed for precipitation at increasing concentration. The starting concentration was 10 mg/ml in PBS buffer at pH 7.4. The cells were centrifuged at 4 degrees 4000 rpm in an ultrafiltration concentrating tube (Millipore), and the centrifugation was stopped every 5-10 minutes and the antibody concentration was sampled until the antibody concentration reached 30 mg/ml and 90 mg/ml. The samples were stored at 4° C. for 14 days and visually observed for precipitation. The antibodies described in this invention remained clear solution at as high as 90 mg/ml, which reference antibody Romosozumab became precipitated and turbid, indicating hAb-1 and hAb-2 are more stable and soluble than Romosozumab in PBS buffer at pH7.4. This result suggests that the antibodies described in this invent can be stable in high concentration formulations like 90 mg/ml.

| Antibody | Concentration (mg/ml) | Day 14 |
|---|---|---|
| hAb-1 | 10 | Clear solution |
| | 30 | Clear solution |
| | 90 | Clear solution |
| hAb-2 | 10 | Clear solution |
| | 30 | Clear solution |
| | 90 | Clear solution |

-continued

| Antibody | Concentration (mg/ml) | Day 14 |
|---|---|---|
| Romosozumab | 10 | Clear solution |
| | 30 | Clear solution |
| | 90 | Sedimentation and turbid solution observed |

Example 9. Generation of Bispecific Antibodies

Bispecific antibodies that target both Sclerostin and DKK1 or RANKL were generated. See Tables 9 and 10 for sequences of the exemplary antibodies that target DKK1 or RANKL.

TABLE 9

CDR Sequences of exemplary anti-DKK1 antibodies

| | $11H10-V_H44V_L32$ (11H10) | RH2-18 | 71G6G8 |
|---|---|---|---|
| HC-CDR1 | GFTFSDYAMA (SEQ ID NO: 42) | GYTFTDYYIH (SEQ ID NO: 48) | GFTFSSYAIS (SEQ ID NO: 54) |
| HC-CDR2 | THIYDGSSTYYR DSVKG (SEQ ID NO: 43) | WIHSNSGAT TYAQKFQA (SEQ ID NO: 49) | SVSGTGLGFQTY YPDSVKG (SEQ ID NO: 55) |
| HC-CDR3 | GLGIATDYFDY (SEQ ID NO: 44) | EDY (SEQ ID NO: 50) | SLENYAFDY (SEQ ID NO: 56) |
| LC-CDR1 | LASEDIYSDLA (SEQ ID NO: 45) | TGSSNIGAGYDVH (SEQ ID NO: 51) | RASESVDDFGISFIN (SEQ ID NO: 57) |
| LC-CDR2 | NANSLQN (SEQ ID NO: 46) | GYSNRPS (SEQ ID NO: 52) | AGSKQGS (SEQ ID NO: 58) |
| LC-CDR3 | QQYNNYPPT (SEQ ID NO: 47) | AGSKQGS (SEQ ID NO: 58) | QQLKEVPPT (SEQ ID NO: 59) |

TABLE 10

CDR Sequences of exemplary anti-RANKL antibody

| | Denosumab |
|---|---|
| HC-CDR1 | GFTFSSYAMS (SEQ ID NO: 66) |
| HC-CDR2 | GITGSGGSTYYADSVKG (SEQ ID NO: 67) |
| HC-CDR3 | DPGTTVIMSWFDP (SEQ ID NO: 68) |
| LC-CDR1 | RASQSVRGRYLA (SEQ ID NO: 69) |
| LC-CDR2 | GASSRAT (SEQ ID NO: 70) |
| LC-CDR3 | QQYGSSPRT (SEQ ID NO: 71) |

Specifically, the following Sclerostin/DKK1 and Sclerostin/RANKL pairings were generated: hAb-1×11H10-$V_H44V_L32$, hAb-2×11H10-$V_H44V_L32$, hAb-1×Denosumab, hAb-2×Denosumab.

Figure 5:
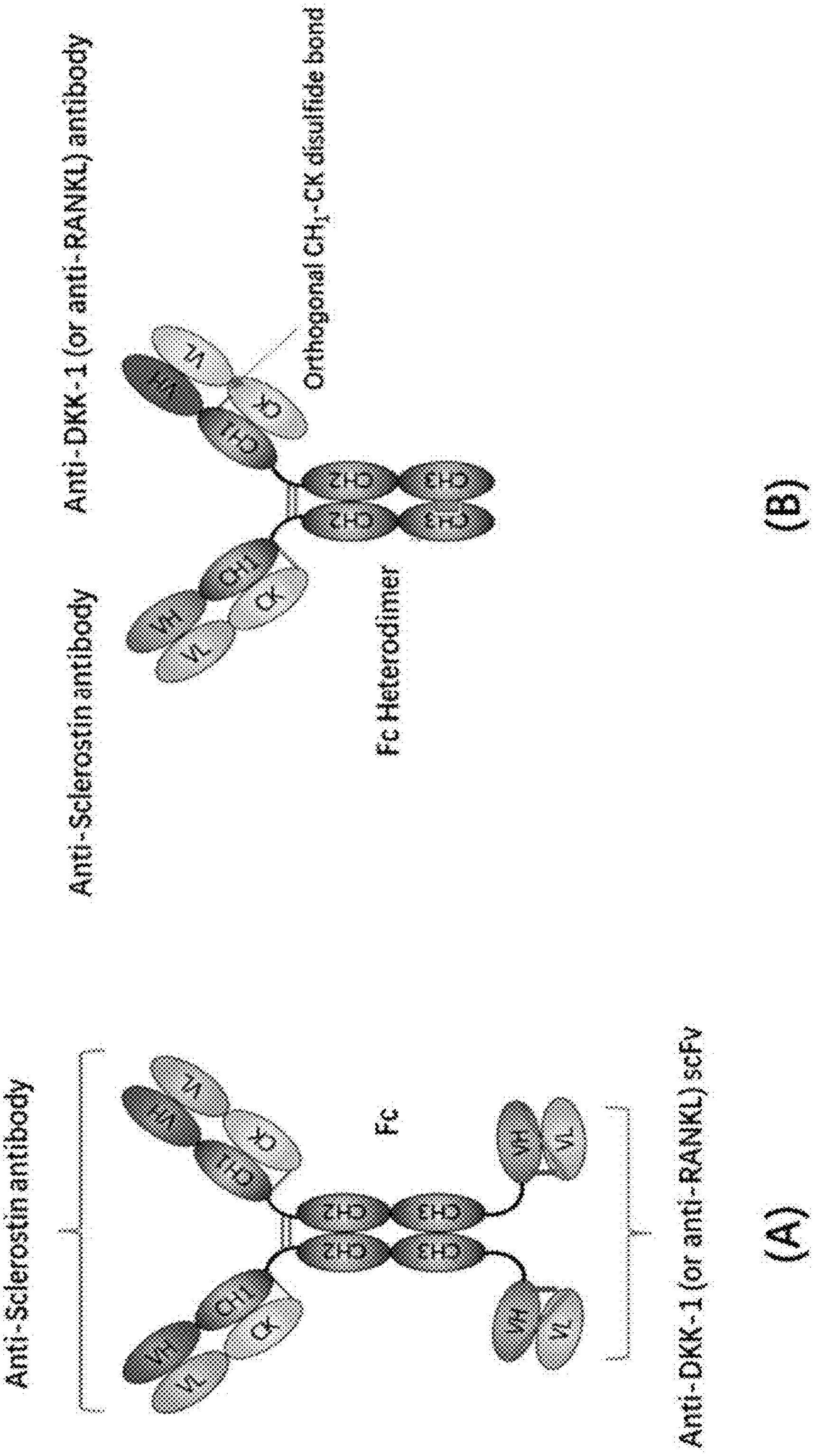
FIG. 5 shows schematic diagrams of exemplary bispecific antibody structures.

In one embodiment (see (A) of FIG. 5), anti-DKK1 11H10-$V_H44V_L32$ (or anti-RANKL Denosumab) Fv domain was transformed into scFvs with two different orientations of $V_H$ and $V_L$, linked by a $(GGGGS)_4$ (SEQ ID NO: 77) linker. There are mutations like G100C in $V_H$ and G44C in $V_L$ to facilitate correct assembly of scFvs. Two anti-DKK1 (or anti-RANKL) scFvs are linked to each of two IgG heavy chain C-termini of anti-Sclerostin humanized antibodies respectively by one GGGGSGGGGSGGGGS (SEQ ID NO: 76) linker to form bispecific of IgG-scFv.

In another embodiment (see (B) of FIG. 5), anti-Sclerostin antibodies and anti-DKK1 11H10-$V_H$44$V_L$32 (or anti-RANKL Denosumab) were transformed into 'Knob-into-Hole' bispecific antibodies with asymmetric IgG structure. The CL domain of anti-DKK1 11H10-$V_H$44$V_L$32 (or anti-RANKL Denosumab) contains mutations of S176C and C214S, and the CH1 domain contains mutations like F170C and C131S to form orthogonal CH1-CK disulfide bond to enable light chains correct paring.

Table 11 below lists format and sequences of various anti-Sclerostin bispecific antibodies.

TABLE 11

Anti-Sclerostin bispecific antibodies

| Bispecific antibodies | Format | Heavy chain (from N-terminus to C-terminus) | Light chain (from N-terminus to C-terminus) |
|---|---|---|---|
| BAP0017 | Anti-Sclerostin scFv ($V_H$-$V_L$) fused to C-terminus of heavy chains of anti-DKK1 full length antibody | 11H10 $V_H$2-CH1-CH2-CH3-L1-93B1B7 $V_H$-L2-93B1B7 $V_L$ (SEQ ID NO: 91) | 11H10 $V_L$2-CL (SEQ ID NO: 93) |
| BAP0018 | Anti-Sclerostin scFv ($V_L$-$V_H$) fused to C-terminus of heavy chains of anti-DKK1 full length antibody | 11H10 $V_H$2-CH1-CH2-CH3-L1-93B1B7 $V_L$-L2-93B1B7 $V_H$ (SEQ ID NO: 92) | 11H10 $V_L$2-CL (SEQ ID NO: 93) |
| BAP0019 | Anti-DKK1 scFv ($V_H$-$V_L$) fused to C-terminus of heavy chains of anti-Sclerostin full length antibody | 93B1B7 $V_H$-CH1-CH2-CH3-L1-11H10 $V_H$2-L2-11H10 $V_L$2 (SEQ ID NO: 94) | 93B1B7 $V_L$-CL (SEQ ID NO: 96) |
| BAP0020 | Anti-DKK1 scFv ($V_L$-$V_H$) fused to C-terminus of heavy chains of anti-Sclerostin full length antibody | 93B1B7 $V_H$-CH1-CH2-CH3-L1-11H10 $V_L$2-L2-11H10 $V_H$2 (SEQ ID NO: 95) | 93B1B7 $V_L$-CL (SEQ ID NO: 96) |
| BAP0021 | Anti-Sclerostin scFv ($V_H$-$V_L$) fused to N-terminus of heavy chains of anti-DKK1 full length antibody | 93B1B7 $V_H$-L1-93B1B7 $V_L$-L2-11H10 $V_H$2-CH1-CH2-CH3 (SEQ ID NO: 97) | 11H10 $V_L$2-CL (SEQ ID NO: 99) |
| BAP0022 | Anti-Sclerostin scFv ($V_L$-$V_H$) fused to N-terminus of heavy chains of anti-DKK1 full length antibody | 93B1B7 $V_L$-L1-93B1B7 $V_H$-L2-11H10 $V_H$2-CH1-CH2-CH3 (SEQ ID NO: 98) | 11H10 $V_L$2-CL (SEQ ID NO: 99) |
| BAP0023 | Anti-DKK1 scFv ($V_H$-$V_L$) fused to N-terminus of heavy chains of anti-Sclerostin full length antibody | 11H10 $V_H$2-L1-11H10 $V_L$2-L2-93B1B7 $V_H$-CH1-CH2-CH3 (SEQ ID NO: 100) | 93B1B7 $V_L$-CL (SEQ ID NO: 102) |
| BAP0024 | Anti-DKK1 scFv ($V_L$-$V_H$) fused to N-terminus of heavy chains of anti-Sclerostin full length antibody | 11H10 $V_L$2-L1-11H10 $V_H$2-L2-93B1B7 $V_H$-CH1-CH2-CH3 (SEQ ID NO: 101) | 93B1B7 $V_L$-CL (SEQ ID NO: 102) |
| BAP0025 | Anti-Sclerostin scFv ($V_H$-$V_L$) fused to N-terminus of light chains of anti-DKK1 full length antibody | 11H10 $V_H$2-CH1-CH2-CH3 (SEQ ID NO: 103) | 93B1B7 $V_H$-L1-93B1B7 $V_L$-L2-11H10 $V_L$2-CL (SEQ ID NO: 104) |
| BAP0026 | Anti-Sclerostin scFv ($V_L$-$V_H$) fused to N-terminus of light chains of anti-DKK1 full length antibody | 11H10 $V_H$2-CH1-CH2-CH3 (SEQ ID NO: 103) | 93B1B7 $V_L$-L1-93B1B7 $V_H$-L2-11H10 $V_L$2-CL (SEQ ID NO: 105) |
| BAP0027 | Anti-DKK1 scFv ($V_H$-$V_L$) fused to N-terminus of light chains of anti-Sclerostin full length antibody | 93B1B7 $V_H$-CH1-CH2-CH3 (SEQ ID NO: 106) | 11H10 $V_H$2-L1-11H10 $V_L$2-L2-93B1B7 $V_L$-CL (SEQ ID NO: 107) |
| BAP0028 | Anti-DKK1 scFv ($V_L$-$V_H$) fused to N-terminus of light chains of anti-Sclerostin full length antibody | 93B1B7 $V_H$-CH1-CH2-CH3 (SEQ ID NO: 106) | 11H10 $V_L$2-L1-11H10 $V_H$2-L2-93B1B7 $V_L$-CL (SEQ ID NO: 108) |
| BAP0029 | Anti-Sclerostin scFv ($V_H$-$V_L$) fused to C-terminus of light chains of anti-DKK1 full length antibody | 11H10 $V_H$2-CH1-CH2-CH3 (SEQ ID NO: 109) | 11H10 $V_L$2-CL-L1-93B1B7 $V_H$-L2-93B1B7 $V_L$ (SEQ ID NO: 110) |

TABLE 11-continued

| Anti-Sclerostin bispecific antibodies | | | |
|---|---|---|---|
| Bispecific antibodies | Format | Heavy chain (from N-terminus to C-terminus) | Light chain (from N-terminus to C-terminus) |
| BAP0030 | Anti-Sclerostin scFv ($V_L$-$V_H$) fused to C-terminus of light chains of anti-DKK1 full length antibody | 11H10 $V_H$2-CH1-CH2-CH3 (SEQ ID NO: 109) | 11H10 $V_L$2-CL-L1-93B1B7 $V_L$-L2-93B1B7 $V_H$ (SEQ ID NO: 111) |
| BAP0031 | Anti-DKK1 scFv ($V_H$-$V_L$) fused to C-terminus of light chains of anti-Sclerostin full length antibody | 93B1B7 $V_H$-CH1-CH2-CH3 (SEQ ID NO: 112) | 93B1B7 $V_L$-CL-L1-11H10 $V_H$2-L2-11H10 $V_L$2 (SEQ ID NO: 113) |
| BAP0032 | Anti-DKK1 scFv ($V_L$-$V_H$) fused to C-terminus of light chains of anti-Sclerostin full length antibody | 93B1B7 $V_H$-CH1-CH2-CH3 (SEQ ID NO: 112) | 93B1B7 $V_L$-CL-L1-11H10 $V_L$2-L2-11H10 $V_H$2 (SEQ ID NO: 114) |
| BAP0033 | Anti-Sclerostin scFv ($V_L$-$V_H$) fused to C-terminus of heavy chains of anti-DKK1 full length antibody | 11H10 $V_H$-CH1-CH2-CH3-L1-hAb2 $V_L$2-L2-hAb $V_H$2 (SEQ ID NO: 115) | 11H10 $V_L$-CL (SEQ ID NO: 119) |
| BAP0034 | Anti-Sclerostin scFv ($V_H$-$V_L$) fused to C-terminus of heavy chains of anti-DKK1 full length antibody | 11H10 $V_H$-CH1-CH2-CH3-L1-hAb $V_H$2-L2-hAb2 $V_L$2 (SEQ ID NO: 116) | 11H10 $V_L$3-CL (SEQ ID NO: 119) |
| BAP0035 | Anti-Sclerostin scFv ($V_L$-$V_H$) fused to C-terminus of heavy chains of anti-DKK1 full length antibody | 11H10 $V_H$-CH1-CH2-CH3-L1-hAb1 $V_L$2-L2-hAb $V_H$2 (SEQ ID NO: 117) | 11H10 $V_L$3-CL (SEQ ID NO: 119) |
| BAP0036 | Anti-Sclerostin scFv ($V_H$-$V_L$) fused to C-terminus of heavy chains of anti-DKK1 full length antibody | 11H10 $V_H$-CH1-CH2-CH3-L1-hAb $V_H$2-L2-hAb1 $V_L$2 (SEQ ID NO: 118) | 11H10 $V_L$3-CL (SEQ ID NO: 119) |
| BAP0037 | Anti-DKK1 scFv ($V_H$-$V_L$) fused to C-terminus of heavy chains of anti-Sclerostin full length antibody | hAb $V_H$-CH1-CH2-CH3-L1-11H10 $V_H$3-L2-11H10 $V_L$3 (SEQ ID NO: 120) | hAb-2 $V_L$-CL (SEQ ID NO: 122) |
| BAP0038 | Anti-DKK1 scFv ($V_L$-$V_H$) fused to C-terminus of heavy chains of anti-Sclerostin full length antibody | hAb $V_H$-CH1-CH2-CH3-L1-11H10 $V_L$3-L2-11H10 $V_H$3 (SEQ ID NO: 121) | hAb-2 $V_L$-CL (SEQ ID NO: 122) |
| BAP0039 | Anti-DKK1 scFv ($V_H$-$V_L$) fused to C-terminus of heavy chains of anti-Sclerostin full length antibody | hAb $V_H$-CH1-CH2-CH3-L1-11H10 $V_H$3-L2-11H10 $V_L$3 (SEQ ID NO: 123) | hAb-1 $V_L$-CL (SEQ ID NO: 125) |
| BAP0040 | Anti-DKK1 scFv ($V_L$-$V_H$) fused to C-terminus of heavy chains of anti-Sclerostin full length antibody | hAb $V_H$-CH1-CH2-CH3-L1-11H10 $V_L$3-L2-11H10 $V_H$3 (SEQ ID NO: 124) | hAb-1 $V_L$-CL (SEQ ID NO: 125) |
| BAP0050 | Anti-Sclerostin scFv ($V_L$-$V_H$) fused to C-terminus of heavy chains of anti-RANKL full length antibody | Denosumab $V_H$-CH1-CH2-CH3-L1-hAb-2 $V_L$2-L2-hAb $V_H$2 (SEQ ID NO: 126) | Denosumab $V_L$-CL (SEQ ID NO: 129) |
| BAP0051 | Anti-Sclerostin scFv ($V_L$-$V_H$) fused to N-terminus of heavy chains of anti-RANKL full length antibody | hAb-2 $V_L$2-L1-hAb $V_H$2-L2-Denosumab $V_H$-CH1-CH2-CH3 (SEQ ID NO: 127) | Denosumab $V_L$-CL (SEQ ID NO: 129) |
| BAP0052 | Anti-Sclerostin scFv ($V_L$-$V_H$) fused to C-terminus of heavy chains of anti-RANKL full length antibody | Denosumab $V_H$-CH1-CH2-CH3-L1-hAb-2 $V_L$2-L2-hAb $V_H$2 (SEQ ID NO: 128) | Denosumab $V_L$-CL (SEQ ID NO: 129) |
| BAP0053 | Anti-Sclerostin scFv ($V_L$-$V_H$) fused to C-terminus of light chains of anti-RANKL full length antibody | Denosumab $V_H$-CH1-CH2-CH3 (SEQ ID NO: 133) | Denosumab $V_L$-CL-L1-hAb-2 $V_L$2-L2-hAb $V_H$2 (SEQ ID NO: 130) |
| BAP0054 | Anti-Sclerostin scFv ($V_L$-$V_H$) fused to N-terminus of light chains of anti-RANKL full length antibody | Denosumab $V_H$-CH1-CH2-CH3 (SEQ ID NO: 133) | hAb-2 $V_L$2-L1-hAb $V_H$2-L2-Denosumab $V_L$-CL (SEQ ID NO: 131) |

TABLE 11-continued

| Anti-Sclerostin bispecific antibodies | | | |
|---|---|---|---|
| Bispecific antibodies | Format | Heavy chain (from N-terminus to C-terminus) | Light chain (from N-terminus to C-terminus) |
| BAP0055 | Anti-Sclerostin scFv ($V_L$-$V_H$) fused to C-terminus of light chains of anti-RANKL full length antibody | Denosumab $V_H$-CH1-CH2-CH3 (SEQ ID NO: 133) | Denosumab $V_L$-CL-L1-hAb-1 $V_L2$-L2-hAb $V_H2$ (SEQ ID NO: 132) |
| BAP0041 | A full length antibody having a) first pair of $V_H$-$V_L$ (a first Fab) recognizing Sclerostin and b) second pair of $V_H$-$V_L$ (a second Fab) recognizing DKK1 | 1st heavy chain: 93B1B7 $V_H$-CH1-CH2-CH3 (SEQ ID NO: 134) 2nd heavy chain: 11H10 $V_H2$-CH1-CH2-CH3 (SEQ ID NO: 136) | 1st light chain: 93B1B7 $V_L$-CL (SEQ ID NO: 135) 2nd light chain: 11H10 $V_L2$-CL (SEQ ID NO: 137) |
| BAP0042 | A full length antibody having a) first pair of $V_H$-$V_L$ (a first Fab) recognizing Sclerostin and b) second pair of $V_H$-$V_L$ (a second Fab) recognizing DKK1 | 1st heavy chain: 93B1B7 $V_H$-CH1-CH2-CH3 (SEQ ID NO: 134) 2nd heavy chain: 11H10 $V_H2$-CH1-CH2-CH3 (SEQ ID NO: 138) | 1st light chain: 93B1B7 $V_L$-CL (SEQ ID NO: 135) 2nd light chain: 11H10 $V_L2$-CL (SEQ ID NO: 139) |
| BAP0043 | A full length antibody having a) first pair of $V_H$-$V_L$ (a first Fab) recognizing Sclerostin and b) second pair of $V_H$-$V_L$ (a second Fab) recognizing DKK1 | 1st heavy chain: 93B1B7 $V_H$-CH1-CH2-CH3 (SEQ ID NO: 134) 2nd heavy chain: 11H10 $V_H2$-CH1-CH2-CH3 (SEQ ID NO: 140) | 1st light chain: 93B1B7 $V_L$-CL (SEQ ID NO: 135) 2nd light chain: 11H10 $V_L2$-CL (SEQ ID NO: 141) |
| BAP0044 | A full length antibody having a) first pair of $V_H$-$V_L$ (a first Fab) recognizing Sclerostin and b) second pair of $V_H$-$V_L$ (a second Fab) recognizing DKK1 | 1st heavy chain: 93B1B7 $V_H$-CH1-CH2-CH3 (SEQ ID NO: 134) 2nd heavy chain: 11H10 $V_H2$-CH1-CH2-CH3 (SEQ ID NO: 142) | 1st light chain: 93B1B7 $V_L$-CL (SEQ ID NO: 135) 2nd light chain: 11H10 $V_L2$-CL (SEQ ID NO: 143) |
| BAP0045 | A full length antibody having a) first pair of $V_H$-$V_L$ (a first Fab) recognizing Sclerostin and b) second pair of $V_H$-$V_L$ (a second Fab) recognizing DKK1 | 1st heavy chain: 93B1B7 $V_H$-CH1-CH2-CH3 (SEQ ID NO: 134) 2nd heavy chain: 11H10 $V_H2$-CH1-CH2-CH3 (SEQ ID NO: 144) | 1st light chain: 93B1B7 $V_L$-CL (SEQ ID NO: 135) 2nd light chain: 11H10 $V_L2$-CL (SEQ ID NO: 145) |
| BAP0061 | A full length antibody having a) first pair of $V_H$-$V_L$ (a first Fab) recognizing Sclerostin and b) second pair of $V_H$-$V_L$ (a second Fab) recognizing DKK1 | 1st heavy chain: hAb $V_H$-CH1-CH2-CH3 (SEQ ID NO: 146) 2nd heavy chain: 11H10 $V_H$-CH1-CH2-CH3 (SEQ ID NO: 148) | 1st light chain: hAb-2 $V_L$-CL (SEQ ID NO: 147) 2nd light chain: 11H10 $V_L$-CL SEQ ID NO: 149) |
| BAP0062 | A full length antibody having a) first pair of $V_H$-$V_L$ (a first Fab) recognizing Sclerostin and b) second pair of $V_H$-$V_L$ (a second Fab) recognizing DKK1 | 1st heavy chain: hAb $V_H$-CH1-CH2-CH3 (SEQ ID NO: 146) 2nd heavy chain: 11H10 $V_H$-CH1-CH2-CH3 (SEQ ID NO: 150) | 1st light chain: hAb-2 $V_L$-CL (SEQ ID NO: 147) 2nd light chain: 11H10 $V_L$-CL SEQ ID NO: 151) |
| BAP0063 | A full length antibody having a) first pair of $V_H$-$V_L$ (a first Fab) recognizing Sclerostin and b) second pair of $V_H$-$V_L$ (a second Fab) recognizing DKK1 | 1st heavy chain: hAb $V_H$-CH1-CH2-CH3 (SEQ ID NO: 146) 2nd heavy chain: 11H10 $V_H$-CH1-CH2-CH3 (SEQ ID NO: 152) | 1st light chain: hAb-2 $V_L$-CL (SEQ ID NO: 147) 2nd light chain: 11H10 $V_L$-CL SEQ ID NO: 153) |
| BAP0064 | A full length antibody having a) first pair of $V_H$-$V_L$ (a first Fab) recognizing | 1st heavy chain: hAb $V_H$-CH1-CH2-CH3 | 1st light chain: hAb-2 $V_L$-CL (SEQ ID NO: 147) |

TABLE 11-continued

| Anti-Sclerostin bispecific antibodies | | | |
|---|---|---|---|
| Bispecific antibodies | Format | Heavy chain (from N-terminus to C-terminus) | Light chain (from N-terminus to C-terminus) |
| | Sclerostin and b) second pair of $V_H$-$V_L$ (a second Fab) recognizing DKK1 | (SEQ ID NO: 146) $2^{nd}$ heavy chain: 11H10 $V_H$-CH1-CH2-CH3 (SEQ ID NO: 154) | $2^{nd}$ light chain: 11H10 $V_L$-CL SEQ ID NO: 155) |
| BAP0065 | A full length antibody having a) first pair of $V_H$-$V_L$ (a first Fab) recognizing Sclerostin and b) second pair of $V_H$-$V_L$ (a second Fab) recognizing RANKL | $1^{st}$ heavy chain: hAb $V_H$-CH1-CH2-CH3 (SEQ ID NO: 146) $2^{nd}$ heavy chain: Denosumab $V_H$-CH1-CH2-CH3 (SEQ ID NO: 156) | $1^{st}$ light chain: hAb-2 $V_L$-CL (SEQ ID NO: 147) $2^{nd}$ light chain: Denosumab $V_L$-CL SEQ ID NO: 157) |
| BAP0066 | A full length antibody having a) first pair of $V_H$-$V_L$ (a first Fab) recognizing Sclerostin and b) second pair of $V_H$-$V_L$ (a second Fab) recognizing RANKL | $1^{st}$ heavy chain: hAb $V_H$-CH1-CH2-CH3 (SEQ ID NO: 146) $2^{nd}$ heavy chain: Denosumab $V_H$-CH1-CH2-CH3 (SEQ ID NO: 158) | $1^{st}$ light chain: hAb-2 $V_L$-CL (SEQ ID NO: 147) $2^{nd}$ light chain: Denosumab $V_L$-CL SEQ ID NO: 159) |
| BAP0067 | A full length antibody having a) first pair of $V_H$-$V_L$ (a first Fab) recognizing Sclerostin and b) second pair of $V_H$-$V_L$ (a second Fab) recognizing RANKL | $1^{st}$ heavy chain: hAb $V_H$-CH1-CH2-CH3 (SEQ ID NO: 146) $2^{nd}$ heavy chain: Denosumab $V_H$-CH1-CH2-CH3 (SEQ ID NO: 162) | $1^{st}$ light chain: hAb-2 $V_L$-CL (SEQ ID NO: 147) $2^{nd}$ light chain: Denosumab $V_L$-CL SEQ ID NO: 163) |
| BAP0068 | A full length antibody having a) first pair of $V_H$-$V_L$ (a first Fab) recognizing Sclerostin and b) second pair of $V_H$-$V_L$ (a second Fab) recognizing RANKL | $1^{st}$ heavy chain: hAb $V_H$-CH1-CH2-CH3 (SEQ ID NO: 146) $2^{nd}$ heavy chain: Denosumab $V_H$-CH1-CH2-CH3 (SEQ ID NO: 160) | $1^{st}$ light chain: hAb-2 $V_L$-CL (SEQ ID NO: 147) $2^{nd}$ light chain: Denosumab $V_L$-CL SEQ ID NO: 161) |
| BAP0069 | Anti-RANKL scFv (VL-VH) fused to C-terminus of heavy chains of anti-Sclerostin full length antibody | hAb $V_H$-CH1-CH2-CH3-L1-Denosumab $V_L$-L2-Denosumab $V_H$ (SEQ ID NO: 177) | hAb-1 $V_L$-CL (SEQ ID NO: 125) |
| BAP0070 | Anti-RANKL scFv (VH-VL) fused to C-terminus of heavy chains of anti-Sclerostin full length antibody | hAb $V_H$-CH1-CH2-CH3-L1-Denosumab $V_H$-L2-Denosumab $V_L$ (SEQ ID NO: 178) | hAb-1 $V_L$-CL (SEQ ID NO: 125) |
| BAP0071 | Anti-RANKL scFv (VH-VL) fused to C-terminus of heavy chains of anti-Sclerostin full length antibody | hAb $V_H$-CH1-CH2-CH3-L1-Denosumab $V_H$-L2-Denosumab $V_L$ (SEQ ID NO: 178) | hAb-2 $V_L$-CL (SEQ ID NO: 122) |
| BAP0072 | Anti-RANKL scFv (VH-VL) fused to C-terminus of heavy chains of anti-Sclerostin full length antibody | hAb $V_H$-CH1-CH2-CH3-L1-Denosumab $V_H$-L2-Denosumab $V_L$ (SEQ ID NO: 179) | hAb-2 $V_L$-CL (SEQ ID NO: 122) |
| BAP0073 | Anti-RANKL scFv (VH-VL) fused to C-terminus of heavy chains of anti-Sclerostin full length antibody | hAb $V_H$-CH1-CH2-CH3-L1-Denosumab $V_H$-L2-Denosumab $V_L$ (SEQ ID NO: 180) | hAb-2 $V_L$-CL (SEQ ID NO: 122) |
| BAP0074 | A full length antibody having a) first pair of $V_H$-$V_L$ (a first Fab) recognizing Sclerostin and b) second pair of $V_H$-$V_L$ (a second Fab) recognizing RANKL | $1^{st}$ heavy chain: hAb $V_H$-CH1-CH2-CH3 (SEQ ID NO: 171) $2^{nd}$ heavy chain: Denosumab $V_H$-CH1-CH2-CH3 (SEQ ID NO: 172) | $1^{st}$ light chain: hAb-2 $V_L$-CL (SEQ ID NO: 147) $2^{nd}$ light chain: Denosumab $V_L$-CL SEQ ID NO: 163) |
| BAP0075 | A full length antibody having a) first pair of $V_H$-$V_L$ (a first Fab) recognizing | $1^{st}$ heavy chain: hAb $V_H$-CH1-CH2-CH3 | $1^{st}$ light chain: hAb-2 $V_L$-CL (SEQ ID NO: 147) |

TABLE 11-continued

Anti-Sclerostin bispecific antibodies

| Bispecific antibodies | Format | Heavy chain (from N-terminus to C-terminus) | Light chain (from N-terminus to C-terminus) |
|---|---|---|---|
| | Sclerostin and b) second pair of $V_H$-$V_L$ (a second Fab) recognizing RANKL | (SEQ ID NO: 173) 2nd heavy chain: Denosumab $V_H$-CH1-CH2-CH3 (SEQ ID NO: 174) | 2nd light chain: Denosumab $V_L$-CL SEQ ID NO: 163) |
| BAP0076 | A full length antibody having a) first pair of $V_H$-$V_L$ (a first Fab) recognizing Sclerostin and b) second pair of $V_H$-$V_L$ (a second Fab) recognizing RANKL | 1st heavy chain: hAb $V_H$-CH1-CH2-CH3 (SEQ ID NO: 175) 2nd heavy chain: Denosumab $V_H$-CH1-CH2-CH3 (SEQ ID NO: 176) | 1st light chain: hAb-2 $V_L$-CL (SEQ ID NO: 147) 2nd light chain: Denosumab $V_L$-CL SEQ ID NO: 163) |

Bispecific molecules were transiently expressed in adherence-adapted 293 6E cells in 96-well plates. Adherent 293 6E cells were seeded in Poly-D-Lysine coated 96-well tissue culture plates at 5E4 cells per well in Serum-free KOP293 medium (Zhuhai Kairui Biotech #K03252) at 25 μg/ml, and 5% FBS 24 hours prior to the transfection and incubated overnight at 37° C. in 5% $CO_2$. On the day of transfection, 100 ng (40 ng/μl) of each corresponding HC and LC DNA of the binding molecules were mixed together. Serum-free media KOP293 25 μl/well was added to the DNA mixtures. After incubation at RT for 15-30 min, the transfection mixtures were added to the culture plates which were seeded the day before and mixed with gentle rocking motions. The culture plates were put back into the 37° C., 5% $CO_2$ incubator overnight. The next day, media and transfection mixtures were aspirated and replaced with 130 μl of serum free media containing 0.5% Tryptone. The plates were incubated for another 6 days. Conditioned media (CM) was harvested on day 7 after transfection. The plates were spun at 1000 rpm for 5 min to pellet any cell debris. Supernatants were carefully transferred into sterile polypropylene blocks.

Antibodies were purified by protein A affinity chromatography, and buffer exchanged in PBS (pH 7.2). The concentrations of purified antibodies were determined by reading the absorbance at 280 nm using the theoretically determined extinction coefficient for that protein.

Example 10. The Binding Kinetics and Affinities of Anti-Sclerostin×Anti-DKK1 and Anti-Sclerostin×Anti-RANKL Bispecific Antibodies Binding kinetics and affinities of anti-Sclerostin×anti-DKK1 and anti-Sclerostin×anti-RANKL bispecific antibodies were measured with Gator® (Probe Life) bio-layer interferometry (BLI). Antibodies were immobilized on an anti-hFc biosensor, using a 5 μg/ml solution. Serial dilutions of sclerostin (from 1 μg/ml), DKK1 (from 2 μg/ml), or RANKL (from 4 μg/ml) by two folds in kinetics buffer (PBS, pH 7.4, 0.05% Tween™-20, 0.2% BSA) were used as the analytes. Affinity ($K_D$) and kinetic parameters ($K_{on}$ and $K_{off}$) were calculated from a global fit (1:1) of the data using the Gator® software. The results are summarized in Table 12.

TABLE 12

Summary of binding kinetics of the bispecific antibodies to human Sclerostin, DKK1 and RANKL

| Antibody | Antigen | $k_{off}$ (1/s) | $k_{on}$ (1/Ms) | $K_D$ (M)[b] |
|---|---|---|---|---|
| BAP0037 | hSclerostin | LOD[a] | $1.88 \times 10^{6}$ | Estimated $10^{-11}$ |
| | hDKK1 | $3.01 \times 10^{-4}$ | $2.97 \times 10^{5}$ | $1.01 \times 10^{-9}$ |
| BAP0039 | hSclerostin | $9.74 \times 10^{-5}$ | $1.88 \times 10^{6}$ | $5.2 \times 10^{-11}$ |
| | hDKK1 | $4.32 \times 10^{-5}$ | $3.09 \times 10^{5}$ | $1.4 \times 10^{-10}$ |
| BAP0061 | hSclerostin | LOD | $2.62 \times 10^{6}$ | Estimated $10^{-11}$ |
| | hDKK1 | LOD | $3.30 \times 10^{5}$ | Estimated $10^{-11}$ |
| BAP0063 | hSclerostin | LOD | $2.59 \times 10^{6}$ | Estimated $10^{-11}$ |
| | hDKK1 | LOD | $1.29 \times 10^{5}$ | Estimated $10^{-11}$ |
| BAP0069 | hSclerostin | LOD | $7.57 \times 10^{5}$ | Estimated $10^{-11}$ |
| | hRANKL | LOD | $8.67 \times 10^{4}$ | Estimated $10^{-11}$ |
| BAP0075 | hSclerostin | LOD | $5.78 \times 10^{5}$ | Estimated $10^{-11}$ |
| | hRANKL | LOD | $1.45 \times 10^{5}$ | Estimated $10^{-11}$ |

[a]Limit of detection, which indicates the off-rate is very slow and beyond the quantification limit of Gator

[b]The affinity $K_D$ values are calculated by $K_{off}/K_{on}$, in the case that $K_{off}$ is LOD, the $K_D$ values are estimated around 10 pM, which is the detection limit of Gator

Figure 6:
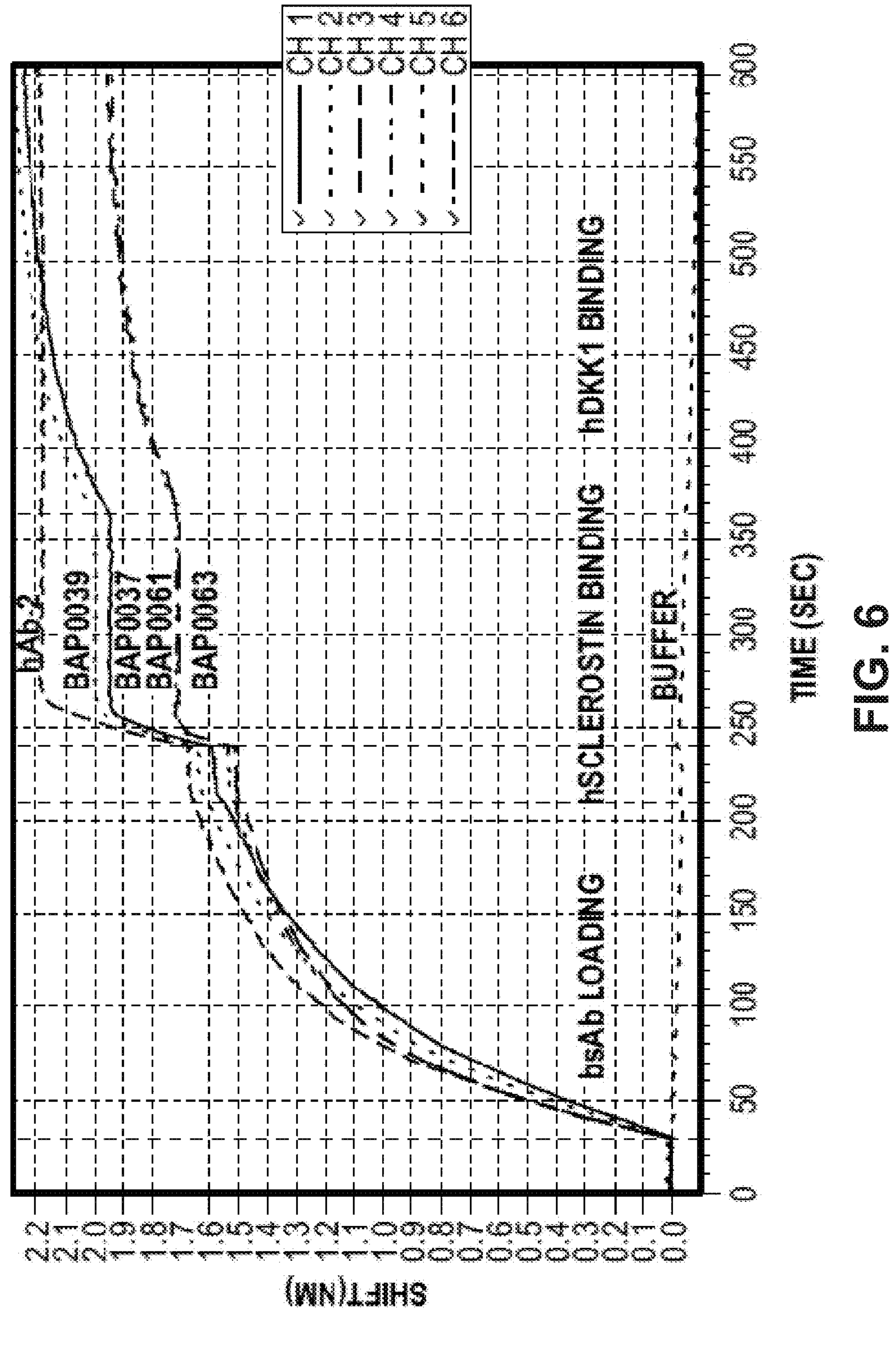
FIG. 6 shows results from BioLayer Interferometry (BLI) sensorgram that demonstrate the incremental binding of human Sclerostin and DKK1 to bispecific antibodies.

Example 11. Simultaneous Binding of Human Sclerostin and DKK1 to bsAbs Using BLI The simultaneous binding of human Sclerostin and DKK1 to bsAbs was confirmed using BLI. The bsAb constructs (5 μg/ml) were captured to the anti-hFc HFC probe, then sequentially adding hSclerostin (2 μg/ml) and hDKK1 (2 μg/ml) in kinetics buffer (PBS, pH 7.4, 0.05% Tween™-20, 0.2% BSA). Two incremental binding responses were observed for four bsAbs but not for blank buffer or anti-Sclerostin mAb as shown in FIG. 6, indicating that the bispecific antibodies can bind Sclerostin and DKK1 at the same time and the binding of one target protein does not block that of the other target.

Example 12. Sclerostin/DKK1-Neutralisation Activity of Bispecific Antibodies on HEK293/TCF/LEF/Wnt1 Cells The WNT signaling assays were performed as described in Example 7, where 1 μg/ml human Sclerostin and DKK1 were added separately. All bsAbs were able to fully neutralize Wnt-antagonizing effect from both sclerostin and DKK1 in a dose dependent manner. The $EC_{50}$ activities as shown in Table 13.

TABLE 13

Sclerostin and DKK1 neutralization activity in HEK293/TCF/LEF/Wnt1 reporter gene assay for anti-Sclerostin × anti-DKK1 bispecific antibodies

| | $EC_{50}$ (nM) | |
|---|---|---|
| Antibody | Sclerostin | DKK1 |
| BAP0037 | 23.63 | 24.13 |
| BAP0039 | 26.66 | 20.87 |
| BAP0061 | 63.83 | 41.39 |
| BAP0063 | 65.44 | 44.72 |

Example 13. Pharmacokinetics Study of Bispecific Antibodies

Naive male cynomolgus monkeys were purchased from Guangzhou Huazhen Laboratory Animal Co., Ltd. The animals weighed between 2.7 kg and 3.5 kg and were 3-5 years old at the initiation of dosing. The animals were randomly assigned to 4 dose groups (n=3 per group). On the day of dosing, 30 mg/kg of antibodies were administered subcutaneously. Blood samples were collected on days 1 (pre-dose, 12 and 24 hr after dosing), 2, 3, 5, 7, 10, 14, 18, 21, 28 after dosing. The PK sampling scheme used in this study was based on known PK properties of other human IgG therapeutic mAbs in cynomolgus monkeys.

The assay for the determination of bsAbs in cynomolgus monkey serum employed a qualified fit-for-purpose sandwich ELISA method. CORNING® High binding 96 well polystyrene Microplates were coated with a specific human IgG-heavy and light chain monkey-adsorbed Antibody. Standard, quality control and unknown samples were loaded into the wells, and any human antibody present was bound by the immobilized antibody. After washing away any unbound substances, a human IgG-heavy and light chain monkey-adsorbed Antibody Conjugate HRP and TMB Substrate Solution for ELISA were added to the wells. Only the samples that contain human bsAbs bound to both the capture and detection antibody produced absorption signal at 450 nm. The signal produced was proportional to the amount of human bsAb present. The lowest quantifiable concentration (LLOQ) of antibodies in a sample was 0.1 μg/ml.

Figure 7:
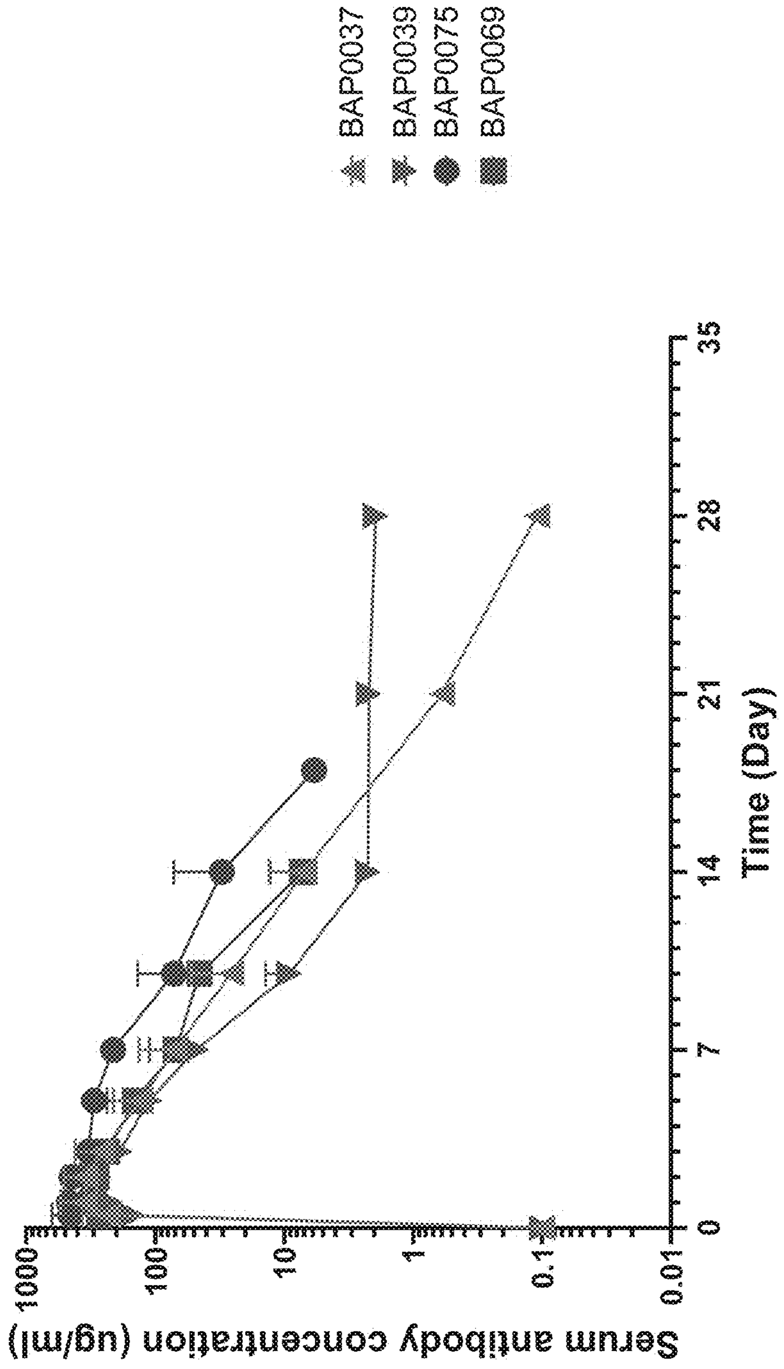
FIG. 7 shows serum concentrations of bispecific antibodies following 30 mg/kg subcutaneous administration in cynomolgus monkeys.

The serum concentrations of the bispecific antibodies in cynomolgus monkeys are shown in FIG. 7. Data are presented as mean±S.E. n=3. The half-lives were calculated to range from 17 to 286 hours.

Example 14. Pharmacodynamics Study of Bispecific Antibodies

The bone formation biomarker procollagen type I N-terminal propeptide (PINP) as well as bone resorption biomarker C-terminal end of the telopeptide of type I collagen (CTX-1) are two widely accepted specific bone homeostatic indicators. To test the pharmacodynamic effects of the bispecific antibodies, normal male cynomolgus monkeys were subjected subcutaneous injection of different bispecific antibodies described above at 30 mg/kg. The blood samples were obtained on day 3 after the injection. Serum samples were then separated by centrifugation. Serum PINP and CTX-1 levels were measured using PINP Test Kit (PC-007, Guangzhou Phicon Biotech Co. Guangzhou, China) and Serum CrossLaps® ELISA kit (AC-021FIR, Immunodiagnostic Systems, UK) respectively following the manufacturer's instruction. The results showed that the administration of bispecific antibody caused a dramatic increase in serum PINP levels only 3 days after the injection. When compared to the pre-dose baseline, serum PINP levels at day 3 were increased between 104.50±8.5% and 212.75±20.6% for different bispecific antibodies (Table 14). Moreover, the serum CTX-1 levels decreased between 46.73±2.5% and 90.11±6.8% for different bispecific antibodies (Table 14) compared to the baseline in response to bispecific antibody injection on day 3. This result indicated that the bispecific antibodies could robustly increase bone formation and decrease bone resorption simultaneously, suggesting their profound therapeutic efficacy to treat diseases or conditions associated with low bone mass or poor bone quality such as osteopenia or osteoporosis in both men and women, osteogenesis imperfecta, multiple myeloma bone diseases. Data was shown in Table 14.

TABLE 14

The serum concentrations of P1NP and CTX-1 in cynomolgus monkeys 3 days after injection

| | % Change from pre-dose (mean ± S.E. n = 3) | |
|---|---|---|
| Antibody | Serum P1NP | Serum CTX-1 |
| BAP0037 | 212.75 ± 20.6 | −90.11 ± 6.8 |
| BAP0039 | 127.92 ± 18.8 | −75.03 ± 10.1 |
| BAP0061 | 180.39 ± 23.8 | −46.73 ± 2.5 |
| BAP0063 | 117.12 ± 16.0 | −68.81 ± 12.5 |
| BAP0069 | 104.50 ± 8.5 | −75.07 ± 2.9 |

Furthermore, when using the bispecific antibody to treat sham operated (Sham) or long-term ovariectomized (OVX) female cynomolgus monkeys, a very well validated postmenopausal osteoporosis animal model, single injection of 10 mg/kg of the bispecific antibody induced a significant increase in serum PINP and a reduction in serum CTX-1 levels. Compared with pre-dose baseline value, serum PINP level increases 241.36±60.9% in OVX monkeys while it increases 182.67=60.1% in Sham monkeys at 14 days post-dosing respectively. Simultaneously, serum CTX-1 decreased-52.12±5.9% in OVX monkeys while it decreases-17.43±8.5% in Sham monkeys at 14 days post-dosing respectively. These data provided further proof of therapeutic efficacy of increasing bone formation and decreasing bone resorption in age-related or postmenopausal osteoporosis.

Example 15. Bispecific Antibodies are Able to Prevent Bone Fractures in Osteogenesis Imperfecta (OI)

The multiscale hierarchical structure of bone is naturally optimized to resist fractures. Enhanced bone formation and reduced bone absorption are two important process to keep the bone strength strong and healthy. In osteogenesis imperfecta (OI) or brittle bone disease, genetic mutations affect the quality and/or the quantity of collagen and dramatically increased bone fracture risk. Clinically, low bone mass and strength, extreme bone fragility and skeletal deformities, as well as frequent fractures becomes the hallmark of the disease. The treatment to reduce the fracture rates in OI is the ultimate goal for clinical improvement. Therefore, we investigated the bispecific antibodies in osteogenesis imperfecta (OI) mouse model (oim/oim) where a spontaneous mutation in the pro-a2 chain of type I collagen causes poor bone quality and lower bone mass resulted in frequent brittle bone fractures. At age of 4 weeks-old, the homozygous oim/oim mouse started to have fractures in their long bones. After 6 weeks of subcutaneous administration of either individual or bispecific antibodies (25 mg/kg, once per week for each antibody), the number of newly occurred fractures were reduced dramatically less than that in vehicle treated animals at 10 weeks-old. In vehicle treated control group, from age of 4 weeks to 10 weeks (6 weeks observation period), the number of fractures was increased by 2.27±0.7 per mouse, counting on X-ray images. Treatment of either sclerostin antibody or DKK1 antibody alone caused a reduction in number of fractures per mouse (0.75±0.2, 1.44±0.4, respectively) as compared with vehicle treatment controls. More dramatically, oim/oim mice treated with the bispecific antibody completely prevent the newly occurred fractures (0.00±0.5 new fracture per mouse from age 4 weeks to 10 weeks), much more superior than either of the mono-therapeutic alone. These results suggest that the bispecific antibodies achieved a synergistic bone anabolic effect by preventing further fractures when neutralizing Sclerostin and DKK1 at the same time. Given that both sclerostin and DKK1 binds to Wnt receptor LRP5/6 and act as antagonists to block the anabolic property of the signaling pathway, it is noticeable if blocking either one of the binding site with specific antibody would cause a up regulation of other antagonists by compensatory mechanism, as demonstrated by the observed up regulation of DKK1 after the treatment with anti-sclerostin antibody in osteoporosis patients (Holdsworth G, 2018, Bone 107, 93-103) Therefore, the above results from current study strongly suggested the synergistic effects on bone by preventing further fractures. This promising result clearly suggested the bispecific antibody is capable to reduce the unmet need of OI patients and to reduce the burden of repeated fractures.

Example 16. Bispecific Antibodies Suppress In Vitro Growth of RPMI8226 Multiple Myeloma Cell The bispecific antibodies are also evaluated in RPMI8226 human multiple myeloma (MM) cells. As indicated in numerous scientific reports demonstrated that DKK1 expression levels are increased in MM patients and are associated with the severity of the disease (Fulciniti M. et al. *Blood,* 2009; 114(2): 371-379., Feng Y et al. *Cancer Biomarkers.* 2018; 1:1-7). Furthermore, studies have shown that about 80-90% of MM patients develop MM related bone disorder (MMBD). The major clinical expression of MMBD is osteolytic lesions and fractures due to increased activities of bone resorption and suppression of bone formation. Therefore, the nature of the bispecific antibodies will benefit MMBD patients by providing bone resorptive inhibition as well as by inhibiting DKK1 expression that leads to increase bone formation. Our preliminary studies demonstrated that in vitro cell culture of MM cells (RPMI 8226) subjected to the molecule showed a decrease in cell surface marker CD138 levels, suggesting the cells might be undergone apoptosis process. Furthermore, CCK8 analysis of tumor growth showed a dose dependent reduction in tumor cell numbers. When administration of the bispecific antibody at 100 μg/ml to the RPMI8226 MM cells for 48 hours, the viable cell numbers dropped about 28%. This evidence indicated that the bispecific antibody could cause the RPMI8226 MM cells apoptosis and arrested the tumor cell growth. The results suggested the therapeutic application to treat MMBD and tumor metastatic related bone disorders by not only preventing bone disorders (as data shown in Example 14 and 15) but also directly inhibiting tumor growth.

SEQUENCE TABLE

| SEQ ID NO. | Description | Nucleotide or Amino Acid Sequence |
|---|---|---|
| | Exemplary anti-Sclerostin mAb sequences | |
| 1. | HC-CDR1 | DYEIH |
| 2. | HC-CDR1 | DFEMH |
| 3. | HC-CDR1 | DYEMH |
| 4. | HC-CDR1 | SYWMH |
| 5. | HC-CDR2 | AIDPETGGTAYNQKFKG |
| 6. | HC-CDR2 | AIDPETGGTAYNQKFKA |
| 7. | HC-CDR2 | AIDPETGGTAYNQKFTA |
| 8. | HC-CDR2 | MIHPNSGSSNYNEKFKS |
| 9. | HC-CDR3 | YDYVTY |
| 10. | HC-CDR3 | YDYVSY |
| 11. | HC-CDR3 | DYDDEGFAY |
| 12. | HC-CDR1 consensus sequence | $DX_1EX_2H$<br>$X_1$ = Y or F, $X_2$ = M or I. |
| 13. | HC-CDR2 consensus sequence | $AIDPETGGX_1AX_2NQKFX_3X_4$<br>$X_1$ = T or S, $X_2$ = Y or N,<br>$X_3$ = K or T, $X_4$ = A, G, or S. |

-continued

SEQUENCE TABLE

| SEQ ID NO. | Description | Nucleotide or Amino Acid Sequence |
|---|---|---|
| 14. | HC-CDR3 consensus sequence | YDYVX$_1$Y<br>X$_1$ = T or S |
| 15 | LC-CDR1 | KSSQSLLYSDGRTYLN |
| 16. | LC-CDR1 | KSSQSLLYSDGKTYLN |
| 17. | LC-CDR1 | KASQSVSNDVA |
| 18. | LC-CDR2 | LVSKLDS |
| 19. | LC-CDR2 | YASNRCT |
| 20. | LC-CDR3 | WQGTHLPHT |
| 21. | LC-CDR3 | QQDYSSPWT |
| 22. | 93B1B7 VH | QAQLQQSGAELVRPGASVTLSCKASGYTFTDYEIHWM<br>KQTPVHGLEWIGAIDPETGGTAYNQKFKGKAILTADRS<br>SSTAYLELRSLTSEDSAVYYCYSYDYVTYWGQGTLVT<br>VSA |
| 23. | 93B1B7 VL | DVVMTQTPLTWSITIGQPASISCKSSQSLLYSDGRTYLN<br>WLLQRPGQSPKRLIYLVSKLDSGVPDRFSGSGSGTDFTL<br>KISRVEAEDLGFYYCWQGTHLPHTFGAGTKLELK |
| 24. | 94B12D3 $V_H$ | QVQLQQSGAELVRPGASVTLSCKASGYTFTDYEIHWVK<br>QTPVHGLEWIGAIDPETGGTAYNQKFKAKAILTADRSSS<br>TAYMELRSLTSEDSAVYYSFSYDYVSYWGQGTLVTVS<br>A |
| 25. | 94B12D3 VL | DVVMTQTPLTLSVTIGQPASISCKSSQSLLYSDGRTYLN<br>WLLQRPGQSPKRLIYLVSKLDSGVPDRFAGSGSGTDFSL<br>KISRVEAEDLGVYYCWQGTHLPHTFGAGTKLELK |
| 26. | 71G6G8 VH | QAQLQQSGAELVRPGASVTLSCKASGYTFTDYEIHWVK<br>QTPVHGLEWIGAIDPETGGTAYNQKFKGKAILTADRSSS<br>TAYLELRSLTSEDSAVYYCFSYDYVTYWGQGTLVTVT<br>A |
| 27. | 71G6G8 VL | DVVMTQTPLTWSITIGQPASISCKSSQSLLYSDGRTYLN<br>WLLQRPGQSPKRLIYLVSKLDSGVPDRFTGSGSGTDFTL<br>KISRVEAEDLGFYYCWQGTHLPHTFGAGTKLELK |
| 28. | 56E5C10 VH | QVQLQQSGAELVRPGASVTLSCKASGYTFTDFEMHWV<br>KQTPVHGLEWIGAIDPETGGTAYNQKFTAKAILTADRS<br>SSTAYMELRSLTSEDSAVYYCFSYDYVSYWGQGTLVT<br>VSA |
| 29. | 56E5C10 VL | DVMMTQTPLTLSVTIGQPASISCKSSQSLLYSDGRTYLN<br>WLLQRPGQSPKRLIYLVSKLDSGVPDRFTGSGSGTDFTL<br>KISRVEAEDLGVYYCWQGTHLPHTFGAGTKLELK |
| 30. | 91F6D10 VH | QVQLQQSGAELVRPGASVTLSCKASGYTFTDYEMHWV<br>KQTPVHGLEWIGAIDPETGGTAYNQKFKAKAILTADRS<br>SSTAYMELRSLTSEDSAVYYCFSYDYVSYWGQGTLVT<br>VSA |
| 31. | 91F6D10 VL | DVVMTQTPLTLSVTIGQPASISCKSSQSLLYSDGRTYLN<br>WLLQRPGQSPKRLIYLVSKLDSGVPDRFTGSGSGTDFTL<br>KISRVEAEDLGVYYCWQGTHLPHTFGVGTKLELK |
| 32. | 51E8D4 VH | QVQLQQSGAELVRPGASVTLSCKASGYTFTDFEIHWMK<br>QTPVPGLEWIGAIDPETGGTAYNQKFKGKALLTADKSS<br>STAYMDLRSLTSEDSAVYFCFSYDYVSYWGQGTLVTV<br>SA |
| 33. | 51E8D4 VL | DVVMTQTPLTLSVTFGQPASISCKSSQSLLYSDGKTYLN<br>WLLQRPGQSPKRLIYLVSKLDSGVPDRFTGSGSGTAFTL<br>KISRVEAEDLGVYYCWQGTHLPHTFGAGTKLELR |

-continued

SEQUENCE TABLE

| SEQ ID NO. | Description | Nucleotide or Amino Acid Sequence |
|---|---|---|
| 34. | 97C11D7 VH | QVQLQQSGAELVRPGASVTLSCKASGYTFTDYEMHWV KQTPVHGLEWIGAIDPETGGSANNQKFKAKAILTADRS SSTAYMELRSLTSEDSAVYYCFSYDYVSYWGQGTLVT VSA |
| 35. | 97C11D7 VL | DVVMTQTPLTLSVTIGQPASISCKSSQSLLYSDGRTYLN WLLQRPGQSPKRLIYLVSKLDSGVPDRFTGSGSGTDFTL KIGRVEAEDLGVYYCWQGTHLPHTFGAGTKLELK |
| 36. | 81B2B6 VH | QVQLQQSGAELVRPGASVTLSCKASGYTFTDYEMHWV KQTPVHGLEWIGAIDPETGGTAYNQKFKAKAILTADRS SSTAYMELRSLTSEDSAVYYCFSYDYVSYWGQGTLVT VSA |
| 37. | 81B2B6 VL | DVVMTQTPLTLSVTLGQPASISCKSSQSLLYSDGRTYLN WLLQRPGQSPKRLIYLVSKLDSGVPDRFTGSGSGTDFTL KISRVEAEDLGLYYCWQGTHLPHTFGAGTKLELK |
| 38. | 84F2D5 VH | QVQLQQSGAELVRPGASVTLSCKASGYTFTDFEIHWLK QTPVPGLEWIGAIDPETGGTAYNQKFKGKALLTADKSS STAYMELRSLTSEDSAVYYCFSYDYVSYWGQGTLVTV SA |
| 39. | 84F2D5 VL | DVVMTQTPLTLSVTIGQPASISCKSSQSLLYSDGKTYLN WLLQRPGQSPKRLIYLVSKLDSGVPDRFTGSGSGTAFTL KISRVEAEDLGVYYCWQGTHLPHTFGAGTKLELR |
| 40. | 65B12C9 VH | QVQLQQPGAELVKPGASVKLSCKASGYTFTSYWMHW VKQRPGQGLEWIGMIHPNSGSSNYNEKFKSKATLTVDK SSSTAYMQLSSLTSEDSAVYYCANDYDDEGFAYWGQG TLVTVSA |
| 41. | 65B12C9 VL | SIVMTQTPKFLLVSAGDRVTITCKASQSVSNDVAWYQQ KPGQSPKLLIYYASNRCTGVPDRFTGSGYGTDFTFTIST VQAEDLAVYFCQQDYSSPWTFGGGTKLEIK |
| | Exemplary anti-DKK1 sequences | |
| 42. | 11H10-VH44VL32 HC-CDR1 | GFTFSDYAMA |
| 43. | 11H10-VH44VL32 HC-CDR2 | THIYDGSSTYYRDSVKG |
| 44. | 11H10-VH44VL32 HC-CDR3 | GLGIATDYFDY |
| 45. | 11H10-VH44VL32 LC-CDR1 | LASEDIYSDLA |
| 46. | 11H10-VH44VL32 LC-CDR2 | NANSLQN |
| 47. | 11H10-VH44VL32 LC-CDR3 | QQYNNYPPT |
| 48. | RH2-18 HC-CDR1 | GYTFTDYYIH |
| 49. | RH2-18 HC-CDR2 | WIHSNSGATTYAQKFQA |
| 50. | RH2-18 HC-CDR3 | EDY |
| 51. | RH2-18 LC-CDR1 | TGSSNIGAGYDVH |

-continued

| SEQUENCE TABLE | | |
|---|---|---|
| SEQ ID NO. | Description | Nucleotide or Amino Acid Sequence |
| 52. | RH2-18 LC-CDR2 | GYSNRPS |
| 53. | RH2-18 LC-CDR3 | QSYDNSLSSYV |
| 54. | 71G6G8 HC-CDR1 | GFTFSSYAIS |
| 55. | 71G6G8 HC-CDR2 | SVSGTGLGFQTYYPDSVKG |
| 56. | 71G6G8 HC-CDR3 | SLENYAFDY |
| 57. | 71G6G8 LC-CDR1 | RASESVDDFGISFIN |
| 58. | 71G6G8 LC-CDR2 | AGSKQGS |
| 59. | 71G6G8 LC-CDR3 | QQLKEVPPT |
| 60. | 11H10-VH44VL32 VH (11H10 VH) | EVQLVESGGGVVQPGRSLRLSCAASGFTFSDYAMAWV RQAPGKGLEWVATIIYDGSSTYYRDSVKGRFTISRDNS KNTLYLQMNSLRAEDTAVYYCATGLGIATDYFDYWG QGTLVTVSS |
| 61. | 11H10-VH44VL32 VL (11H10 VL) | DIRMTQSPFSLSASVGDRVTITCLASEDIYSDLAWYQQK PAKAPKLFIYNANSLQNGVPSRFSGSGSGTDYTLTISSL QPEDFATYYCQQYNNYPPTFGGGTKVEIK |
| 62. | RH2-18 VH | EVQLVQSGAEVKKPGASVKVSCKASGYTFTDYYIHWV RQAPGQGLEWMGWIHSNSGATTYAQKFQARVTMSRD TSSSTAYMELSRLESDDTAMYFCSREDYWGQGTLVTV SS |
| 63. | RH2-18 VL | QSVLTQPPSVSGAPGQRVTISCTGSSNIGAGYDVHWYQ QLPGTAPKLLIYGYSNRPSGVPDRFSGSKSGASASLAIT GLRPDDEADYYCQSYDNSLSSYVFGGGTQLTVL |
| 64. | 71G6G8 VH | EVQLVESGGGLVQPGGSLRLSCAASGFTFSSYAISWVR QAPGKGLEWVASVSGTGLGFQTYYPDSVKGRFTISRDN AKNSLYLQMNSLRAEDTAVYYCATSLENYAFDYWGQ GTTVTVSS |
| 65. | 71G6G8 VL | EIVLTQSPATLSLSPGERATLSCRASESVDDFGISFINWY QQKPGQAPRLLIYAGSKQGSGIPARFSGSGSGTDFTLTIS SLEPEDFAVYYCQQLKEVPPTFGGGTKVEIK |
| Exemplary anti-RANKL sequences | | |
| 66. | Denosumab HC-CDR1 | GFTFSSYAMS |
| 67. | Denosumab HC-CDR2 | GITGSGGSTYYADSVKG |
| 68. | Denosumab HC-CDR3 | DPGTTVIMSWFDP |
| 69. | Denosumab LC-CDR1 | RASQSVRGRYLA |
| 70. | Denosumab LC-CDR2 | GASSRAT |
| 71. | Denosumab LC-CDR3 | QQYGSSPRT |

-continued

| SEQUENCE TABLE | | |
|---|---|---|
| SEQ ID NO. | Description | Nucleotide or Amino Acid Sequence |
| 72. | Denosumab VH | EVQLLESGGGLVQPGGSLRLSCAASGFTFSSYAMSWVR QAPGKGLEWVSGITGSGGSTYYADSVKGRFTISRDNSK NTLYLQMNSLRAEDTAVYYCAKDPGTTVIMSWFDPW GQGTLVTVSS |
| 73. | Denosumab VL | EIVLTQSPGTLSLSPGERATLSCRASQSVRGRYLAWYQ QKPGQAPRLLIYGASSRATGIPDRFSGSGSGTDFTLTISR LEPEDFAVFYCQQYGSSPRTFGQGTKVEIK |
| | Exemplary linker sequences | |
| 74. | Linker | GGGGS |
| 75. | Linker | GGGGSGGGGS |
| 76. | Linker | GGGGSGGGGSGGGGS |
| 77. | Linker | GGGGSGGGGSGGGGSGGGGS |
| 78. | Linker | $(G)_n$, n > = 1 |
| 79. | Linker | $(GS)_n$, 8 > = n > = 1 |
| 80. | Linker | $(GSGGS)_n$, 8 > = n > = 1 |
| 81. | Linker | $(GGGGS)_n$, 8 > = n > = 1 |
| 82. | Linker | $(GGGS)_n$, 8 > = n > = 1 |
| 83. | Linker | $(GGGGS)_6$ |
| 84. | Linker | $(GSTSGSGKPGSGEGS)_n$ 3 > = n > = 1 |
| | Exemplary humanized anti-sclerostin antibody sequences | |
| 85. | hAb-2 LC-CDR1 | RSSQSLLYSDGRTYLN |
| 86. | hAb-3 LC-CDR1 | RSSQSLLYSDSRTYLN |
| 87. | hAb-1/hAb-2/ hAb-3 VH (hAb VH) | EVQLVQSGAEVKKPGASVKVSCKASGYTFTDYEIHWV RQAPGKGLEWMGAIDPETGGTAYNQKFKGRVTMTTDT STSTAYMELRSLRSDDTAVYYCYSYDYVTYWGQGTTV TVSS |
| 88. | hAb-1 VL | DVVMTQSPLSLSVSPGERASLSCKSSQSLLYSDGRTYLN WYLQKPGQSPQRLIYLVSKLDSGVPDRFSGSGSGTDFTL KISRVQSEDVGVYYCWQGTHLPHTFGGGTKVEIK |
| 89. | hAb-2 VL | DIQMTQSPSSLSASVGDRVTITCRSSQSLLYSDGRTYLN WYQQKPGKSPKRLIYLVSKLDSGVPDRFSGSGSGTDFT LTISSLQPEDFATYYCWQGTHLPHTFGGGTKVEIK |
| 90. | hAb-3 VL | DIQMTQSPSSLSASVGDRVTITCRSSQSLLYSDSRTYLN WLQQKPGKSPKRLIYLVSKLDSGVPDRFSGSGSGTDFTL TISSLQPEDFATYYCWQGTHLPHTFGGGTKVEIK |
| | Exemplary bispecific anti-sclerostin antibody sequences | |
| 91. | BAP0017 | EVQLVESGGGLVQPANSLKLSCAASGFTFSDYAMAWV RQSPKKGLEWVATIIYDGSSTYYRDSVKGRFTISRDNAK STLYLQMDSLRSEDTATYYCATGLGIATDYFDYWGQG VLVTVSSAETTAPSVYPLAPGTALKSNSMVTLGCLVKG YFPEPVTVTWNSGALSSGVHTFPAVLQSGLYTLTSSVT VPSSTWPSQTVTCNVAHPASSTKVDKKIVPRNCGGDCK PCICTGSEVSSVFIFPPKPKDVLTITLTPKVTCVVVDISQD DPEVHFSWFVDDVEVHTAQTRPPEEQFNSTFRSVSELPI LHQDWLNGRTFRCKVTSAAFPSPIEKTISKPEGRTQVPH VYTMSPTKEEMTQNEVSITCMVKGFYPPDIYVEWQMN GQPQENYKNTPPTMDTDGSYFLYSKLNVKKEKWQQG NTFTCSVLHEGLHNHHTEKSLSHSPGKGGGGSGGGGSG |

-continued

| SEQUENCE TABLE | | |
|---|---|---|
| SEQ ID NO. | Description | Nucleotide or Amino Acid Sequence |
| | | GGGSQAQLQQSGAELVRPGASVTLSCKASGYTFTDYEI HWMKQTPVHGLEWIGAIDPETGGTAYNQKFKGKAILT ADRSSSTAYLELRSLTSEDSAVYYCYSYDYVTYWGQG TLVTVSAGGGGSGGGGSGGGGSGGGGSDVVMTQTPLT WSITIGQPASISCKSSQSLLYSDGRTYLNWLLQRPGQSP KRLIYLVSKLDSGVPDRFSGSGSGTDFTLKISRVEAEDL GFYYCWQGTHLPHTFGAGTKLELK |
| 92. | heavy chain BAP0018 heavy chain | EVQLVESGGGLVQPANSLKLSCAASGFTFSDYAMAWV RQSPKKGLEWVATIIYDGSSTYYRDSVKGRFTISRDNAK STLYLQMDSLRSEDTATYYCATGLGIATDYFDYWGQG VLVTVSSAETTAPSVYPLAPGTALKSNSMVTLGCLVKG YFPEPVTVTWNSGALSSGVHTFPAVLQSGLYTLTSSVT VPSSTWPSQTVTCNVAHPASSTKVDKKIVPRNCGGDCK PCICTGSEVSSVFIFPPKPKDVLTITLTPKVTCVVVDISQD DPEVHFSWFVDDVEVHTAQTRPPEEQFNSTFRSVSELPI LHQDWLNGRTFRCKVTSAAFPSPIEKTISKPEGRTQVPH VYTMSPTKEEMTQNEVSITCMVKGFYPPDIYVEWQMN GQPQENYKNTPPTMDTDGSYFLYSKLNVKKEKWQQG NTFTCSVLHEGLHNHHTEKSLSHSPGKGGGGSGGGGSG GGGSDVVMTQTPLTWSITIGQPASISCKSSQSLLYSDGR TYLNWLLQRPGQSPKRLIYLVSKLDSGVPDRFSGSGSGT DFTLKISRVEAEDLGFYYCWQGTHLPHTFGAGTKLELK GGGGSGGGGSGGGGSGGGGSQAQLQQSGAELVRPGAS VTLSCKASGYTFTDYEIHWMKQTPVHGLEWIGAIDPET GGTAYNQKFKGKAILTADRSSSTAYLELRSLTSEDSAV YYCYSYDYVTYWGQGTLVTVSA |
| 93. | BAP0017/ BAP0018 light chain | DIRMTQSPASLSASLGETVNIECLASEDIYSDLAWYQQK PGKSPQLLIYNANSLQNGVPSRFSGSGSGTQYSLKINSL QSEDVATYFCQQYNNYPPTFGGGTKLELKRADAAPTVS IFPPSTEQLATGGASVVCLMNNFYPRDISVKWKIDGTER RDGVLDSVTDQDSKDSTYSMSSTLSLTKADYESHNLYT CEVVHKTSSSPVVKSFNRNEC |
| 94. | BAP0019 heavy chain | QAQLQQSGAELVRPGASVTLSCKASGYTFTDYEIHWM KQTPVHGLEWIGAIDPETGGTAYNQKFKGKAILTADRS SSTAYLELRSLTSEDSAVYYCYSYDYVTYWGQGTLVT VSAAKTTPPSVYPLAPGSAAQTNSMVTLGCLVKGYFPE PVTVTWNSGSLSSGVHTFPAVLQSDLYTLSSSVTVPSSP RPSETVTCNVAHPASSTKVDKKIVPRDCGCKPCICTVPE VSSVFIFPPKPKDVLTITLTPKVTCVVVDISKDDPEVQFS WFVDDVEVHTAQTQPREEQFNSTFRSVSELPIMHQDWL NGKEFKCRVNSAAFPAPIEKTISKTKGRPKAPQVYTIPPP KEQMAKDKVSLTCMITDFFPEDITVEWQWNGQPAENY KNTQPIMNTNGSYFVYSKLNVQKSNWEAGNTFTCSVL HEGLHNHHTEKSLSHSPGKGGGGSGGGGSGGGGSEVQ LVESGGGLVQPANSLKLSCAASGFTFSDYAMAWVRQS PKKGLEWVATIIYDGSSTYYRDSVKGRFTISRDNAKSTL YLQMDSLRSEDTATYYCATGLGIATDYFDYWGQGVLV TVSSGGGGSGGGGSGGGGSGGGGSDIRMTQSPASLSAS LGETVNIECLASEDIYSDLAWYQQKPGKSPQLLIYNANS LQNGVPSRFSGSGSGTQYSLKINSLQSEDVATYFCQQY NNYPPTFGGGTKLELK |
| 95. | BAP0020 heavy chain | QAQLQQSGAELVRPGASVTLSCKASGYTFTDYEIHWM KQTPVHGLEWIGAIDPETGGTAYNQKFKGKAILTADRS SSTAYLELRSLTSEDSAVYYCYSYDYVTYWGQGTLVT VSAAKTTPPSVYPLAPGSAAQTNSMVTLGCLVKGYFPE PVTVTWNSGSLSSGVHTFPAVLQSDLYTLSSSVTVPSSP RPSETVTCNVAHPASSTKVDKKIVPRDCGCKPCICTVPE VSSVFIFPPKPKDVLTITLTPKVTCVVVDISKDDPEVQFS WFVDDVEVHTAQTQPREEQFNSTFRSVSELPIMHQDWL NGKEFKCRVNSAAFPAPIEKTISKTKGRPKAPQVYTIPPP KEQMAKDKVSLTCMITDFFPEDITVEWQWNGQPAENY KNTQPIMNTNGSYFVYSKLNVQKSNWEAGNTFTCSVL HEGLHNHHTEKSLSHSPGKGGGGSGGGGSGGGGSDIR MTQSPASLSASLGETVNIECLASEDIYSDLAWYQQKPG KSPQLLIYNANSLQNGVPSRFSGSGSGTQYSLKINSLQSE DVATYFCQQYNNYPPTFGGGTKLELKGGGGSGGGGSG GGGSGGGGSEVQLVESGGGLVQPANSLKLSCAASGFTF SDYAMAWVRQSPKKGLEWVATIIYDGSSTYYRDSVKG RFTISRDNAKSTLYLQMDSLRSEDTATYYCATGLGIATD YFDYWGQGVLVTVSS |

-continued

SEQUENCE TABLE

| SEQ ID NO. | Description | Nucleotide or Amino Acid Sequence |
|---|---|---|
| 96. | BAP0019/ BAP0020 light chain | DVVMTQTPLTWSITIGQPASISCKSSQSLLYSDGRTYLN WLLQRPGQSPKRLIYLVSKLDSGVPDRFSGSGSGTDFTL KISRVEAEDLGFYYCWQGTHLPHTFGAGTKLELKRAD AAPTVSIFPPSSEQLTSGGASVVCFLNNFYPKDINVKWK IDGSERQNGVLNSWTDQDSKDSTYSMSSTLTLTKDEYE RHNSYTCEATHKTSTSPIVKSFNRNEC |
| 97. | BAP0021 heavy chain | QAQLQQSGAELVRPGASVTLSCKASGYTFTDYEIHWM KQTPVHGLEWIGAIDPETGGTAYNQKFKGKAILTADRS SSTAYLELRSLTSEDSAVYYCYSYDYVTYWGQGTLVT VSAGGGGSGGGGSGGGGSGGGGSDVVMTQTPLTWSIT IGQPASISCKSSQSLLYSDGRTYLNWLLQRPGQSPKRLIY LVSKLDSGVPDRFSGSGSGTDFTLKISRVEAEDLGFYYC WQGTHLPHTFGAGTKLELKGGGGSGGGGSGGGGSEVQ LVESGGGLVQPANSLKLSCAASGFTFSDYAMAWVRQS PKKGLEWVATIIYDGSSTYYRDSVKGRFTISRDNAKSTL YLQMDSLRSEDTATYYCATGLGIATDYFDYWGQGVLV TVSSAETTAPSVYPLAPGTALKSNSMVTLGCLVKGYFP EPVTVTWNSGALSSGVHTFPAVLQSGLYTLTSSVTVPSS TWPSQTVTCNVAHPASSTKVDKKIVPRNCGGDCKPCIC TGSEVSSVFIFPPKPKDVLTITLTPKVTCVVVDISQDDPE VHFSWFVDDVEVHTAQTRPPEEQFNSTFRSVSELPILHQ DWLNGRTFRCKVTSAAFPSPIEKTISKPEGRTQVPHVYT MSPTKEEMTQNEVSITCMVKGFYPPDIYVEWQMNGQP QENYKNTPPTMDTDGSYFLYSKLNVKKEKWQQGNTFT CSVLHEGLHNHHTEKSLSHSPGK |
| 98. | BAP0022 heavy chain | DVVMTQTPLTWSITIGQPASISCKSSQSLLYSDGRTYLN WLLQRPGQSPKRLIYLVSKLDSGVPDRFSGSGSGTDFTL KISRVEAEDLGFYYCWQGTHLPHTFGAGTKLELKGGG GSGGGGSGGGGSGGGGSQAQLQQSGAELVRPGASVTL SCKASGYTFTDYEIHWMKQTPVHGLEWIGAIDPETGGT AYNQKFKGKAILTADRSSSTAYLELRSLTSEDSAVYYC YSYDYVTYWGQGTLVTVSAGGGGSGGGGSGGGGSEV QLVESGGGLVQPANSLKLSCAASGFTFSDYAMAWVRQ SPKKGLEWVATIIYDGSSTYYRDSVKGRFTISRDNAKST LYLQMDSLRSEDTATYYCATGLGIATDYFDYWGQGVL VTVSSAETTAPSVYPLAPGTALKSNSMVTLGCLVKGYF PEPVTVTWNSGALSSGVHTFPAVLQSGLYTLTSSVTVPS STWPSQTVTCNVAHPASSTKVDKKIVPRNCGGDCKPCI CTGSEVSSVFIFPPKPKDVLTITLTPKVTCVVVDISQDDP EVHFSWFVDDVEVHTAQTRPPEEQFNSTFRSVSELPILH QDWLNGRTFRCKVTSAAFPSPIEKTISKPEGRTQVPHVY TMSPTKEEMTQNEVSITCMVKGFYPPDIYVEWQMNGQ PQENYKNTPPTMDTDGSYFLYSKLNVKKEKWQQGNTF TCSVLHEGLHNHHTEKSLSHSPGK |
| 99. | BAP0021/ BAP0022 light chain | DIRMTQSPASLSASLGETVNIECLASEDIYSDLAWYQQK PGKSPQLLIYNANSLQNGVPSRFSGSGSGTQYSLKINSL QSEDVATYFCQQYNNYPPTFGGGTKLELKRADAAPTVS IFPPSTEQLATGGASVVCLMNNFYPRDISVKWKIDGTER RDGVLDSVTDQDSKDSTYSMSSTLSLTKADYESHNLYT CEVVHKTSSSPVVKSFNRNEC |
| 100. | BAP0023 heavy chain | EVQLVESGGGLVQPANSLKLSCAASGFTFSDYAMAWV RQSPKKGLEWVATIIYDGSSTYYRDSVKGRFTISRDNAK STLYLQMDSLRSEDTATYYCATGLGIATDYFDYWGQG VLVTVSSGGGGSGGGGSGGGGSGGGGSDIRMTQSPASL SASLGETVNIECLASEDIYSDLAWYQQKPGKSPQLLIYN ANSLQNGVPSRFSGSGSGTQYSLKINSLQSEDVATYFCQ QYNNYPPTFGGGTKLELKGGGGSGGGGSGGGGSQAQL QQSGAELVRPGASVTLSCKASGYTFTDYEIHWMKQTPV HGLEWIGAIDPETGGTAYNQKFKGKAILTADRSSSTAY LELRSLTSEDSAVYYCYSYDYVTYWGQGTLVTVSAAK TTPPSVYPLAPGSAAQTNSMVTLGCLVKGYFPEPVTVT WNSGSLSSGVHTFPAVLQSDLYTLSSSVTVPSSPRPSET VTCNVAHPASSTKVDKKIVPRDCGCKPCICTVPEVSSVF IFPPKPKDVLTITLTPKVTCVVVDISKDDPEVQFSWFVD DVEVHTAQTQPREEQFNSTFRSVSELPIMHQDWLNGKE FKCRVNSAAFPAPIEKTISKTKGRPKAPQVYTIPPPKEQ MAKDKVSLTCMITDFFPEDITVEWQWNGQPAENYKNT QPIMNTNGSYFVYSKLNVQKSNWEAGNTFTCSVLHEG LHNHHTEKSLSHSPGK |

-continued

SEQUENCE TABLE

| SEQ ID NO. | Description | Nucleotide or Amino Acid Sequence |
|---|---|---|
| 101. | BAP0024 heavy chain | DIRMTQSPASLSASLGETVNIECLASEDIYSDLAWYQQK PGKSPQLLIYNANSLQNGVPSRFSGSGSGTQYSLKINSL QSEDVATYFCQQYNNYPPTFGGGTKLELKGGGGSGGG GSGGGGSGGGGSEVQLVESGGGLVQPANSLKLSCAAS GFTFSDYAMAWVRQSPKKGLEWVATIIYDGSSTYYRDS VKGRFTISRDNAKSTLYLQMDSLRSEDTATYYCATGLG IATDYFDYWGQGVLVTVSSGGGGSGGGGSGGGGSQAQ LQQSGAELVRPGASVTLSCKASGYTFTDYEIHWMKQTP VHGLEWIGAIDPETGGTAYNQKFKGKAILTADRSSSTA YLELRSLTSEDSAVYYCYSYDYVTYWGQGTLVTVSAA KTTPPSVYPLAPGSAAQTNSMVTLGCLVKGYFPEPVTV TWNSGSLSSGVHTFPAVLQSDLYTLSSSVTVPSSPRPSET VTCNVAHPASSTKVDKKIVPRDCGCKPCICTVPEVSSVF IFPPKPKDVLTITLTPKVTCVVVDISKDDPEVQFSWFVD DVEVHTAQTQPREEQFNSTFRSVSELPIMHQDWLNGKE FKCRVNSAAFPAPIEKTISKTKGRPKAPQVYTIPPPKEQ MAKDKVSLTCMITDFFPEDITVEWQWNGQPAENYKNT QPIMNTNGSYFVYSKLNVQKSNWEAGNTFTCSVLHEG LHNHHTEKSLSHSPGK |
| 102. | BAP0023/ BAP0024 light chain | DVVMTQTPLTWSITIGQPASISCKSSQSLLYSDGRTYLN WLLQRPGQSPKRLIYLVSKLDSGVPDRFSGSGSGTDFTL KISRVEAEDLGFYYCWQGTHLPHTFGAGTKLELKRAD AAPTVSIFPPSSEQLTSGGASVVCFLNNFYPKDINVKWK IDGSERQNGVLNSWTDQDSKDSTYSMSSTLTLTKDEYE RHNSYTCEATHKTSTSPIVKSFNRNEC |
| 103. | BAP0025/ BAP0026 heavy chain | EVQLVESGGGLVQPANSLKLSCAASGFTFSDYAMAWV RQSPKKGLEWVATIIYDGSSTYYRDSVKGRFTISRDNAK STLYLQMDSLRSEDTATYYCATGLGIATDYFDYWGQG VLVTVSSAETTAPSVYPLAPGTALKSNSMVTLGCLVKG YFPEPVTVTWNSGALSSGVHTFPAVLQSGLYTLTSSVT VPSSTWPSQTVTCNVAHPASSTKVDKKIVPRNCGGDCK PCICTGSEVSSVFIFPPKPKDVLTITLTPKVTCVVVDISQD DPEVHFSWFVDDVEVHTAQTRPPEEQFNSTFRSVSELPI LHQDWLNGRTFRCKVTSAAFPSPIEKTISKPEGRTQVPH VYTMSPTKEEMTQNEVSITCMVKGFYPPDIYVEWQMN GQPQENYKNTPPTMDTDGSYFLYSKLNVKKEKWQQG NTFTCSVLHEGLHNHHTEKSLSHSPGK |
| 104. | BAP0025 light chain | QAQLQQSGAELVRPGASVTLSCKASGYTFTDYEIHWM KQTPVHGLEWIGAIDPETGGTAYNQKFKGKAILTADRS SSTAYLELRSLTSEDSAVYYCYSYDYVTYWGQGTLVT VSAGGGGSGGGGSGGGGSGGGGSDVVMTQTPLTWSIT IGQPASISCKSSQSLLYSDGRTYLNWLLQRPGQSPKRLIY LVSKLDSGVPDRFSGSGSGTDFTLKISRVEAEDLGFYYC WQGTHLPHTFGAGTKLELKGGGGSGGGGSGGGGSDIR MTQSPASLSASLGETVNIECLASEDIYSDLAWYQQKPG KSPQLLIYNANSLQNGVPSRFSGSGSGTQYSLKINSLQSE DVATYFCQQYNNYPPTFGGGTKLELKRADAAPTVSIFP PSTEQLATGGASVVCLMNNFYPRDISVKWKIDGTERRD GVLDSVTDQDSKDSTYSMSSTLSLTKADYESHNLYTCE VVHKTSSSPVVKSFNRNEC |
| 105. | BAP0026 light chain | DVVMTQTPLTWSITIGQPASISCKSSQSLLYSDGRTYLN WLLQRPGQSPKRLIYLVSKLDSGVPDRFSGSGSGTDFTL KISRVEAEDLGFYYCWQGTHLPHTFGAGTKLELKGGG GSGGGGSGGGGSGGGGSQAQLQQSGAELVRPGASVTL SCKASGYTFTDYEIHWMKQTPVHGLEWIGAIDPETGGT AYNQKFKGKAILTADRSSSTAYLELRSLTSEDSAVYYC YSYDYVTYWGQGTLVTVSAGGGGSGGGGSGGGGSDIR MTQSPASLSASLGETVNIECLASEDIYSDLAWYQQKPG KSPQLLIYNANSLQNGVPSRFSGSGSGTQYSLKINSLQSE DVATYFCQQYNNYPPTFGGGTKLELKRADAAPTVSIFP PSTEQLATGGASVVCLMNNFYPRDISVKWKIDGTERRD GVLDSVTDQDSKDSTYSMSSTLSLTKADYESHNLYTCE VVHKTSSSPVVKSFNRNEC |
| 106. | BAP0027/ BAP0028 heavy chain | QAQLQQSGAELVRPGASVTLSCKASGYTFTDYEIHWM KQTPVHGLEWIGAIDPETGGTAYNQKFKGKAILTADRS SSTAYLELRSLTSEDSAVYYCYSYDYVTYWGQGTLVT VSAAKTTPPSVYPLAPGSAAQTNSMVTLGCLVKGYFPE PVTVTWNSGSLSSGVHTFPAVLQSDLYTLSSSVTVPSSP |

-continued

SEQUENCE TABLE

| SEQ ID NO. | Description | Nucleotide or Amino Acid Sequence |
| --- | --- | --- |
| | | RPSETVTCNVAHPASSTKVDKKIVPRDCGCKPCICTVPE VSSVFIFPPKPKDVLTITLTPKVTCVVVDISKDDPEVQFS WFVDDVEVHTAQTQPREEQFNSTFRSVSELPIMHQDWL NGKEFKCRVNSAAFPAPIEKTISKTKGRPKAPQVYTIPPP KEQMAKDKVSLTCMITDFFPEDITVEWQWNGQPAENY KNTQPIMNTNGSYFVYSKLNVQKSNWEAGNTFTCSVL HEGLHNHHTEKSLSHSPGK |
| 107. | BAP0027 light chain | EVQLVESGGGLVQPANSLKLSCAASGFTFSDYAMAWV RQSPKKGLEWVATIIYDGSSTYYRDSVKGRFTISRDNAK STLYLQMDSLRSEDTATYYCATGLGIATDYFDYWGQG VLVTVSSGGGGSGGGGSGGGGSGGGGSDIRMTQSPASL SASLGETVNIECLASEDIYSDLAWYQQKPGKSPQLLIYN ANSLQNGVPSRFSGSGSGTQYSLKINSLQSEDVATYFCQ QYNNYPPTFGGGTKLELKGGGGSGGGGSGGGGSDVV MTQTPLTWSITIGQPASISCKSSQSLLYSDGRTYLNWLL QRPGQSPKRLIYLVSKLDSGVPDRFSGSGSGTDFTLKISR VEAEDLGFYYCWQGTHLPHTFGAGTKLELKRADAAPT VSIFPPSSEQLTSGGASVVCFLNNFYPKDINVKWKIDGS ERQNGVLNSWTDQDSKDSTYSMSSTLTLTKDEYERHN SYTCEATHKTSTSPIVKSFNRNEC |
| 108. | BAP0028 light chain | DIRMTQSPASLSASLGETVNIECLASEDIYSDLAWYQQK PGKSPQLLIYNANSLQNGVPSRFSGSGSGTQYSLKINSL QSEDVATYFCQQYNNYPPTFGGGTKLELKGGGGSGGG GSGGGGSGGGGSEVQLVESGGGLVQPANSLKLSCAAS GFTFSDYAMAWVRQSPKKGLEWVATIIYDGSSTYYRDS VKGRFTISRDNAKSTLYLQMDSLRSEDTATYYCATGLG IATDYFDYWGQGVLVTVSSGGGGSGGGGSGGGGSDVV MTQTPLTWSITIGQPASISCKSSQSLLYSDGRTYLNWLL QRPGQSPKRLIYLVSKLDSGVPDRFSGSGSGTDFTLKISR VEAEDLGFYYCWQGTHLPHTFGAGTKLELKRADAAPT VSIFPPSSEQLTSGGASVVCFLNNFYPKDINVKWKIDGS ERQNGVLNSWTDQDSKDSTYSMSSTLTLTKDEYERHN SYTCEATHKTSTSPIVKSFNRNEC |
| 109. | BAP0029/ BAP0030 heavy chain | EVQLVESGGGLVQPANSLKLSCAASGFTFSDYAMAWV RQSPKKGLEWVATIIYDGSSTYYRDSVKGRFTISRDNAK STLYLQMDSLRSEDTATYYCATGLGIATDYFDYWGQG VLVTVSSAETTAPSVYPLAPGTALKSNSMVTLGCLVKG YFPEPVTVTWNSGALSSGVHTFPAVLQSGLYTLTSSVT VPSSTWPSQTVTCNVAHPASSTKVDKKIVPRNCGGDCK PCICTGSEVSSVFIFPPKPKDVLTITLTPKVTCVVVDISQD DPEVHFSWFVDDVEVHTAQTRPPEEQFNSTFRSVSELPI LHQDWLNGRTFRCKVTSAAFPSPIEKTISKPEGRTQVPH VYTMSPTKEEMTQNEVSITCMVKGFYPPDIYVEWQMN GQPQENYKNTPPTMDTDGSYFLYSKLNVKKEKWQQG NTFTCSVLHEGLHNHHTEKSLSHSPGK |
| 110. | BAP0029 light chain | DIRMTQSPASLSASLGETVNIECLASEDIYSDLAWYQQK PGKSPQLLIYNANSLQNGVPSRFSGSGSGTQYSLKINSL QSEDVATYFCQQYNNYPPTFGGGTKLELKRADAAPTVS IFPPSTEQLATGGASVVCLMNNFYPRDISVKWKIDGTER RDGVLDSVTDQDSKDSTYSMSSTLSLTKADYESHNLYT CEVVHKTSSSPVVKSFNRNECGGGGSGGGGSGGGGSQ AQLQQSGAELVRPGASVTLSCKASGYTFTDYEIHWMK QTPVHGLEWIGAIDPETGGTAYNQKFKGKAILTADRSSS TAYLELRSLTSEDSAVYYCYSYDYVTYWGQGTLVTVS AGGGGSGGGGSGGGGSGGGGSDVVMTQTPLTWSITIG QPASISCKSSQSLLYSDGRTYLNWLLQRPGQSPKRLIYL VSKLDSGVPDRFSGSGSGTDFTLKISRVEAEDLGFYYC WQGTHLPHTFGAGTKLELK |
| 111. | BAP0030 light chain | DIRMTQSPASLSASLGETVNIECLASEDIYSDLAWYQQK PGKSPQLLIYNANSLQNGVPSRFSGSGSGTQYSLKINSL QSEDVATYFCQQYNNYPPTFGGGTKLELKRADAAPTVS IFPPSTEQLATGGASVVCLMNNFYPRDISVKWKIDGTER RDGVLDSVTDQDSKDSTYSMSSTLSLTKADYESHNLYT CEVVHKTSSSPVVKSFNRNECGGGGSGGGGSGGGGSD VVMTQTPLTWSITIGQPASISCKSSQSLLYSDGRTYLNW LLQRPGQSPKRLIYLVSKLDSGVPDRFSGSGSGTDFTLKI SRVEAEDLGFYYCWQGTHLPHTFGAGTKLELKGGGGS GGGGSGGGGSGGGGSQAQLQQSGAELVRPGASVTLSC KASGYTFTDYEIHWMKQTPVHGLEWIGAIDPETGGTAY |

SEQUENCE TABLE

| SEQ ID NO. | Description | Nucleotide or Amino Acid Sequence |
|---|---|---|
| | | NQKFKGKAILTADRSSSTAYLELRSLTSEDSAVYYCYSY DYVTYWGQGTLVTVSA |
| 112. | BAP0031/ BAP0032 heavy chain | QAQLQQSGAELVRPGASVTLSCKASGYTFTDYEIHWM KQTPVHGLEWIGAIDPETGGTAYNQKFKGKAILTADRS SSTAYLELRSLTSEDSAVYYCYSYDYVTYWGQGTLVT VSAAKTTPPSVYPLAPGSAAQTNSMVTLGCLVKGYFPE PVTVTWNSGSLSSGVHTFPAVLQSDLYTLSSSVTVPSSP RPSETVTCNVAHPASSTKVDKKIVPRDCGCKPCICTVPE VSSVFIFPPKPKDVLTITLTPKVTCVVVDISKDDPEVQFS WFVDDVEVHTAQTQPREEQFNSTFRSVSELPIMHQDWL NGKEFKCRVNSAAFPAPIEKTISKTKGRPKAPQVYTIPPP KEQMAKDKVSLTCMITDFFPEDITVEWQWNGQPAENY KNTQPIMNTNGSYFVYSKLNVQKSNWEAGNTFTCSVL HEGLHNHHTEKSLSHSPGK |
| 113. | BAP0031 light chain | DVVMTQTPLTWSITIGQPASISCKSSQSLLYSDGRTYLN WLLQRPGQSPKRLIYLVSKLDSGVPDRFSGSGSGTDFTL KISRVEAEDLGFYYCWQGTHLPHTFGAGTKLELKRAD AAPTVSIFPPSSEQLTSGGASVVCFLNNFYPKDINVKWK IDGSERQNGVLNSWTDQDSKDSTYSMSSTLTLTKDEYE RHNSYTCEATHKTSTSPIVKSFNRNECGGGGSGGGGSG GGGSEVQLVESGGGLVQPANSLKLSCAASGFTFSDYAM AWVRQSPKKGLEWVATIIYDGSSTYYRDSVKGRFTISR DNAKSTLYLQMDSLRSEDTATYYCATGLGIATDYFDY WGQGVLVTVSSGGGGSGGGGSGGGGSGGGGSDIRMT QSPASLSASLGETVNIECLASEDIYSDLAWYQQKPGKSP QLLIYNANSLQNGVPSRFSGSGSGTQYSLKINSLQSEDV ATYFCQQYNNYPPTFGGGTKLELK |
| 114. | BAP0032 light chain | DVVMTQTPLTWSITIGQPASISCKSSQSLLYSDGRTYLN WLLQRPGQSPKRLIYLVSKLDSGVPDRFSGSGSGTDFTL KISRVEAEDLGFYYCWQGTHLPHTFGAGTKLELKRAD AAPTVSIFPPSSEQLTSGGASVVCFLNNFYPKDINVKWK IDGSERQNGVLNSWTDQDSKDSTYSMSSTLTLTKDEYE RHNSYTCEATHKTSTSPIVKSFNRNECGGGGSGGGGSG GGGSDIRMTQSPASLSASLGETVNIECLASEDIYSDLAW YQQKPGKSPQLLIYNANSLQNGVPSRFSGSGSGTQYSL KINSLQSEDVATYFCQQYNNYPPTFGGGTKLELKGGGG SGGGGSGGGGSGGGGSEVQLVESGGGLVQPANSLKLS CAASGFTFSDYAMAWVRQSPKKGLEWVATIIYDGSSTY YRDSVKGRFTISRDNAKSTLYLQMDSLRSEDTATYYCA TGLGIATDYFDYWGQGVLVTVSA |
| 115. | BAP0033 heavy chain | EVQLVESGGGVVQPGRSLRLSCAASGFTFSDYAMAWV RQAPGKGLEWVATIIYDGSSTYYRDSVKGRFTISRDNSK NTLYLQMNSLRAEDTAVYYCATGLGIATDYFDYWGQG TLVTVSSASTKGPSVFPLAPCSRSTSESTAALGCLVKDY FPEPVTVSWNSGALTSGVHTFPAVLQSSGLYSLSSVVTV PSSSLGTKTYTCNVDHKPSNTKVDKRVESKYGPPCPPCP APEFLGGPSVFLFPPKPKDTLMISRTPEVTCVVVDVSQE DPEVQFNWYVDGVEVHNAKTKPREEQFNSTYRVVSVL TVLHQDWLNGKEYKCKVSNKGLPSSIEKTISKAKGQPR EPQVYTLPPSQEEMTKNQVSLTCLVKGFYPSDIAVEWE SNGQPENNYKTTPPVLDSDGSFFLYSRLTVDKSRWQEG NVFSCSVMHEALHNHYTQKSLSLSLGKGGGGSGGGGS GGGGSDIQMTQSPSSLSASVGDRVTITCRSSQSLLYSDG RTYLNWYQQKPGKSPKRLIYLVSKLDSGVPDRFSGSGS GTDFTLTISSLQPEDFATYYCWQGTHLPHTFGCGTKVEI KGGGGSGGGGSGGGGSGGGGSEVQLVQSGAEVKKPG ASVKVSCKASGYTFTDYEIHWVRQAPGKCLEWMGAID PETGGTAYNQKFKGRVTMTTDTSTSTAYMELRSLRSDD TAVYYCYSYDYVTYWGQGTTVTVSA |
| 116. | BAP0034 heavy chain | EVQLVESGGGVVQPGRSLRLSCAASGFTFSDYAMAWV RQAPGKGLEWVATIIYDGSSTYYRDSVKGRFTISRDNSK NTLYLQMNSLRAEDTAVYYCATGLGIATDYFDYWGQG TLVTVSSASTKGPSVFPLAPCSRSTSESTAALGCLVKDY FPEPVTVSWNSGALTSGVHTFPAVLQSSGLYSLSSVVTV PSSSLGTKTYTCNVDHKPSNTKVDKRVESKYGPPCPPCP APEFLGGPSVFLFPPKPKDTLMISRTPEVTCVVVDVSQE DPEVQFNWYVDGVEVHNAKTKPREEQFNSTYRVVSVL TVLHQDWLNGKEYKCKVSNKGLPSSIEKTISKAKGQPR EPQVYTLPPSQEEMTKNQVSLTCLVKGFYPSDIAVEWE |

-continued

SEQUENCE TABLE

| SEQ ID NO. | Description | Nucleotide or Amino Acid Sequence |
|---|---|---|
| | | SNGQPENNYKTTPPVLDSDGSFFLYSRLTVDKSRWQEG NVFSCSVMHEALHNHYTQKSLSLSLGKGGGGSGGGGS GGGGSEVQLVQSGAEVKKPGASVKVSCKASGYTFTDY EIHWVRQAPGKCLEWMGAIDPETGGTAYNQKFKGRVT MTTDTSTSTAYMELRSLRSDDTAVYYCYSYDYVTYWG QGTTVTVSSGGGGSGGGGSGGGGSGGGGSDIQMTQSPS SLSASVGDRVTITCRSSQSLLYSDGRTYLNWYQQKPGK SPKRLIYLVSKLDSGVPDRFSGSGSGTDFTLTISSLQPED FATYYCWQGTHLPHTFGCGTKVEIK |
| 117. | BAP0035 heavy chain | EVQLVESGGGVVQPGRSLRLSCAASGFTFSDYAMAWV RQAPGKGLEWVATIIYDGSSTYYRDSVKGRFTISRDNSK NTLYLQMNSLRAEDTAVYYCATGLGIATDYFDYWGQG TLVTVSSASTKGPSVFPLAPCSRSTSESTAALGCLVKDY FPEPVTVSWNSGALTSGVHTFPAVLQSSGLYSLSSVVTV PSSSLGTKTYTCNVDHKPSNTKVDKRVESKYGPPCPPCP APEFLGGPSVFLFPPKPKDTLMISRTPEVTCVVVDVSQE DPEVQFNWYVDGVEVHNAKTKPREEQFNSTYRVVSVL TVLHQDWLNGKEYKCKVSNKGLPSSIEKTISKAKGQPR EPQVYTLPPSQEEMTKNQVSLTCLVKGFYPSDIAVEWE SNGQPENNYKTTPPVLDSDGSFFLYSRLTVDKSRWQEG NVFSCSVMHEALHNHYTQKSLSLSLGKGGGGSGGGGS GGGGSDVVMTQSPLSLSVSPGERASLSCKSSQSLLYSDG RTYLNWYLQKPGQSPQRLIYLVSKLDSGVPDRFSGSGS GTDFTLKISRVQSEDVGVYYCWQGTHLPHTFGCGTKVE IKGGGGSGGGGSGGGGSGGGGSEVQLVQSGAEVKKPG ASVKVSCKASGYTFTDYEIHWVRQAPGKCLEWMGAID PETGGTAYNQKFKGRVTMTTDTSTSTAYMELRSLRSDD TAVYYCYSYDYVTYWGQGTTVTVSA |
| 118. | BAP0036 heavy chain | EVQLVESGGGVVQPGRSLRLSCAASGFTFSDYAMAWV RQAPGKGLEWVATIIYDGSSTYYRDSVKGRFTISRDNSK NTLYLQMNSLRAEDTAVYYCATGLGIATDYFDYWGQG TLVTVSSASTKGPSVFPLAPCSRSTSESTAALGCLVKDY FPEPVTVSWNSGALTSGVHTFPAVLQSSGLYSLSSVVTV PSSSLGTKTYTCNVDHKPSNTKVDKRVESKYGPPCPPCP APEFLGGPSVFLFPPKPKDTLMISRTPEVTCVVVDVSQE DPEVQFNWYVDGVEVHNAKTKPREEQFNSTYRVVSVL TVLHQDWLNGKEYKCKVSNKGLPSSIEKTISKAKGQPR EPQVYTLPPSQEEMTKNQVSLTCLVKGFYPSDIAVEWE SNGQPENNYKTTPPVLDSDGSFFLYSRLTVDKSRWQEG NVFSCSVMHEALHNHYTQKSLSLSLGKGGGGSGGGGS GGGGSEVQLVQSGAEVKKPGASVKVSCKASGYTFTDY EIHWVRQAPGKCLEWMGAIDPETGGTAYNQKFKGRVT MTTDTSTSTAYMELRSLRSDDTAVYYCYSYDYVTYWG QGTTVTVSSGGGGSGGGGSGGGGSGGGGSDVVMTQSP LSLSVSPGERASLSCKSSQSLLYSDGRTYLNWYLQKPG QSPQRLIYLVSKLDSGVPDRFSGSGSGTDFTLKISRVQSE DVGVYYCWQGTHLPHTFGCGTKVEIK |
| 119. | BAP0033/ BAP0034/ BAP0035/BAP0036 light chain | DIRMTQSPFSLSASVGDRVTITCLASEDIYSDLAWYQQK PAKAPKLFIYNANSLQNGVPSRFSGSGSGTDYTLTISSLQ PEDFATYYCQQYNNYPPTFGGGTKVEIKRTVAAPSVFIF PPSDEQLKSGTASVVCLLNNFYPREAKVQWKVDNALQ SGNSQESVTEQDSKDSTYSLSSTLTLSKADYEKHKVYA CEVTHQGLSSPVTKSFNRGEC |
| 120. | BAP0037 heavy chain | EVQLVQSGAEVKKPGASVKVSCKASGYTFTDYEIHWV RQAPGKGLEWMGAIDPETGGTAYNQKFKGRVTMTTDT STSTAYMELRSLRSDDTAVYYCYSYDYVTYWGQGTTV TVSSASTKGPSVFPLAPCSRSTSESTAALGCLVKDYFPEP VTVSWNSGALTSGVHTFPAVLQSSGLYSLSSVVTVPSSS LGTKTYTCNVDHKPSNTKVDKRVESKYGPPCPPCPAPE FLGGPSVFLFPPKPKDTLMISRTPEVTCVVVDVSQEDPE VQFNWYVDGVEVHNAKTKPREEQFNSTYRVVSVLTVL HQDWLNGKEYKCKVSNKGLPSSIEKTISKAKGQPREPQ VYTLPPSQEEMTKNQVSLTCLVKGFYPSDIAVEWESNG QPENNYKTTPPVLDSDGSFFLYSRLTVDKSRWQEGNVF SCSVMHEALHNHYTQKSLSLSLGKGGGGSGGGGSGGG GSEVQLVESGGGVVQPGRSLRLSCAASGFTFSDYAMA WVRQAPGKCLEWVATIIYDGSSTYYRDSVKGRFTISRD NSKNTLYLQMNSLRAEDTAVYYCATGLGIATDYFDYW GQGTLVTVSSGGGGSGGGGSGGGGSGGGGSDIRMTQS PFSLSASVGDRVTITCLASEDIYSDLAWYQQKPAKAPKL |

-continued

SEQUENCE TABLE

| SEQ ID NO. | Description | Nucleotide or Amino Acid Sequence |
|---|---|---|
| | | FIYNANSLQNGVPSRFSGSGSGTDYTLTISSLQPEDFATY YCQQYNNYPPTFGCGTKVEIK |
| 121. | BAP0038 heavy chain | EVQLVQSGAEVKKPGASVKVSCKASGYTFTDYEIHWV RQAPGKGLEWMGAIDPETGGTAYNQKFKGRVTMTTDT STSTAYMELRSLRSDDTAVYYCYSYDYVTYWGQGTTV TVSSASTKGPSVFPLAPCSRSTSESTAALGCLVKDYFPEP VTVSWNSGALTSGVHTFPAVLQSSGLYSLSSVVTVPSSS LGTKTYTCNVDHKPSNTKVDKRVESKYGPPCPPCPAPE FLGGPSVFLFPPKPKDTLMISRTPEVTCVVVDVSQEDPE VQFNWYVDGVEVHNAKTKPREEQFNSTYRVVSVLTVL HQDWLNGKEYKCKVSNKGLPSSIEKTISKAKGQPREPQ VYTLPPSQEEMTKNQVSLTCLVKGFYPSDIAVEWESNG QPENNYKTTPPVLDSDGSFFLYSRLTVDKSRWQEGNVF SCSVMHEALHNHYTQKSLSLSLGKGGGGSGGGGSGGG GSDIRMTQSPFSLSASVGDRVTITCLASEDIYSDLAWYQ QKPAKAPKLFIYNANSLQNGVPSRFSGSGSGTDYTLTIS SLQPEDFATYYCQQYNNYPPTFGCGTKVEIKGGGGSGG GGSGGGGSGGGGSEVQLVESGGGVVQPGRSLRLSCAA SGFTFSDYAMAWVRQAPGKCLEWVATIIYDGSSTYYR DSVKGRFTISRDNSKNTLYLQMNSLRAEDTAVYYCATG LGIATDYFDYWGQGTLVTVSA |
| 122. | BAP0037/ BAP0038/ BAP0071/ BAP0072/BAP0073 light chain | DIQMTQSPSSLSASVGDRVTITCRSSQSLLYSDGRTYLN WYQQKPGKSPKRLIYLVSKLDSGVPDRFSGSGSGTDFT LTISSLQPEDFATYYCWQGTHLPHTFGGGTKVEIKRTVA APSVFIFPPSDEQLKSGTASVVCLLNNFYPREAKVQWK VDNALQSGNSQESVTEQDSKDSTYSLSSTLTLSKADYE KHKVYACEVTHQGLSSPVTKSFNRGEC |
| 123. | BAP0039 heavy chain | EVQLVQSGAEVKKPGASVKVSCKASGYTFTDYEIHWV RQAPGKGLEWMGAIDPETGGTAYNQKFKGRVTMTTDT STSTAYMELRSLRSDDTAVYYCYSYDYVTYWGQGTTV TVSSASTKGPSVFPLAPCSRSTSESTAALGCLVKDYFPE PVTVSWNSGALTSGVHTFPAVLQSSGLYSLSSVVTVPSSS LGTKTYTCNVDHKPSNTKVDKRVESKYGPPCPPCPAPE FLGGPSVFLFPPKPKDTLMISRTPEVTCVVVDVSQEDPE VQFNWYVDGVEVHNAKTKPREEQFNSTYRVVSVLTVL HQDWLNGKEYKCKVSNKGLPSSIEKTISKAKGQPREPQ VYTLPPSQEEMTKNQVSLTCLVKGFYPSDIAVEWESNG QPENNYKTTPPVLDSDGSFFLYSRLTVDKSRWQEGNVF SCSVMHEALHNHYTQKSLSLSLGKGGGGSGGGGSGGG GSEVQLVESGGGVVQPGRSLRLSCAASGFTFSDYAMA WVRQAPGKCLEWVATIIYDGSSTYYRDSVKGRFTISRD NSKNTLYLQMNSLRAEDTAVYYCATGLGIATDYFDYW GQGTLVTVSSGGGGSGGGGSGGGGSGGGGSDIRMTQS PFSLSASVGDRVTITCLASEDIYSDLAWYQQKPAKAPKL FIYNANSLQNGVPSRFSGSGSGTDYTLTISSLQPEDFATY YCQQYNNYPPTFGCGTKVEIK |
| 124. | BAP0040 heavy chain | EVQLVQSGAEVKKPGASVKVSCKASGYTFTDYEIHWV RQAPGKGLEWMGAIDPETGGTAYNQKFKGRVTMTTDT STSTAYMELRSLRSDDTAVYYCYSYDYVTYWGQGTTV TVSSASTKGPSVFPLAPCSRSTSESTAALGCLVKDYFPEP VTVSWNSGALTSGVHTFPAVLQSSGLYSLSSVVTVPSSS LGTKTYTCNVDHKPSNTKVDKRVESKYGPPCPPCPAPE FLGGPSVFLFPPKPKDTLMISRTPEVTCVVVDVSQEDPE VQFNWYVDGVEVHNAKTKPREEQFNSTYRVVSVLTVL HQDWLNGKEYKCKVSNKGLPSSIEKTISKAKGQPREPQ VYTLPPSQEEMTKNQVSLTCLVKGFYPSDIAVEWESNG QPENNYKTTPPVLDSDGSFFLYSRLTVDKSRWQEGNVF SCSVMHEALHNHYTQKSLSLSLGKGGGGSGGGGSGGG GSDIRMTQSPFSLSASVGDRVTITCLASEDIYSDLAWYQ QKPAKAPKLFIYNANSLQNGVPSRFSGSGSGTDYTLTIS SLQPEDFATYYCQQYNNYPPTFGCGTKVEIKGGGGSGG GGSGGGGSGGGGSEVQLVESGGGVVQPGRSLRLSCAA SGFTFSDYAMAWVRQAPGKCLEWVATIIYDGSSTYYR DSVKGRFTISRDNSKNTLYLQMNSLRAEDTAVYYCATG LGIATDYFDYWGQGTLVTVSA |
| 125. | BAP0039/ BAP0040/ BAP0069/BAP0070 light chain | DVVMTQSPLSLSVSPGERASLSCKSSQSLLYSDGRTYLN WYLQKPGQSPQRLIYLVSKLDSGVPDRFSGSGSGTDFTL KISRVQSEDVGVYYCWQGTHLPHTFGGGTKVEIKRTVA APSVFIFPPSDEQLKSGTASVVCLLNNFYPREAKVQWK |

-continued

SEQUENCE TABLE

| SEQ ID NO. | Description | Nucleotide or Amino Acid Sequence |
|---|---|---|
| | | VDNALQSGNSQESVTEQDSKDSTYSLSSTLTLSKADYE KHKVYACEVTHQGLSSPVTKSFNRGEC |
| 126. | BAP0050 heavy chain | EVQLLESGGGLVQPGGSLRLSCAASGFTFSSYAMSWVR QAPGKGLEWVSGITGSGGSTYYADSVKGRFTISRDNSK NTLYLQMNSLRAEDTAVYYCAKDPGTTVIMSWFDPWG QGTLVTVSSASTKGPSVFPLAPCSRSTSESTAALGCLVK DYFPEPVTVSWNSGALTSGVHTFPAVLQSSGLYSLSSV VTVPSSNFGTQTYTCNVDHKPSNTKVDKTVERKCCVEC PPCPAPPVAGPSVFLFPPKPKDTLMISRTPEVTCVVVDV SHEDPEVQFNWYVDGVEVHNAKTKPREEQFNSTFRVV SVLTVVHQDWLNGKEYKCKVSNKGLPAPIEKTISKTKG QPREPQVYTLPPSREEMTKNQVSLTCLVKGFYPSDIAVE WESNGQPENNYKTTPPMLDSDGSFFLYSKLTVDKSRW QQGNVFSCSVMHEALHNHYTQKSLSLSPGKGGGGSGG GGSGGGGSDIQMTQSPSSLSASVGDRVTITCRSSQSLLY SDGRTYLNWYQQKPGKSPKRLIYLVSKLDSGVPDRFSG SGSGTDFTLTISSLQPEDFATYYCWQGTHLPHTFGCGTK VEIKGGGGSGGGGSGGGGSGGGGSEVQLVQSGAEVKK PGASVKVSCKASGYTFTDYEIHWVRQAPGKCLEWMGA IDPETGGTAYNQKFKGRVTMTTDTSTSTAYMELRSLRS DDTAVYYCYSYDYVTYWGQGTTVTVSA |
| 127. | BAP0051 heavy chain | DIQMTQSPSSLSASVGDRVTITCRSSQSLLYSDGRTYLN WYQQKPGKSPKRLIYLVSKLDSGVPDRFSGSGSGTDFT LTISSLQPEDFATYYCWQGTHLPHTFGCGTKVEIKGGG GSGGGGSGGGGSGGGGSEVQLVQSGAEVKKPGASVKV SCKASGYTFTDYEIHWVRQAPGKCLEWMGAIDPETGG TAYNQKFKGRVTMTTDTSTSTAYMELRSLRSDDTAVY YCYSYDYVTYWGQGTTVTVSSGGGGSGGGGSGGGGS EVQLLESGGGLVQPGGSLRLSCAASGFTFSSYAMSWVR QAPGKGLEWVSGITGSGGSTYYADSVKGRFTISRDNSK NTLYLQMNSLRAEDTAVYYCAKDPGTTVIMSWFDPWG QGTLVTVSSASTKGPSVFPLAPCSRSTSESTAALGCLVK DYFPEPVTVSWNSGALTSGVHTFPAVLQSSGLYSLSSV VTVPSSNFGTQTYTCNVDHKPSNTKVDKTVERKCCVEC PPCPAPPVAGPSVFLFPPKPKDTLMISRTPEVTCVVVDV SHEDPEVQFNWYVDGVEVHNAKTKPREEQFNSTFRVV SVLTVVHQDWLNGKEYKCKVSNKGLPAPIEKTISKTKG QPREPQVYTLPPSREEMTKNQVSLTCLVKGFYPSDIAVE WESNGQPENNYKTTPPMLDSDGSFFLYSKLTVDKSRW QQGNVFSCSVMHEALHNHYTQKSLSLSPGK |
| 128. | BAP0052 heavy chain | EVQLLESGGGLVQPGGSLRLSCAASGFTFSSYAMSWVR QAPGKGLEWVSGITGSGGSTYYADSVKGRFTISRDNSK NTLYLQMNSLRAEDTAVYYCAKDPGTTVIMSWFDPWG QGTLVTVSSASTKGPSVFPLAPCSRSTSESTAALGCLVK DYFPEPVTVSWNSGALTSGVHTFPAVLQSSGLYSLSSV VTVPSSNFGTQTYTCNVDHKPSNTKVDKTVERKCCVEC PPCPAPPVAGPSVFLFPPKPKDTLMISRTPEVTCVVVDV SHEDPEVQFNWYVDGVEVHNAKTKPREEQFNSTFRVV SVLTVVHQDWLNGKEYKCKVSNKGLPAPIEKTISKTKG QPREPQVYTLPPSREEMTKNQVSLTCLVKGFYPSDIAVE WESNGQPENNYKTTPPMLDSDGSFFLYSKLTVDKSRW QQGNVFSCSVMHEALHNHYTQKSLSLSPGKGGGGSGG GGSGGGGSDVVMTQSPLSLSVSPGERASLSCKSSQSLLY SDGRTYLNWYLQKPGQSPQRLIYLVSKLDSGVPDRFSG SGSGTDFTLKISRVQSEDVGVYYCWQGTHLPHTFGCGT KVEIKGGGGSGGGGSGGGGSGGGGSEVQLVQSGAEVK KPGASVKVSCKASGYTFTDYEIHWVRQAPGKCLEWMG AIDPETGGTAYNQKFKGRVTMTTDTSTSTAYMELRSLR SDDTAVYYCYSYDYVTYWGQGTTVTVSA |
| 129. | BAP0050/ BAP0051/BAP0052 light chain | EIVLTQSPGTLSLSPGERATLSCRASQSVRGRYLAWYQQ KPGQAPRLLIYGASSRATGIPDRFSGSGSGTDFTLTISRL EPEDFAVFYCQQYGSSPRTFGQGTKVEIKRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC |
| 130. | BAP0053 light chain | EIVLTQSPGTLSLSPGERATLSCRASQSVRGRYLAWYQQ KPGQAPRLLIYGASSRATGIPDRFSGSGSGTDFTLTISRL EPEDFAVFYCQQYGSSPRTFGQGTKVEIKRTVAAPSVFI FPPSDEQLKSGTASVVCLLNNFYPREAKVQWKVDNAL |

-continued

SEQUENCE TABLE

| SEQ ID NO. | Description | Nucleotide or Amino Acid Sequence |
|---|---|---|
| | | QSGNSQESVTEQDSKDSTYSLSSTLTLSKADYEKHKVY ACEVTHQGLSSPVTKSFNRGECGGGGSGGGGSGGGGS DIQMTQSPSSLSASVGDRVTITCRSSQSLLYSDGRTYLN WYQQKPGKSPKRLIYLVSKLDSGVPDRFSGSGSGTDFT LTISSLQPEDFATYYCWQGTHLPHTFGCGTKVEIKGGG GSGGGGSGGGGSGGGGSEVQLVQSGAEVKKPGASVKV SCKASGYTFTDYEIHWVRQAPGKCLEWMGAIDPETGG TAYNQKFKGRVTMTTDTSTSTAYMELRSLRSDDTAVY YCYSYDYVTYWGQGTTVTVSA |
| 131. | BAP0054 light chain | DIQMTQSPSSLSASVGDRVTITCRSSQSLLYSDGRTYLN WYQQKPGKSPKRLIYLVSKLDSGVPDRFSGSGSGTDFT LTISSLQPEDFATYYCWQGTHLPHTFGCGTKVEIKGGG GSGGGGSGGGGSGGGGSEVQLVQSGAEVKKPGASVKV SCKASGYTFTDYEIHWVRQAPGKCLEWMGAIDPETGG TAYNQKFKGRVTMTTDTSTSTAYMELRSLRSDDTAVY YCYSYDYVTYWGQGTTVTVSSGGGGSGGGGSGGGGS EIVLTQSPGTLSLSPGERATLSCRASQSVRGRYLAWYQQ KPGQAPRLLIYGASSRATGIPDRFSGSGSGTDFTLTISRL EPEDFAVFYCQQYGSSPRTFGQGTKVEIKRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC |
| 132. | BAP0055 light chain | EIVLTQSPGTLSLSPGERATLSCRASQSVRGRYLAWYQQ KPGQAPRLLIYGASSRATGIPDRFSGSGSGTDFTLTISRL EPEDFAVFYCQQYGSSPRTFGQGTKVEIKRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGECGGGGSGGGGSGGGGS DVVMTQSPLSLSVSPGERASLSCKSSQSLLYSDGRTYLN WYLQKPGQSPQRLIYLVSKLDSGVPDRFSGSGSGTDFTL KISRVQSEDVGVYYCWQGTHLPHTFGCGTKVEIKGGG GSGGGGSGGGGSGGGGSEVQLVQSGAEVKKPGASVKV SCKASGYTFTDYEIHWVRQAPGKCLEWMGAIDPETGG TAYNQKFKGRVTMTTDTSTSTAYMELRSLRSDDTAVY YCYSYDYVTYWGQGTTVTVSA |
| 133. | BAP0053/ PBA0054/ BAP0055 heavy chain | EVQLLESGGGLVQPGGSLRLSCAASGFTFSSYAMSWVR QAPGKGLEWVSGITGSGGSTYYADSVKGRFTISRDNSK NTLYLQMNSLRAEDTAVYYCAKDPGTTVIMSWFDPWG QGTLVTVSSASTKGPSVFPLAPCSRSTSESTAALGCLVK DYFPEPVTVSWNSGALTSGVHTFPAVLQSSGLYSLSSV VTVPSSNFGTQTYTCNVDHKPSNTKVDKTVERKCCVEC PPCPAPPVAGPSVFLFPPKPKDTLMISRTPEVTCVVVDV SHEDPEVQFNWYVDGVEVHNAKTKPREEQFNSTFRVV SVLTVVHQDWLNGKEYKCKVSNKGLPAPIEKTISKTKG QPREPQVYTLPPSREEMTKNQVSLTCLVKGFYPSDIAVE WESNGQPENNYKTTPPMLDSDGSFFLYSKLTVDKSRW QQGNVFSCSVMHEALHNHYTQKSLSLSPGK |
| 134. | BAP0041/ BAP0042/ BAP0043/ BAP0044/BAP0045 heavy chain #1 | QAQLQQSGAELVRPGASVTLSCKASGYTFTDYEIHWM KQTPVHGLEWIGAIDPETGGTAYNQKFKGKAILTADRS SSTAYLELRSLTSEDSAVYYCYSYDYVTYWGQGTLVT VSSASTKGPSVFPLAPCSRSTSESTAALGCLVKDYFPEP VTVSWNSGALTSGVHTFPAVLQSSGLYSLSSVVTVPSSS LGTKTYTCNVDHKPSNTKVDKRVESKYGPPCPPCPAPE FLGGPSVFLFPPKPKDTLMISRTPEVTCVVVDVSQEDPE VQFNWYVDGVEVHNAKTKPREEQFNSTYRVVSVLTVL HQDWLNGKEYKCKVSNKGLPSSIEKTISKAKGQPREPQ VYTLPPSQEEMTKNQVSLSCAVKGFYPSDIAVEWESNG QPENNYKTTPPVLDSDGSFFLVSRLTVDKSRWQEGNVF SCSVMHEALHNRFTQKSLSLSLGK |
| 135. | BAP0041/ BAP0042/ BAP0043/ BAP0044/BAP0045 light chain #1 | DVVMTQTPLTWSITIGQPASISCKSSQSLLYSDGRTYLN WLLQRPGQSPKRLIYLVSKLDSGVPDRFSGSGSGTDFTL KISRVEAEDLGFYYCWQGTHLPHTFGAGTKLELKRTVA APSVFIFPPSDEQLKSGTASVVCLLNNFYPREAKVQWK VDNALQSGNSQESVTEQDSKDSTYSLSSTLTLSKADYE KHKVYACEVTHQGLSSPVTKSFNRGEC |
| 136. | BAP0041 heavy chain #2 | EVQLVESGGGLVQPANSLKLSCAASGFTFSDYAMAWV RQSPKKGLEWVATIIYDGSSTYYRDSVKGRFTISRDNAK STLYLQMDSLRSEDTATYYCATGLGIATDYFDYWGQG |

-continued

SEQUENCE TABLE

| SEQ ID NO. | Description | Nucleotide or Amino Acid Sequence |
|---|---|---|
| | | VLVTVSSASTKGPSVCPLAPSSRSTSESTAALGCLVKDY FPEPVTVSWNSGALTSGVHTFPAVLQSSGLYSLSSVVTV PSSSLGTKTYTCNVDHKPSNTKVDKRVESKYGPPCPPCP APEFLGGPSVFLFPPKPKDTLMISRTPEVTCVVVDVSQE DPEVQFNWYVDGVEVHNAKTKPREEQFNSTYRVVSVL TVLHQDWLNGKEYKCKVSNKGLPSSIEKTISKAKGQPR EPQVYTLPPSQEEMTKNQVSLWCLVKGFYPSDIAVEWE SNGQPENNYKTTPPVLDSDGSFFLYSRLTVDKSRWQEG NVFSCSVMHEALHNHYTQKSLSLSLGK |
| 137. | BAP0041 light chain #2 | DIRMTQSPASLSASLGETVNIECLASEDIYSDLAWYQQK PGKSPQLLIYNANSLQNGVPSRFSGSGSGTQYSLKINSL QSEDVATYFCQQYNNYPPTFGGGTKLELKRTVAAPSVF IFPPCDEQLKSGTASVVCLLNNFYPREAKVQWKVDNAL QSGNSQESVTEQDSKDSTYSLSSTLTLSKADYEKHKVY ACEVTHQGLSSPVTKSFNRGES |
| 138. | BAP0042 heavy chain #2 | EVQLVESGGGLVQPANSLKLSCAASGFTFSDYAMAWV RQSPKKGLEWVATIIYDGSSTYYRDSVKGRFTISRDNAK STLYLQMDSLRSEDTATYYCATGLGIATDYFDYWGQG VLVTVSSASTKGPSVFPCAPSSRSTSESTAALGCLVKDY FPEPVTVSWNSGALTSGVHTFPAVLQSSGLYSLSSVVTV PSSSLGTKTYTCNVDHKPSNTKVDKRVESKYGPPCPPCP APEFLGGPSVFLFPPKPKDTLMISRTPEVTCVVVDVSQE DPEVQFNWYVDGVEVHNAKTKPREEQFNSTYRVVSVL TVLHQDWLNGKEYKCKVSNKGLPSSIEKTISKAKGQPR EPQVYTLPPSQEEMTKNQVSLWCLVKGFYPSDIAVEWE SNGQPENNYKTTPPVLDSDGSFFLYSRLTVDKSRWQEG NVFSCSVMHEALHNHYTQKSLSLSLGK |
| 139. | BAP0042 light chain #2 | DIRMTQSPASLSASLGETVNIECLASEDIYSDLAWYQQK PGKSPQLLIYNANSLQNGVPSRFSGSGSGTQYSLKINSL QSEDVATYFCQQYNNYPPTFGGGTKLELKRTVAAPSVF ICPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGES |
| 140. | BAP0043 heavy chain #2 | EVQLVESGGGLVQPANSLKLSCAASGFTFSDYAMAWV RQSPKKGLEWVATIIYDGSSTYYRDSVKGRFTISRDNAK STLYLQMDSLRSEDTATYYCATGLGIATDYFDYWGQG VLVTVSSASTKGPSVFPLAPSSRSTSESTAALGCLVKDY FPEPVTVSWNSGALTSGVHTCPAVLQSSGLYSLSSVVT VPSSSLGTKTYTCNVDHKPSNTKVDKRVESKYGPPCPP CPAPEFLGGPSVFLFPPKPKDTLMISRTPEVTCVVVDVS QEDPEVQFNWYVDGVEVHNAKTKPREEQFNSTYRVVS VLTVLHQDWLNGKEYKCKVSNKGLPSSIEKTISKAKGQ PREPQVYTLPPSQEEMTKNQVSLWCLVKGFYPSDIAVE WESNGQPENNYKTTPPVLDSDGSFFLYSRLTVDKSRWQ EGNVFSCSVMHEALHNHYTQKSLSLSLGK |
| 141. | BAP0043 light chain #2 | DIRMTQSPASLSASLGETVNIECLASEDIYSDLAWYQQK PGKSPQLLIYNANSLQNGVPSRFSGSGSGTQYSLKINSL QSEDVATYFCQQYNNYPPTFGGGTKLELKRTVAAPSVF IFPPSDEQLKSGTASVVCLLNNFYPREAKVQWKVDNAL QSGNSQESVTEQDSKDSTYSLCSTLTLSKADYEKHKVY ACEVTHQGLSSPVTKSFNRGES |
| 142. | BAP0044 heavy chain #2 | EVQLVESGGGLVQPANSLKLSCAASGFTFSDYAMAWV RQSPKKGLEWVATIIYDGSSTYYRDSVKGRFTISRDNAK STLYLQMDSLRSEDTATYYCATGLGIATDYFDYWGQG VLVTVSSASTKGPSVFPLAPSSRSTSESTAALGCLVKDY FPEPVTVSWNSGALTSGVHTFPACLQSSGLYSLSSVVTV PSSSLGTKTYTCNVDHKPSNTKVDKRVESKYGPPCPPCP APEFLGGPSVFLFPPKPKDTLMISRTPEVTCVVVDVSQE DPEVQFNWYVDGVEVHNAKTKPREEQFNSTYRVVSVL TVLHQDWLNGKEYKCKVSNKGLPSSIEKTISKAKGQPR EPQVYTLPPSQEEMTKNQVSLWCLVKGFYPSDIAVEWE SNGQPENNYKTTPPVLDSDGSFFLYSRLTVDKSRWQEG NVFSCSVMHEALHNHYTQKSLSLSLGK |
| 143. | BAP0044 light chain #2 | DIRMTQSPASLSASLGETVNIECLASEDIYSDLAWYQQK PGKSPQLLIYNANSLQNGVPSRFSGSGSGTQYSLKINSL QSEDVATYFCQQYNNYPPTFGGGTKLELKRTVAAPSVF IFPPSDEQLKSGTASVVCLLNNFYPREAKVQWKVDNAL |

-continued

SEQUENCE TABLE

| SEQ ID NO. | Description | Nucleotide or Amino Acid Sequence |
|---|---|---|
| | | QSGNSCESVTEQDSKDSTYSLSSTLTLSKADYEKHKVY ACEVTHQGLSSPVTKSFNRGES |
| 144. | BAP0045 heavy chain #2 | EVQLVESGGGLVQPANSLKLSCAASGFTFSDYAMAWV RQSPKKGLEWVATIIYDGSSTYYRDSVKGRFTISRDNAK STLYLQMDSLRSEDTATYYCATGLGIATDYFDYWGQG VLVTVSSASTKGPSVFPLAPSSRSTSESTAALGCLVKDY FPEPVTVSWNSGALTSGVHTFPACLQSSGLYSLSSVVTV PSSSLGTKTYTCNVDHKPSNTKVDKRVESKYGPPCPPCP APEFLGGPSVFLFPPKPKDTLMISRTPEVTCVVVDVSQE DPEVQFNWYVDGVEVHNAKTKPREEQFNSTYRVVSVL TVLHQDWLNGKEYKCKVSNKGLPSSIEKTISKAKGQPR EPQVYTLPPSQEEMTKNQVSLWCLVKGFYPSDIAVEWE SNGQPENNYKTTPPVLDSDGSFFLYSRLTVDKSRWQEG NVFSCSVMHEALHNHYTQKSLSLSLGK |
| 145. | BAP0045 light chain #2 | DIRMTQSPASLSASLGETVNIECLASEDIYSDLAWYQQK PGKSPQLLIYNANSLQNGVPSRFSGSGSGTQYSLKINSL QSEDVATYFCQQYNNYPPTFGGGTKLELKRTVAAPSVF IFPPSDEQLKSGTASVVCLLNNFYPREAKVQWKVDNAL QSGNSCESVTEQDSKDSTYSLSSTLTLSKADYEKHKVY ACEVTHQGLSSPVTKSFNRGES |
| 146. | BAP0061/ BAP0062/ BAP0063/ BAP0064/ BAP0065/ BAP0066/ BAP0067/ BAP0068 heavy chain #1 | EVQLVQSGAEVKKPGASVKVSCKASGYTFTDYEIHWV RQAPGKGLEWMGAIDPETGGTAYNQKFKGRVTMTTDT STSTAYMELRSLRSDDTAVYYCYSYDYVTYWGQGTTV TVSSASTKGPSVFPLAPCSRSTSESTAALGCLVKDYFPEP VTVSWNSGALTSGVHTFPAVLQSSGLYSLSSVVTVPSSS LGTKTYTCNVDHKPSNTKVDKRVESKYGPPCPPCPAPE FLGGPSVFLFPPKPKDTLMISRTPEVTCVVVDVSQEDPE VQFNWYVDGVEVHNAKTKPREEQFNSTYRVVSVLTVL HQDWLNGKEYKCKVSNKGLPSSIEKTISKAKGQPREPQ VYTLPPSQEEMTKNQVSLSCAVKGFYPSDIAVEWESNG QPENNYKTTPPVLDSDGSFFLVSRLTVDKSRWQEGNVF SCSVMHEALHNRFTQKSLSLSLGK |
| 147. | BAP0061/ BAP0062/ BAP0063/ BAP0064/ BAP0065/ BAP0066/ BAP0067/ BAP0068/ BAP0074/ PBA0075/ BAP0076 light chain #1 | DIQMTQSPSSLSASVGDRVTITCRSSQSLLYSDGRTYLN WYQQKPGKSPKRLIYLVSKLDSGVPDRFSGSGSGTDFT LTISSLQPEDFATYYCWQGTHLPHTFGGGTKVEIKRTVA APSVFIFPPSDEQLKSGTASVVCLLNNFYPREAKVQWK VDNALQSGNSQESVTEQDSKDSTYSLSSTLTLSKADYE KHKVYACEVTHQGLSSPVTKSFNRGEC |
| 148. | BAP0061 heavy chain #2 | EVQLVESGGGVVQPGRSLRLSCAASGFTFSDYAMAWV RQAPGKGLEWVATIIYDGSSTYYRDSVKGRFTISRDNSK NTLYLQMNSLRAEDTAVYYCATGLGIATDYFDYWGQG TLVTVSSASTKGPSVFPCAPSSRSTSESTAALGCLVKDY FPEPVTVSWNSGALTSGVHTFPAVLQSSGLYSLSSVVTV PSSSLGTKTYTCNVDHKPSNTKVDKRVESKYGPPCPPCP APEFLGGPSVFLFPPKPKDTLMISRTPEVTCVVVDVSQE DPEVQFNWYVDGVEVHNAKTKPREEQFNSTYRVVSVL TVLHQDWLNGKEYKCKVSNKGLPSSIEKTISKAKGQPR EPQVYTLPPSQEEMTKNQVSLWCLVKGFYPSDIAVEWE SNGQPENNYKTTPPVLDSDGSFFLYSRLTVDKSRWQEG NVFSCSVMHEALHNHYTQKSLSLSLGK |
| 149. | BAP0061 light chain #2 | DIRMTQSPFSLSASVGDRVTITCLASEDIYSDLAWYQQK PAKAPKLFIYNANSLQNGVPSRFSGSGSGTDYTLTISSLQ PEDFATYYCQQYNNYPPTFGGGTKVEIKRTVAAPSVFIC PPSDEQLKSGTASVVCLLNNFYPREAKVQWKVDNALQ SGNSQESVTEQDSKDSTYSLSSTLTLSKADYEKHKVYA CEVTHQGLSSPVTKSFNRGES |
| 150. | BAP0062 heavy chain #2 | EVQLVESGGGVVQPGRSLRLSCAASGFTFSDYAMAWV RQAPGKGLEWVATIIYDGSSTYYRDSVKGRFTISRDNSK NTLYLQMNSLRAEDTAVYYCATGLGIATDYFDYWGQG TLVTVSSASTKGPSVFPLAPSSRSTSESTAALGCLVKDY |

-continued

SEQUENCE TABLE

| SEQ ID NO. | Description | Nucleotide or Amino Acid Sequence |
|---|---|---|
| | | FPEPVTVSWNSGALTSGVHTCPAVLQSSGLYSLSSVVT VPSSSLGTKTYTCNVDHKPSNTKVDKRVESKYGPPCPP CPAPEFLGGPSVFLFPPKPKDTLMISRTPEVTCVVVDVS QEDPEVQFNWYVDGVEVHNAKTKPREEQFNSTYRVVS VLTVLHQDWLNGKEYKCKVSNKGLPSSIEKTISKAKGQ PREPQVYTLPPSQEEMTKNQVSLWCLVKGFYPSDIAVE WESNGQPENNYKTTPPVLDSDGSFFLYSRLTVDKSRWQ EGNVFSCSVMHEALHNHYTQKSLSLSLGK |
| 151. | BAP0062 light chain #2 | DIRMTQSPFSLSASVGDRVTITCLASEDIYSDLAWYQQK PAKAPKLFIYNANSLQNGVPSRFSGSGSGTDYTLTISSLQ PEDFATYYCQQYNNYPPTFGGGTKVEIKRTVAAPSVFIF PPSDEQLKSGTASVVCLLNNFYPREAKVQWKVDNALQ SGNSQESVTEQDSKDSTYSLCSTLTLSKADYEKHKVYA CEVTHQGLSSPVTKSFNRGES |
| 152. | BAP0063 heavy chain #2 | EVQLVESGGGVVQPGRSLRLSCAASGFTFSDYAMAWV RQAPGKGLEWVATIIYDGSSTYYRDSVKGRFTISRDNSK NTLYLQMNSLRAEDTAVYYCATGLGIATDYFDYWGQG TLVTVSSASTKGPSVFPLAPSSRSTSESTAALGCLVKDY FPEPVTVSWNSGALTSGVHTFPACLQSSGLYSLSSVVTV PSSSLGTKTYTCNVDHKPSNTKVDKRVESKYGPPCPPCP APEFLGGPSVFLFPPKPKDTLMISRTPEVTCVVVDVSQE DPEVQFNWYVDGVEVHNAKTKPREEQFNSTYRVVSVL TVLHQDWLNGKEYKCKVSNKGLPSSIEKTISKAKGQPR EPQVYTLPPSQEEMTKNQVSLWCLVKGFYPSDIAVEWE SNGQPENNYKTTPPVLDSDGSFFLYSRLTVDKSRWQEG NVFSCSVMHEALHNHYTQKSLSLSLGK |
| 153. | BAP0063 light chain #2 | DIRMTQSPFSLSASVGDRVTITCLASEDIYSDLAWYQQK PAKAPKLFIYNANSLQNGVPSRFSGSGSGTDYTLTISSLQ PEDFATYYCQQYNNYPPTFGGGTKVEIKRTVAAPSVFIF PPSDEQLKSGTASVVCLLNNFYPREAKVQWKVDNALQ SGNSCESVTEQDSKDSTYSLSSTLTLSKADYEKHKVYA CEVTHQGLSSPVTKSFNRGES |
| 154. | BAP0064 heavy chain #2 | EVQLVESGGGVVQPGRSLRLSCAASGFTFSDYAMAWV RQAPGKGLEWVATIIYDGSSTYYRDSVKGRFTISRDNSK NTLYLQMNSLRAEDTAVYYCATGLGIATDYFDYWGQG TLVTVSSASTKGPSVCPLAPSSRSTSESTAALGCLVKDY FPEPVTVSWNSGALTSGVHTFPAVLQSSGLYSLSSVVTV PSSSLGTKTYTCNVDHKPSNTKVDKRVESKYGPPCPPCP APEFLGGPSVFLFPPKPKDTLMISRTPEVTCVVVDVSQE DPEVQFNWYVDGVEVHNAKTKPREEQFNSTYRVVSVL TVLHQDWLNGKEYKCKVSNKGLPSSIEKTISKAKGQPR EPQVYTLPPSQEEMTKNQVSLWCLVKGFYPSDIAVEWE SNGQPENNYKTTPPVLDSDGSFFLYSRLTVDKSRWQEG NVFSCSVMHEALHNHYTQKSLSLSLGK |
| 155. | BAP0064 light chain #2 | DIRMTQSPFSLSASVGDRVTITCLASEDIYSDLAWYQQK PAKAPKLFIYNANSLQNGVPSRFSGSGSGTDYTLTISSLQ PEDFATYYCQQYNNYPPTFGGGTKVEIKRTVAAPSVFIC PPSDEQLKSGTASVVCLLNNFYPREAKVQWKVDNALQ SGNSQESVTEQDSKDSTYSLSSTLTLSKADYEKHKVYA CEVTHQGLSSPVTKSFNRGES |
| 156. | BAP0065 heavy chain #2 | EVQLLESGGGLVQPGGSLRLSCAASGFTFSSYAMSWVR QAPGKGLEWVSGITGSGGSTYYADSVKGRFTISRDNSK NTLYLQMNSLRAEDTAVYYCAKDPGTTVIMSWFDPWG QGTLVTVSSASTKGPSVFPCAPSSRSTSESTAALGCLVK DYFPEPVTVSWNSGALTSGVHTFPAVLQSSGLYSLSSV VTVPSSSLGTKTYTCNVDHKPSNTKVDKRVESKYGPPC PPCPAPEFLGGPSVFLFPPKPKDTLMISRTPEVTCVVVDV SQEDPEVQFNWYVDGVEVHNAKTKPREEQFNSTYRVV SVLTVLHQDWLNGKEYKCKVSNKGLPSSIEKTISKAKG QPREPQVYTLPPSQEEMTKNQVSLWCLVKGFYPSDIAV EWESNGQPENNYKTTPPVLDSDGSFFLYSRLTVDKSRW QEGNVFSCSVMHEALHNHYTQKSLSLSLGK |
| 157. | BAP0065 light chain #2 | EIVLTQSPGTLSLSPGERATLSCRASQSVRGRYLAWYQQ KPGQAPRLLIYGASSRATGIPDRFSGSGSGTDFTLTISRL EPEDFAVFYCQQYGSSPRTFGQGTKVEIKRTVAAPSVFI |

-continued

SEQUENCE TABLE

| SEQ ID NO. | Description | Nucleotide or Amino Acid Sequence |
|---|---|---|
| | | CPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGES |
| 158. | BAP0066 heavy chain #2 | EVQLLESGGGLVQPGGSLRLSCAASGFTFSSYAMSWVR QAPGKGLEWVSGITGSGGSTYYADSVKGRFTISRDNSK NTLYLQMNSLRAEDTAVYYCAKDPGTTVIMSWFDPWG QGTLVTVSSASTKGPSVFPLAPSSRSTSESTAALGCLVK DYFPEPVTVSWNSGALTSGVHTCPAVLQSSGLYSLSSV VTVPSSSLGTKTYTCNVDHKPSNTKVDKRVESKYGPPC PPCPAPEFLGGPSVFLFPPKPKDTLMISRTPEVTCVVVDV SQEDPEVQFNWYVDGVEVHNAKTKPREEQFNSTYRVV SVLTVLHQDWLNGKEYKCKVSNKGLPSSIEKTISKAKG QPREPQVYTLPPSQEEMTKNQVSLWCLVKGFYPSDIAV EWESNGQPENNYKTTPPVLDSDGSFFLYSRLTVDKSRW QEGNVFSCSVMHEALHNHYTQKSLSLSLGK |
| 159. | BAP0066 light chain #2 | EIVLTQSPGTLSLSPGERATLSCRASQSVRGRYLAWYQQ KPGQAPRLLIYGASSRATGIPDRFSGSGSGTDFTLTISRL EPEDFAVFYCQQYGSSPRTFGQGTKVEIKRTVAAPSVFI FPPSDEQLKSGTASVVCLLNNFYPREAKVQWKVDNAL QSGNSQESVTEQDSKDSTYSLCSTLTLSKADYEKHKVY ACEVTHQGLSSPVTKSFNRGES |
| 160. | BAP0067 heavy chain #2 | EVQLLESGGGLVQPGGSLRLSCAASGFTFSSYAMSWVR QAPGKGLEWVSGITGSGGSTYYADSVKGRFTISRDNSK NTLYLQMNSLRAEDTAVYYCAKDPGTTVIMSWFDPWG QGTLVTVSSASTKGPSVCPLAPSSRSTSESTAALGCLVK DYFPEPVTVSWNSGALTSGVHTFPAVLQSSGLYSLSSV VTVPSSSLGTKTYTCNVDHKPSNTKVDKRVESKYGPPC PPCPAPEFLGGPSVFLFPPKPKDTLMISRTPEVTCVVVDV SQEDPEVQFNWYVDGVEVHNAKTKPREEQFNSTYRVV SVLTVLHQDWLNGKEYKCKVSNKGLPSSIEKTISKAKG QPREPQVYTLPPSQEEMTKNQVSLWCLVKGFYPSDIAV EWESNGQPENNYKTTPPVLDSDGSFFLYSRLTVDKSRW QEGNVFSCSVMHEALHNHYTQKSLSLSLGK |
| 161. | BAP0067 light chain #2 | EIVLTQSPGTLSLSPGERATLSCRASQSVRGRYLAWYQQ KPGQAPRLLIYGASSRATGIPDRFSGSGSGTDFTLTISRL EPEDFAVFYCQQYGSSPRTFGQGTKVEIKRTVAAPSVFI CPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGES |
| 162. | BAP0068 heavy chain #2 | EVQLLESGGGLVQPGGSLRLSCAASGFTFSSYAMSWVR QAPGKGLEWVSGITGSGGSTYYADSVKGRFTISRDNSK NTLYLQMNSLRAEDTAVYYCAKDPGTTVIMSWFDPWG QGTLVTVSSASTKGPSVFPLAPSSRSTSESTAALGCLVK DYFPEPVTVSWNSGALTSGVHTFPACLQSSGLYSLSSVV TVPSSSLGTKTYTCNVDHKPSNTKVDKRVESKYGPPCP PCPAPEFLGGPSVFLFPPKPKDTLMISRTPEVTCVVVDVS QEDPEVQFNWYVDGVEVHNAKTKPREEQFNSTYRVVS VLTVLHQDWLNGKEYKCKVSNKGLPSSIEKTISKAKGQ PREPQVYTLPPSQEEMTKNQVSLWCLVKGFYPSDIAVE WESNGQPENNYKTTPPVLDSDGSFFLYSRLTVDKSRWQ EGNVFSCSVMHEALHNHYTQKSLSLSLGK |
| 163. | BAP0068/ BAP0074/ 7BAP005/BAP0076 light chain #2 | EIVLTQSPGTLSLSPGERATLSCRASQSVRGRYLAWYQQ KPGQAPRLLIYGASSRATGIPDRFSGSGSGTDFTLTISRL EPEDFAVFYCQQYGSSPRTFGQGTKVEIKRTVAAPSVFI FPPSDEQLKSGTASVVCLLNNFYPREAKVQWKVDNAL QSGNSCESVTEQDSKDSTYSLSSTLTLSKADYEKHKVY ACEVTHQGLSSPVTKSFNRGES |
| 171. | BAP0074 heavy chain #1 | EVQLVQSGAEVKKPGASVKVSCKASGYTFTDYEIHWV RQAPGKGLEWMGAIDPETGGTAYNQKFKGRVTMTTDT STSTAYMELRSLRSDDTAVYYCYSYDYVTYWGQGTTV TVSSASTKGPSVFPLAPCSRSTSESTAALGCLVKDYFPEP VTVSWNSGALTSGVHTFPAVLQSSGLYSLSSVVTVPSS NFGTQTYTCNVDHKPSNTKVDKTVERKCCVECPPCPAP PVAGPSVFLFPPKPKDTLMISRTPEVTCVVVDVSHEDPE VQFNWYVDGVEVHNAKTKPREEQFNSTFRVVSVLTVV HQDWLNGKEYKCKVSNKGLPAPIEKTISKTKGQPREPQ VYTLPPCREEMTKNQVSLWCLVKGFYPSDIAVEWESN |

-continued

SEQUENCE TABLE

| SEQ ID NO. | Description | Nucleotide or Amino Acid Sequence |
|---|---|---|
| | | GQPENNYKTTPPMLDSDGSFFLYSKLTVDKSRWQQGN VFSCSVMHEALHNHYTQKSLSLSPGK |
| 172. | BAP0074 heavy chain #2 | EVQLLESGGGLVQPGGSLRLSCAASGFTFSSYAMSWVR QAPGKGLEWVSGITGSGGSTYYADSVKGRFTISRDNSK NTLYLQMNSLRAEDTAVYYCAKDPGTTVIMSWFDPWG QGTLVTVSSASTKGPSVFPLAPSSRSTSESTAALGCLVK DYFPEPVTVSWNSGALTSGVHTFPACLQSSGLYSLSSVV TVPSSNFGTQTYTCNVDHKPSNTKVDKTVERKCCVECP PCPAPPVAGPSVFLFPPKPKDTLMISRTPEVTCVVVDVS HEDPEVQFNWYVDGVEVHNAKTKPREEQFNSTFRVVS VLTVVHQDWLNGKEYKCKVSNKGLPAPIEKTISKTKGQ PREPQVCTLPPSREEMTKNQVSLSCAVKGFYPSDIAVE WESNGQPENNYKTTPPMLDSDGSFFLVSKLTVDKSRW QQGNVFSCSVMHEALHNRFTQKSLSLSPGK |
| 173. | BAP0075 heavy chain #1 | EVQLVQSGAEVKKPGASVKVSCKASGYTFTDYEIHWV RQAPGKGLEWMGAIDPETGGTAYNQKFKGRVTMTTDT STSTAYMELRSLRSDDTAVYYCYSYDYVTYWGQGTTV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKKVEPKSCDKTHTCPPC PAPEAAGGPSVFLFPPKPKDTLMISRTPEVTCVVVDVSH EDPEVKFNWYVDGVEVHNAKTKPREEQYNSTYRVVSV LTVLHQDWLNGKEYKCKVSNKALPAPIEKTISKAKGQP REPQVCTLPPSRDELTKNQVSLSCAVKGFYPSDIAVEWE SNGQPENNYKTTPPVLDSDGSFFLVSKLTVDKSRWQQG NVFSCSVMHEALHNRFTQKSLSLSPGK |
| 174. | BAP0075 heavy chain #2 | EVQLLESGGGLVQPGGSLRLSCAASGFTFSSYAMSWVR QAPGKGLEWVSGITGSGGSTYYADSVKGRFTISRDNSK NTLYLQMNSLRAEDTAVYYCAKDPGTTVIMSWFDPWG QGTLVTVSSASTKGPSVFPLAPSSKSTSGGTAALGCLVK DYFPEPVTVSWNSGALTSGVHTFPACLQSSGLYSLSSVV TVPSSSLGTQTYICNVNHKPSNTKVDKKVEPKSSDKTH TCPPCPAPEAAGGPSVFLFPPKPKDTLMISRTPEVTCVV VDVSHEDPEVKFNWYVDGVEVHNAKTKPREEQYNSTY RVVSVLTVLHQDWLNGKEYKCKVSNKALPAPIEKTISK AKGQPREPQVYTLPPCRDELTKNQVSLWCLVKGFYPSD IAVEWESNGQPENNYKTTPPVLDSDGSFFLYSKLTVDK SRWQQGNVFSCSVMHEALHNHYTQKSLSLSPGK |
| 175. | BAP0076 heavy chain #1 | EVQLVQSGAEVKKPGASVKVSCKASGYTFTDYEIHWV RQAPGKGLEWMGAIDPETGGTAYNQKFKGRVTMTTDT STSTAYMELRSLRSDDTAVYYCYSYDYVTYWGQGTTV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKKVEPKSCDKTHTCPPC PAPEAAGGPSVFLFPPKPKDTLMISRTPEVTCVVVDVSH EDPEVKFNWYVDGVEVHNAKTKPREEQYNSTYRVVSV LTVLHQDWLNGKEYKCKVSNKALPAPIEKTISKAKGQP REPQVCTLPPSRDELTKNQVSLSCAVKGFYPSDIAVEWE SNGQPENNYKTTPPVLDSDGSFFLVSKLTVDKSRWQQG NVFSCSVLHEALHARFTQKSLSLSPGK |
| 176. | BAP0076 heavy chain #2 | EVQLLESGGGLVQPGGSLRLSCAASGFTFSSYAMSWVR QAPGKGLEWVSGITGSGGSTYYADSVKGRFTISRDNSK NTLYLQMNSLRAEDTAVYYCAKDPGTTVIMSWFDPWG QGTLVTVSSASTKGPSVFPLAPSSKSTSGGTAALGCLVK DYFPEPVTVSWNSGALTSGVHTFPACLQSSGLYSLSSVV TVPSSSLGTQTYICNVNHKPSNTKVDKKVEPKSSDKTH TCPPCPAPEAAGGPSVFLFPPKPKDTLMISRTPEVTCVV VDVSHEDPEVKFNWYVDGVEVHNAKTKPREEQYNSTY RVVSVLTVLHQDWLNGKEYKCKVSNKALPAPIEKTISK AKGQPREPQVYTLPPCRDELTKNQVSLWCLVKGFYPSD IAVEWESNGQPENNYKTTPPVLDSDGSFFLYSKLTVDK SRWQQGNVFSCSVLHEALHAHYTQKSLSLSPGK |
| 177. | BAP0069 heavy chain | EVQLVQSGAEVKKPGASVKVSCKASGYTFTDYEIHWV RQAPGKGLEWMGAIDPETGGTAYNQKFKGRVTMTTDT STSTAYMELRSLRSDDTAVYYCYSYDYVTYWGQGTTV TVSSASTKGPSVFPLAPCSRSTSESTAALGCLVKDYFPEP VTVSWNSGALTSGVHTFPAVLQSSGLYSLSSVVTVPSSS LGTKTYTCNVDHKPSNTKVDKRVESKYGPPCPPCPAPE |

-continued

SEQUENCE TABLE

| SEQ ID NO. | Description | Nucleotide or Amino Acid Sequence |
|---|---|---|
| | | AAGGPSVFLFPPKPKDTLMISRTPEVTCVVVDVSQEDPE VQFNWYVDGVEVHNAKTKPREEQFNSTYRVVSVLTVL HQDWLNGKEYKCKVSNKGLPSSIEKTISKAKGQPREPQ VYTLPPSQEEMTKNQVSLTCLVKGFYPSDIAVEWESNG QPENNYKTTPPVLDSDGSFFLYSKLTVDKSRWQEGNVF SCSVMHEALHNHYTQKSLSLSPGKGGGGSGGGGSGGG GSEIVLTQSPGTLSLSPGERATLSCRASQSVRGRYLAWY QQKPGQAPRLLIYGASSRATGIPDRFSGSGSGTDFTLTIS RLEPEDFAVFYCQQYGSSPRTFGCGTKVEIKGGGGSGG GGSGGGGSGGGGSEVQLLESGGGLVQPGGSLRLSCAAS GFTFSSYAMSWVRQAPGKCLEWVSGITGSGGSTYYAD SVKGRFTISRDNSKNTLYLQMNSLRAEDTAVYYCAKDP GTTVIMSWFDPWGQGTLVTVSA |
| 178. | BAP0070/ BAP0071 heavy chain | EVQLVQSGAEVKKPGASVKVSCKASGYTFTDYEIHWV RQAPGKGLEWMGAIDPETGGTAYNQKFKGRVTMTTDT STSTAYMELRSLRSDDTAVYYCYSYDYVTYWGQGTTV TVSSASTKGPSVFPLAPCSRSTSESTAALGCLVKDYFPEP VTVSWNSGALTSGVHTFPAVLQSSGLYSLSSVVTVPSSS LGTKTYTCNVDHKPSNTKVDKRVESKYGPPCPPCPAPE AAGGPSVFLFPPKPKDTLMISRTPEVTCVVVDVSQEDPE VQFNWYVDGVEVHNAKTKPREEQFNSTYRVVSVLTVL HQDWLNGKEYKCKVSNKGLPSSIEKTISKAKGQPREPQ VYTLPPSQEEMTKNQVSLTCLVKGFYPSDIAVEWESNG QPENNYKTTPPVLDSDGSFFLYSKLTVDKSRWQEGNVF SCSVMHEALHNHYTQKSLSLSPGKGGGGSGGGGSGGG GSEVQLLESGGGLVQPGGSLRLSCAASGFTFSSYAMSW VRQAPGKCLEWVSGITGSGGSTYYADSVKGRFTISRDN SKNTLYLQMNSLRAEDTAVYYCAKDPGTTVIMSWFDP WGQGTLVTVSSGGGGSGGGGSGGGGSGGGGSEIVLTQ SPGTLSLSPGERATLSCRASQSVRGRYLAWYQQKPGQA PRLLIYGASSRATGIPDRFSGSGSGTDFTLTISRLEPEDFA VFYCQQYGSSPRTFGCGTKVEIK |
| 179. | BAP0072 heavy chain | EVQLVQSGAEVKKPGASVKVSCKASGYTFTDYEIHWV RQAPGKGLEWMGAIDPETGGTAYNQKFKGRVTMTTDT STSTAYMELRSLRSDDTAVYYCYSYDYVTYWGQGTTV TVSSASTKGPSVFPLAPCSRSTSESTAALGCLVKDYFPEP VTVSWNSGALTSGVHTFPAVLQSSGLYSLSSVVTVPSS NFGTQTYTCNVDHKPSNTKVDKTVERKCCVECPPCPAP PVAGPSVFLFPPKPKDTLMISRTPEVTCVVVDVSHEDPE VQFNWYVDGVEVHNAKTKPREEQFNSTFRVVSVLTVV HQDWLNGKEYKCKVSNKGLPAPIEKTISKTKGQPREPQ VYTLPPSREEMTKNQVSLTCLVKGFYPSDIAVEWESNG QPENNYKTTPPMLDSDGSFFLYSKLTVDKSRWQQGNV FSCSVMHEALHNHYTQKSLSLSPGKGGGGSGGGGSGG GGSEVQLLESGGGLVQPGGSLRLSCAASGFTFSSYAMS WVRQAPGKCLEWVSGITGSGGSTYYADSVKGRFTISRD NSKNTLYLQMNSLRAEDTAVYYCAKDPGTTVIMSWFD PWGQGTLVTVSSGGGGSGGGGSGGGGSGGGGSEIVLT QSPGTLSLSPGERATLSCRASQSVRGRYLAWYQQKPGQ APRLLIYGASSRATGIPDRFSGSGSGTDFTLTISRLEPEDF AVFYCQQYGSSPRTFGCGTKVEIK |
| 180. | BAP0073 heavy chain | EVQLVQSGAEVKKPGASVKVSCKASGYTFTDYEIHWV RQAPGKGLEWMGAIDPETGGTAYNQKFKGRVTMTTDT STSTAYMELRSLRSDDTAVYYCYSYDYVTYWGQGTTV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKKVEPKSCDKTHTCPPC PAPEAAGGPSVFLFPPKPKDTLMISRTPEVTCVVVDVSH EDPEVKFNWYVDGVEVHNAKTKPREEQYNSTYRVVSV LTVLHQDWLNGKEYKCKVSNKALPAPIEKTISKAKGQP REPQVYTLPPSRDELTKNQVSLTCLVKGFYPSDIAVEWE SNGQPENNYKTTPPVLDSDGSFFLYSKLTVDKSRWQQG NVFSCSVMHEALHNHYTQKSLSLSPGKGGGGSGGGGS GGGGSEVQLLESGGGLVQPGGSLRLSCAASGFTFSSYA MSWVRQAPGKCLEWVSGITGSGGSTYYADSVKGRFTIS RDNSKNTLYLQMNSLRAEDTAVYYCAKDPGTTVIMSW FDPWGQGTLVTVSSGGGGSGGGGSGGGGSGGGGSEIV LTQSPGTLSLSPGERATLSCRASQSVRGRYLAWYQQKP GQAPRLLIYGASSRATGIPDRFSGSGSGTDFTLTISRLEPE DFAVFYCQQYGSSPRTFGCGTKVEIK |

-continued

SEQUENCE TABLE

| SEQ ID NO. | Description | Nucleotide or Amino Acid Sequence |
|---|---|---|
| | | Additional exemplary anti-DKK1 or anti-sclerostin sequences |
| 164. | 11H10 VH2 | EVQLVESGGGLVQPANSLKLSCAASGFTFSDYAMAWV RQSPKKGLEWVATIIYDGSSTYYRDSVKGRFTISRDNAK STLYLQMDSLRSEDTATYYCATGLGIATDYFDYWGQG VLVTVSS |
| 165. | 11H10 VL2 | DIRMTQSPASLSASLGETVNIECLASEDIYSDLAWYQQK PGKSPQLLIYNANSLQNGVPSRFSGSGSGTQYSLKINSL QSEDVATYFCQQYNNYPPTFGGGTKLELK |
| 166. | 11H10 VH3 | EVQLVESGGGVVQPGRSLRLSCAAS**GFTFSDYAMA**WV RQAPGKCLEWVA**TIIYDGSSTYYRDSVKG**RFTISRDNS KNTLYLQMNSLRAEDTAVYYCAT**GLGIATDY**FDYWG QGTLVTVSS |
| 167. | 11H10 VL3 | DIRMTQSPFSLSASVGDRVTITCLASEDIYSDLAWYQQK PAKAPKLFIYNANSLQNGVPSRFSGSGSGTDYTLTISSLQ PEDFATYYCQQYNNYPPTFGCGTKVEIK |
| 168. | hAb VH2 | EVQLVQSGAEVKKPGASVKVSCKASGYTFTDYEIHWV RQAPGKCLEWMGAIDPETGGTAYNQKFKGRVTMTTDT STSTAYMELRSLRSDDTAVYYCYSYDYVTYWGQGTTV TVSS |
| 169. | hAb1 VL2 | DVVMTQSPLSLSVSPGERASLSC**KSSQSLLYSDGRTYL** NWYLQKPGQSPQRLIY**LVSKLDS**GVPDRFSGSGSGTDF TLKISRVQSEDVGVYYC**WQGTHLPHT**FGCGTKVEIK |
| 170. | hAb2 VL2 | DIQMTQSPSSLSASVGDRVTITC**RSSQSLLYSDGRTYL**N WYQQKPGKSPKRLIY**LVSKLDS**GVPDRFSGSGSGTDFT LTISSLQPEDFATYYC**WQGTHLPHT**FGCGTKVEIK |
| | | Peptide amino acid sequences on the second loop of Sclerostin |
| 185 | hScl 110-133/ pep1 | GPARLLPNAIGRGKWWRPSGPDFR |
| 186 | hScl 119-126 | IGRGKWWR |
| 187 | pep5 | PNAIGRGKWWR |
| 188 | pep6 | IGRGKWWRPSGP |
| | | Additional sequences |
| 183 | SOST_ HUMAN_Q9BQB4 | QGWQAFKNDATEIIPELGEYPEPPPELENNKTMNRAEN GGRPPHHPFETKDVSEYSCRELHFTRYVTDGPCRSAKP VTELVCSGQCGPARLLPNAIGRGKWWRPSGPDFRCIPD RYRAQRVQLLCPGGEAPRARKVRLVASCKCKRLTRFH NQSELKDFGTEAARPQKGRKPRPRARSAKANQAELEN AY |
| 184 | SOST_ MACFA_ A0A2K5VUE5 | QGWQAFKNDATEIIPELGEYPEPPPDLENNKTMNRAEN GGRPPHHPFETKDVSEYSCRELHFTRYVTDGQCRSAKP VTELVCSGQCGPARLLPNAIGRGKWWRPSGPDFRCIPD RYRAQRVQLLCPGGAAPRARKVRLVASCKCKRLTRFH NQSELKDFGPEAARPQKGRKPRPRARGAKANQAELEN AY |
| 189 | SOST_ MACMU_F6WYL4 | QGWQAFKNDATEIIPELGEYPEPPPELENNKTMNRAEN GGRPPHHPFETKDVSEYSCRELHFTRYVTDGQCRSAKP VTELVCSGQCGPARLLPNAIGRGKWWRPSGPDFRCIPD RYRAQRVQLLCPGGAAPRARKVRLVASCKCKRLTRFH NQSELKDFGPEAARPQKGRKPRPRARGAKANQAELEN AY |
| 190 | SOST_ MOUSE_Q99P68 | QGWQAFRNDATEVIPGLGEYPEPPPENNQTMNRAENG GRPPHHPYDAKDVSEYSCRELHYTRFLTDGQCRSAKPV TELVCSGQCGPARLLPNAIGRVKWWRPNGPDFRCIPDR YRAQRVQLLCPGGAAPRSRKVRLVASCKCKRLTRFHN QSELKDFGPETARPQKGRKPRPGARGAKANQAELENA Y |

-continued

SEQUENCE TABLE

| SEQ ID NO. | Description | Nucleotide or Amino Acid Sequence |
|---|---|---|
| 191 | SOST_RAT_ Q99P67 | QGWQAFKNDATEVIPGLREYPEPPQELENNQTMNRAE NGGRPPHHPYDTKDVSEYSCRELHYTRFVTDGQCRSAK PVTELVCSGQCGPARLLPNAIGRVKWWRPNGPDFRCIP DRYRAQRVQLLCPGGAAPRSRKVRLVASCKCKRLTRF HNQSELKDFGPETARPQKGRKPRPRARGAKANQAELE NAY |
| 192 | Pep2 mSOST | GPARLLPNAIGRVKWWRPNGPDFR |
| 193 | Pep3 h/mSOST | GPARLLPNAIGR |
| 194 | Pep4 hSOST | RLLPNAIGRGK |
| 195 | Pep7 hSOST | KWWRPSGPDFR |
| 196 | Pep8 mSOST | PNAIGRVKWWR |
| 197 | Pep9 mSOST | IGRVKWWRPNGP |
| 198 | Pep10 mSOST | KWWRPNGPDFR |
| 199 | HC-CDR1 | DFEIH |
| 200 | HC-CDR2 | AIDPETGGSANNQKFKA |

The invention claimed is:

1. An anti-human Sclerostin construct, comprising:

a) a first polypeptide comprising a first light chain comprising, from N-terminus to C-terminus, i) a light chain variable region, and ii) a first light chain constant domain;

b) a second polypeptide comprising a first heavy chain comprising, from N-terminus to C-terminus, i) a heavy chain variable region, ii) a first heavy chain constant domain, and iii) a first Fc domain;

c) a third polypeptide comprising a second heavy chain comprising, from N-terminus to C-terminus, i) a second heavy chain variable region, ii) a second heavy chain constant domain, and iii) a second Fc domain; and d) a fourth polypeptide comprising a second light chain comprising, from N-terminus to C-terminus, i) a second light chain variable region, and ii) a second light chain constant domain, wherein the first and the second Fc domains form an Fc fragment, and wherein the first polypeptide comprises the amino acid sequence of SEQ ID NO: 147, the second polypeptide comprises the amino acid sequence of SEQ ID NO: 146, the third polypeptide comprises the amino acid sequence of SEQ ID NO: 148, and the fourth polypeptide comprises the amino acid sequence of SEQ ID NO: 149.

2. A pharmaceutical composition comprising the anti-human Sclerostin construct of claim 1 and a pharmaceutically acceptable carrier.

* * * * *